(12) United States Patent
Wohlstadter et al.

(10) Patent No.: US 7,842,246 B2
(45) Date of Patent: Nov. 30, 2010

(54) ASSAY PLATES, READER SYSTEMS AND METHODS FOR LUMINESCENCE TEST MEASUREMENTS

(75) Inventors: Jacob N. Wohlstadter, Potomac, MD (US); Eli Glezer, Chevy Chase, MD (US); James Wilbur, Germantown, MD (US); George Sigal, Rockville, MD (US); Kent Johnson, Bethesda, MD (US); Charles Clinton, Clarksburg, MD (US); Alan Kishbaugh, Germantown, MD (US); Bandele Jeffrey-Coker, Darnestown, MD (US); Jeff D. Debad, Gaithersburg, MD (US); Alan B. Fischer, Cambridge, MA (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 855 days.

(21) Appl. No.: 10/185,274

(22) Filed: Jun. 28, 2002

(65) Prior Publication Data
US 2004/0022677 A1 Feb. 5, 2004

Related U.S. Application Data

(60) Provisional application No. 60/301,932, filed on Jun. 29, 2001.

(51) Int. Cl.
*B01L 3/00* (2006.01)
(52) U.S. Cl. .................. 422/102; 422/52; 422/82.01; 422/82.02; 435/288.4; 435/305.2

(58) Field of Classification Search .............. 422/102, 422/82.01, 82.02, 52; 435/288.4, 305.2
See application file for complete search history.

(56) References Cited

U.S. PATENT DOCUMENTS

| 4,498,780 | A | 2/1985 | Banno et al. |
| 4,849,330 | A | 7/1989 | Humphries et al. |
| 5,030,310 | A | 7/1991 | Wogoman et al. |
| 5,066,372 | A | 11/1991 | Weetall et al. |
| 5,187,096 | A | 2/1993 | Giaever et al. |

(Continued)

FOREIGN PATENT DOCUMENTS

WO  WO94/19683  2/1994

(Continued)

OTHER PUBLICATIONS

Mendoza, L.G., et al., "High-Throughput Microarray-Based Enzyme-Linked Immunosorbent Assay (ELISA)", *BioTechniques* 27(4): 778-88 (1999).

(Continued)

*Primary Examiner*—Jan M Ludlow
(74) *Attorney, Agent, or Firm*—Scully, Scott, Murphy & Presser, P.C.

(57) ABSTRACT

Luminescence test measurements are conducted using an assay module having integrated electrodes with a reader apparatus adapted to receive assay modules, induce luminescence, preferably electrode induced luminescence, in the wells or assay regions of the assay modules and measure the induced luminescence.

29 Claims, 58 Drawing Sheets

U.S. PATENT DOCUMENTS

| | | | |
|---|---|---|---|
| 5,218,312 A | 6/1993 | Moro | |
| 5,264,103 A | 11/1993 | Yoshioka et al. | |
| 5,389,215 A | 2/1995 | Horiuchi et al. | |
| 5,429,735 A | 7/1995 | Johnson et al. | |
| 5,459,068 A | 10/1995 | Madara | |
| 5,527,670 A | 6/1996 | Stanley | |
| 5,547,555 A | 8/1996 | Schwartz et al. | |
| 5,589,136 A | 12/1996 | Northrup et al. | |
| 5,632,957 A | 5/1997 | Heller et al. | |
| 5,670,322 A | 9/1997 | Eggers et al. | |
| 5,776,672 A | 7/1998 | Hashimoto et al. | |
| 5,849,486 A | 12/1998 | Heller et al. | |
| 5,866,434 A | 2/1999 | Massey et al. | |
| 5,968,745 A | 10/1999 | Thorpe et al. | |
| 5,972,694 A | 10/1999 | Mathus | |
| 6,066,448 A * | 5/2000 | Wohlstadter et al. | 435/6 |
| 6,071,395 A | 6/2000 | Lange | |
| 6,083,763 A | 7/2000 | Balch | |
| 6,090,545 A | 7/2000 | Wohlstadter et al. | |
| 6,127,127 A | 10/2000 | Eckhardt et al. | |
| 6,140,045 A | 10/2000 | Wohlstadter et al. | |
| 6,207,369 B1 | 3/2001 | Wohlstadter et al. | |
| 6,238,869 B1 | 5/2001 | Kris et al. | |
| 6,251,685 B1 | 6/2001 | Dorsel et al. | |
| 6,258,326 B1 | 7/2001 | Modlin | |
| 6,264,814 B1 | 7/2001 | Lange | |
| 6,376,233 B1 * | 4/2002 | Wolf et al. | 435/288.4 |
| 6,413,783 B1 | 7/2002 | Wohlstadter et al. | |
| 6,553,318 B2 * | 4/2003 | Mansky | 702/22 |
| 2001/0006417 A1 | 7/2001 | Modlin et al. | |
| 2001/0029048 A1 | 10/2001 | Ding et al. | |
| 2002/0014415 A1 | 2/2002 | Nakayama et al. | |
| 2002/0025573 A1 | 2/2002 | Maher et al. | |

FOREIGN PATENT DOCUMENTS

| | | | |
|---|---|---|---|
| WO | WO98/36266 | | 2/1998 |
| WO | WO 98/20974 | * | 5/1998 |

OTHER PUBLICATIONS

Popovich, N., "Mediated electrochemical detection of nucleic acids for drug discovery and clinical diagnostics", *IVD Technology*, Apr. 2001: 36-42 (2001).

Moody, M.D., et al., "Array-Based ELISAs for High-Throughput Analysis of Human Cytokines", *BioTechniques*, 31(1): 186-194 (2001).

ViewLux™ Features Guide Brochure, Perkin Elmer Brochure #1430-970-05 (Apr. 2001).

Umek, Robert M., et al., "Electronic Detection of Nucleic Acids—A Versatile Platform for Molecular Diagnostics", *J. Molecular Diagnostics*, 3(2):74-84 (2001).

* cited by examiner

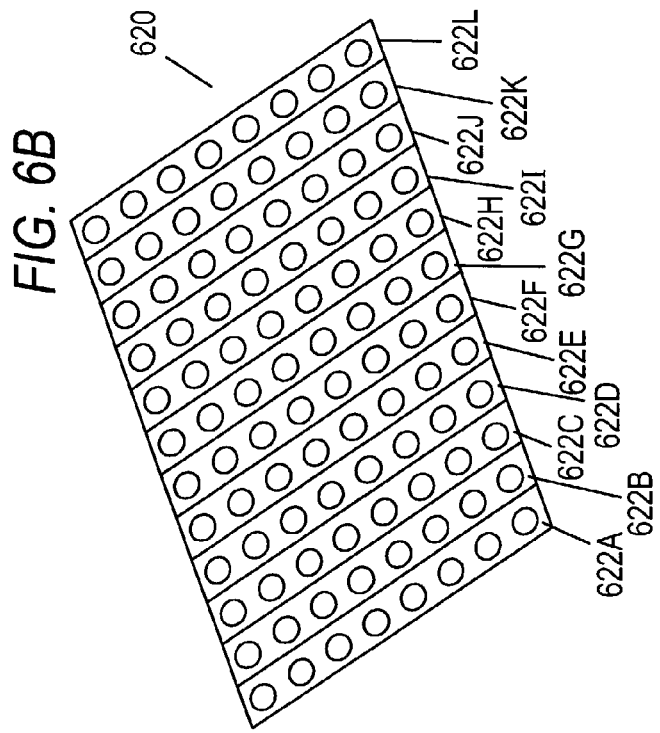
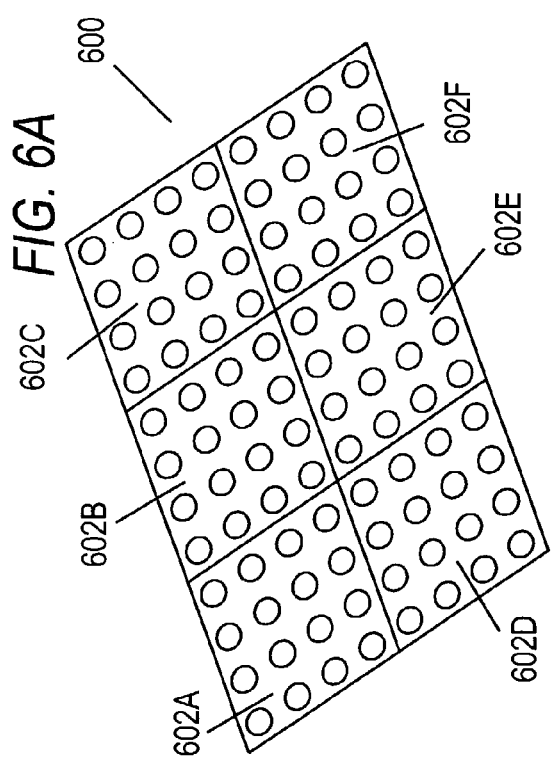
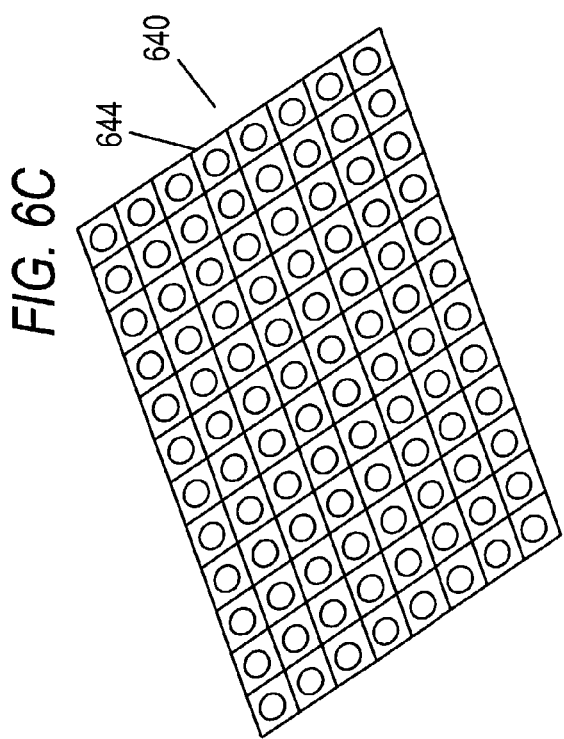

ASSAY PLATES, READER SYSTEMS AND METHODS FOR LUMINESCENCE TEST MEASUREMENTS

CROSS-REFERENCE TO RELATED APPLICATIONS

This application claims priority to U.S. Provisional Application Ser. No. 60/301,932, filed Jun. 29, 2001, hereby incorporated by reference. This application is related to co-pending U.S. patent application Ser. No. 10/185,363, filed Jun. 28, 2002, now U.S. Pat. No. 6,977,722 B2, which is hereby incorporated by reference.

1. FIELD OF THE INVENTION

This application relates to plates, plate components, kits, apparatuses and methods for conducting chemical, biochemical and/or biological assays.

2. BACKGROUND OF THE INVENTION

2.1 Chemical, Biochemical and Biological Assays

Numerous methods and systems have been developed for conducting chemical, biochemical and/or biological assays. These methods and systems are essential in a variety of applications including medical diagnostics, food and beverage testing, environmental monitoring, manufacturing quality control, drug discovery and basic scientific research. Depending on the application, it is desirable that assay methods and systems have one or more of the following characteristics: i) high throughput, ii) high sensitivity, iii) large dynamic range, iv) high precision and/or accuracy, v) low cost, vi) low consumption of reagents, vii) compatibility with existing instrumentation for sample handling and processing, viii) short time to result, ix) insensitivity to interferents and complex sample matrices and x) uncomplicated format. There is substantial value to new assay methods and systems that incorporate improvements in these characteristics or in other performance parameters.

At this time, there are a number of commercially available instruments that utilize electrochemiluminescence (ECL) for analytical measurements. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863, herein incorporated by reference). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody or nucleic acid probe; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants, herein incorporated by reference). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; and 5,589,136 and Published PCT Nos. WO99/63347; WO00/03233; WO99/58962; WO99/32662; WO99/14599; WO98/12539; WO97/36931 and WO98/57154, each of which are herein incorporated by reference.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. The use of a permanent flow cell provides many advantages but also some limitations, for example, in assay throughput. In some applications, for example, the screening of chemical libraries for potential therapeutic drugs, assay instrumentation should perform large numbers of analyses at very high speeds on small quantities of samples. A variety of techniques have been developed for increasing assay throughput. The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates). Multi-well assay plates can take a variety of forms, sizes and shapes. For convenience, some standards have appeared for some instrumentation used to process samples for high throughput assays. Multi-well assay plates typically are made in standard sizes and shapes and having standard arrangements of wells. Some well established arrangements of wells include those found on 96-well plates (12×8 array of wells), 384-well plates (24×16 array of wells) and 1536-well plate (48×32 array of well). The Society for Biomolecular Screening has published recommended microplate specifications for a variety of plate formats (see, http://www.sbsonline.org), the recommended specifications hereby incorporated by reference.

Assays carried out in standardized plate formats can take advantage of readily available equipment for storing and moving these plates as well as readily available equipment for rapidly dispensing liquids in and out of the plates. A variety of instrumentation is commercially available for rapidly measuring radioactivity, fluorescence, chemiluminescence, and optical absorbance in or from the wells of a plate, however, there is no commercial instrument for measuring ECL emitted from the wells of a multi-well assay plate.

2.2 Assay Plates

FIG. 1 depicts a standard 96-well assay plate 100. Assay plate 100 comprises a skirt 112, a periphery wall 114, a upper surface 116 and an 8×12 array of wells 118 separated by spacers 120 and empty base regions 128. Skirt 112 surrounds the base of plate 100 and typically has a width of 3.365 inches and a length of 5.030 inches. To facilitate orientation, skirt 112 and periphery wall 114 include a recess 130. Upper surface 116 extends around plate 100 from periphery wall 114 to respective midlines of the outermost wells of wells 118. Each of wells 118 comprises a cell wall 122 having an inner surface 124 and a cell floor 126, together defining a cylindrical region. Skirt 112, periphery wall 114, upper surface 116, wells 118, spacers 120, cell floors 126 and base regions 128 are integrally molded features of plate 100. Alternatively, plate 100 may omit cell floors 126.

A standard 96-well assay plate is not particularly suited for electrochemiluminescence test measurements. The small size of the wells in such a plate, approximately 0.053 square inches each, presents a considerable obstacle for the introduction of electrodes and/or the efficient collection of light emitted from the surface of such electrodes. The dimensional problems grow even more difficult when plates having even higher well concentrations are considered, e.g. 384-well plates and 1536-well plates.

3. SUMMARY OF THE INVENTION

The invention relates to assay modules (preferably assay plates, more preferably multi-well assay plates), methods and apparatuses for conducting assay measurements. Assay modules of the invention may include one or more, preferably a plurality, of wells, chambers and/or assay regions for conducting one or more assay measurements. Preferably, these wells, chambers and/or assay regions comprise one or more electrodes for inducing luminescence from materials in the wells, chambers and/or assay regions. The assay modules may further comprise assay reagents (in liquid or dry form), preferably in the wells, chambers or assay regions of the assay module. Such assay reagents may be immobilized on electrodes of the module or confined on electrodes of the module (e.g., through the use of appropriately designed dielectric surfaces surrounding the electrode surfaces). Preferably, the module is configured to allow for the measurement of luminescence in portions of the assay module (preferably, more than one assay region, well or chamber at a time, but less than all). One aspect of the invention relates to novel configurations and materials for electrodes and electrical contacts in assay modules. The invention also relates to apparatuses, methods, systems and kits for conducting measurements using assay modules. The invention further relates to methods of manufacturing the assay modules and plates of the invention.

The multi-well assay plates may include several elements, for example, a plate top, a plate bottom, wells, working electrodes, counter electrodes, reference electrodes, dielectric materials, electrical connections, and assay reagents. The wells of the plates may be defined by holes/openings in the plate top. The plate bottom can be affixed to the plate top (either directly or in combination with other components) and can serve as the bottom of the well. Alternatively, the wells of the plates may be defined as indentations or dimples on a surface of a plate. The multi-well assay plates may have any number of wells of any size or shape, arranged in any pattern or configuration, and can be composed of a variety of different materials. Preferred embodiments of the invention use industry standard formats for the number, size, shape and configuration of the plate and wells. Examples of standard formats include 96-, 384-, 1536-, and 9600-well plates, with the wells configured in two-dimensional arrays. Other formats may include single well plates (preferably having a plurality of assay domains), 2 well plates, 6 well plates, 24 well plates, and 6144 well plates.

According to the invention, working, counter and, optionally, reference electrodes can be incorporated into the wells. The present invention describes several novel configurations and materials for electrodes in multi-well assay plates. Multi-well assay plates of the present invention may be used once or may be used multiple times and are well suited to applications where the plates are disposable. Furthermore, the assay reagents, preferably dried reagents and/or wet reagents, may be incorporated into the assay plate, preferably into one or more wells or assay domains. In some embodiments, a well of a multi-well plate may include a plurality of assay domains.

The invention relates to processes that involve the use of an electrode and the generation of light, including methods, apparatuses and assay modules adapted for such processes. The invention further relates to the measurement of light from such processes, for example, in the conduct of assays. Examples of such processes include electrochemiluminescence (also referred to as electrogenerated chemiluminescence), electroluminescence, and chemiluminescence triggered by an electrochemically generated species. For the purposes of the application and for convenience, these three processes will be referred to as "electrode induced luminescence". Electrochemiluminescence involves electrogenerated species and the emission of light. For example, electrochemiluminescence may involve luminescence generated by a process in which one or more reactants are generated electrochemically and undergo one or more chemical reactions to produce species that emits light, preferably repeatedly. The invention also relates to processes that do not require the use of an electrode, for example, chemiluminescence, fluorescence, bioluminescence, phosphorescence, optical density and processes that involve the emission of light from a scintillant. The invention also relates to processes that do not involve luminescence, for example, electrochemical processes (e.g., involving the measurement or generation of current or voltage) or electrical processes (e.g., involving the measurement of resistance or impedance).

The invention further relates to an apparatus that can be used to induce and measure luminescence, preferably electrode induced luminescence, more preferably electrochemiluminescence, in assays conducted in or on assay modules, preferably multi-well assay plates. The invention further relates to an apparatus that can be used to conduct assays by certain optically based assay methodologies that do not use electrode induced luminescence such as fluorescence assays, chemiluminescence assays, bioluminescence assays and phosphorescence assays. The invention also relates to an apparatus that can be used to induce and/or measure current and/or voltage, for example, at an electrode. The measurement of current and/or voltage may occur independently of or concurrently with illumination and/or with the measurement of luminescence (e.g., as in spectroelectrochemical measurements or photoelectrochemical measurements).

The apparatus may incorporate, for example, one or more photodetectors; a light tight enclosure; mechanisms to transport the assay plates into and out of the apparatus (and in particular, into and out of a light tight enclosure); mechanisms to align and orient the assay plates with the photodetector(s) and/or with electrical contacts; mechanisms to track and identify plates (e.g. bar code readers); mechanisms to make electrical connections to plates, one or more sources of electrical energy for inducing luminescence, and appropriate devices, electronics and/or software. The apparatus may also include mechanisms to store, stack, move and/or distribute one or more multi-well assay plates (e.g. plate stackers and/or plate conveyors). The apparatus may be configured to measure light from multi-well assay plates by measuring light sequentially from a plurality of sectors of the plate and/or from the entire plate substantially simultaneously or simultaneously. The apparatus may also incorporate microprocessors and computers to control certain functions within the instrument and to aid in the storage, analysis and presentation of data.

Another aspect of the invention relates to methods for performing assays comprising measuring luminescence from an assay plate. According to the present invention, luminescence is advantageously measured from the assay plate in sectors. Another embodiment relates to methods for performing electrode induced luminescence (preferably electrochemiluminescence) assays in a multi-well plate having a plurality of wells.

Yet another aspect of the invention relates to assay plates and plate components (e.g., plate bottoms, plate tops and multi-well plates) for use in a variety of assays. Thus, one embodiment relates to plate bottoms (e.g., without the plate top) which can be joined with a plate top to form a multi-well plate suitable for assays. For example, a plate bottom having a plurality of patterned electrodes which may be on a top surface, the electrodes arranged in such a manner so that when the bottom is joined with a multi-well plate top, each well has one or more, preferably two or more, conductive electrode surfaces.

Another embodiment relates to an improved plate top having one or more openings configured so that when affixed or placed onto a plate bottom forms one or more assay wells. Preferably, the plate top forms wells having well surfaces with properties and characteristics (e.g., light reflection, surface tension, etc.) for improved assays. For example, plate tops designed to form well surfaces which provide for improved luminescence collection efficiencies.

A still further aspect of the invention relates to systems comprising the apparatus of the present invention combined with the multi-well plate of the invention. Preferably, the system contains all the components necessary for performing assays such as high-throughput assays including a light detector, a source of electrical energy and a plate support with a multi-well plate placed thereon.

A still further aspect of the invention relates to kits for use in the assay plates, apparatuses and methods of the invention. Preferably, the kits include, in one or more containers, a multi-well plate and one or more assay reagents.

4. DESCRIPTION OF THE FIGURES

Figure 2:
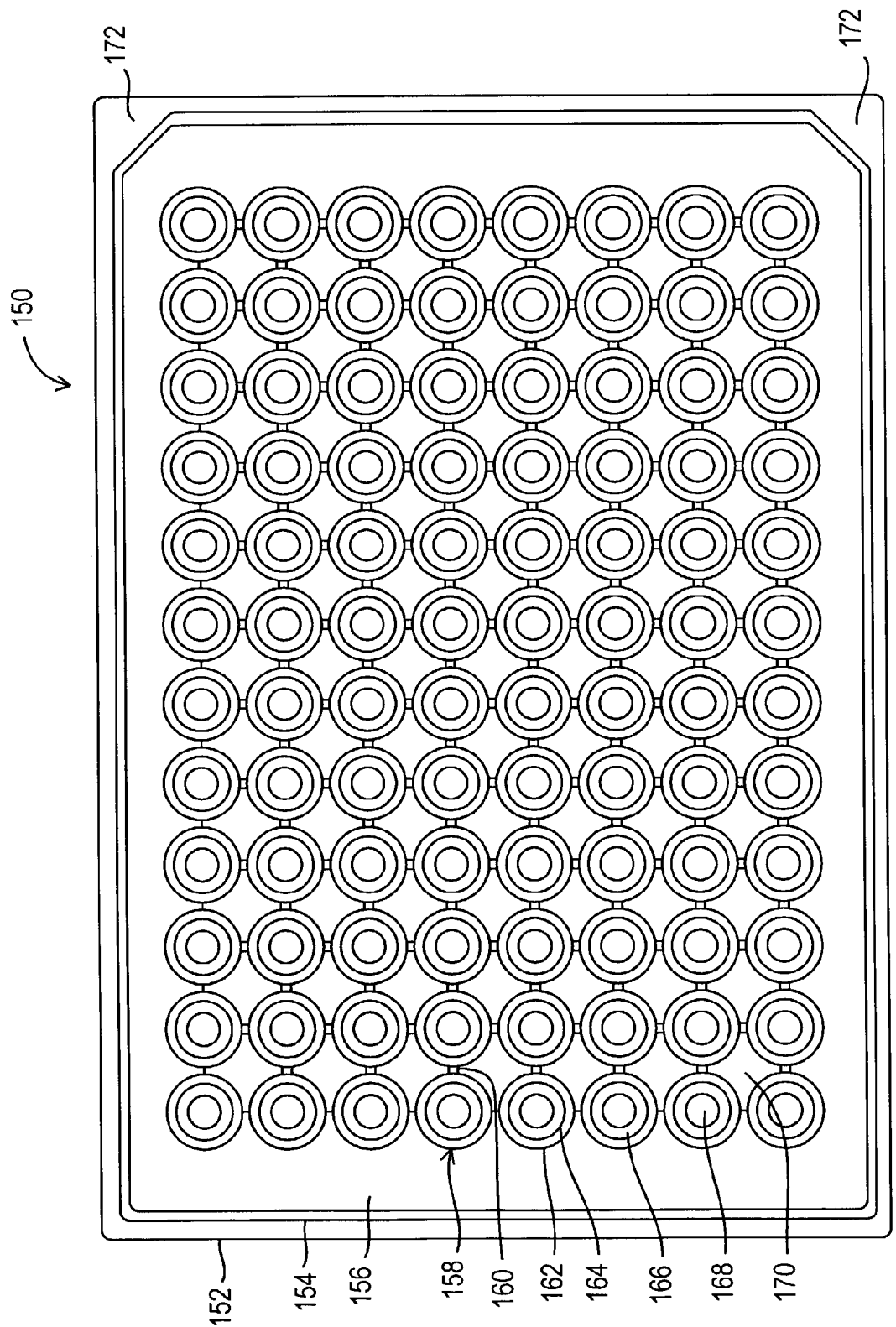
FIG. 2 illustrates a top view of a multi-well assay plate according to one embodiment of the invention.
Figure 2A:
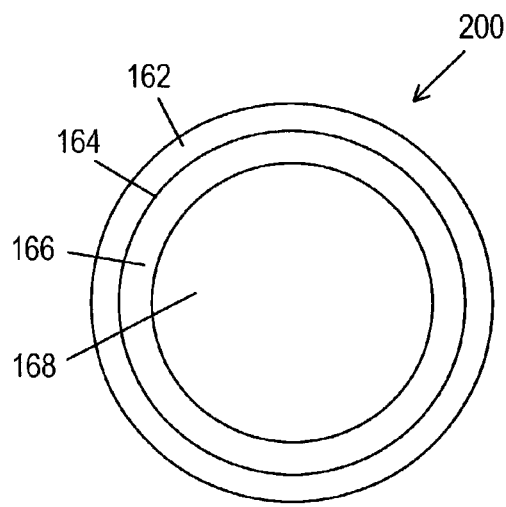

FIG. 2A illustrates a top view of a well 200 of a multi-well assay plate according to another embodiment of the invention. Well 200 has a wall 162, having an inner surface 164; a counter electrode 166; and a working electrode 168 which forms the bottom of well 200.

Figure 2B:
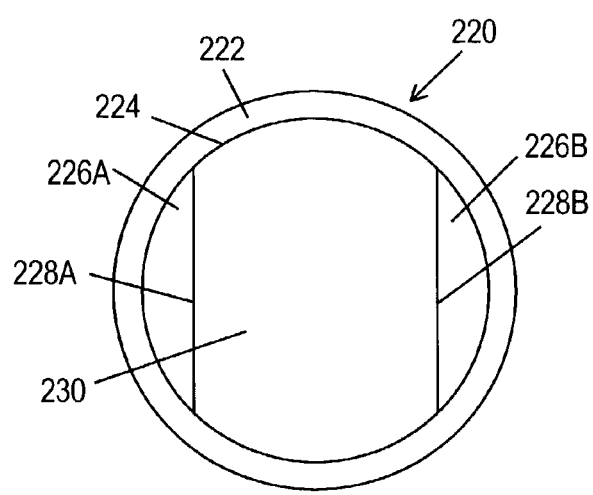

FIG. 2B illustrates a top view of a well 220 of a multi-well assay plate according to the invention. Well 220 has a wall 222, counter electrodes 226A and 226B and a working electrode 230.

Figure 2C:
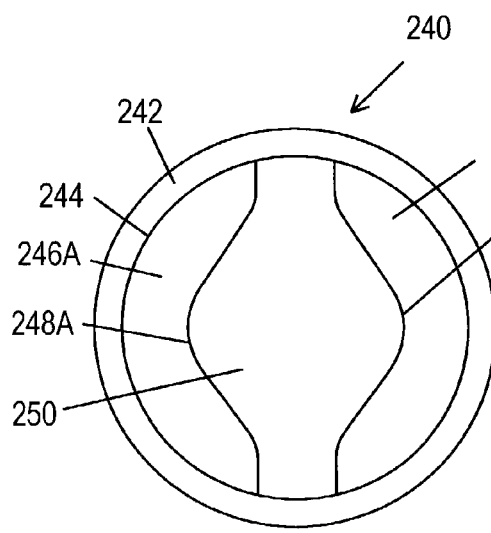

FIG. 2C illustrates a top view of a well 240 of a multi-well assay plate according to the invention. Well 240 has wall 242, counter electrodes 246A and 246B, and working electrode 250.

Figure 2D:
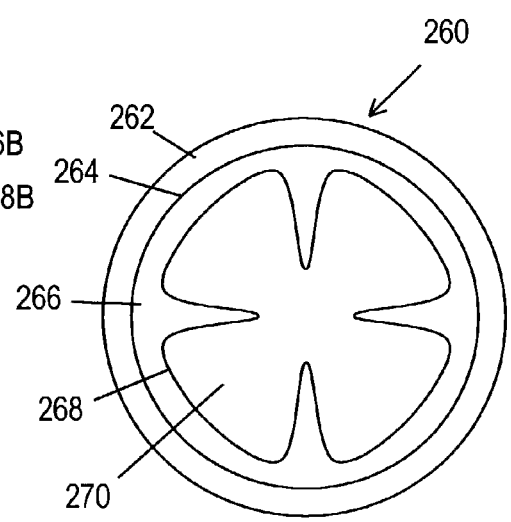

FIG. 2D illustrates a top view of a well 260 of a multi-well assay plate according to the invention. Well 260 has wall 262, counter electrode 266, and working electrode 270.

Figure 2E:
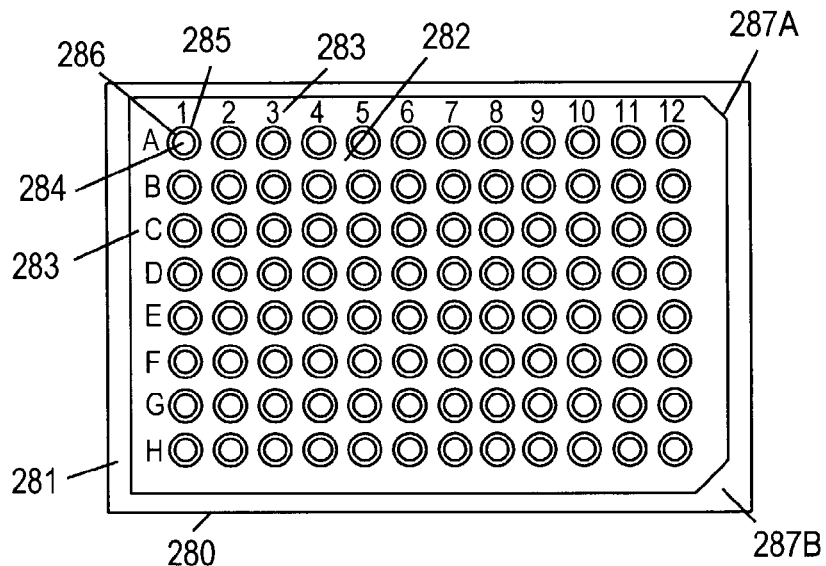

FIG. 2E illustrates a plate top 280 according to the present invention. Plate top 280 comprises a plate top body 281, a top surface 282, wall 285, and inner surface 286. Plate top 280 has holes 284 that may be used in part to form walls for wells in multi-well assay plates of the invention.

Figure 2F:
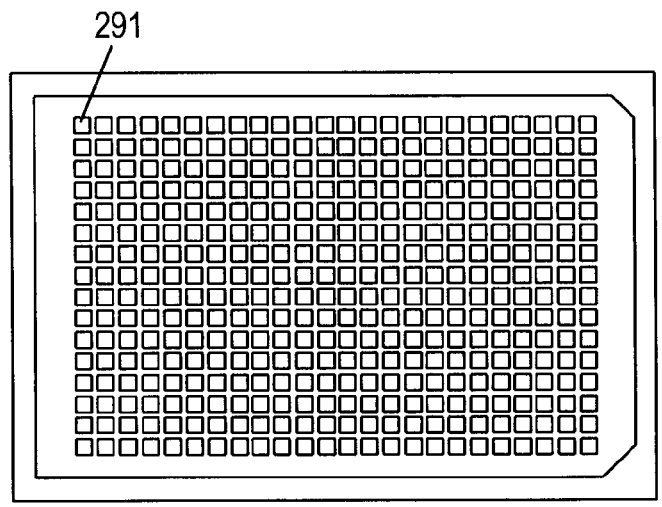

FIG. 2F illustrates a plate top 290 according to the present invention wherein plate top 290 has 384 square holes 291.

Figure 2G:
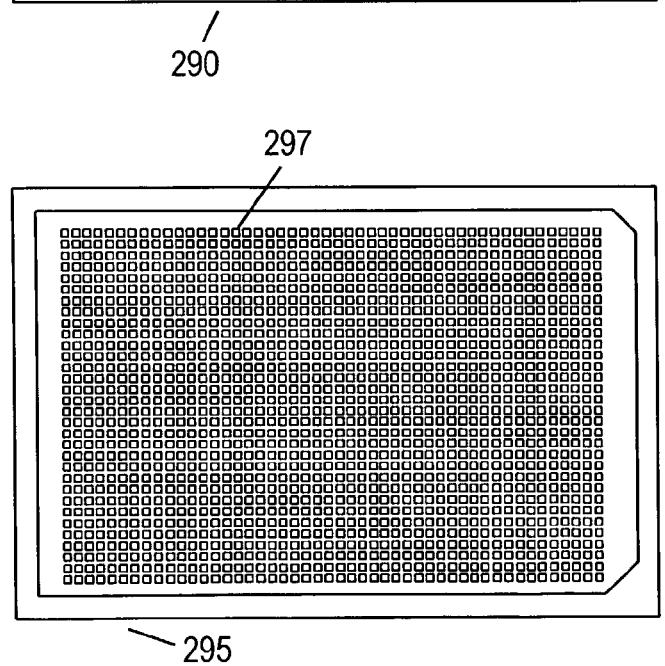

FIG. 2G illustrates a plate top 295 according to the invention wherein plate top 295 has 1536 holes 297.

Figure 2H:
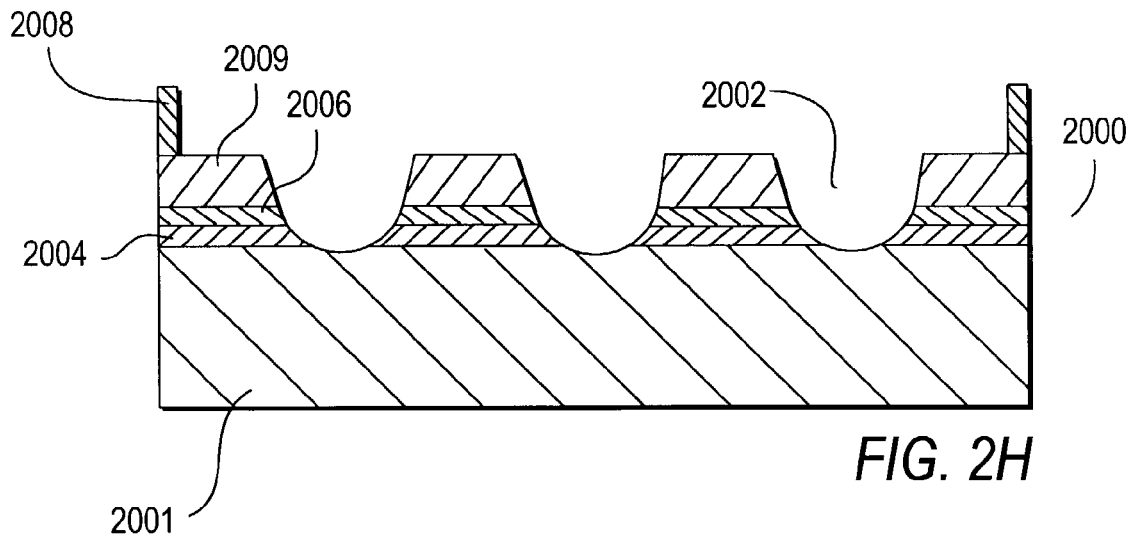

FIG. 2H illustrates a cross sectional view from the side of a multi-well assay plate 2000 according to the present invention. Plate 2000 has a support/working electrode 2001, a plurality of wells 2002, dielectric layer 2004, counter electrode 2006, lip 2008 and plate top 2009. Plate 2000 may also incorporate other features described elsewhere for multi-well assay plates such as assay reagents, electrical connections, supporting materials, etc.

Figure 2I:
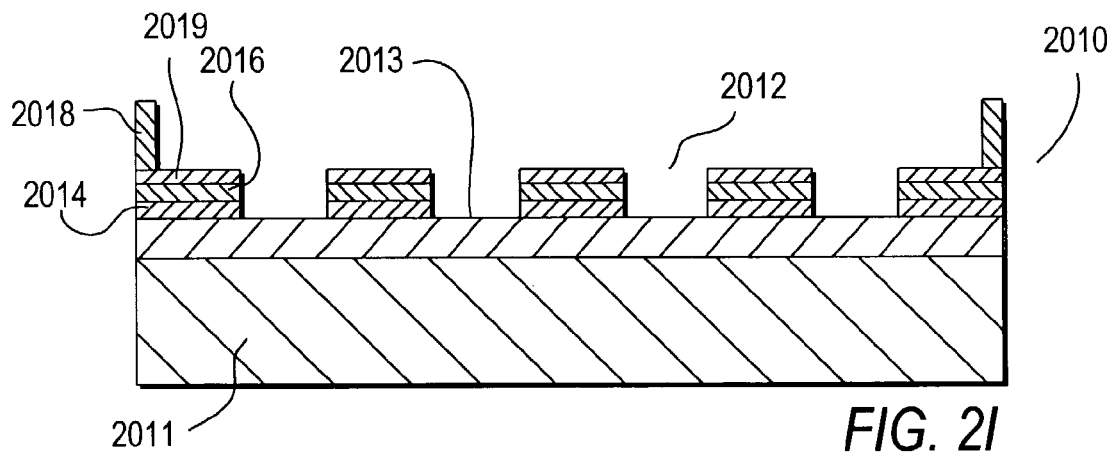

FIG. 2I illustrates cross-sectional view from the side of a multi-well assay plate 2010 of the invention. Multi-well assay plate 2010 has a support 2011, one or more wells 2012, working electrode 2013, dielectric layer 2014, counter electrode 2016, lip 2018 and boundary 2019. Plate 2010 may also incorporate other features described elsewhere for multi-well assay plates such as assay reagents, electrical connections, supporting materials, etc.

Figure 2J:
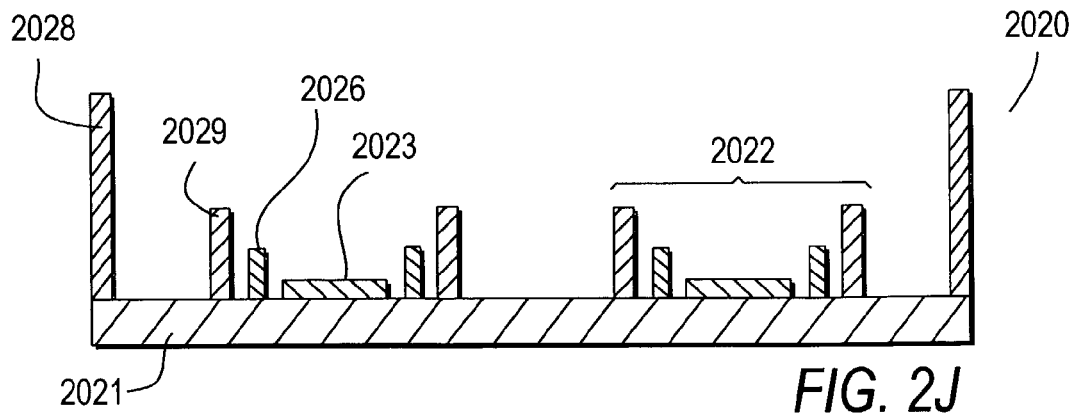

FIG. 2J illustrates a cross sectional view from the side of a multi-well assay plate 2020 of the invention. Plate 2020 has a support 2021, one or more wells 2022, one or more working electrodes 2023, one or more counter electrodes 2026, lip 2028 and one or more boundaries 2029. Plate 2020 may also incorporate other features described above for multi-well assay plates such as assay reagents, electrical connections, supporting materials, etc.

Figures 3A, 3B:
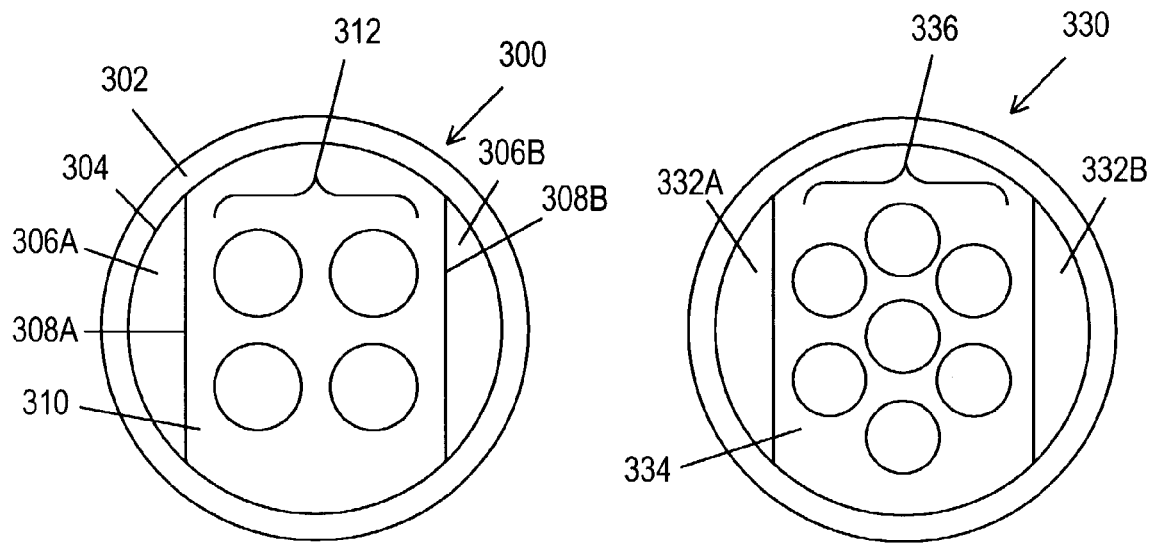

FIG. 3A illustrates a well 300 according to another embodiment of the present invention. Well 300 has a wall 302 having an interior surface 304, counter electrodes 306A and 306B, working electrode 310 and assay domains 312.

FIG. 3B illustrates a well 330 according to the present invention wherein well 330 has a plurality of assay domains 336.

Figure 3C:
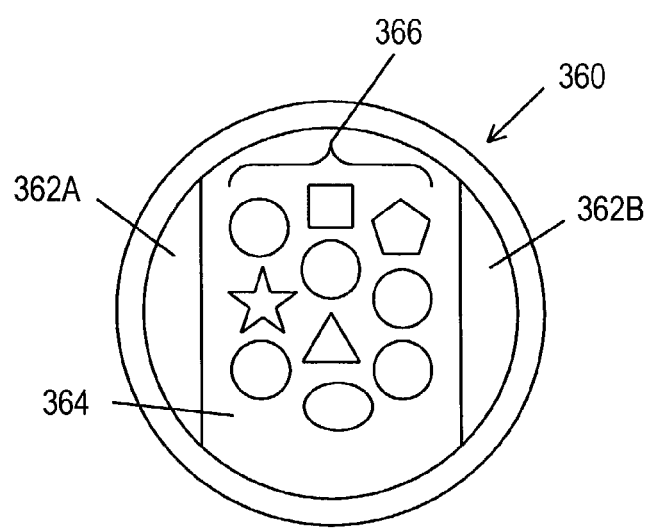

FIG. 3C illustrates a well 360 according to the present invention wherein well 360 has a plurality of assay domains 366.

Figure 4A:
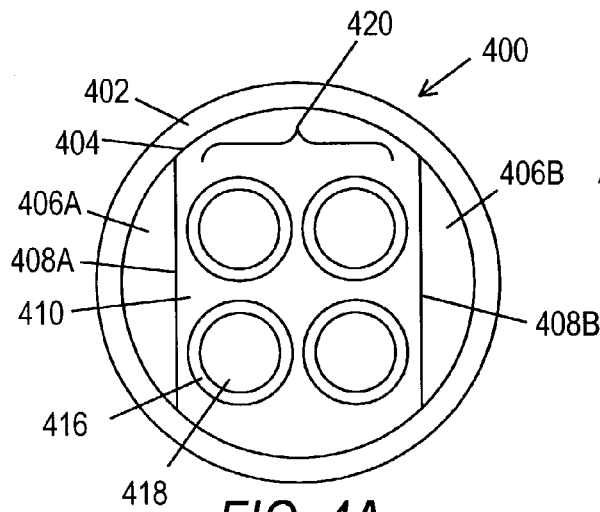

FIG. 4A illustrates a well 400 according to yet another embodiment of the present invention. Well 400 has a wall 402 having an interior surface 404, counter electrodes 406A and 406B, working electrode 410, and boundaries 416 that define domains 418 of working electrode 410.

Figure 4B:
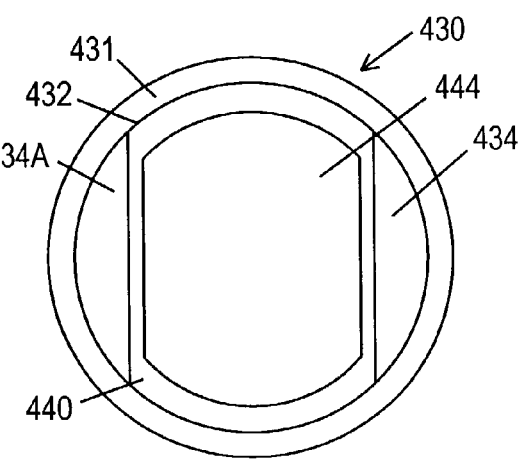

FIG. 4B illustrates a well 430 according to the invention. Boundary 440 separates counter electrodes 434A and 434B from working electrode 444.

Figure 4C:
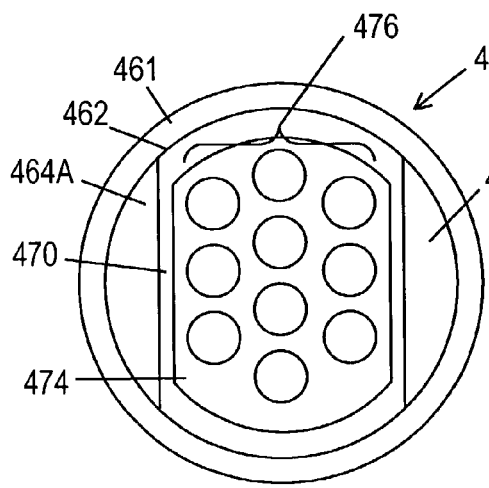

FIG. 4C illustrates a well 460 according to the invention wherein boundary 470 separate counter electrodes 464A and 464B from working electrode 474. Working electrode 474 has a plurality of assay domains 476.

Figure 4D:
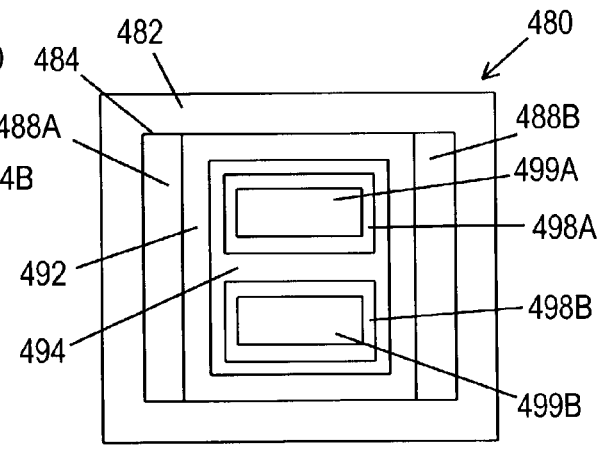

FIG. 4D illustrates a well 480 according to the invention with a wall 482, counter electrodes 488A and 488B, boundary 492, working electrode 494, boundaries 498A and 498B and assay domains 499A and 499B.

Figure 4E:
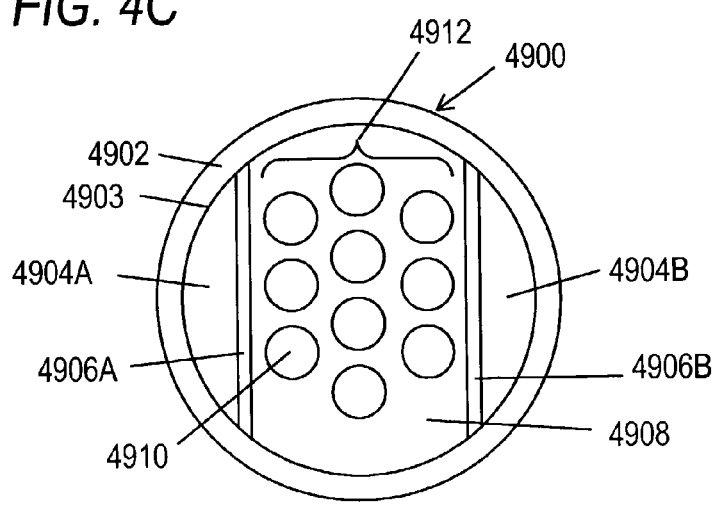

FIG. 4E illustrates a well 4900 according to the present invention. Well 4900 has wall 4902 with interior surface 4903, counter electrodes 4904A and 4904B, gaps 4906A and 4906B exposing a support, barrier 4908 with a plurality of holes 4912 that expose working electrode 4910.

Figure 5:
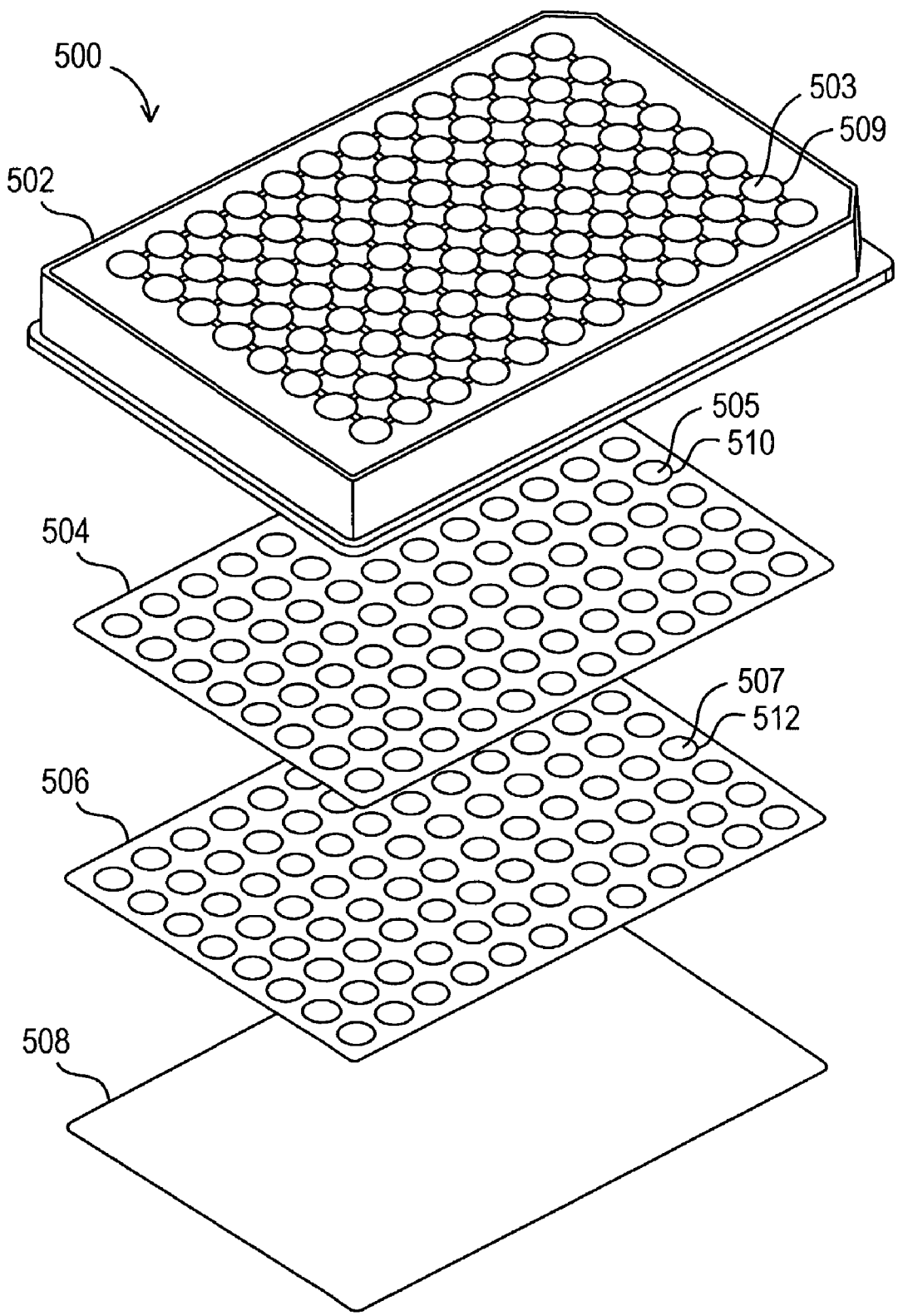

FIG. 5 illustrates a multi-well assay plate 500 according to another embodiment of the invention.

FIG. 6 illustrates examples of sectioned conductive layers in multi-well assay plate of the invention. FIG. 6A shows a conductive layer 600 sectioned into six sections 602A, 602B, 602C, 602D, 602E, and 602F. FIG. 6B shows conductive layer 620 sectioned into 12 sections 622A-L. FIG. 6C shows conductive layer 640 shows sectioned into 96 sections 644.

FIG. 7 illustrates examples of sectioned electrodes in multi-well assay plate of the invention. FIG. 7A shows electrode 700 sectioned into six sections. FIG. 7B shows electrode 720 sectioned into 12 sections. FIG. 7C shows electrode 740 sectioned into 8 sections. FIG. 7D shows electrode 760 sectioned into 96 sections.

Figure 8A:
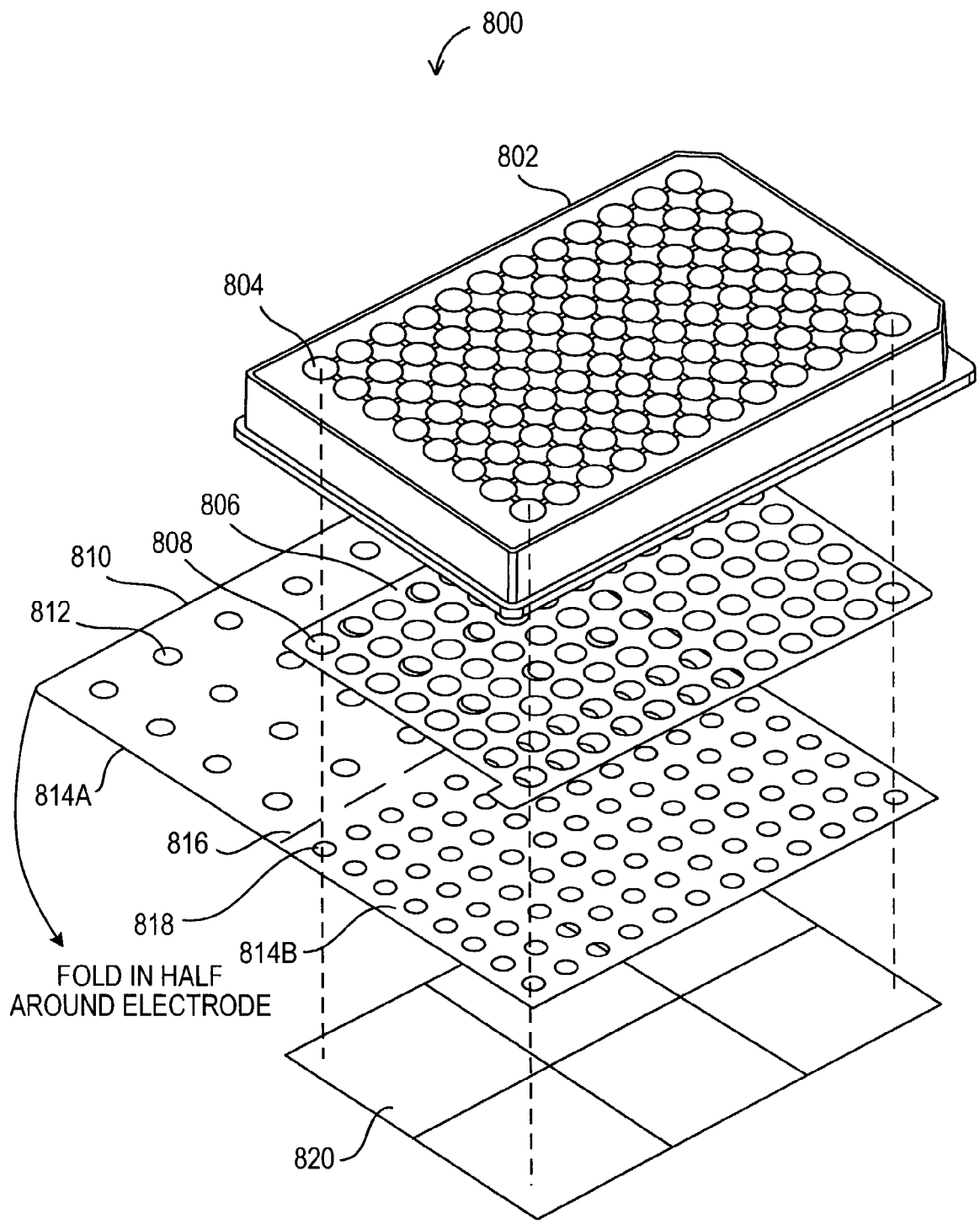

FIG. 8A illustrates a multi-well assay plate 800 of the invention.

Figure 8B:
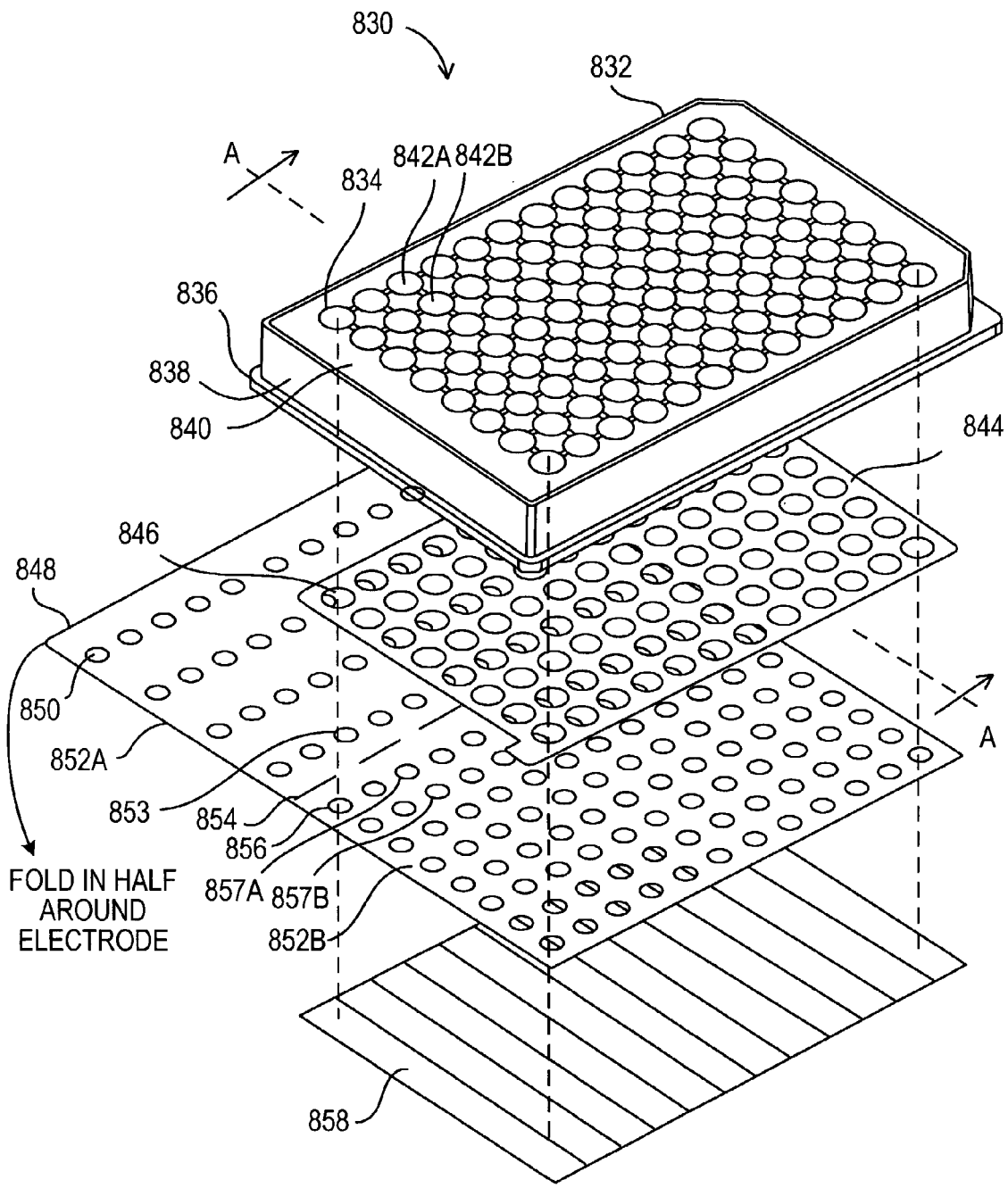

FIG. 8B illustrates a multi-well assay plate 830 of the invention.

Figure 8C:
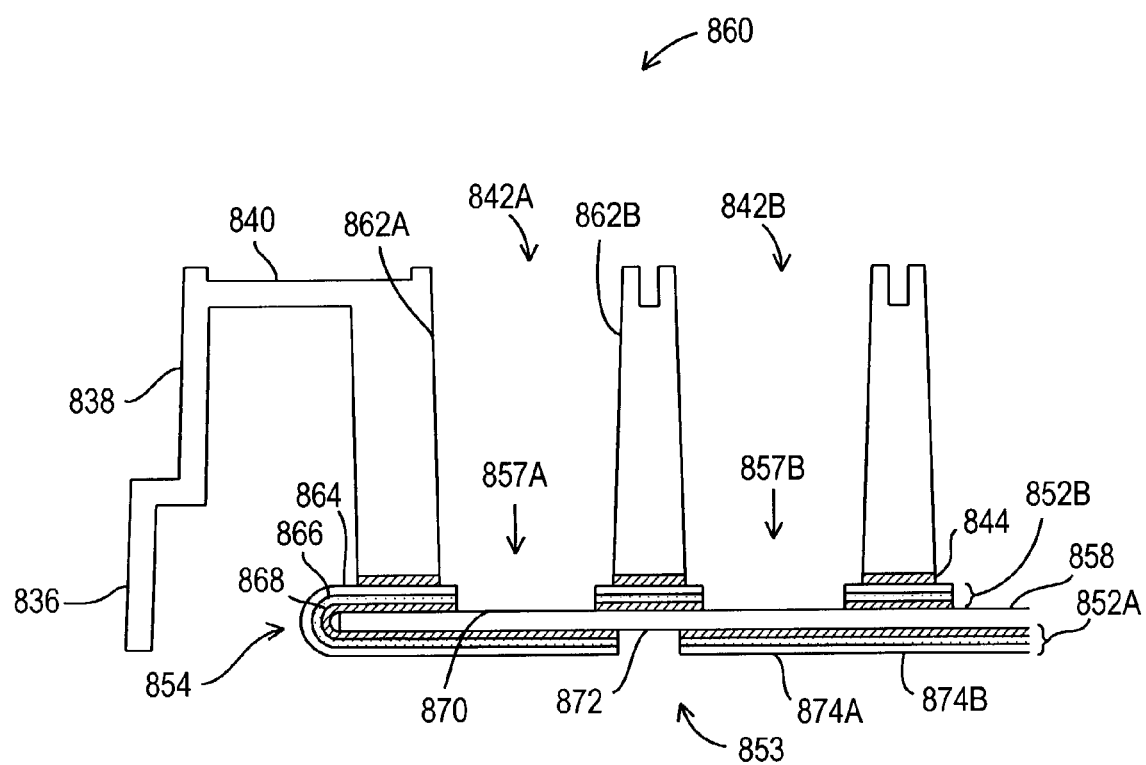

FIG. 8C illustrates a stylized cross sectional view of two wells 842A and 842B from the multi-well assay plate 830 shown in FIG. 8B.

Figure 9A:
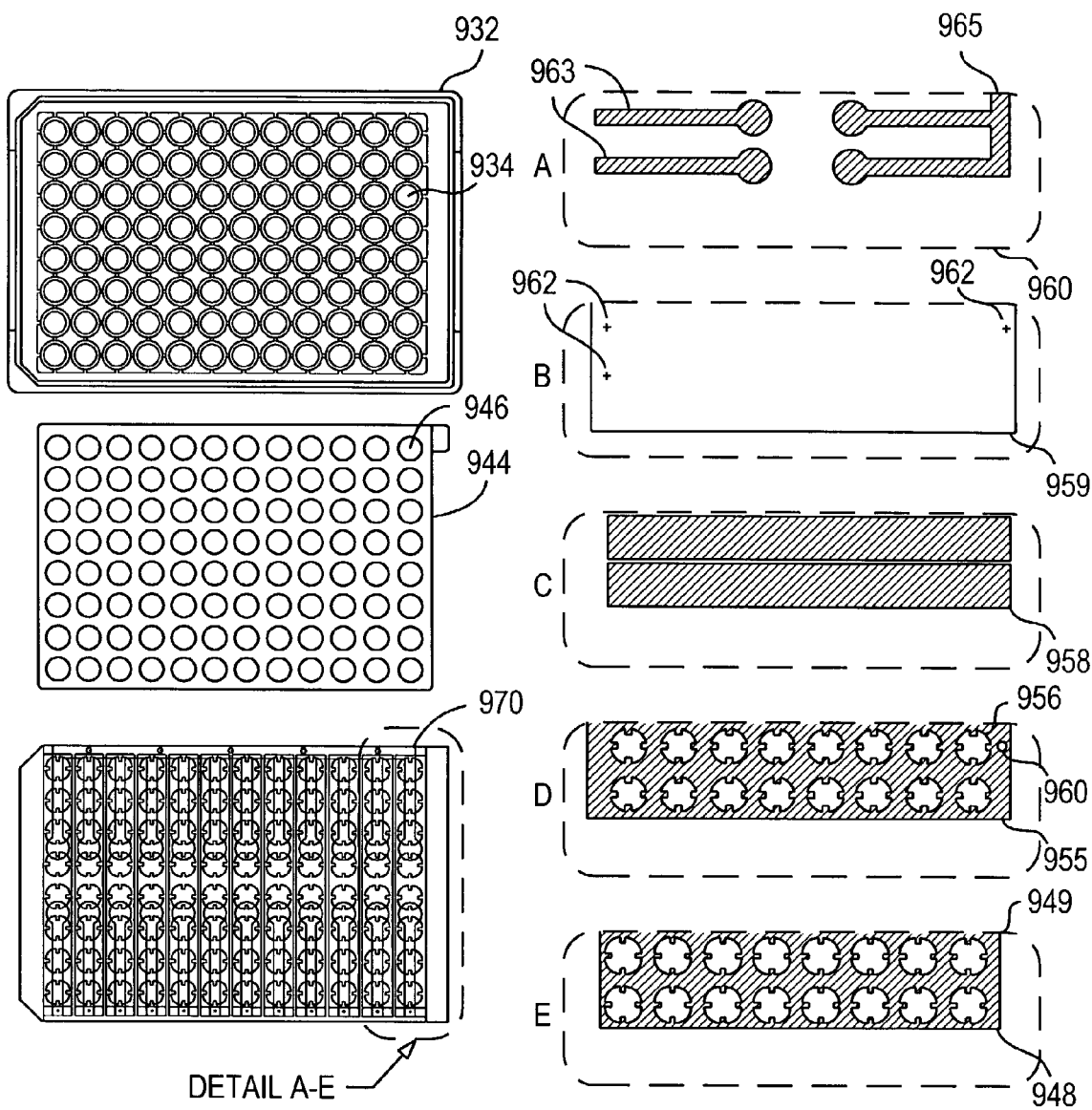
Figure 9B:
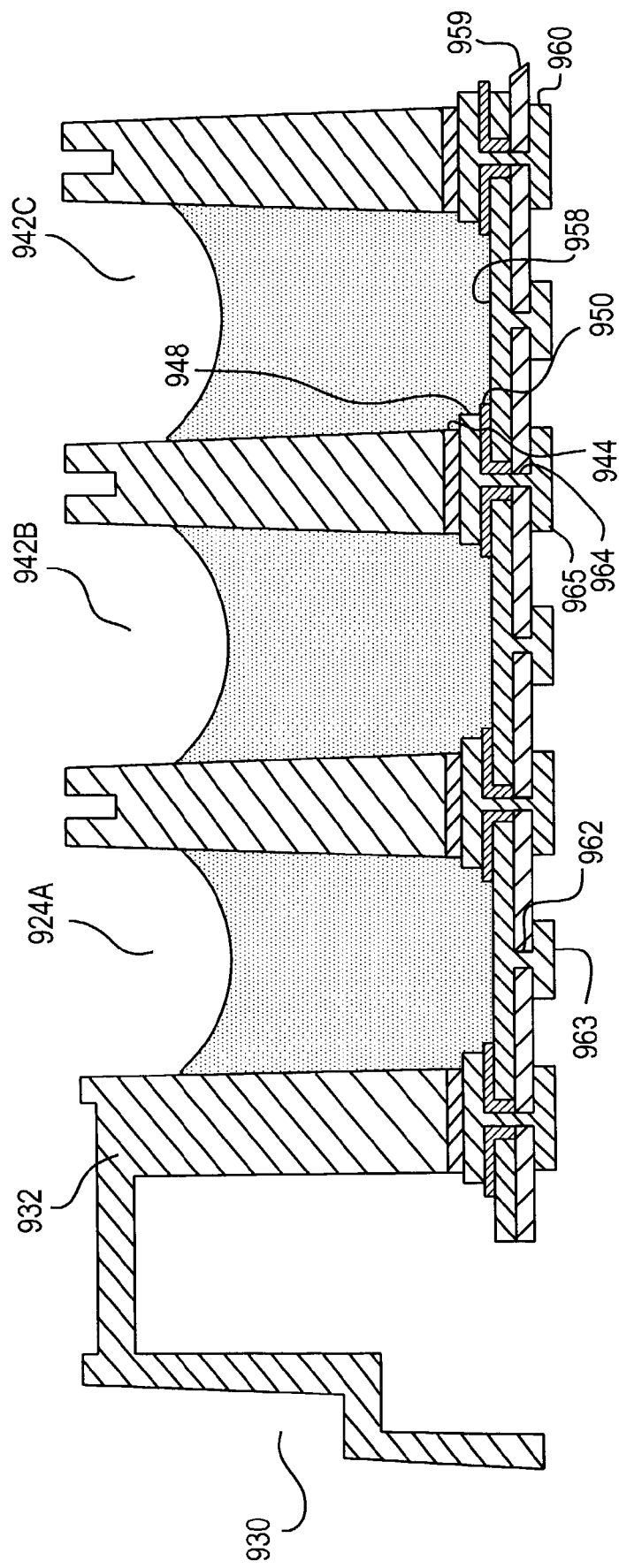

FIG. 9A shows the components of a multi-well plate 930 according to the invention. FIG. 9B shows a stylized cross sectional view of three wells from the multi-well assay plate 930 shown in FIG. 9A.

Figure 10A:
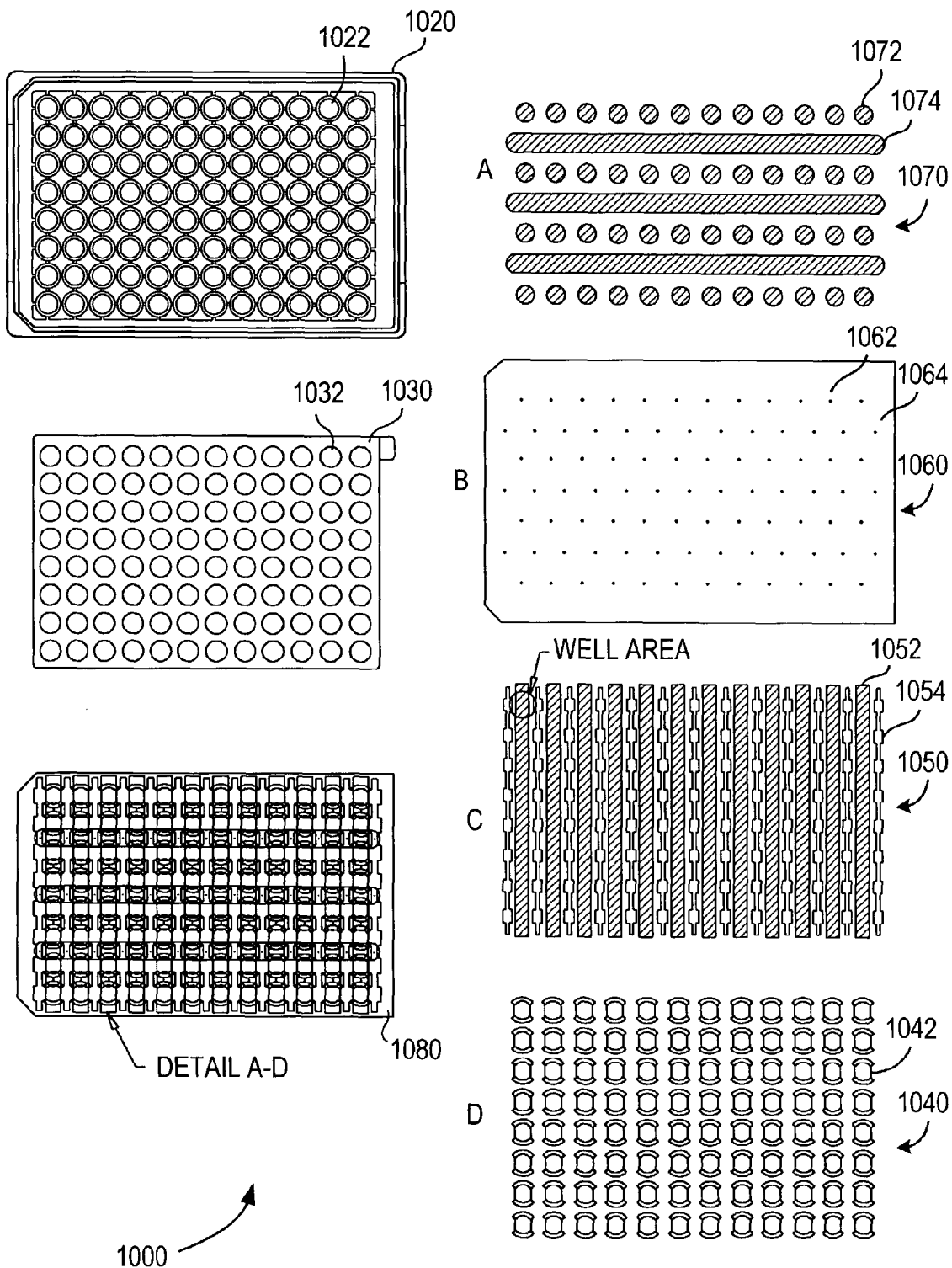

FIG. 10A illustrates a multi-well assay plate 1000 of the invention.

Figure 10B:
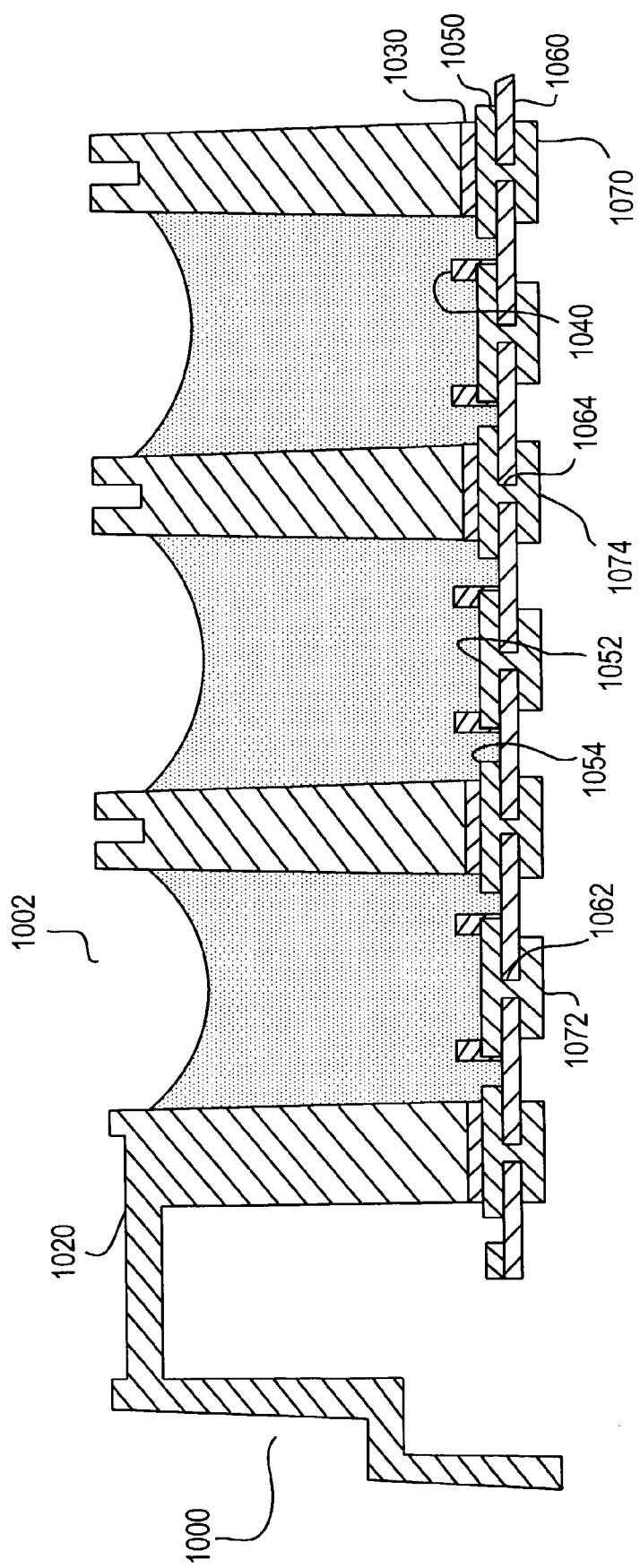

FIG. 10B shows a stylized cross sectional view of three wells from the multi-well assay plate 1000 shown in FIG. 10A.

Figure 11A:
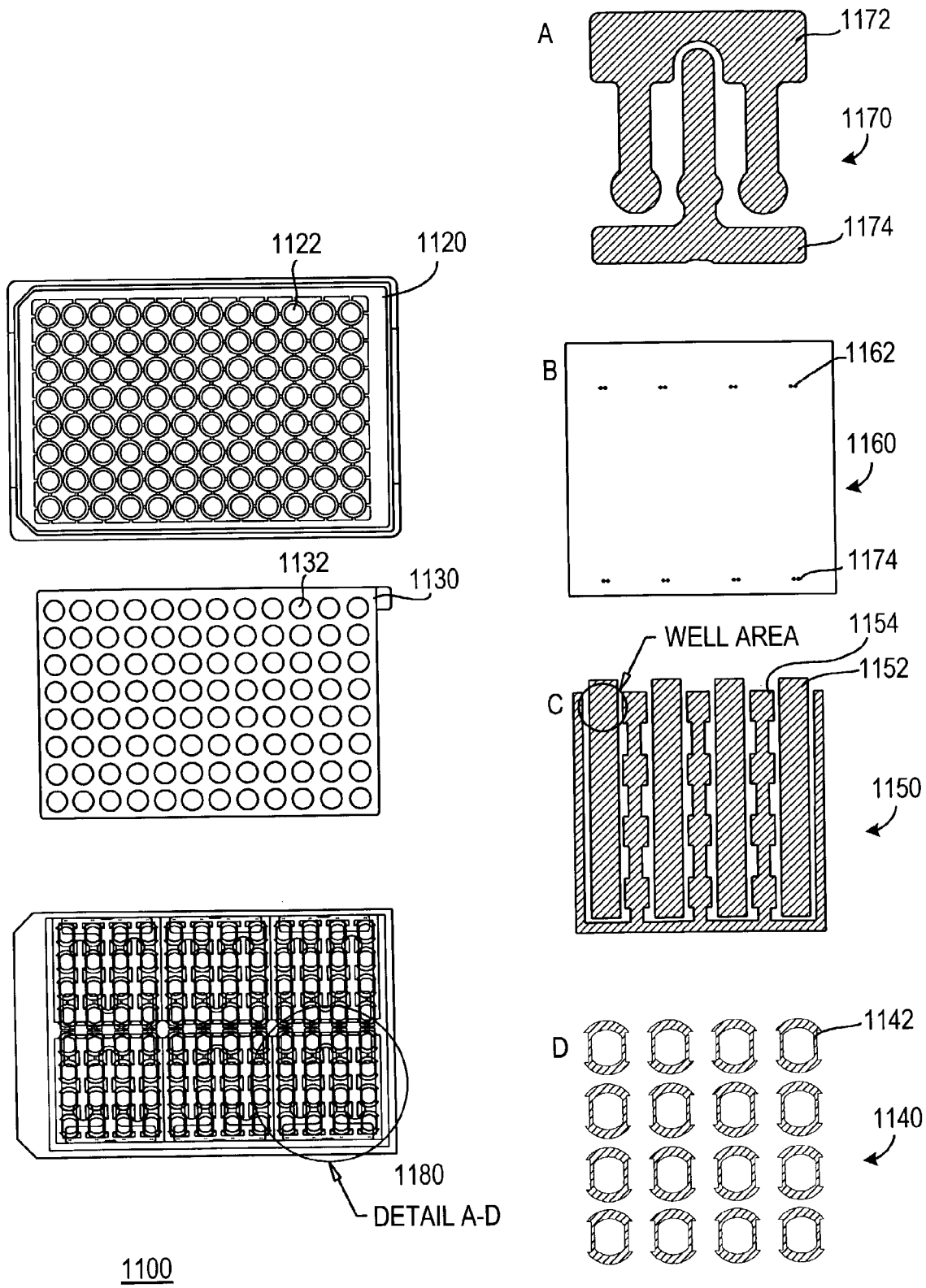

FIG. 11A illustrates a 96-well assay plate 1100 of the invention.

Figure 12A:
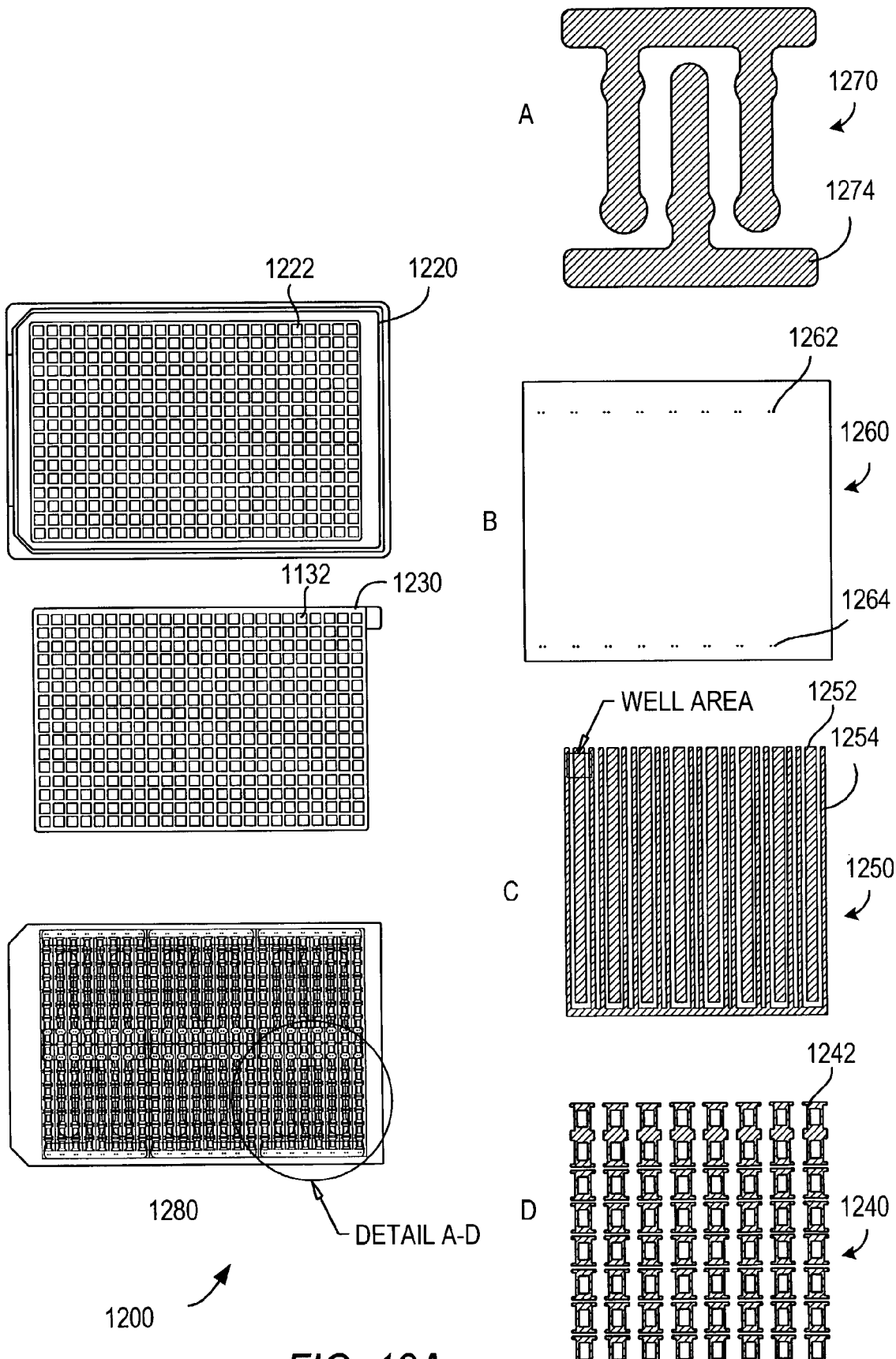

FIG. 12A illustrates a 384-well assay plate 1200 of the invention.

Figure 13A:
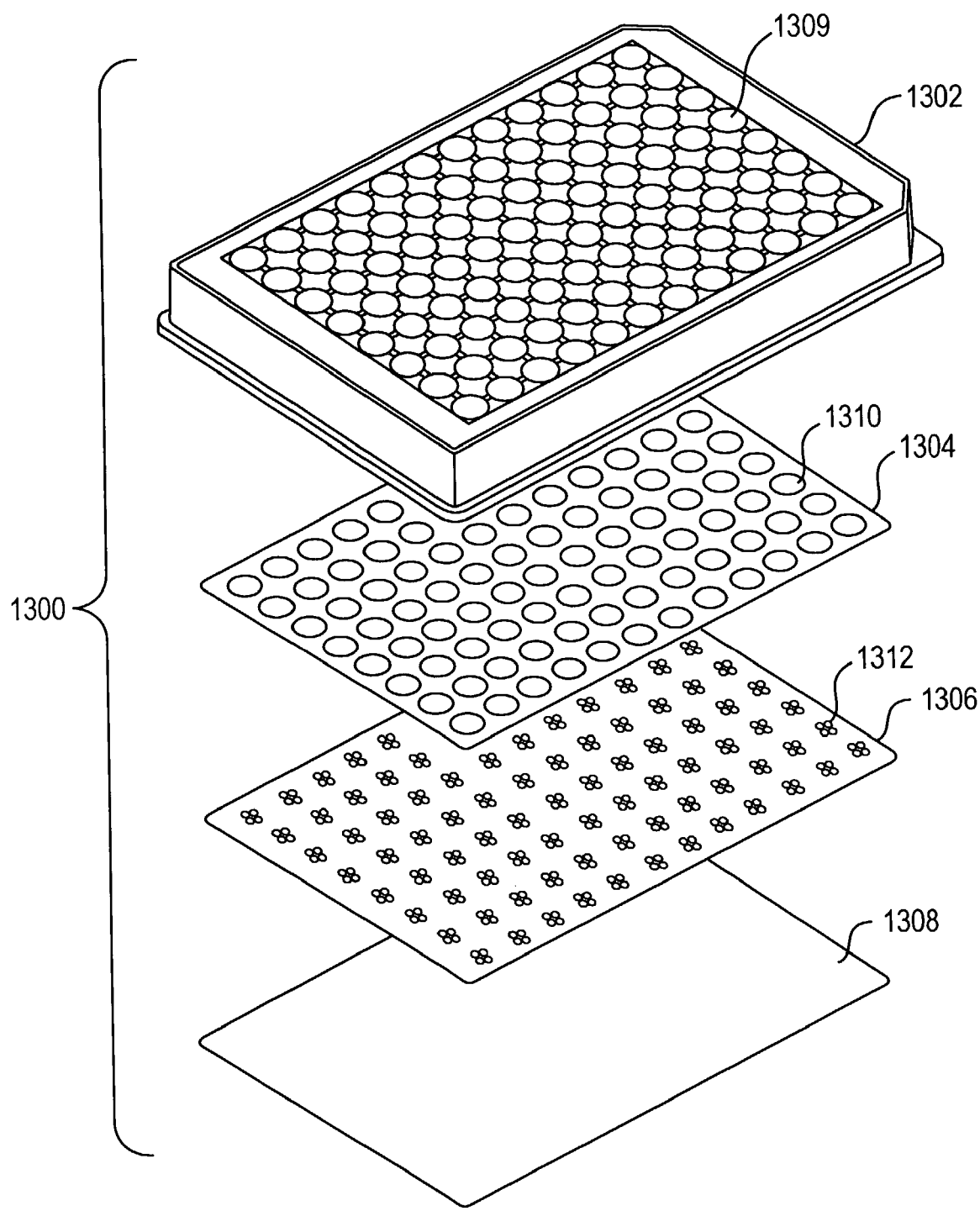

FIG. 13A illustrates a multi-well assay plate 1300 of the invention that has multiple fluid containment regions in each well.

Figure 13B:
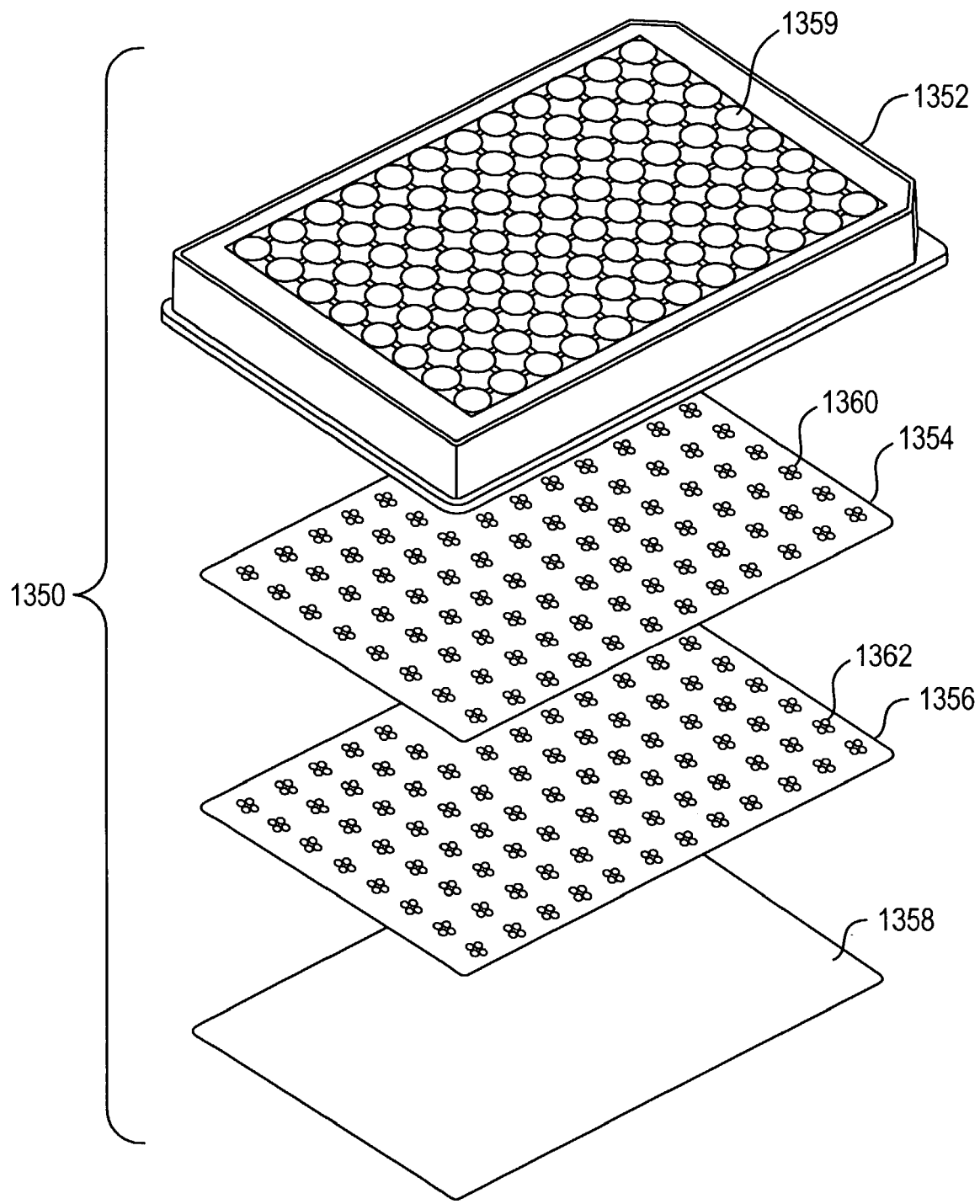

FIG. 13B illustrates a multi-well assay plate 1350 of the invention that has multiple fluid containment regions in each well.

Figure 14A:
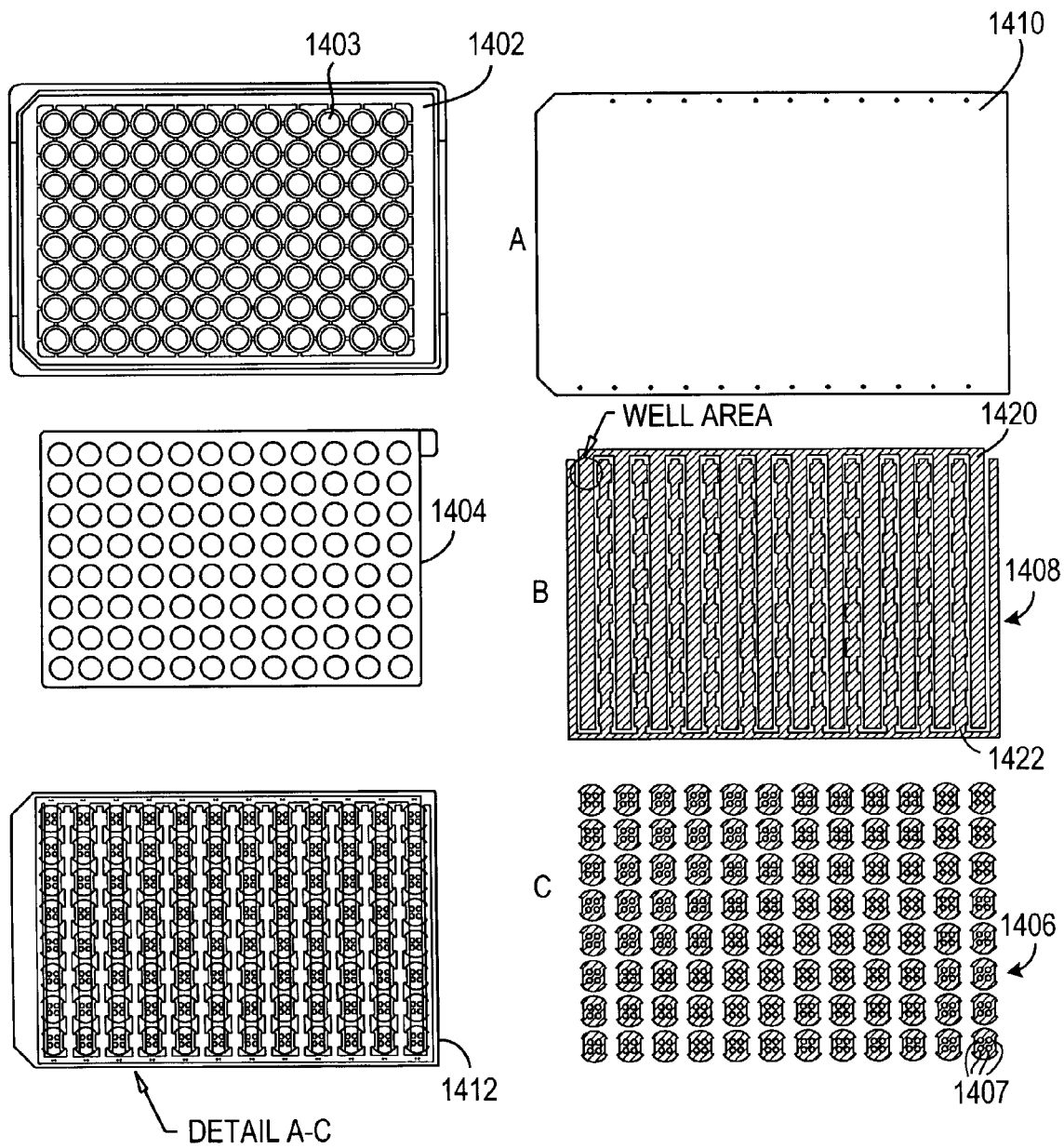

FIG. 14A illustrates a multi-well assay plate 1400 of the invention that has multiple fluid containment regions in each well.

Figure 14B:
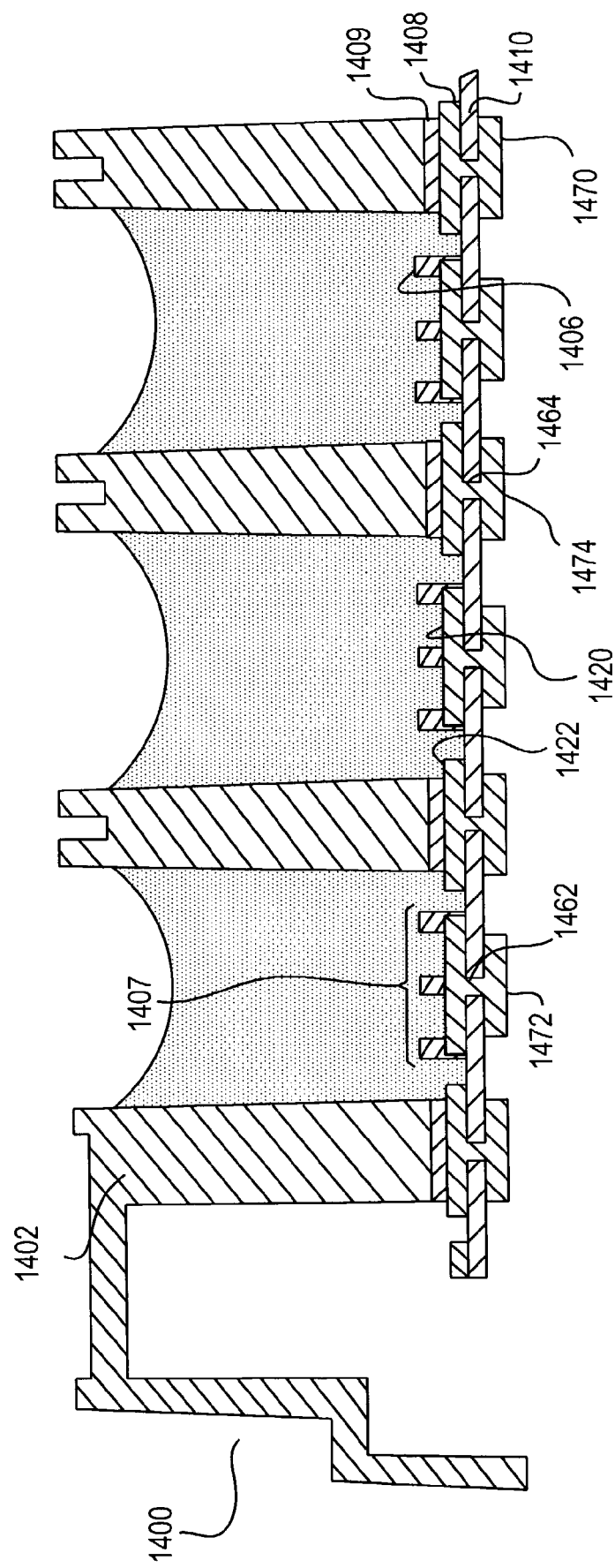

FIG. 14B shows a stylized cross sectional view of three wells from the 96-well assay plate 1400 shown in FIG. 14A.

Figure 15:
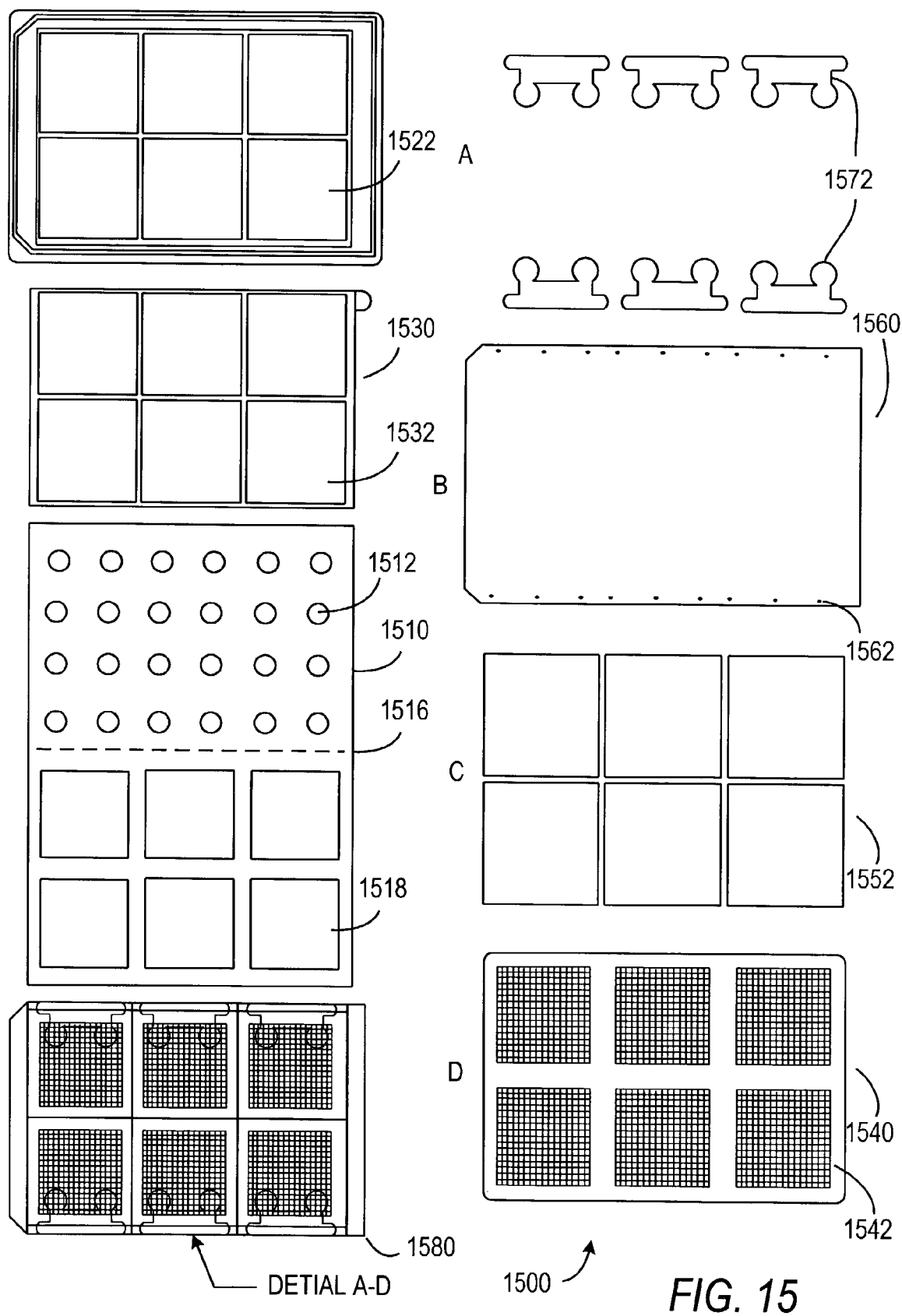

FIG. 15 illustrates a multi-well assay plate 1500 of the invention that has multiple fluid containment regions in each well.

Figure 16A:
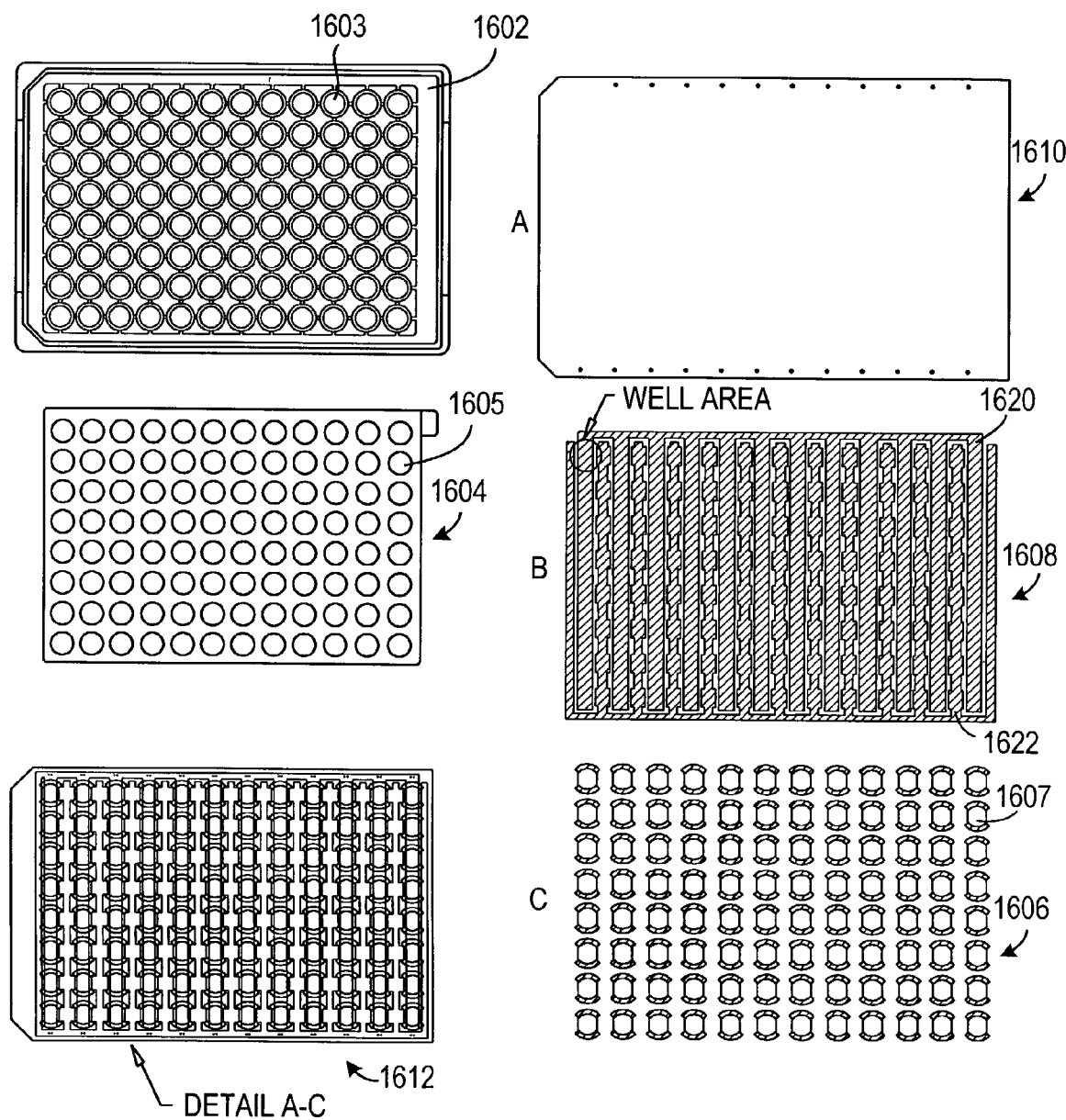
Figure 16B:
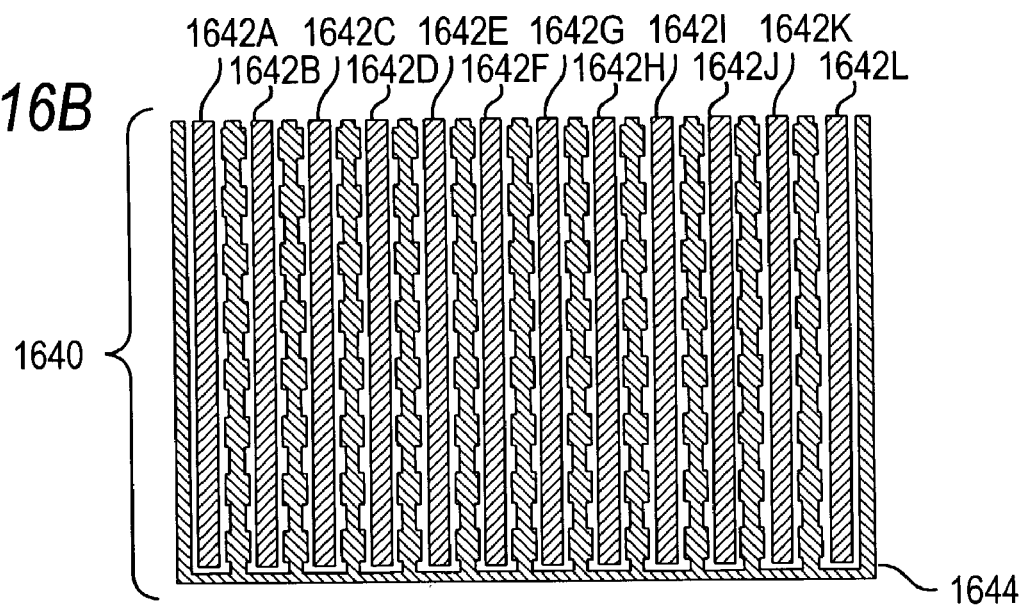
Figure 16C:
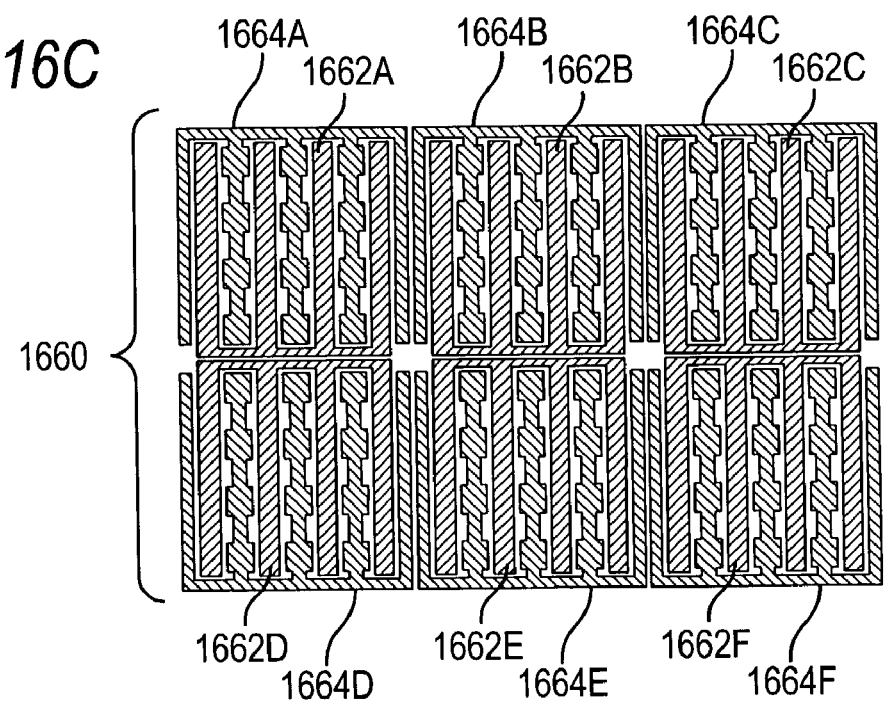

FIG. 16A illustrates a multi-well assay plate 1600 of the invention having a single patterned conductive layer on a substrate. FIG. 16B shows a conductive layer 1640 having a working electrode section 1642 and counter electrode section 1644. FIG. 16C shows plate 1660 and demonstrates alternative schemes for sectioning electrodes in multi-well assay plates.

Figure 17:
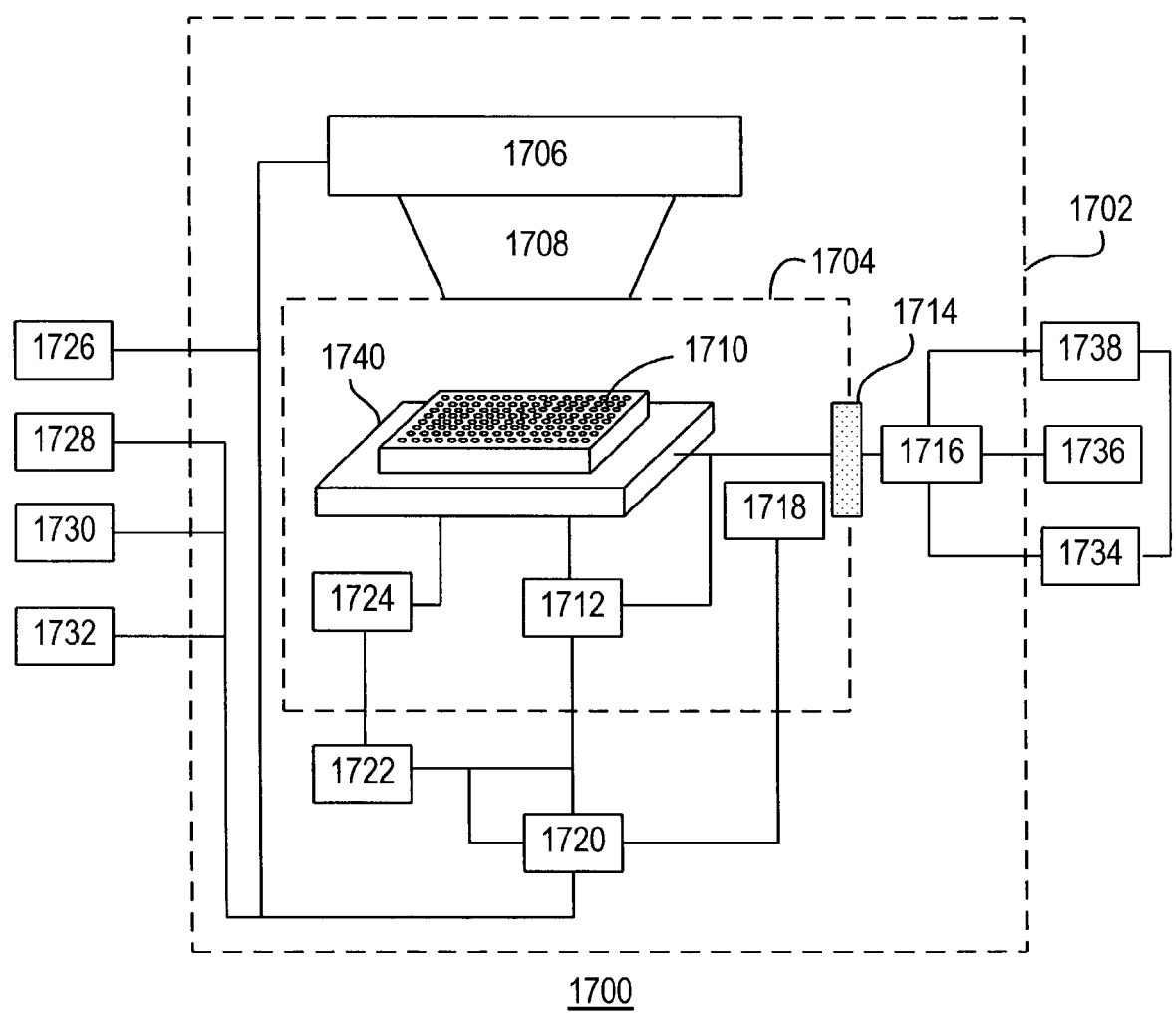

FIG. 17 illustrates an apparatus according to one embodiment of the present invention. Reader 1700 comprises a cover 1702, a light tight enclosure 1704 with one or more doors or apertures 1714, a photodetector 1706, optics 1708, multi-well assay plate 1710, plate aligner 1712, plate transporter 1716, bar code reader 1718, electronics 1720, current/voltage source 1722, plate electrical connector 1724, computer 1726, power supply 1728, data and network connections 1730, indicators 1732, reagent handler 1734, one or more plate stackers 1736, robotics 1738, and plate carrier 1740.

Figure 18:
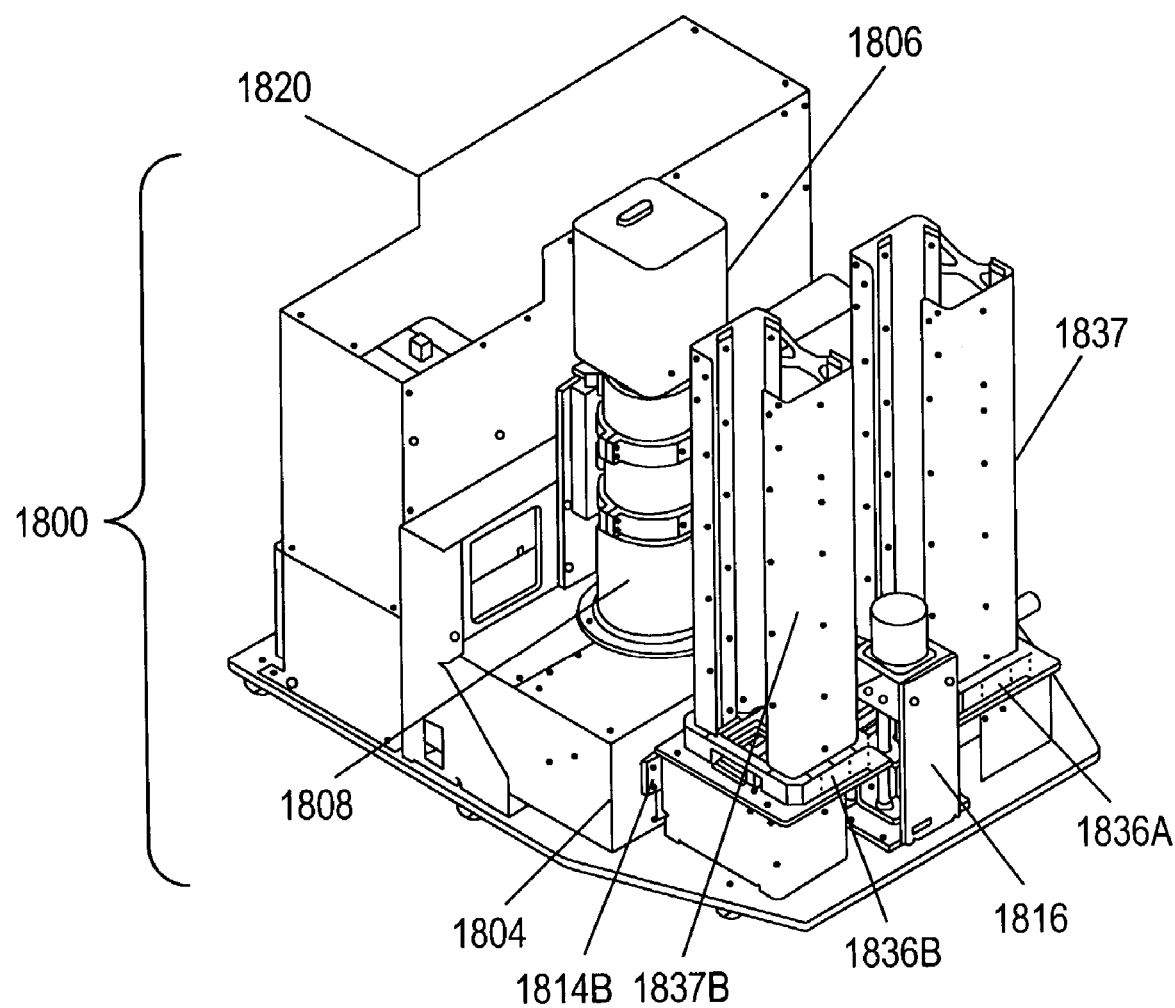

FIG. 18 illustrates an apparatus according to the present invention. Reader 1800, which shows selected elements, illustrates a light tight enclosure 1804, photodetector 1806, optics 1808, plate transporter 1816, plate electronics 1820, input plate stacker 1836A, output plate stacker 1836B, input plate stack 1837A, output plate stack 1837B, and output door or aperture 1814B.

Figure 19:
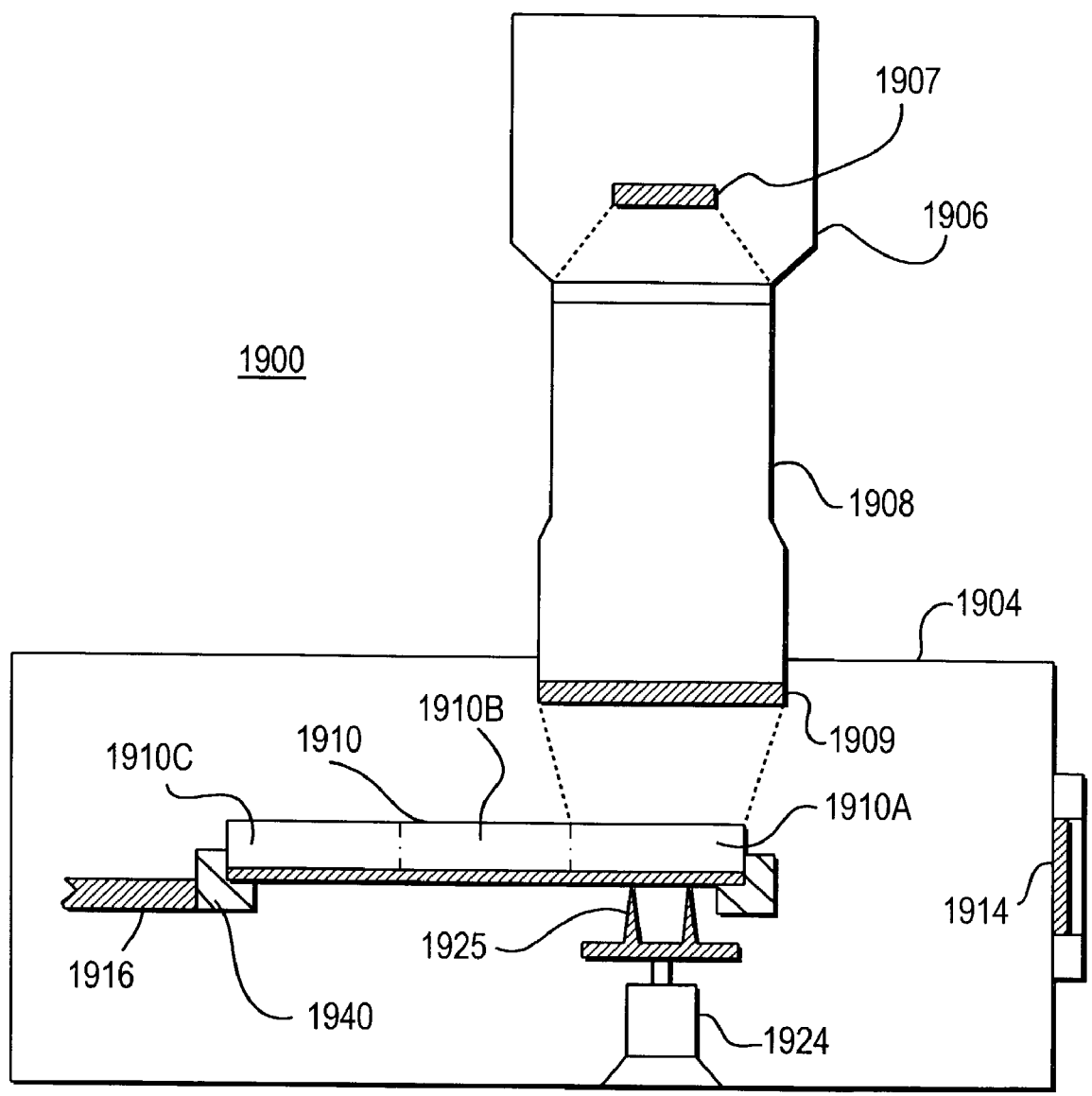

FIG. 19 illustrates selected components of an apparatus according to the present invention wherein the illustration highlights the alignment of optics 1908, photodetector 1907, plate sector 1910A, and plate electrical connector 1924 having contacts 1925. Light tight enclosure 1904, door or aperture 1914, plate 1910, plate carrier 1940 and plate transporter 1916 are also present.

Figure 20:
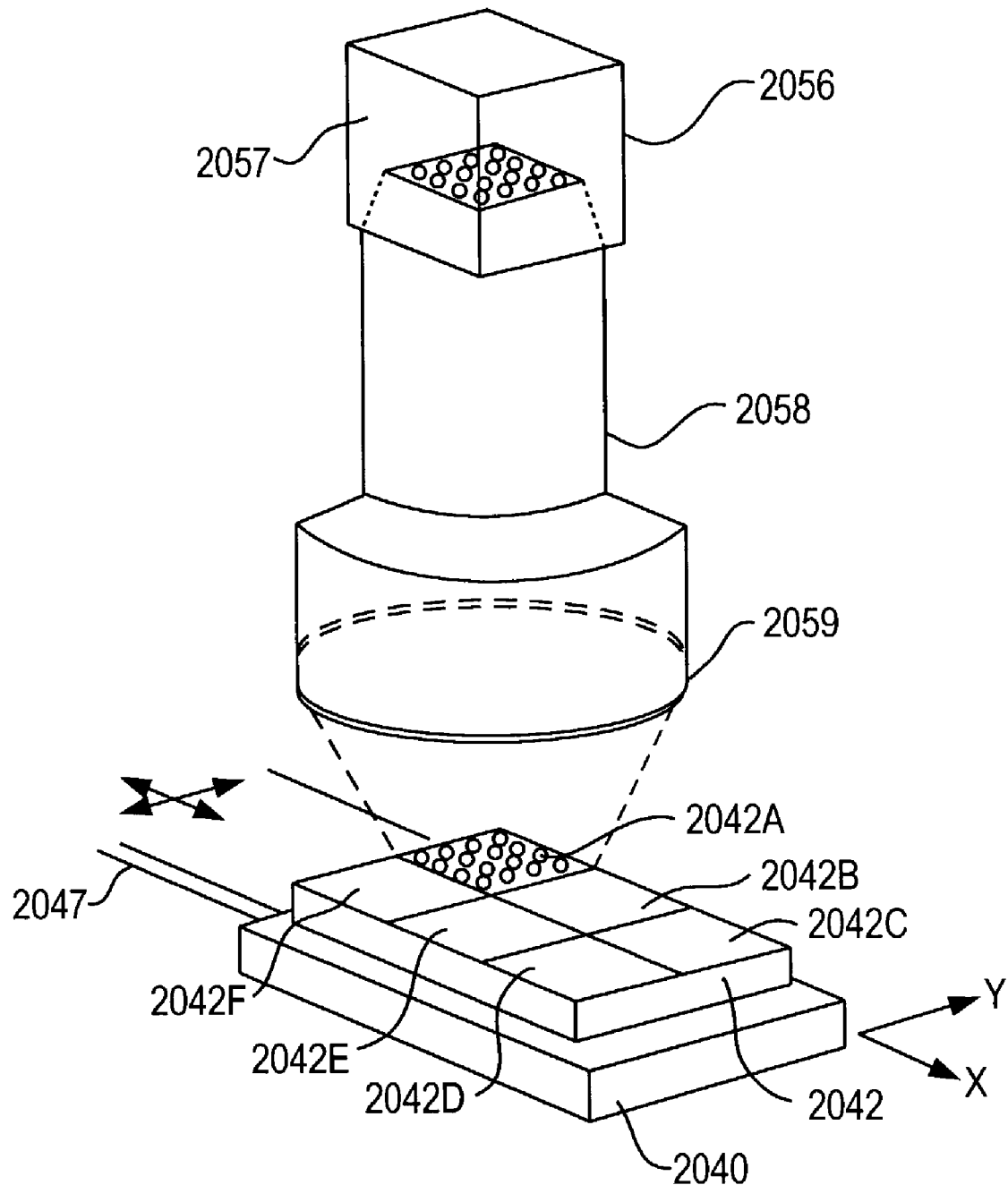

FIG. 20 illustrates selected components of an apparatus according to the present invention wherein the illustration highlights the imaging of a sector 2042A of a multi-well assay plate 2042 of the invention. Photodetector 2057, optics 2058, filter 2059, plate carrier 2040 and plate transporter 2047 are also indicated.

Figure 21:
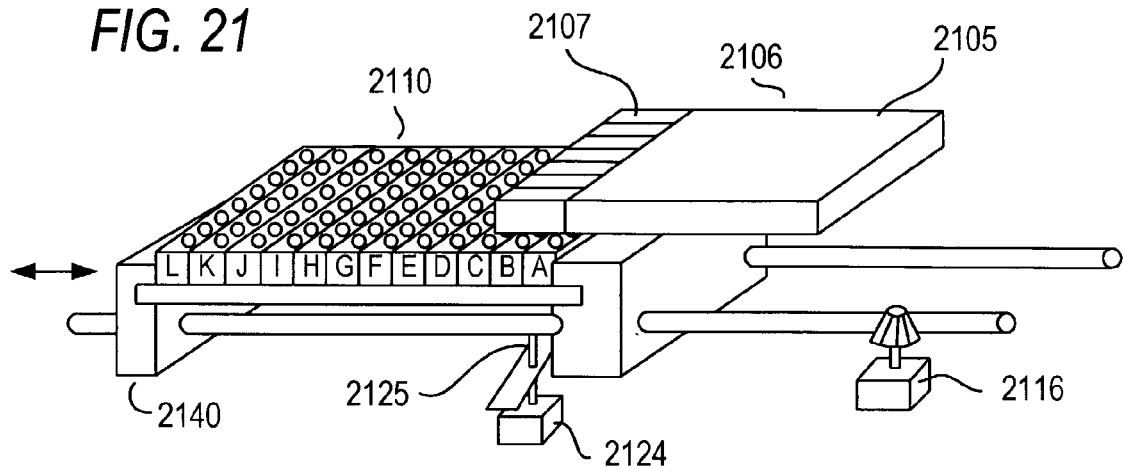

FIG. 21 illustrates selected components of an apparatus of the invention wherein the illustration highlights the relative positions of plate sector 2110A, plate electrical connector 2124 with contacts 2125, and photodiode array 2107 of photodetector 2106. Plate 2110, photodetector circuit board 2105, plate transporter 2116, and plate carrier 2140 are also shown.

Figure 22:
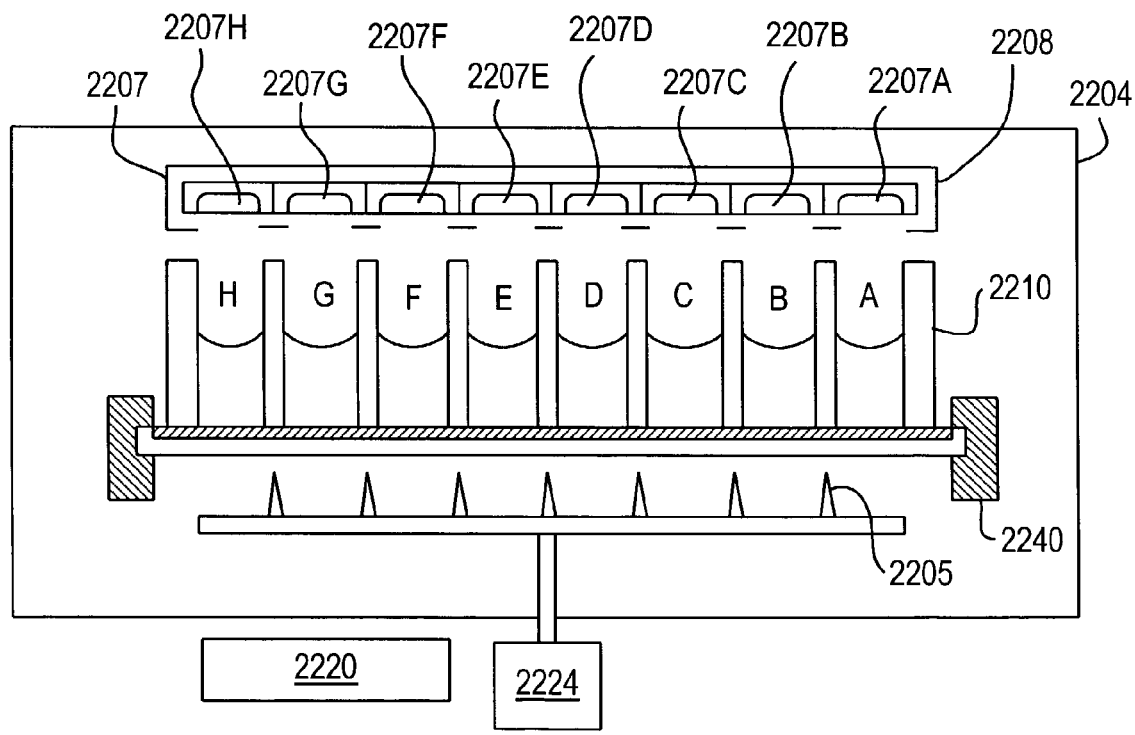

FIG. 22 illustrates selected components of an apparatus of the invention wherein the illustration highlights photodiode array 2207 where the relative positions of photodiodes 2207A-H with wells 2210A-H respectively of multi-well assay plate 2210. Plate electrical connector 2224, electronics 2220, electrical contacts 2205, shield 2208, light tight enclosure 2204 and plate carrier 2240 are also shown.

Figure 23:
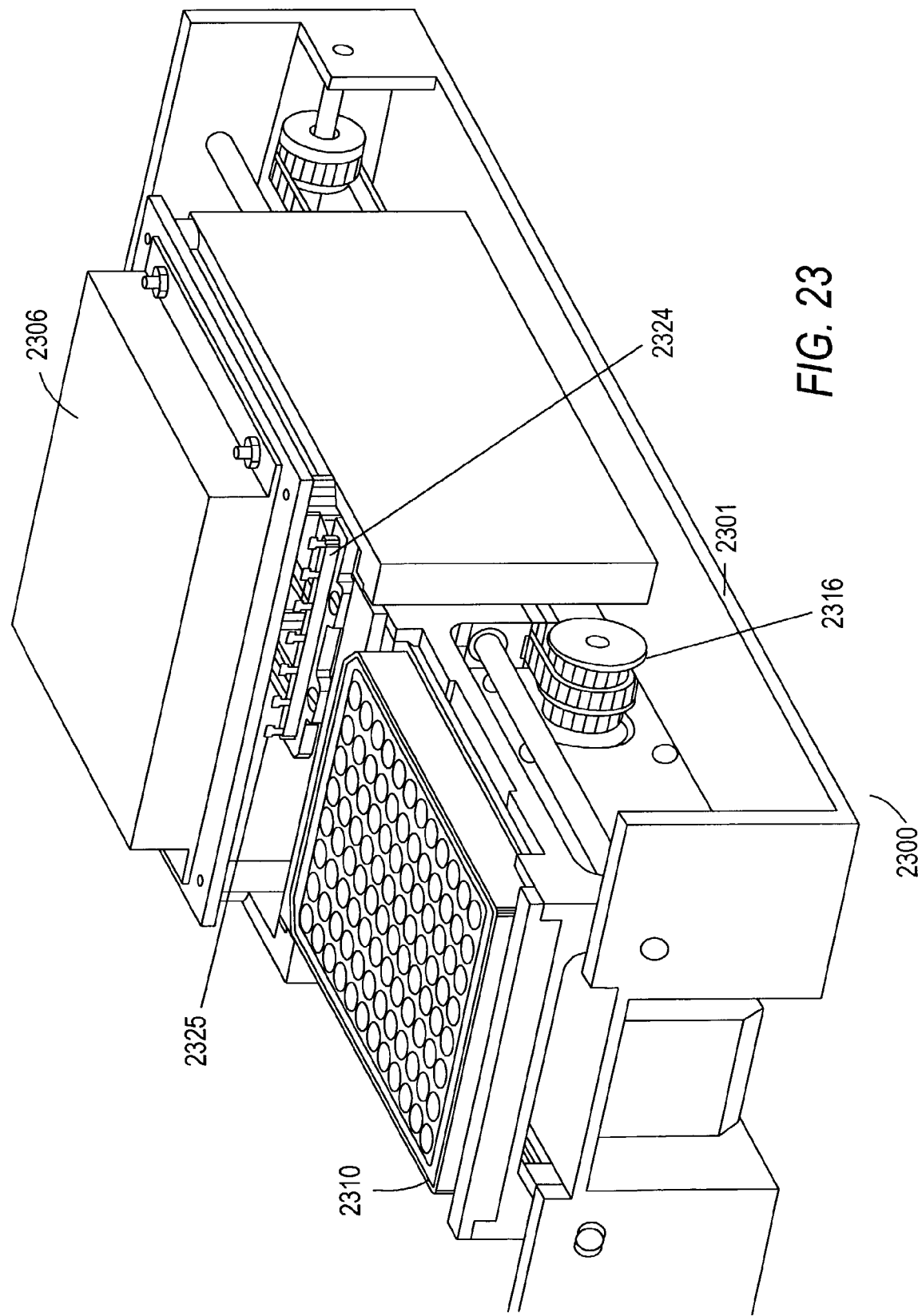

FIG. 23 illustrates an apparatus according to the present invention. Reader 2300, which shows selected elements, illustrates a chassis 2301, photodetector 2306, multi-well assay plate 2310, plate transporter 2316, plate electrical connector 2324 and a plurality of contacts 2325.

Figure 24:
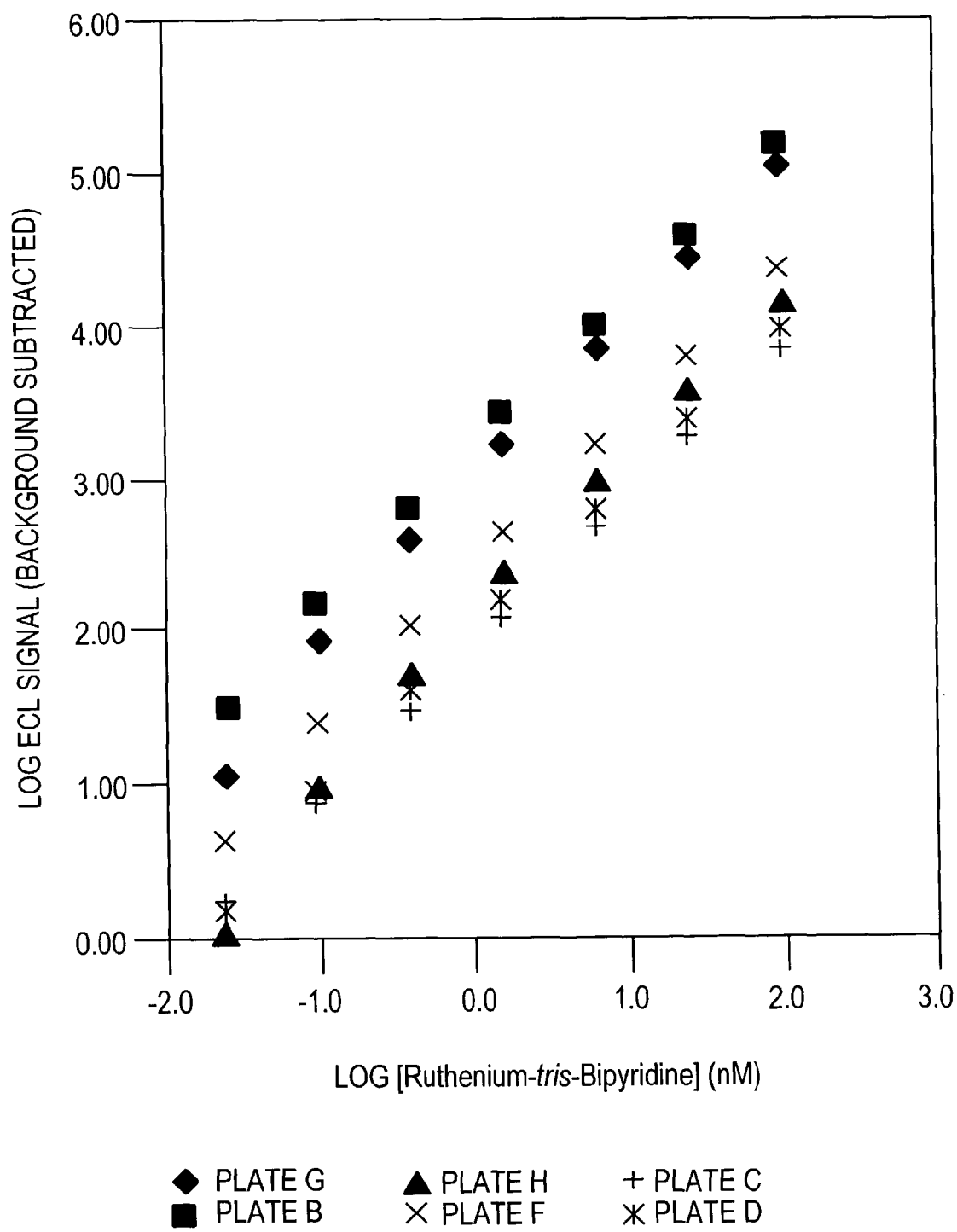

FIG. 24 shows the ECL signal emitted from wells of several embodiments of the multi-well assay plates of the invention as a function of the concentration of ruthenium-tris-bipyridine in the wells. The ECL signal was measured by imaging using a cooled CCD camera.

Figure 25:
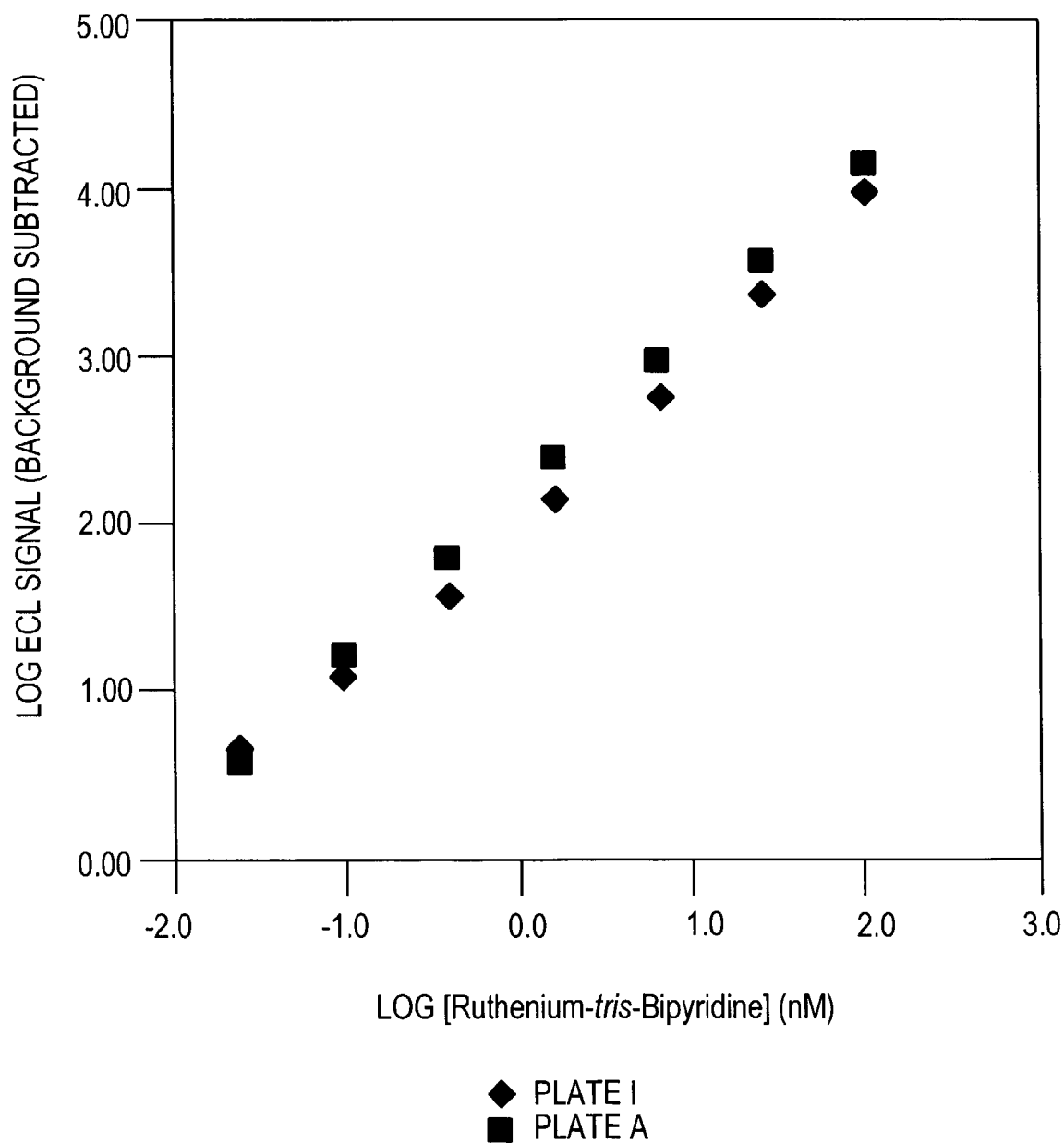

FIG. 25 shows the ECL signal emitted from wells of two embodiments of the multi-well assay plates of the invention as a function of the concentration of ruthenium-tris-bipyridine in the wells. The ECL signal was measured with an array of eight photodiodes.

Figure 26:
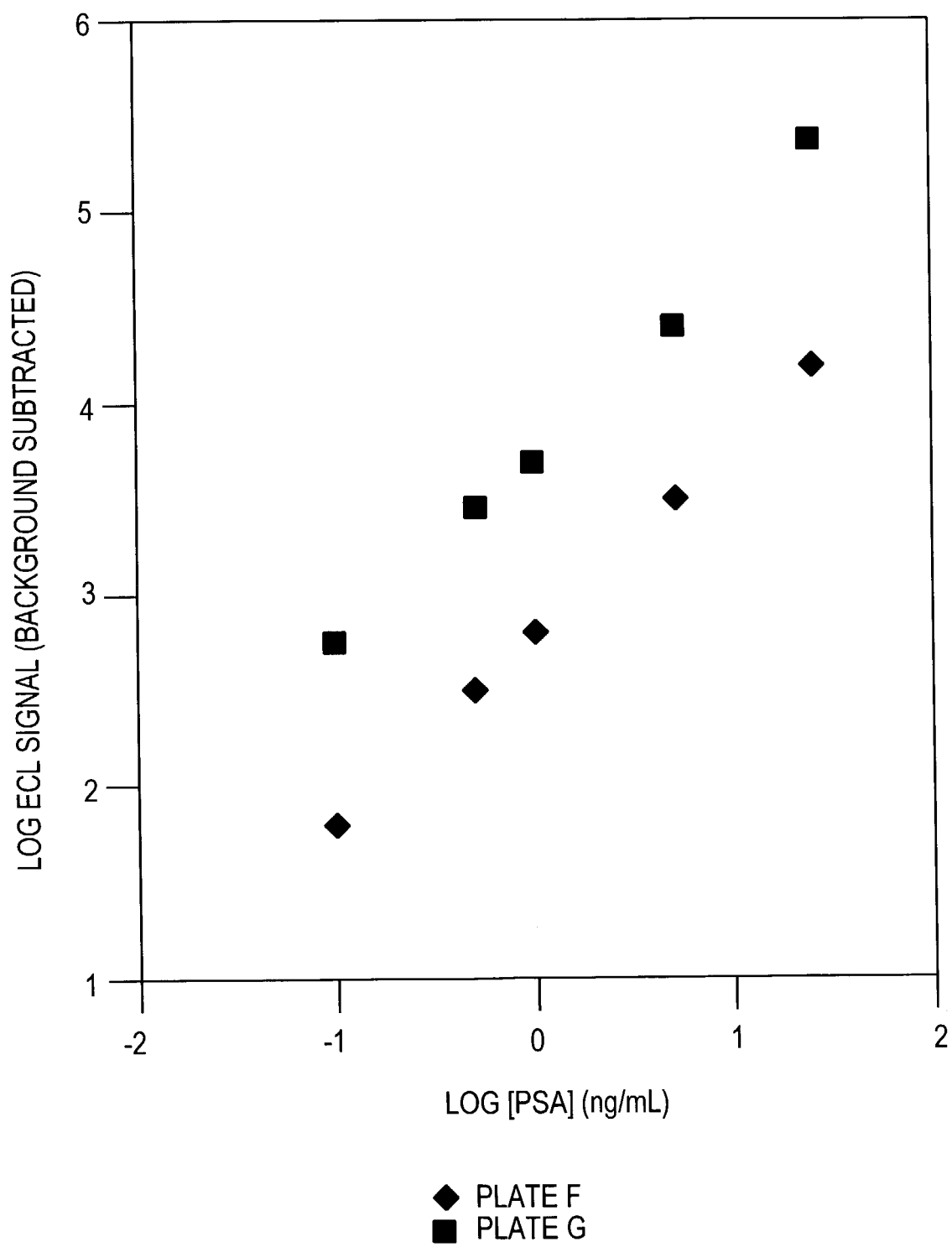

FIG. 26 demonstrates the use of two embodiments of multi-well assay plates of the invention for carrying out sandwich immunoassays for prostate specific antigen (PSA). The plot shows the ECL signal as a function of the concentration of PSA. The ECL signal was measured by imaging with a cooled CCD camera.

Figure 27:
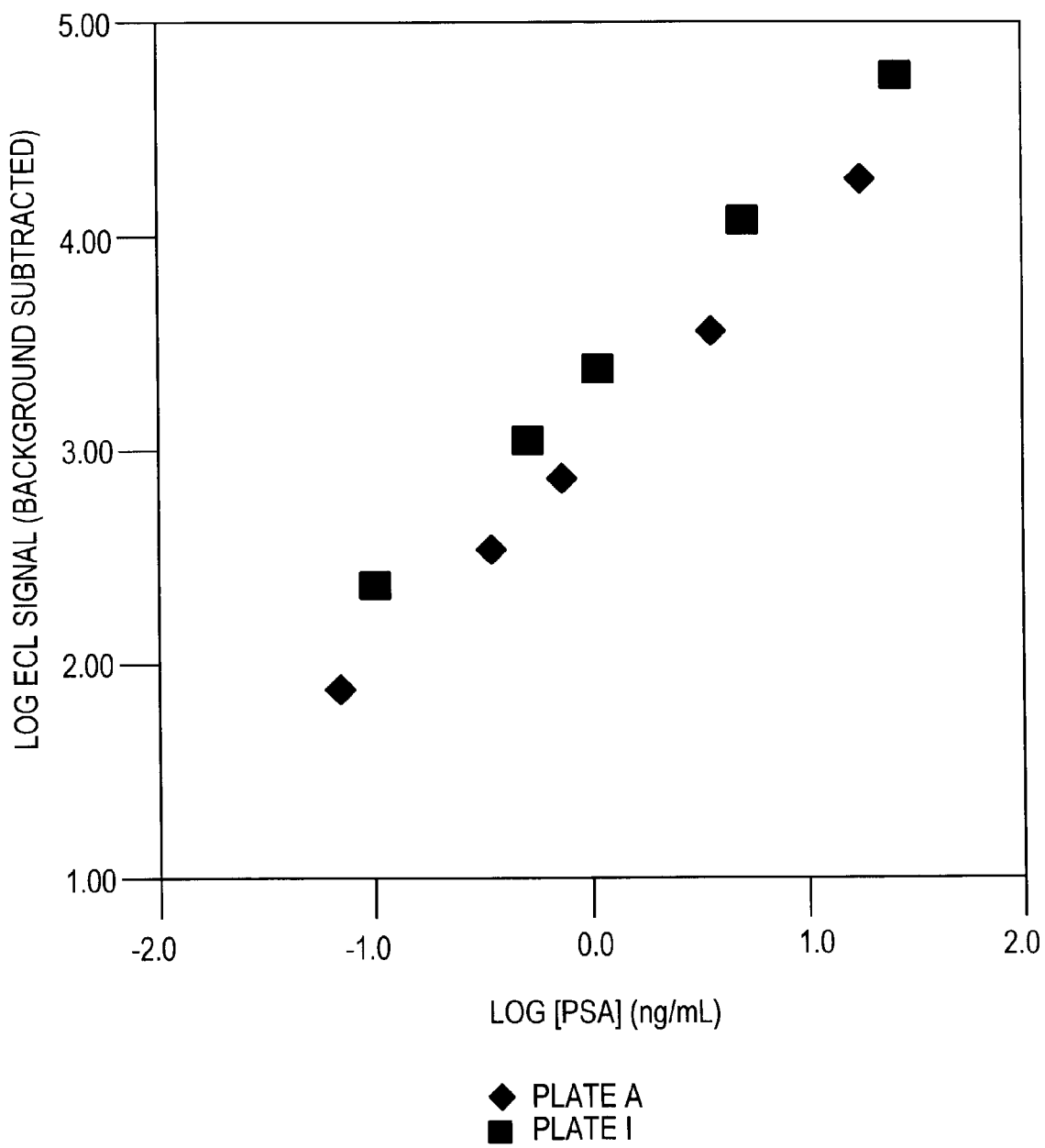

FIG. 27 demonstrates the use of two embodiments of multi-well assay plates of the invention for carrying out sandwich immunoassays for PSA. The plot shows the ECL signal as a function of the concentration of PSA. The ECL signal was measured with an array of eight photodiodes.

Figure 28:
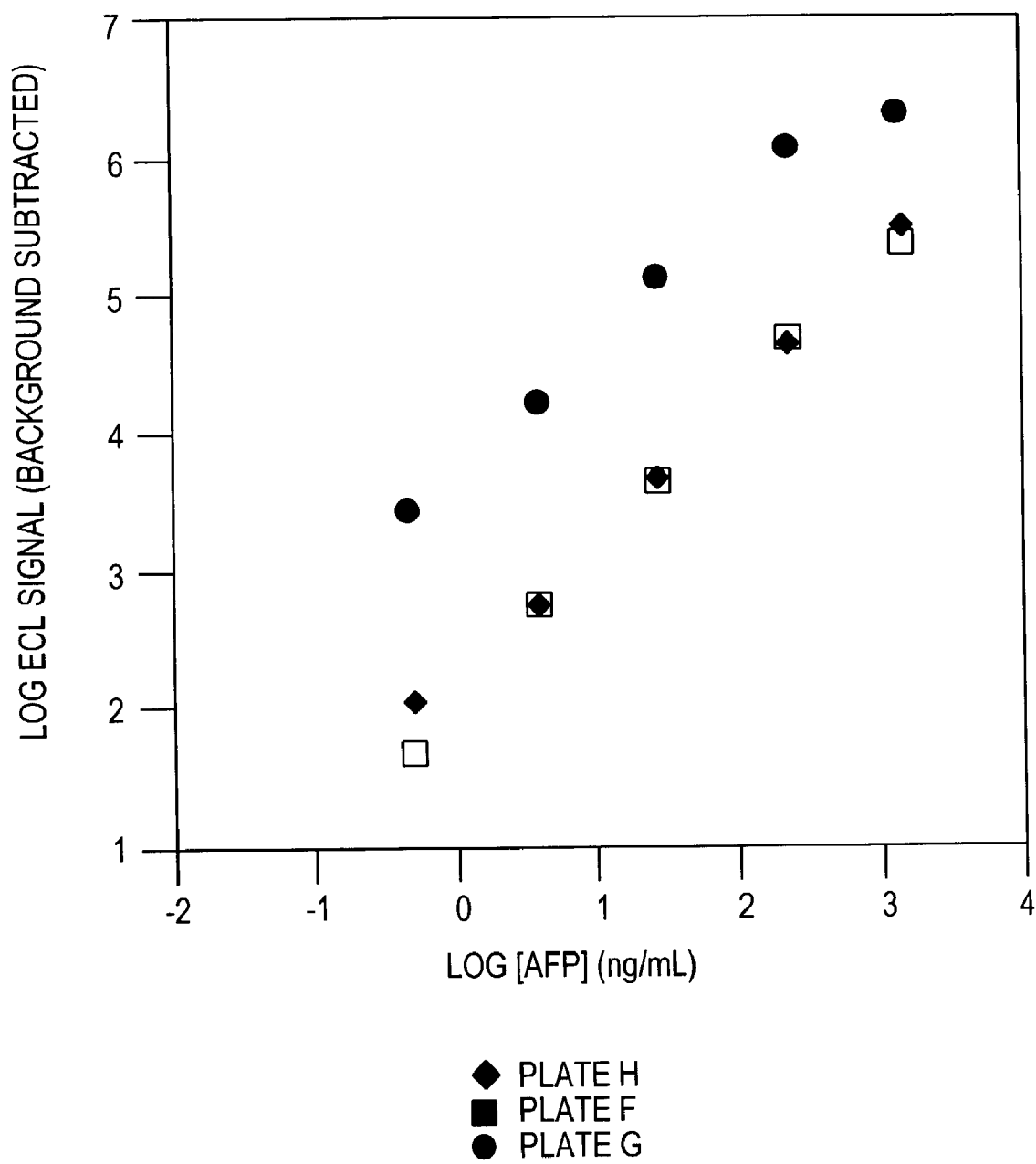

FIG. 28 demonstrates the use of three embodiments of multi-well assay plates of the invention for carrying out sandwich immunoassays for AFP. The plot shows the ECL signal as a function of the concentration of AFP. The ECL signal was measured by imaging with a cooled CCD camera.

Figure 29:
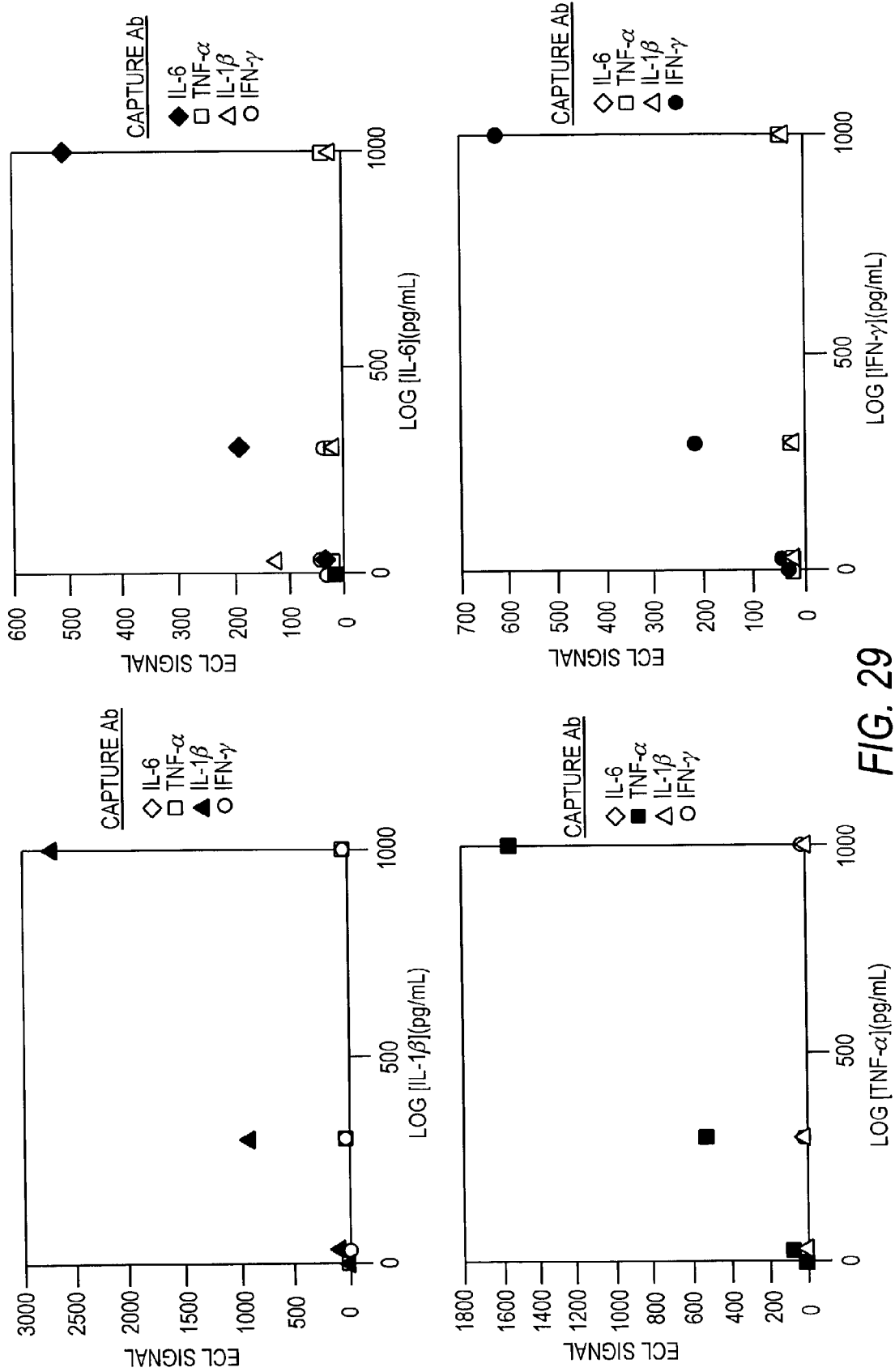

FIG. 29 demonstrates the independent measurement by ECL sandwich immunoassay of four analytes (IL-1β, IL-6, TNF-α and IFN-γ) in wells of a multi-well assay plate. The working electrode in each well is patterned with four assay domains, each assay domain comprising a capture antibody specific for one of the analytes. The plots show the ECL signal emitted from each assay domain as a function of the concentration of each analyte.

Figure 30:
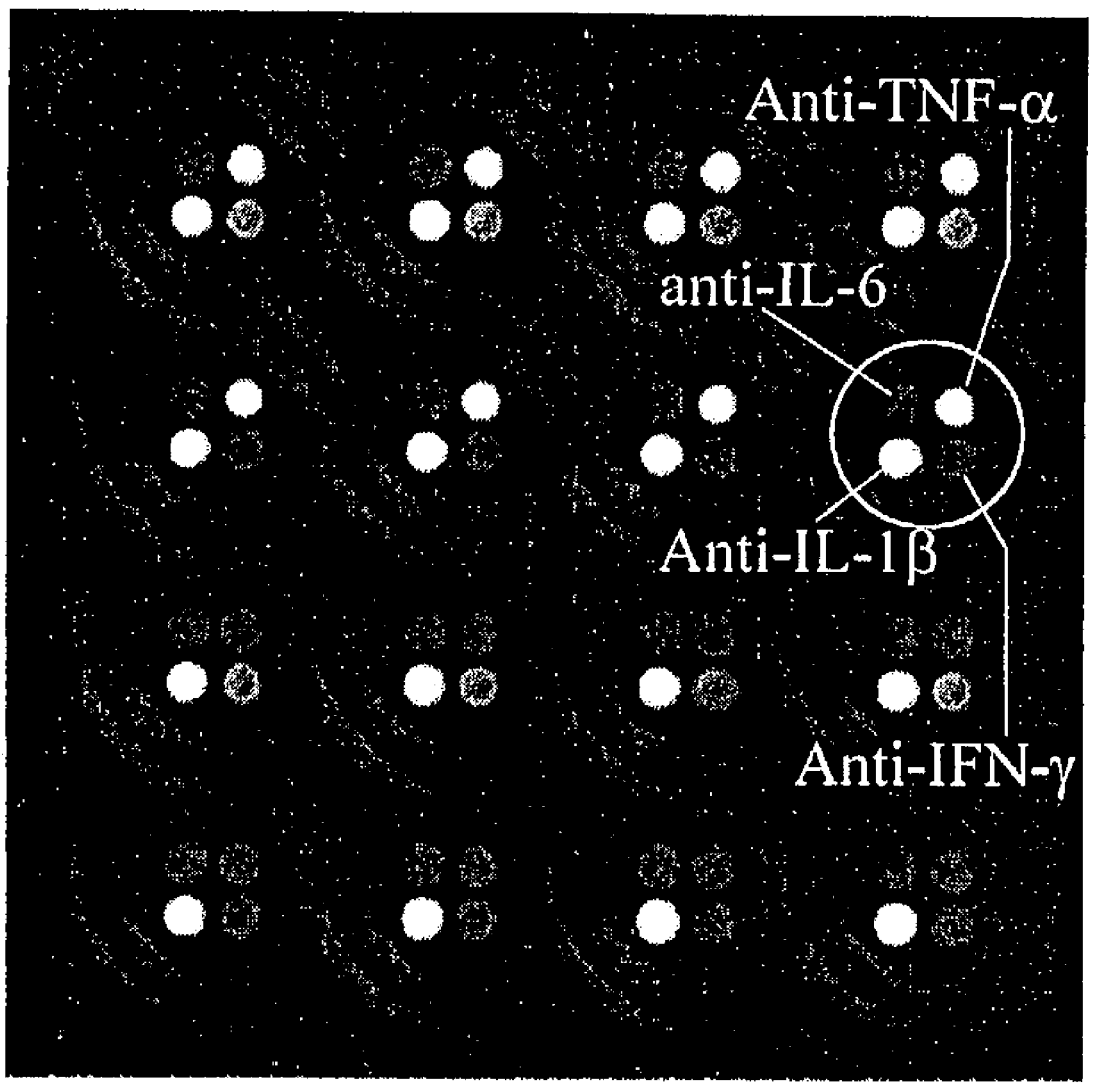

FIG. 30 demonstrates the independent measurement by ECL sandwich immunoassay of four analytes (IL-1β, IL-6, TNF-α and IFN-γ) in wells of a multi-well assay plate. The working electrode in each well is patterned with four assay domains, each assay domain comprising a capture antibody specific for one of the analytes. The figure shows an image of the ECL emitted from a sector of wells used to assay samples containing varying mixtures of the four analytes. The highlighted well is annotated to show the arrangement of the four assay domains. That specific well was used to assay a sample having 250 pg/mL each of IL-1β and TNF-α and 8 pg/mL each of IL-6 and IFN-γ.

Figure 31:
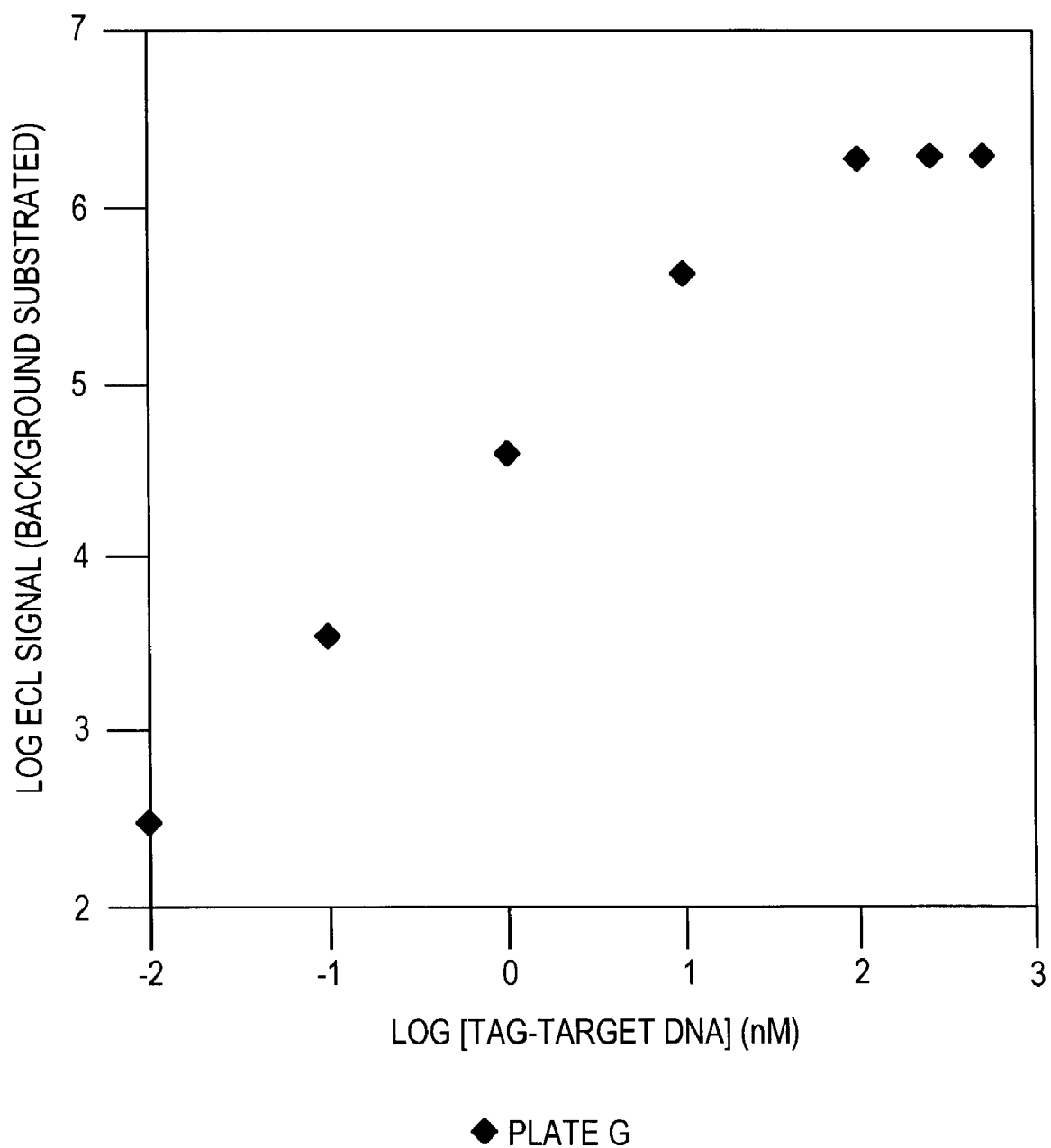

FIG. 31 demonstrates the use of multi-well assay plates of the invention for carrying out a nucleic acid hybridization assay. The plot shows the ECL signal as a function of the concentration of a ruthenium-tris-bipyridine labeled DNA target. The ECL signal was measured by imaging with a cooled CCD camera.

Figure 32:
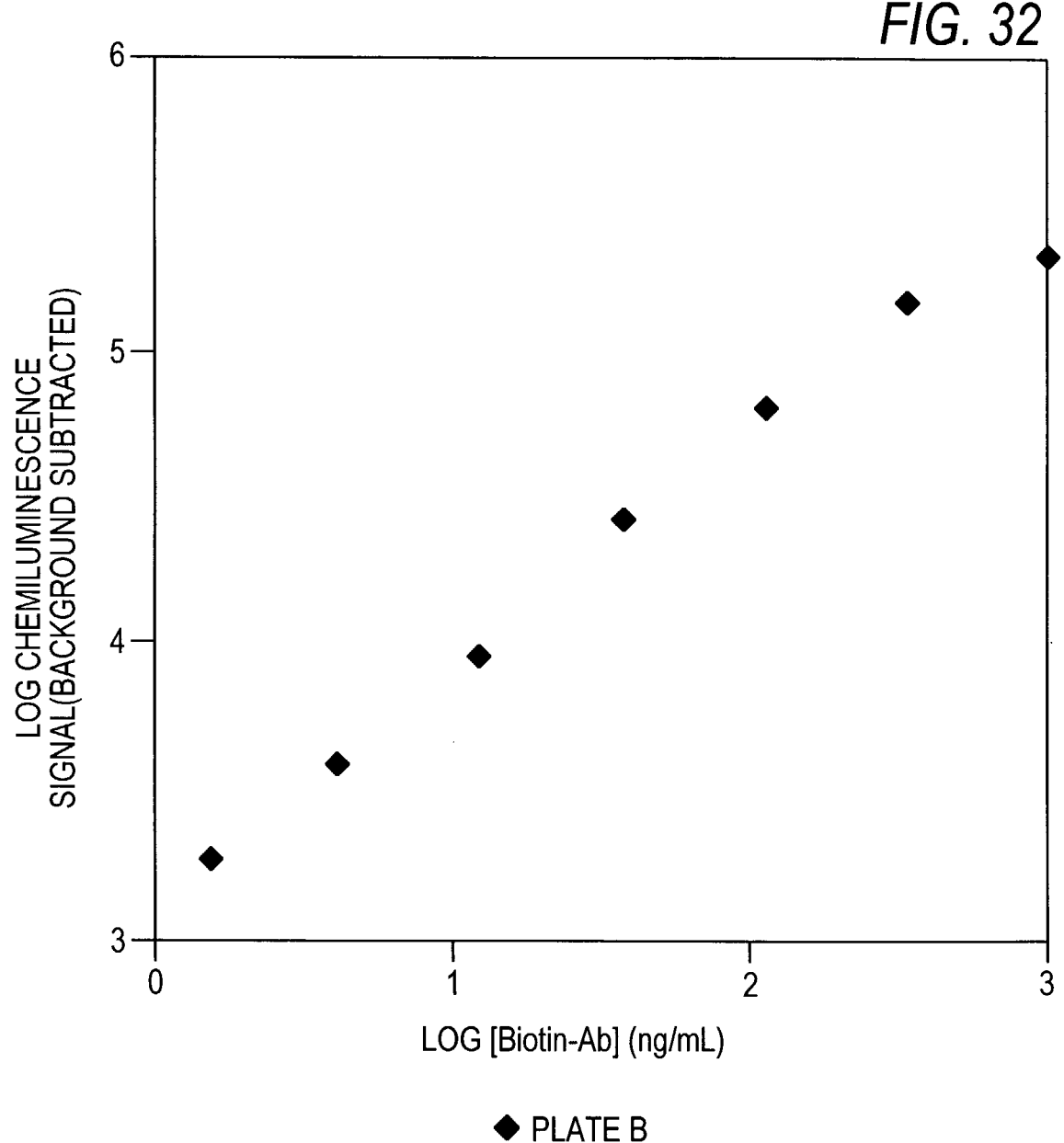

FIG. 32 demonstrates the use of a multi-well assay plate of the invention in a chemiluminescence-based assay.

Figure 33:
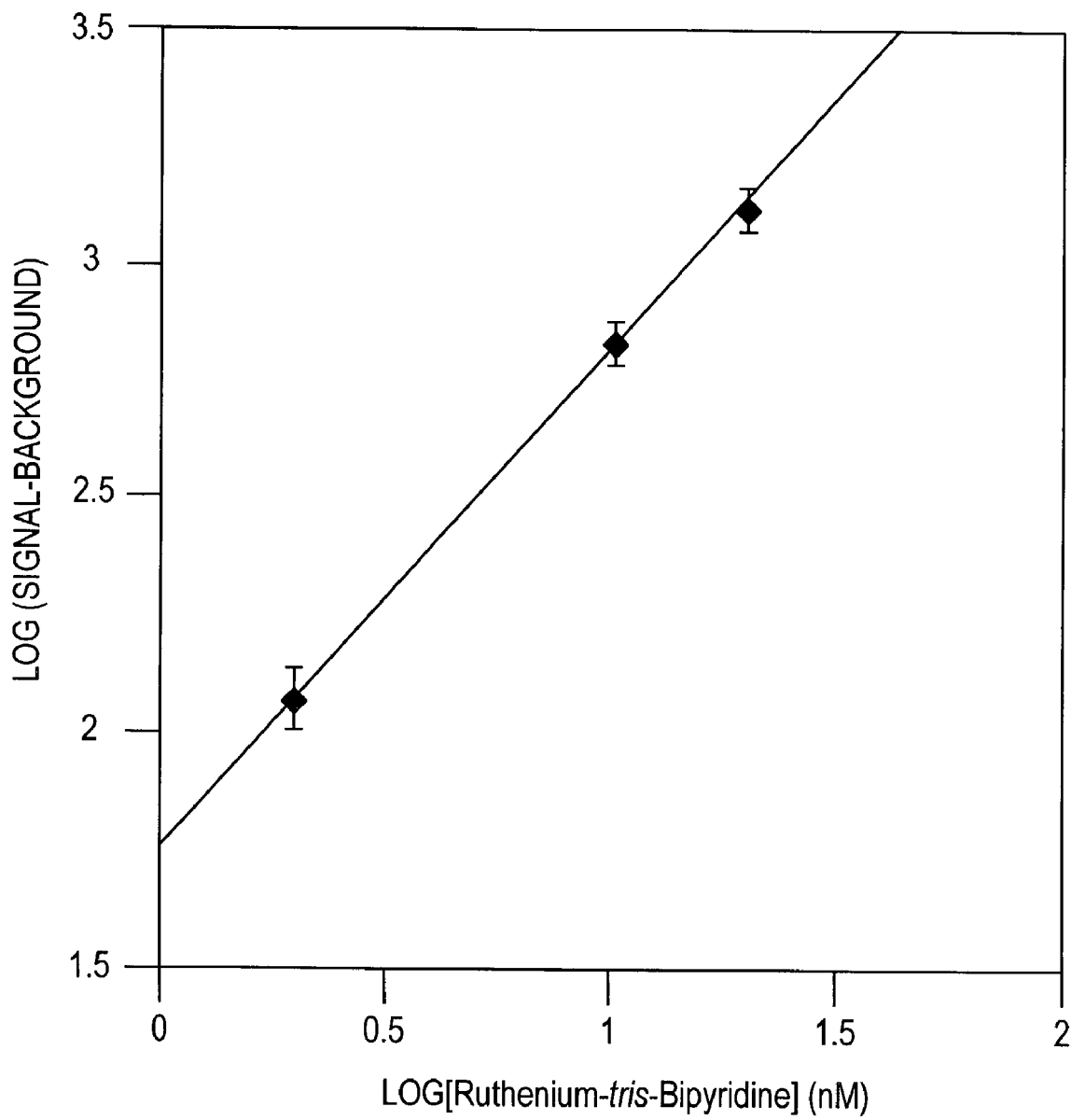

FIG. 33 shows the integrated electrochemiluminescence intensity emitted from a 1536-well plate of the invention as function of the concentration of ruthenium(II)-tris-bipyridine dichloride in the wells.

Figure 34A:
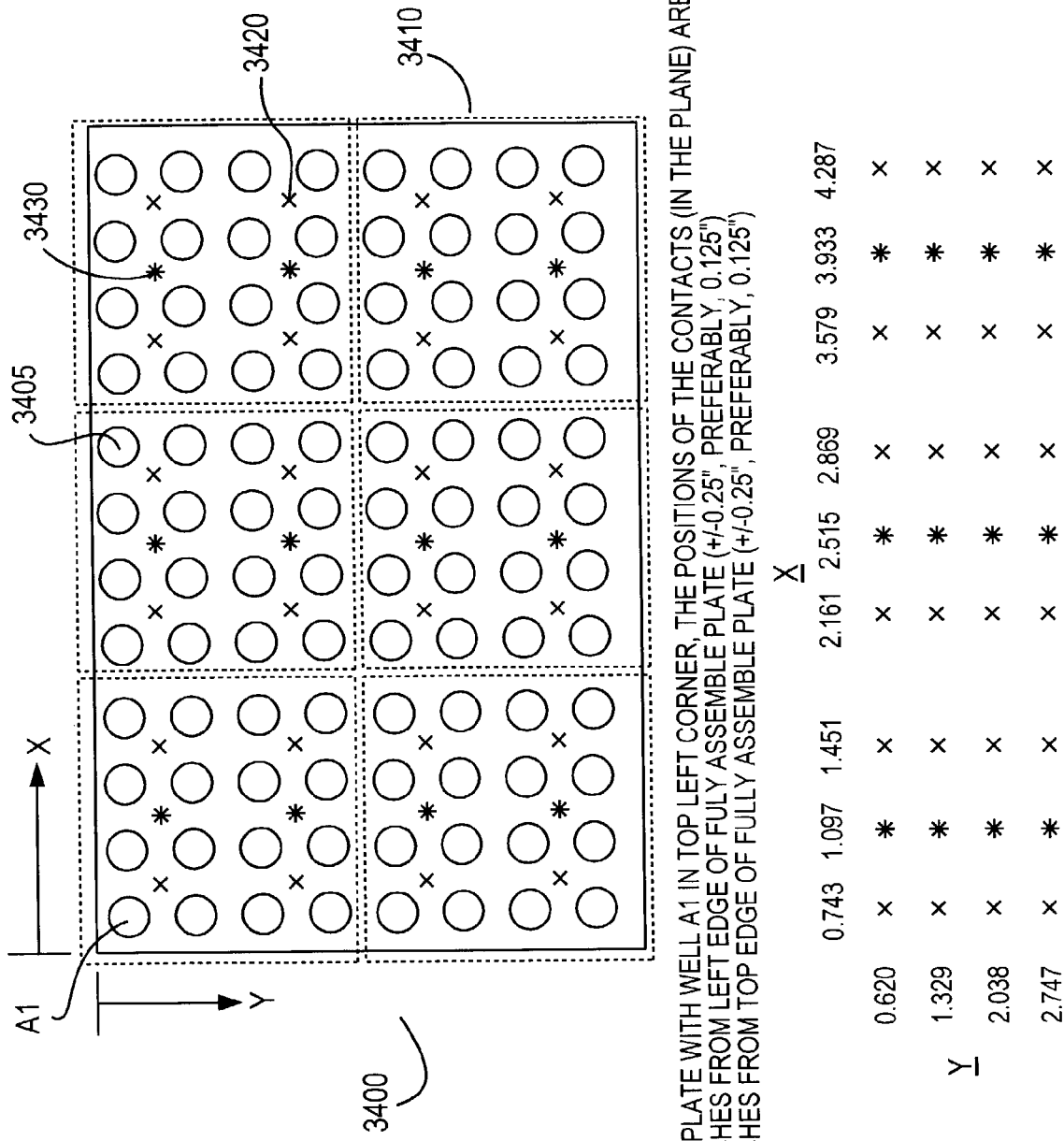

FIG. 34A shows preferred contact locations on assay plate having a 2×3 array of six square sectors.

Figure 34B:
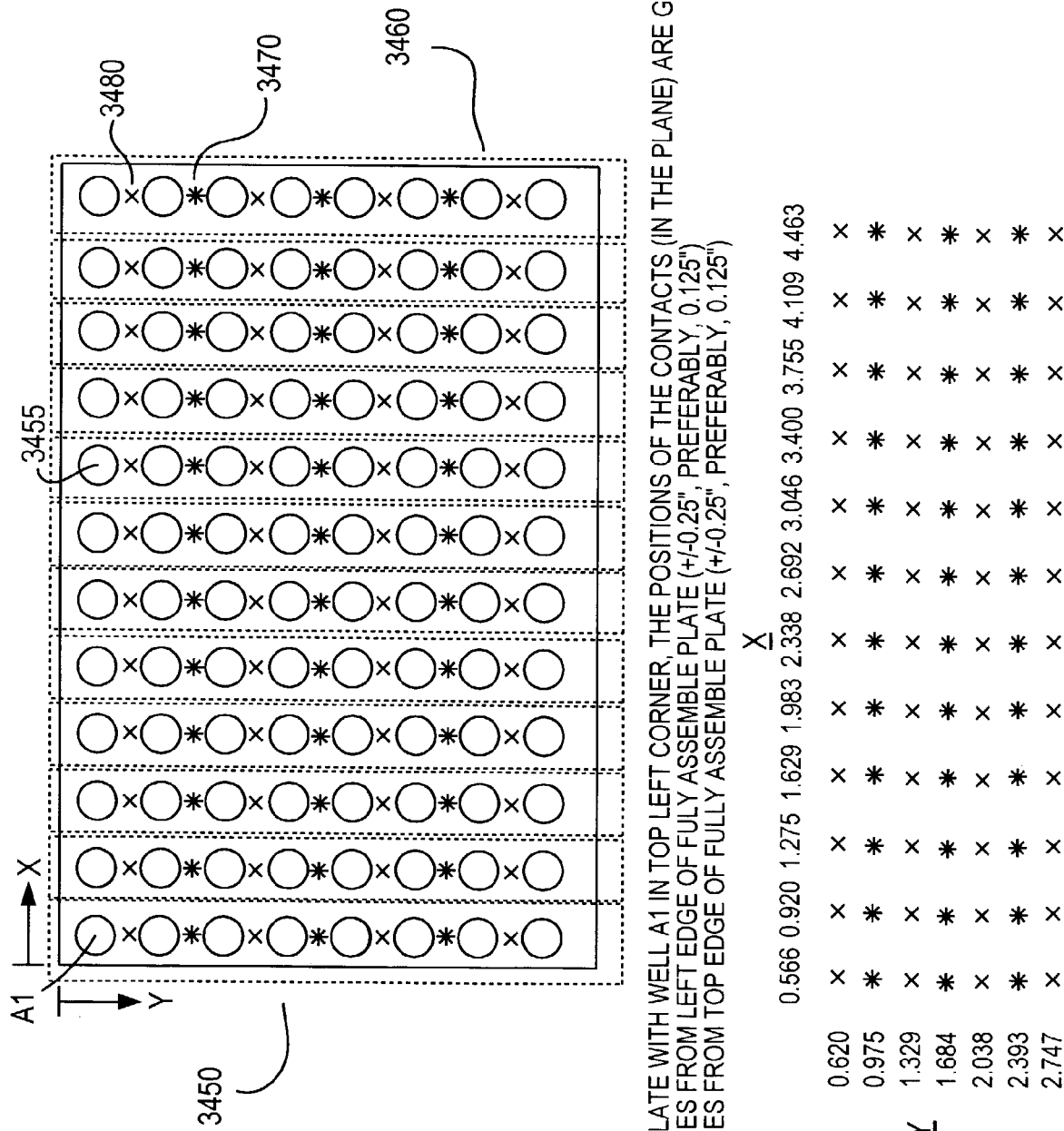

FIG. 34B shows preferred contact locations on assay plate having an array of 12 columnar sectors.

FIGS. 35a-f is a representative block diagram of an automated diagnostic device utilizing a CCD camera.

FIGS. 36a-f is a representative block diagram of an automated diagnostic device utilizing a photodiode array.

Figure 37C:
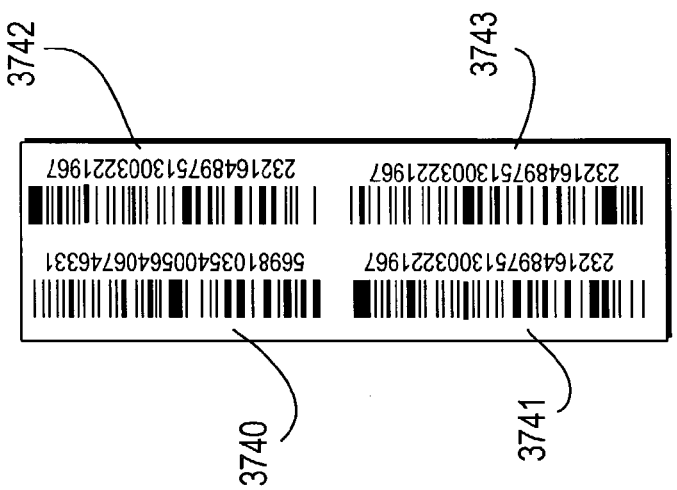
Figure 37A:
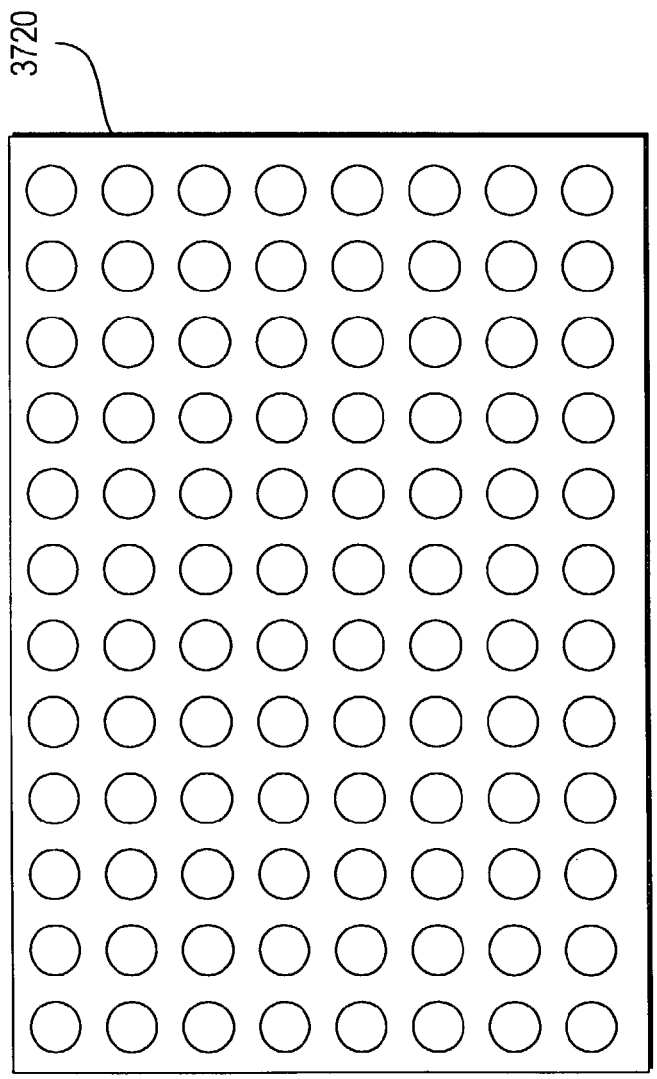
Figure 37B:
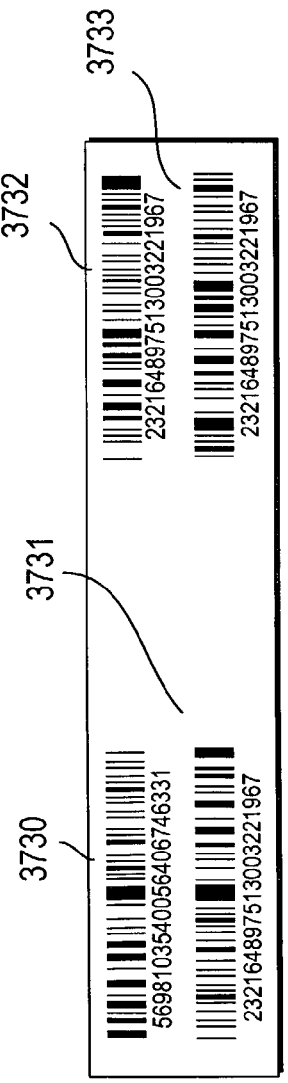

FIG. 37 is a diagram illustrating placement of bar code information along the edges of a microtiter plate.

Figure 38:
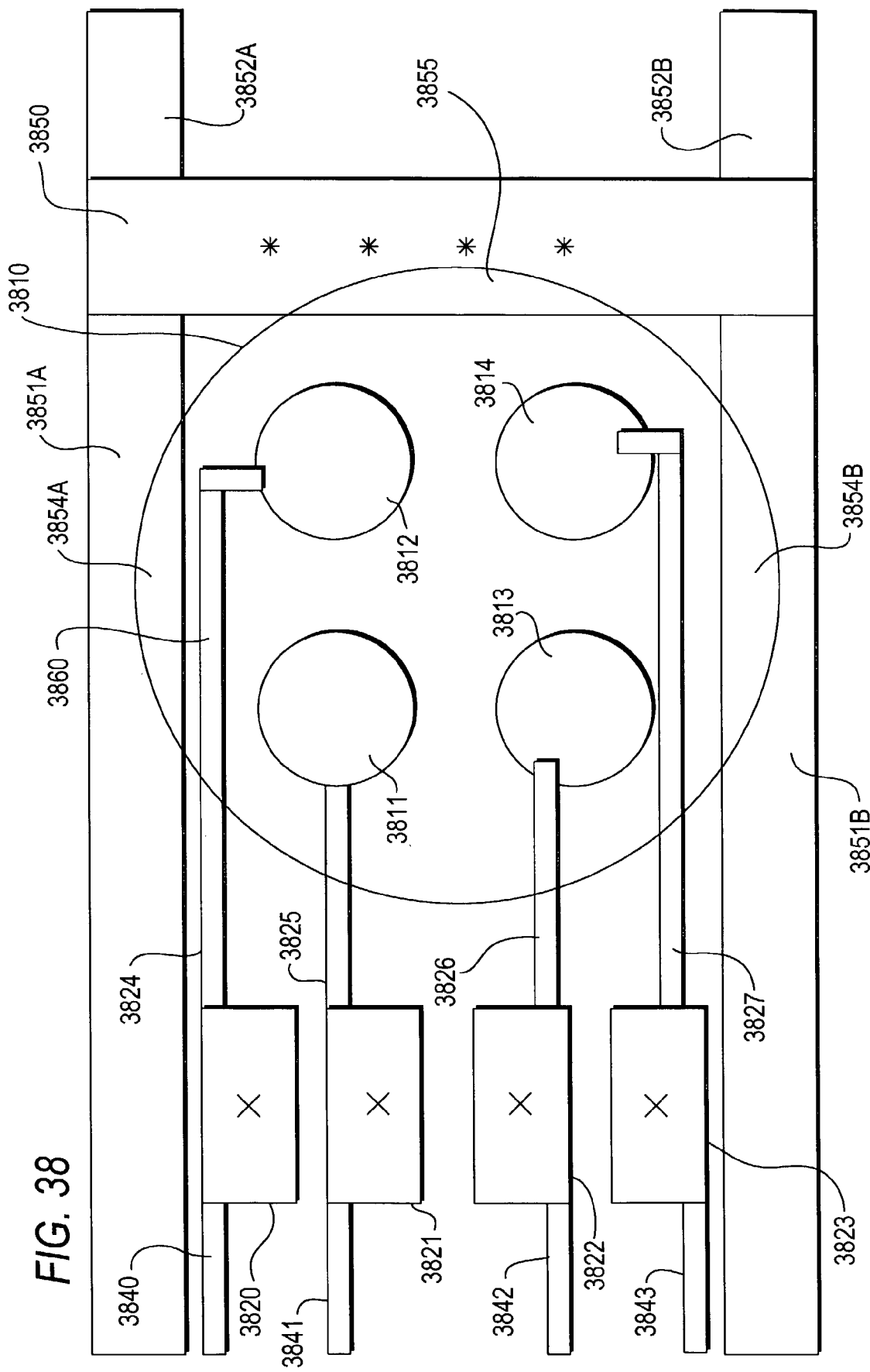

FIG. 38 illustrates a top view of a four spot well configured to be measured by a single light detector according to one embodiment of the invention.

5. DETAILED DESCRIPTION OF THE INVENTION

The invention includes instrumentation and methods for conducting a variety of different types of measurements. The word "measurement" and verb forms of "to measure" as used herein include both quantitative and qualitative determinations.

The invention includes assay modules (e.g., plates, dipsticks, measurement cells, cassettes, cartridges, elements or devices), plate or module components, apparatuses and methods for performing luminescence-based assays. The present invention describes several novel configurations and/or materials for electrodes in assay modules, particularly multi-well assay plates. One embodiment relates to an assay module having a plurality of assay domains or assay regions and, preferably, one or more wells or chambers. The assay modules of the present invention may be used once or may be used multiple times; in preferred embodiments, the modules (e.g., plates) are disposable.

In this specification, inventive concepts may be disclosed in the context of assay plates (e.g., preferred electrode configurations, electrode materials, laminar structures, means for making electrical contacts to an electrode from the bottom of a plate, apparatuses and methods for measuring electrode induced luminescence (preferably electrochemiluminescence)), however, the concepts are also applicable to embodiments relating to other types of assay modules. The preferred embodiments of the invention relate to assay modules, preferably assay plates, having a plurality of assay wells (e.g., "multi-well plates"). Preferred apparatus of the invention are designed to operate with the multi-well assay modules and generally incorporates features for inducing and measuring electrode induced luminescence. The multi-well assay modules and apparatus of the present invention greatly improve among other things the speed, efficiency, quality, ease and cost of luminescence, particularly electrode induced luminescence, more particularly electrochemiluminescence, measurements.

The multi-well assay modules (e.g., plates) of the invention enable the performance of electrode induced luminescence-based assays inside one or more wells or chambers of a multi-well assay module (e.g., the wells of a multi-well assay plate). Multi-well assay plates may include several elements including, for example, a plate top, a plate bottom, wells, working electrodes, counter electrodes, reference electrodes, dielectric materials, contact surfaces for electrical connections, conductive through-holes electrically connecting the electrodes and contact surfaces, adhesives, assay reagents, and identifying markings or labels. The wells of the plates may be defined by holes in the plate top; the inner walls of the holes in the plate top may define the walls of the well. The plate bottom can be affixed to the plate top (either directly or in combination with other components) and can serve as the bottom of the well.

The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Preferably, the wells and/or chambers have at least one first electrode incorporated therein, and more preferably also include at least one second electrode. According to preferred embodiments, the wells and/or chambers have at least one working electrode incorporated therein, and more preferably also include at least one counter electrode. According to a particularly preferred embodiment, working, counter and, optionally, reference electrodes are incorporated into the wells and/or chambers. The assay plates are preferably flat, but may also be curved (not flat).

Moreover, one or more assay reagents may be included in wells, chambers and/or assay domains of an assay module (e.g., in the wells of a multi-well assay plate). These assay reagents may be immobilized or placed on one or more of the surfaces of a well and/or chamber (preferably on the surface of an electrode, most preferably a working electrode) and may be immobilized or placed in one or more distinct assay domains (e.g. in patterned arrays of reagents immobilized on one or more surfaces of a well and/or chamber, preferably on working electrodes and/or counter electrodes, most preferably on working electrodes). The assay reagents may also be contained or localized by features within the well and/or chamber. For example, patterned dielectric materials may confine or localize fluids.

The preferred apparatus of the invention can be used to induce and measure luminescence in assays conducted in assay modules, preferably in multi-well assay plates. It may incorporate, for example, one or more photodetectors; a light tight enclosure; electrical connectors for contacting the assay modules; mechanisms to transport multi-well assay modules into and out of the apparatus (and in particular, into and out of light tight enclosures); mechanisms to align and orient multi-well assay modules with the photodetector(s) and with electrical contacts; mechanisms to track and identify modules (e.g. one or more bar code readers (e.g., one bar code reader for reading one side of a plate or module and another for reading another side of the plate or module); orientation sensor(s); mechanisms to make electrical connections to modules, one or more sources of electrical energy for inducing luminescence in the modules; and appropriate electronics and software.

The apparatus may also include mechanisms to store, stack, move and/or distribute one or more assay modules (e.g. multi-well plate stackers). The apparatus may advantageously use arrays of photodetectors (e.g. arrays of photodiodes) or imaging photodetectors (e.g. CCD cameras) to measure light. These detectors allow the apparatus to measure the light from multiple wells (and/or chambers) simultaneously and/or to image the intensity and spatial distribution of light emitted from an individual well (and/or chamber).

The apparatus can preferably measure light from one or more sectors of an assay module, preferably a multi-well assay plate. In some embodiments, a sector comprises a group of wells (and/or chambers) numbering between one and a number fewer than the total number of wells (and/or chambers) in the assay module (e.g. a row, column, or two-dimensional sub-array of wells in a multi-well plate). In preferred embodiments, a sector comprises between 4 percent and 50 percent of the wells of a multi-well plate. In especially preferred embodiments, multi-well assay plates are divided into columnar sectors (each sector having one row or column of wells) or square sectors (e.g., a standard sized multi-well plate can be divided into six square sectors of equal size). In some embodiments, a sector may comprise one or more wells with more than one fluid containment region within the wells. The apparatus, preferably, is adapted to sequentially induce ECL in and/or sequentially measure ECL from the sectors in a given module, preferably plate.

The apparatus may also incorporate microprocessors and computers to control certain functions within the instrument and to aid in the storage, analysis and presentation of data. These microprocessors and computers may reside in the apparatus, or may reside in remote locations that interact with the apparatus (e.g. through network connections).

In a general description of a preferred measurement operation, samples, reactants, and reagents for electrode induced luminescence (preferably electrochemiluminescence) assays are introduced into assay modules (preferably, into one or more wells of multi-well assay plates). The modules (e.g., the plates and the contents of their wells) are introduced into the measurement apparatus, either one at a time, or in multiples (e.g., by using a plate stacker). A module is, preferably, transported into an enclosed region of the apparatus and, in particular, into a light-tight enclosure. The apparatus positions the module so that one or more (preferably, one) sectors are in alignment with the photodetector(s) and/or with electrical connector mechanisms. After making electrical contact to a sector, the apparatus applies a voltage and/or current waveform and induces luminescence from labels within that sector. The apparatus measures the emitted light with photodetector(s) and stores the results. The apparatus may then sequentially repeat the measurements on other sectors (preferably, one sector at a time). The sequential measurement of sectors may involve making electrical contact to a plurality of sectors and then sequentially applying electrical energy to the appropriate sectors and/or it may involve moving the module, photodetector(s) and/or electrical contacts with respect to each other so as to align the photodetectors and/or electrical contacts with the appropriate sector before firing. In an alternate embodiment, the apparatus may be adapted to measure the entire module at once. After all measurements are complete, the module is then, preferably, transported out of the light-tight enclosure.

In particularly preferred embodiments, the assay modules (in particular, the multi-well assay plates) and apparatus according to the present invention can greatly improve the speed and efficiency with which luminescence measurements may be conducted. By incorporating the ability to induce electrode induced luminescence directly in a well of a multi-well assay plate, the invention overcomes an important limitation of the prior art, namely, the need to transfer the contents of a well in a standard multi-well plate (which lacks the features necessary for electrode induced luminescence tests) into a separate instrument that can conduct electrode induced luminescence-based measurements. In preferred examples of the present invention, multiple electrode induced luminescence (preferably electrochemiluminescence) test measurements may be conducted in different wells of the same plate simultaneously. Such simultaneous operation dramatically increases the rate at which samples may be processed, eliminates cross-contamination of samples, significantly improves overall testing efficiency and enables the measurement of multiple analytes simultaneously. Because the preferred embodiments of the present invention incorporate electrodes into each well of the multi-well assay plates, it eliminates the need for a permanent, reusable measurement cell in the apparatus, which significantly reduces the cost and complexity of the apparatus. By measuring luminescence from sectors in a multi-well assay plate, the apparatus balances the desirable characteristics of rapid measurement times and high optical collection efficiencies.

An important advantage of the multi-well assay plates according to the present invention is the ability to make them compatible with other apparatus already adapted to handle industry-standard multi-well plates. Compatibility with existing plate handling equipment facilitates rapid, efficient and economic loading, processing, storage and disposal of assay plates. Standard plate handling equipment may be used to transport assay plates from one apparatus to another or to and from storage. Existing fluid transfer equipment, such as automatic pipetting equipment, plate washers and mixing stations may be used to transfer samples, reactants, solutions and other reagents to and from the individual wells of a multi-well assay plate. Advantageously, the shape and size of the assay plates is compatible with standard apparatuses for the conduct of pre-processing reactions, shaking or mixing operations or storage. Compatibility with existing equipment and sample handling processes allow for ready integration of the multi-well assay plates and apparatus of the present invention with existing laboratory equipment for handling and processing plates (such equipment may be incorporated, in whole or in part, into the apparatus and/or functionally linked or adjoined to the apparatus). This compatibility may be particularly advantageous in high throughput screening operations.

5.1 Multi-Well Assay Plates

One aspect of the invention relates to improved assay modules (e.g., plates) adapted for use in assays, preferably luminescence assays, more preferably electrode induced luminescence assays, even more preferably electrochemiluminescence assays. The assay modules of the invention are preferably suitable not only for ECL assays, but also suitable for fluorescence assays, chemiluminescence assays, bioluminescence assays, phosphorescence assays, optical transmittance assays (e.g., measurements of optical density or light scattering) and electrochemical assays (e.g., wherein the measurement involves measuring current or voltage).

According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particularly preferred embodiment, the assay plate is a multi-well assay plate having a standard well configuration (e.g., 6 well, 24 well, 96 well, 384 well, 1536 well, 6144 well or 9600 well).

An electrode induced luminescence well (preferably electrochemiluminescence well (i.e., a well adapted for electrochemiluminescence)) or electrode induced luminescence domain (preferably electrochemiluminescence assay domain (i.e., an assay domain adapted for electrochemiluminescence assays)) may include a first electrode surface (such as a working electrode surface) and, preferably also includes a second electrode surface (such as a counter electrode surface).

The invention also relates to a multi-well module, preferably an assay plate, for conducting one or more assays, the module having a plurality of wells (and/or chambers), wherein two or more of the plurality of wells (and/or chambers) comprise at least one first electrode surface and, preferably at least one counter electrode surface. According to a preferred embodiment, two or more of the plurality of wells (and/or chambers) comprise a working electrode surface and, preferably a counter electrode surface, adapted to induce luminescence in the wells. The invention also relates to a multi-well module, preferably a plate, for conducting one or more assays, the module having a plurality of wells, wherein one or more of the plurality of wells comprise a working electrode surface and a counter electrode surface adapted to induce luminescence in the wells. Preferably, all or substantially all of the wells comprise an electrode surface.

Another embodiment relates to a multi-well assay module, preferably an assay plate, for conducting electrode induced luminescence (preferably electrochemiluminescence) assays, the module, preferably plate, having a plurality of wells, wherein each of the plurality of wells comprises at least one first electrode surface (e.g., a working electrode) and, preferably, at least one second electrode surface (e.g., a counter electrode).

Another embodiment relates to an assay plate for conducting one or more electrode induced luminescence (preferably electrochemiluminescence) assays, the plate having a plurality of wells or assay regions comprising electrode surfaces, wherein the electrode surfaces consist essentially of at least one working electrode surface and at least one counter electrode surface.

Preferably, the assay regions or assay wells are free of reference electrodes allowing for a greater density of assay domains and simplified instrumentation for inducing and measuring luminescence.

Preferably, the working electrode is adjacent, but not physically contacting the counter electrode. Preferably, the working electrode surface and counter electrode surface are at substantially the same height or at the same height within the well.

According to another embodiment, the spacing between the working electrode and counter electrode is preferably small, more preferably less than 0.5 inch, even more preferably less than 0.2 inch, even more preferably less than 0.1 inch, even more preferably less then 0.05, even more preferably less than 0.01 inch and most preferred less than 0.005 inch. Preferably, the electrodes are integrated into the assay module, preferably assay plate, allowing luminescence, preferably electrode induced luminescence, more preferably electrochemiluminescence, to be induced without the use of an external electrode probe. Preferably, an assay reagent is immobilized on the working electrode (discussed further below). In another preferred embodiment no assay reagent is immobilized on the working electrode (discussed further below). In yet another preferred embodiment, one or more assay reagents are immobilized on the working electrode (discussed further below). In yet another preferred embodiment, two or more assay reagents are immobilized on the working electrode (discussed further below).

In order to enhance luminescence collection efficiency and/or reduce the size of the imaging surface and/or number of light detectors, the module is preferably electrically addressable in sectors. That is, rather than measuring light from a single well, chamber, or assay domain at a time (which is time inefficient) or measuring light from the entire module (which reduces light collection efficiencies, requires multiple light detectors or requires the use of larger light detectors), the module and apparatus are configured to allow for the measurement of luminescence in portions of the assay module (preferably, more than one assay domain, well or chamber at a time, but less than all). Preferably, the portions of the assay module are in sectors, where the terms "sector" or "sectors" when used in the context of a plate or module is used herein to refer to independently addressable groups of one or more (preferably two or more) jointly addressable assay wells, assay chambers or assay domains. Preferably, the sectors comprise one or more electrodes, more preferably two or more jointly addressable (e.g., electrically connected) working electrodes.

One embodiment relates to an assay module (preferably, an assay plate, more preferably a multi-well plate) for conducting luminescence assays (preferably electrode induced luminescence assays, more preferably electrochemiluminescence assays) comprising a substrate surface having a plurality of electrodes patterned thereon, wherein the plurality of electrodes are patterned so as to form independently addressable sectors comprising jointly addressable electrodes.

According to another embodiment, the assay module (preferably a multi-well plate) has a plurality of wells, each well comprising a first electrode surface (preferably suitable for use as a working electrode in an electrode induced luminescence assay) and, preferably, a second electrode surface (preferably suitable for use as a counter electrode in the electrode induced luminescence assay). Referring to FIG. 2, each well 158 of multi-well assay plate 150 according to a particularly preferred embodiment of the invention comprises a working electrode 168 and a counter electrode 166.

The working electrode surface area may be smaller, the same or larger than the counter electrode surface area. In some embodiments, the working electrode surface is preferably much larger than the counter electrode surface. See FIGS. 2A, 2B and 2D, for example. This configuration allows for a greater working electrode surface on which to immobilize assay reagents. Preferably, the surface ratio of the working electrode surface to the counter electrode surface is at least 2 to 1, more preferably at least 5 to 1, even more preferably at least 10 to 1, still more preferred at least 50 to 1, even more preferably at least 100 to 1 and most preferred at least 500 to 1. Surprisingly, the assay modules of the invention provide for the performance of electrochemiluminescence assays with very little counter electrode surface. Preferably, the working electrode is substantially centered within the well so as to maximize the percentage of ECL emitted from the electrode that can be captured by a light detector placed above the well.

According to another embodiment, the first electrode surface (e.g., working electrode surface) is centered at the bottom of each well and the second electrode surface (e.g., counter electrode surface) is adjacent the periphery of the bottom of each well. In some embodiments, the working electrode surface is centered at the bottom of each well and is completely surrounded by the counter electrode surface. Referring to FIG. 2D, working electrode 270 is completely surrounded by counter electrode 266. Preferably, the counter electrode surface is adjacent, but not in contact, with the working electrode (being separated by gap and/or insulating material 268).

Another embodiment of the invention relates to a multi-well assay module having a plurality of wells, each well having a well bottom comprising a first electrode surface, a second electrode surface and a dielectric surface (preferably the dielectric surface is the surface of the bottom of the well between the first electrode surface and the second electrode surface), wherein the ratio of the first electrode surface and the dielectric surface is at least 5 to 1, preferably 10 to 1, more preferably 30 to 1.

According to another embodiment the well bottom comprises 30 to 99.1% working electrode surface, 0.1 to 50% counter electrode surface and 0.01 to 70% dielectric surface. Preferably, the well bottom comprises 30 to 99.1% working electrode surface, 0.1 to 30% counter electrode surface and 0.01 to 70% dielectric surface, more preferably the well bottom comprises 50 to 99.1% working electrode surface, 0.1 to 20% counter electrode surface and 0.01 to 70% dielectric surface, even more preferably 75 to 99.1% working electrode surface, 0.1 to 10% counter electrode surface and 0.01 to 70% dielectric surface, even more preferably 80 to 99.1% working electrode surface, 0.1 to 5% counter electrode surface and 0.01 to 70% dielectric surface and most preferably 85 to 99.1% working electrode surface, 0.1 to 1% counter electrode surface and 0.01 to 70% dielectric surface.

Alternatively, for some applications it is desirable that working electrode surfaces be small, e.g., relative to the surface area of a well or well bottom. In some applications, this configuration may reduce non-specific signals. According to one embodiment of the invention, the multi-well assay module has a plurality of wells, each well having a well bottom comprising a first electrode surface, a second electrode surface and a dielectric surface (preferably the dielectric surface is the surface of the bottom of the well between the first electrode surface and the second electrode surface), wherein the ratio of the first electrode surface and the dielectric surface (or alternatively the surface of the well bottom) is less than 1 to 5, preferably 1 to 10, more preferably 1 to 30.

According to one preferred embodiment of the invention, the assay module comprises a first electrode surface (preferably a working electrode surface) that is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary). Preferably, the first electrode surface has a contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface.

According to another embodiment, an assay module comprises one or more (preferably two or more) wells, the wells having one or more first electrode surfaces (preferably one or more working electrode surfaces) and a plurality of assay domains immobilized therein. Preferably, at least two of the plurality of the assay domains comprises different binding reagents. Preferably, each well comprises at least four, more preferably at least seven, even more preferably at least ten assay domains and most preferred at least 15 assay domains. One preferred embodiment is a 24 well plate wherein each well comprises at least 16, preferably at least 25, more preferably at least 64, even more preferably at least 100 assay domains per well and most preferably at least 250 assay domains per well.

Another embodiment of the invention relates to a multi-well module (preferably a multi-well plate) having a plurality of wells, wherein the wells comprise a plurality of working electrode surfaces having assay domains immobilized thereon. Preferably, the assay domains are independently addressable. For example, a well may comprise a plurality of assay domains, wherein each assay domain comprises an electrode which is independently addressable from the other assay domains within the well. In another example, a group of wells may each comprise a plurality of assay domains, wherein each assay domain comprises an electrode which is independently addressable from the other assay domains within the well, but which is jointly addressable with an assay domain in each of the other wells.

As discussed above and described in more detail below, one aspect of the invention may involve detecting emitted luminescence using an imaging system. According to a preferred embodiment, the apparatus may employ a camera, which images the assay module (e.g., a multi-well plate). Since the distance between the camera or imaging surface and the source of luminescence (e.g., working electrode surface) can impact the quality of the image, controlling such distances is preferred. For example, if the working electrode surfaces (e.g., the surfaces at which luminescence may be induced or generated) are formed on well bottoms and two or more wells are imaged simultaneously, the height of the working electrode surface (and corresponding distance to the camera) is preferably substantially the same. Preferably, the variation is less than 0.01 inches, more preferably less than 0.005 inches and most preferably less than 0.001 inches. Thus, the parameters, which may cause such variation, are preferably controlled (e.g., electrode thickness and height, flexing or warping of the assay module, etc.).

Thus, the plate bottom of an assay plate is preferably flat. For example, when a multi-well assay plate is placed on a flat surface, the variation in height measured from the flat surface to the electrode surfaces in each of the plurality of wells is preferably less than 0.01 inches, more preferably less than 0.005 inches and most preferably less than 0.001 inches. That is, referring to the cross-sectional view in FIGS. 2H, 2I and 2J and FIGS. 8C, 9B, 10B and 14B, the vertical height of each working electrode surface in each of the wells is preferably substantially the same (i.e., the same vertical height throughout the well or assay region). Preferably, the vertical height within at least the wells within each sector is the same (i.e., the same vertical height throughout the sector). Even more preferably, the vertical height within each sector of a plate is substantially the same (i.e., the same vertical height throughout the plate). Otherwise, the light detector or imaging system may need to be re-focused for each sector to optimize the measurement (discussed further below in Section 5.8).

Accordingly, another embodiment relates to a multi-well plate comprising:
(a) a plurality of wells, the wells having well bottoms; and
(b) a plate substrate;
wherein when the multi-well plate is placed on a flat surface, the well bottom is elevated from the flat surface 0.050 to 0.150 inches, preferably, 0.103 to 0.107 inches, more preferably 0.104-0.106, and most preferred about 0.105.

Providing a more uniform and consistent well bottom elevation enables control of the electrode surface height variation, even for different plate formats. Preferably, the plate comprises greater than 100 wells or less than 90 wells. Thus, the height may be maintained whether the plate is a 96 well plate, a 6 well plate, a 384 well plate or otherwise. This allows for the use of different plate configurations without distorting the image or without having to refocus the imaging system. That is, one may use a variety of different plate formats without re-focusing the imaging system if the distance between the camera and working electrode surface is maintained from plate to plate. This is particularly advantageous, for example, if a plate stack including a number of plates having different plate formats is being used.

Preferably, the plate bottom has a thickness less than 10 cm, preferably less than 5 cm, even more preferably less than 1 cm, even more preferably less than 5 mm, even more preferably less than 1 mm, even more preferably 0.1 mm, even more preferably 0.01 mm, and most preferred 0.001 mm.

Figure 1:
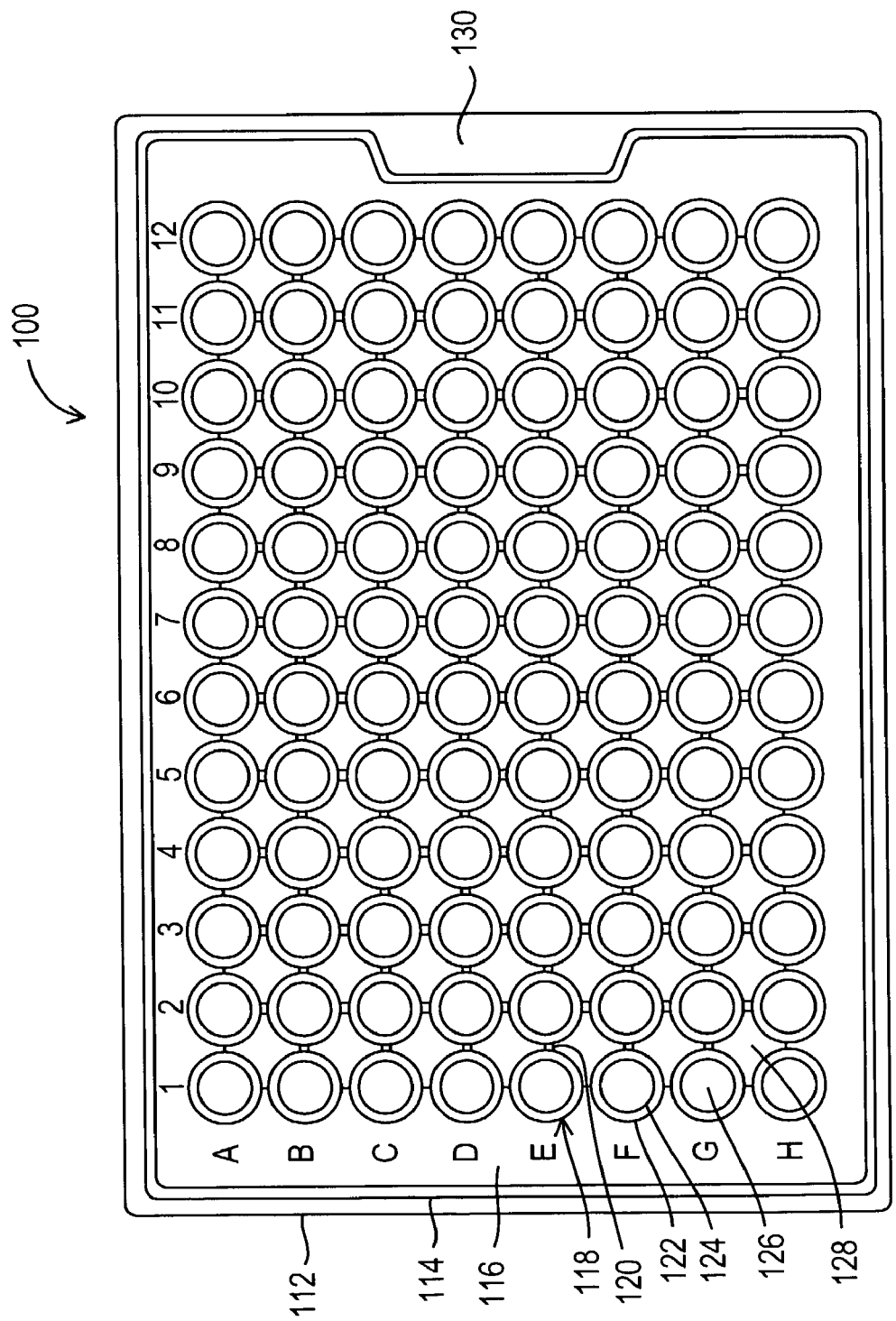
FIG. 1 illustrates an industry standard multi-well assay plate having 96 wells.

According to one embodiment, the plate bottom elevation is provided using "legs" or a skirt to elevate the plate off any surface on which it rests. FIG. 1 illustrates skirt 112 and FIG. 8C illustrates skirt 836, both of which are embodiments of "skirts" according to the invention that may be configured to elevate the plate. Preferably, the plate is elevated to maintain the distance between the working electrode surface and the imaging surface or camera. Thus, although the well depth of the 384 well plate may be different than that of a 96 well plate, the legs on the 96 well plate would be configured to adjust its working electrode surface to be comparable to that of the 384 well plate. Advantageously, the skirt and/or the elevation of the plate bottom are also configured so as to prevent contact between top edge or lip of the well of one plate in a stack with the bottom surface of the next higher plate in the stack. Preventing such contact prevents the plates from sticking together and reduces condensation from occurring on the bottom of plates. Alternatively, the plates may be adapted to form a seal when stacked (e.g., to reduce or prevent contamination and/or the evaporation of the well contents).

According to one embodiment, an adhesive layer 944 may be employed to both attach a plate top to a plate bottom and also provide sealing between the wells. (See also, for example, adhesive layer 806 of FIG. 8A; adhesive layer 844 of FIG. 8B; adhesive layer 1030 of FIG. 10A; adhesive layer 1530 of FIG. 15; and adhesive layer 1604 of FIG. 16A). Preferably, the thickness of the adhesive layer is 0.0002-0.01 inches, more preferably 0.0005-0.008 inches, even more preferably 0.002-0.006 inches and most preferably approximately 0.005 inches. Preferably, in such embodiments, the well walls are at least 0.03 inches, or more preferably, at least 0.05 inches thick to allow for reliable and leak-free sealing. According to one preferred embodiment, the adhesive layer is a double coated film preferably comprising at least a 0.5 mil (0.02 mm) carrier film (e.g., polyester) coated on both sides with an adhesive (preferably an acrylic based adhesive) of at least 2 mils (0.08 mm). The carrier provides dimensional stability and the 2 mil adhesive coat prevents leaks. Preferably, the adhesive layer is Keystone Tapes W-546, 3M 4768 or a combination thereof, more preferably 3M 4768. Other suitable adhesives or adhesive layers may include Ideal (887), 3M (444, 442, 415), Morgan IB-2100, Nashua 943, Permacel P-941, Tesa 4972, Avery Dennison adhesives (e.g., UVA tape) and Adhesives Research adhesives.

Preferably, the wells are separated from each adjacent well by between 0.03 and 0.3 inches, preferably (for 96 well plates) between about 0.09 and 0.11 inches, most preferred about 0.104 inches. Optimizing the well wall thickness and well separation advantageously reduces and preferably prevents sample leakage from one well into another well. This may be a problem, for example, if the electrical contacts of the apparatus push up onto the well bottoms causing flexing.

Another way to mitigate the problem of well leakage involves improving the sealing between the wells. Referring to FIG. 9B, working electrode surface 958 and dielectric layer 950 preferably extend beyond well 942. Thus, one embodiment of the invention relates to a multi-well plate comprising a dielectric surface and a working electrode layer, wherein the dielectric surface is comprised of a dielectric layer formed on a portion of the working electrode layer wherein the working electrode layer and the dielectric layer extend beyond the well walls. According to another embodiment, the working electrode layer and the dielectric layer are deposited onto a plate bottom or substrate and extend beyond the well helping to seal the wells. Preferably, at least a portion of the working electrode surface, the counter electrode surface, and/or the dielectric layer extend beyond the well wall.

According to another aspect of the invention, one or more of the electrodes are integrated into a plate bottom or assay module substrate. In one embodiment of the invention, an assay module is formed by combining such a plate bottom or assay module substrate with a suitable assay module top. The top may comprise holes, wells, channels, tubes, compartments, etc. that define wells, chambers, channels, tubes and/or microfluidics within the assay module. Thus, the invention also relates to plate bottoms or assay module substrates having a variety of electrodes, electrical contacts and conductive through-hole combinations. Also included within the scope of the invention are multi-well plates, formed by attaching a suitable plate top to the plate bottom and apparatuses and methods adapted to perform assays using such plates.

Thus, another aspect of the invention relates to assay module substrates, preferably multi-well plate bottoms (e.g., having no plate top). For example, such plate bottoms can be affixed with the plate top thus forming a multi-well plate for use in conducting assays.

FIG. 2 illustrates a multi-well assay plate 150 according to a preferred embodiment of the present invention. A 96-well assay plate 150 comprises an outer lip 152, an inner lip 154, a top surface 156, and 96 individual wells 158 separated by spacers 160. Defined between wells 158 and spacers 160 are inter-well regions 170.

Preferably, the majority of plate 150 (e.g., all but the bottom surfaces of wells 158) is a unitary molded structure made from rigid thermoplastic material such as polystyrene, polyethylene or polypropylene (alternatively, the entire plate, including the bottom surface of wells 158, may be a unitary structure). According to one preferred embodiment, the material comprises polystyrene blended with High Impact Polystyrene (HIPS) to reduce the brittleness of the material. Preferably, between 4 and 16 wt % HIPS is blended with the polystyrene, more preferably between about 8 and 12 wt %.

Optimally, the unitary structure of plate 150 is formed of inexpensive material that is generally impervious to reagents typically encountered in ECL measurements, resistant to the adsorption of biomolecules, and can withstand modest levels of heat and light. Advantageously, the plate materials (including any adhesives used to seal the wells) are impervious to organic solvents typically used to dissolve chemical libraries for high throughput screening (preferably the plate is unaffected by 10% aqueous solutions of DMSO or methanol, more preferably by 20% aqueous solutions of DMSO or methanol, or most preferably by 100% DMSO or methanol). Preferably the use of silicone-containing materials is avoided in the components used to make up a plate since silicones can contaminate surfaces of the plate and affect wetting, adsorptive and/or electrode properties of surfaces (preferably, the plate or a given component of the plate contains less than 1 wt % silicone, more preferably less than 0.1 wt % silicone or, most preferably, less than 0.01% silicone).

Different colored material for plate 150 may be used to improve the results of certain ECL measurement processes. It is preferable to use a material that does not transmit light so as to prevent cross-talk between wells. A highly reflective metallic coating or constituent material may provide an especially reflective interior surface for each of wells 158 to increase the efficiency with which light can be transmitted to photodetectors. An opaque white plastic material such as a plastic filled with light scattering particles (e.g., lead oxide, alumina, silica or, preferably, titanium dioxide particles) may provide an interior surface for each of wells 158 that is highly light scattering thereby improving light gathering efficiency. Alternatively, an opaque black material for plate 150 may advantageously prevent the reflection or scattering of ECL-generated light from different locations within a well 158 so as to prevent reflective interference during ECL test measurements. In general, when imaging light emitted from a well (e.g., when using a camera to produce an image of light emitted from the well) it is advantageous that the interior surface of wells 158 comprise an absorptive (e.g., black) non-scattering material since the detection of scattered light will reduce the fidelity of the image. In general, when detecting light in a non-imaging mode (e.g., when a single light detector is used to detect all the light emitted from a well) it is advantageous that the interior surface of wells 158 comprise a reflective or highly scattering material so as to maximize the collection of light at the detector.

Plate 150 may be composed of several parts joined together. In many embodiments plate 150 and elements outer lip 152, inner lip 154, top surface 156, spacers 160, inter-well region 170, corner recesses or chamfers 172, and wall 162 (having interior surface 164) comprise a plate top. The plate top of plate 150 may have holes, the sides of which are defined by interior surface 164 of wall 162. The plate top can then be combined with a plate bottom that defines, together with the plate top, wells 158. The plate bottom advantageously comprises a working electrode 168 and may further comprise a counter electrode 166. The plate bottom may, optionally, comprise one or more independent reference electrodes (not shown). Preferably, reference electrodes are not included. The plate bottom may be a continuous element or may be composed of many elements, either coupled together or completely distinct. Working electrode(s) 168 may comprise the predominant structure for the plate bottom or, alternatively, may be supported on another element that provides appropriate structural properties. The plate bottom may be affixed to the plate top by a variety of means, for example, by using adhesives or other bonding agents, conducting or dielectric films, by bonding, fusing or welding the constituent parts, by mechanical fasteners such as clamps, screws, tabs and slots, or by other structures or means known in the art.

Alternatively, plate 150 may be formed from any material that can be formed into an appropriate shape. Materials such as plastics, elastomers, ceramics, composites, glasses, metals, carbon materials or the like can be used. While it is preferred that the majority of plate 150 be a single unitary structure, it is within the scope of the present invention to provide plate 150 with removable or otherwise contiguable components, particularly wells 158. Plate 150 can be conductive or non-conductive. In applications in which plate 150 is conductive, plate 150 may be grounded or itself function as a counter electrode or a working electrode.

Outer lip 152 extends downwardly and inwardly to provide a rigid lip extending around the entire periphery of plate 150. Outer lip 152 may function to aid in the alignment and orientation of plate 150 and may function to allow robotic systems to handle the plate. As shown, outer lip 152 preferably includes two recessed corner recesses 172 that provide identifying physical indicia for plate 150. In particular, corner recesses 172 facilitate the alignment and handling of plate 150 and assist in distinguishing plate 150 from other plates having different configurations of recessed areas along their respective peripheries. Advantageously, the dimensions and structure of outer lip 152 are preferably in accordance with, or at least compatible with, industry standards for the footprints of similar types of assay plate.

Inner lip 154 extends upwardly from the top surface of outer lip 152 to a height slightly above top surface 156. Top surface 156 is thus recessed within inner lip 154. The otherwise rectangular shape of inner lip 154 is interrupted at two corners by corner cutouts shaped to define part of corner recesses 172.

Top surface 156 extends around the periphery of plate 150 within the confines of inner lip 154. Preferably, top surface 156 extends inward to the mid point of each of the outer most of wells 158. Alternatively, top surface 156 is a continuous surface extending throughout the areas defined between wells 158. As preferred, spacers 160 structurally connect wells 158 to each other and, in conjunction with the outside surfaces of wells 158, define inter-well regions 170.

Each of wells 158, preferably, comprise a wall 162, an interior surface 164, a counter electrode 166, and a working electrode 168. As shown, wall 162 may define a cylindrical volume extending above top surface 156 and downwardly to at least counter electrode 166 or working electrode 168. Alternatively, wall 162 may not extend to electrodes 166 or 168 and may be flush with top surface 156. In another embodiment, not shown, wall 162 is rectilinear with a quadrilateral cross-sectional, preferably square or rectangular.

Wall 162 has an interior surface 164 that is preferably cylindrical in shape and defines a volume of well 158. Inner surface 164 preferably extends the depth of well 158. At bottom, or at a position near the bottom of well 158, counter electrode 166 and/or working electrode 168 comprise a bottom surface of well 158. Such bottom surface is preferably not integral to plate 150 or well 158 in that it is formed of different materials. Counter electrode 166 and working electrode 168 may be coplanar or at different depths within well 158. Preferably, interior surface 164, counter electrode 166 and working electrode 168 together form a container suitable for holding liquids as well as solids, gels and similar states of matter.

Inter-well regions 170 may be open passages extending through plate 150 or, preferably, include base structure integral to plate 150. Such base structure may bear indicia identifying wells 158 individually. In addition to corner recesses 172, plate 150 may bear other identifying indicia. For example, plate 150 may include a bar code identification stripe pattern on top surface 156, on the exterior of inner lip 154, on the exterior surface of outer lip 152, on the underside of plate 150, or elsewhere on plate 150.

In alternate preferred embodiments, plate 150 may be configured as a multi-well assay plate having any number of wells. For example, 1-well, 6-well, 24-well, 96-well, 384-well, 1536-well, 6144-well and 9600-well plates may be constructed in accordance with the present invention as described herein. Multi-well assay plates of the invention may have a number of wells ranging from 1 to 2, 2 to 6, 6 to 24, 24 to 96, 96 to 384, 384 to 1536, 1536 to 9600, 6144 to 100,000, or greater than 100,000. Preferred embodiments have wells that range in volume from 10 nL to 100 nL, 100 nL to 1 uL, from 1 uL to 100 uL, from 100 uL to 1 mL and from 500 uL to 10 mL. The wells 158 of plate 150 may be configured in many different shapes and sizes, such as wells with rectangular cross sections, very shallow wells or depressions (dimples) or the like, to accommodate particular reaction criteria or existing equipment and implement integrated ECL electrode technology according to the present invention.

Assay reagents (e.g., binding reagents, coreactants, ECL labels) may be immobilized on the bottom surface of the well 158. These reagents may be covalently or non-covalently immobilized on the bottom surface. Advantageously, reagents are immobilized on the working electrode 168. In preferred embodiments, assay reagents are immobilized in assay domains on working electrode 168. These assay domains may be distinct or contiguous. In some embodiments, multiple distinct assay domains containing assay reagents are present on the working electrode 168.

According to one embodiment, the plate further comprises a cover or lid or plate seal ("cover") adapted to cover the wells and thereby reduce or prevent evaporation and/or prevent contamination. The cover may be, for example, a hard plastic cover or an adhesive flexible tape. The cover may be disposable and/or reusable.

According to one embodiment, the cover is opaque to protect light sensitive components within the plate. In this embodiment, the cover is removed prior to measurement of the luminescence. According to another embodiment, the cover is transparent, preferably transparent enough to allow luminescence to be measured through it. Preferably, at least the bottom surface of the cover is treated (e.g., with a hydrophilic or hydrophobic coating) to prevent detrimental clouding of the lid. According to one embodiment, the bottom surface is hydrophobic to reduce condensation and thereby reduce clouding. According to an alternative embodiment, the bottom surface is hydrophilic to promote uniform wetting and thereby also reduce clouding.

5.1.1 Embodiments of Wells in a Multi-Well Assay Plate

FIGS. 2A-D, 3A-C, and 4A-E provide views of a number of alternative configurations for wells 158. These figures show wells having first electrodes (preferably working electrodes), second electrodes (preferably counter electrodes), and in some cases, boundaries. The figures show the exposed surfaces of the components. In some embodiments of the invention some of these components may have additional surfaces buried under other components. Preferably, the first and second electrodes are not in electrical contact (e.g., there is a least a small gap or some interposing material between the electrodes in the vertical and/or horizontal dimensions). In the figures, a line shown dividing working and counter electrode surfaces may represent such a gap or interposing material. Preferably, the working electrode is placed at or substantially at the center of the well bottom, so as to minimize shadowing by the well walls of luminescence generated at the working electrode; preferably, the counter electrode is placed at or substantially at the edges of the wells. FIG. 2A illustrates well 200 comprising wall 162, having an inner surface 164; a counter electrode 166; and a working electrode 168. Well 200 may, optionally, comprise a reference electrode (not shown). As shown, interior surface 164 of wall 162 defines a cylindrical volume. At or near the bottom of such cylindrical volume, counter electrode 166 extends in a ring-shape area between interior surface 164 and circular working electrode 168. Wall 162 is preferably comprised of materials described previously for plates 150. It may also, however, be comprised of other materials and/or have coatings on its surface 164. Counter electrode 166 may be coplanar with the surface of working electrode 168 or it may be at a different depth. It may also be a material or coating affixed to inner surface 164. It is preferred that counter electrode 166 itself defines a cylindrical volume above working electrode 168. Preferably, counter electrode 166 has an inner radius which is at least 20% of the radius of inner surface 164, more preferably is at least 50% of the radius of inner surface 164 and most preferably is at least 80% of the radius of inner surface 164. Preferably, counter electrode 166 is not in direct electrical contact with working electrode 168 and a gap or insulating layer (not shown) is interposed between electrodes 166 and 168.

FIG. 2B illustrates well 220, another embodiment of well 158. Well 220 comprises wall 222 having an interior surface 224; counter electrode 226A and 226B; and working electrode 230. Preferably, counter electrodes 226A and 226B are symmetrical electrode areas abutting opposite sides of interior surface 224. Preferably, counter electrodes 226A and 226B are electrically isolated from working electrode 230 by a gap or insulating layer interposed between the electrodes. Preferably, each of counter electrodes 226A and 226B is less than 40% of the cross-sectional area defined by inner surface 224, more preferably is less than 20% of such area, and most preferably is less than 10% of such area. Well 220 may, optionally, comprise a reference electrode (not shown).

FIG. 2C illustrates well 240, another embodiment of well 158. Well 240 comprises wall 242 having an interior surface 244, counter electrodes 246A and 246B, and working electrode 250. Preferable counter electrodes 246A and 246B abut opposite sides of interior surface 244. Preferably, counter electrodes 246A and 246B are electrically isolated from working electrode 250 by a gap (or insulating layer) 248A and 248B interposed between the electrodes. Preferably, each of counter electrodes 246A and 246B is less than 40% of the cross-sectional area defined by inner surface 244, more preferably is less than 20% of such area, and most preferably is less than 10% of such area. Well 240 may, optionally, comprise a reference electrode (not shown).

FIG. 2D illustrates well 260, another embodiment of well 158. Well 260 comprises wall 262 having an interior surface 264, counter electrode 266, and working electrode 270. Preferable counter electrode 266 abuts interior surface 264. Preferably, counter electrode 266 is electrically isolated from working electrode 270 by a gap (or insulating layer) 268 interposed between the electrodes. Preferably, counter electrode 266 is less than 40% of the cross-sectional area defined by inner surface 264, more preferably is less than 20% of such area, even more preferably less than 10% of such area, even more preferably less than 5% of such area and most preferably is less than 1% of such area. Well 260 may, optionally, comprise a reference electrode (not shown).

FIG. 3A illustrates well 300, another embodiment of well 158. Well 300 comprises wall 302 having an interior surface 304, counter electrodes 306A and 306B and working electrode 310. Well 300 may, optionally, comprise a reference electrode (not shown). Preferably counter electrodes 306A and 306B abut interior surface 304. Counter electrodes 306A and 306B are preferably electrically isolated from working electrode 310 by a gap (or insulating layer) 308A and 308B interposed between the electrodes. Working electrode 310 may be, but is not necessarily, in contact with interior surface 304. Working electrode 310 has one or more assay domains 312. Assay domains 312 may contain assay reagents. Preferably assay domains 312 comprise assay binding reagents (so as to form binding domains), reaction substrates (e.g., substrates of enzymatic activities) or calibration reagents. Assay domains 312 may comprise assay reagents in dry, liquid, gel or solid form. The reagents may be immobilized on working electrode 310. Assay domains 312 may comprise binding reagents for one or more analytes in a sample, and each assay domain may contain the same or different assay reagents. Assay domains 312 may be formed by depositing reagents (e.g., by a variety of methods understood for depositing reagents) on specified locations on the surface of working electrode 310 or may be incorporated into working electrode 310 (e.g., as reagents entrained in the material that composes working electrode 310). In another embodiment, assay domains 310 are defined as regions of working electrode 310 with different physical, chemical or compositional properties relative to each other and/or to other regions of the surface of working electrode 310. For example, assay domains may represent especially hydrophilic or hydrophobic regions, regions of high or low surface area, depressions or protrusions, regions surrounded by physical barriers and/or regions of high or low conductivity. They may also comprise regions with one or more materials (e.g., a gel) deposited on the surface of the electrode. FIGS. 3B and 3C illustrate wells 330 and 360 respectively, which show additional embodiments. Well 330 has assay domains 336 which are arranged in a different pattern than assay domains 312. Well 360 has assay domains 366 which illustrate different shapes for assay domains 366. It will be appreciated that the shape, number, pattern of distribution and properties of assay domains as described herein can have many variations, all of which are encompassed by the present invention. Preferably, each well comprises one or more, preferably at least two domains, more preferably at least four, even more preferably at least seven, even more preferably at least 15 and most preferably at least 20 assay domains. Other preferred embodiments include plates wherein each well comprises at least 50, more preferably at least 75, even more preferably at least 100 assay domains per well.

FIGS. 4A through 4E show embodiments of well 158 that illustrate the use of boundaries to define one or more distinct exposed regions and/or assay domains on a working electrode. While each figure shows specific numbers, shapes and arrangements of the exposed regions or assay domains, it is understood that the invention encompasses wells varying in these parameters. FIG. 4A illustrates well 400, another embodiment of well 158, and shows the use of boundaries to form distinct regions on an electrode (in particular, assay domains as described above). Well 400 comprises wall 402 having an interior surface 404, counter electrodes 406A and 406B and working electrode 410. Well 400 may, optionally, comprise a reference electrode (not shown). Preferably counter electrodes 406A and 406B abut interior surface 404. Counter electrodes 406A and 406B are electrically isolated from working electrode 410 by a gap (or insulating layer) 408A and 408B interposed between the electrodes. Working electrode 410 may be, but is not necessarily, in contact with interior surface 404. Working electrode 410 has a plurality of regions 420, each having an inner region 418 defined by boundaries 416 (in an alternate embodiment well 400 has only one region 420). Boundary 416 may be comprised of a material deposited on working electrode 410 or may be comprised of the same material as working electrode 410. Boundary 416 may be a region in which material has been removed from working electrode 410. Boundary 416 may also comprise regions of working electrode 410 with different physical, chemical or compositional properties. For example, boundary 416 may, relative to interior regions 416, be hydrophilic or hydrophobic, have high or low surface area, have a different height and/or have a high or low conductivity. Preferably, boundary 416 is composed of non-conducting or dielectric materials deposited on the surface of working electrode 410. Boundary 416 may be coplanar with working electrode 410 and may extend out from or into the surface of working electrode 410. Inner regions 418 may comprise assay domains as described above. In preferred embodiments, boundary 416 confines materials (e.g. liquids, assay reagents, and the like) on working electrode 410. Boundaries 416 may be used to aid in or direct the deposition of materials to regions 420, for example, by preventing spreading of liquids deposited in inner regions 418 to surrounding regions of working electrode 410 or to counter electrodes 406A and 406B (e.g., so as to allow the controlled immobilization of reagents onto defined assay domains on working electrode 410). In one embodiment, the meniscus of fluids or other materials confined within boundary 416 may act as a lens. Boundary 416 may also serve as an indicia during measurements using the apparatus of the present invention, e.g., to allow the location or identification of an assay domain. FIG. 4B illustrates well 430, another embodiment of well 158. Well 430 comprises wall 431 having an interior surface 432, counter electrodes 434A and 434B and working electrode 444. Well 430 may, optionally, comprise a reference electrode (not shown). The exposed region of working electrode 444 is defined by boundary 440 having an inner perimeter and an outer perimeter (alternatively, a plurality of holes in boundary 440 may define a plurality of exposed regions of working electrode 444). Boundary 440 may abut counter electrodes 434A and 434B and may abut interior surface 432. Alternatively, boundary 440 may extend below counter electrodes 434A and 434B or, alternatively, at least partially above counter electrodes 434A and 434B. In some embodiments, boundary 440 extends beneath counter electrodes 434A and 434B and electrically isolates them from working electrode 444. Boundary 440 may be comprised of a material deposited on working electrode 444 and may or may not be comprised on the same material as working electrode 444. Boundary 440 may be a region in which material has been removed from working electrode 444. Boundary 440 may also comprise a region of working electrode 444 with different physical, chemical or compositional properties. Preferably, boundary 440 is composed of a dielectric material deposited on the surface of working electrode 444. Boundary 440 may be coplanar with working electrode 444 and may extend out from or into the surface of working electrode 444. Working electrode 444 may have assay domains as described above. In preferred embodiments, boundary 440 confines materials (e.g. liquids, assay reagents, and the like) on working electrode 444 (e.g., so as to allow the controlled immobilization of reagents onto working electrode 444). Boundary 440 may be used to aid in or direct the deposition of materials to working electrode 444, for example, by preventing spreading of liquids to surrounding regions of working electrode 444 or to counter electrodes 434A and 434B. Boundary 440 may also serve as indicia during measurements using the apparatus of the present invention. In a preferred embodiment: working electrode 444 is a conducting material, either self supporting or supported on another material; boundary 440 is a non-conducting material deposited on working electrode 444 that covers working electrode 444 except in regions defined by the inner perimeter of boundary 440; counter electrodes 434A and 434B are deposited on boundary 440 and are electrically isolated from working electrode 444 by boundary 440; and wall 431 with interior surface 432 serves to define the outer boundaries of counter electrodes 434A and 434B and define the interior walls of well 430. In another embodiment, boundary 440 does not extend beneath counter electrodes 434A and 434B.

FIG. 4C illustrates well 460, another embodiment of well 158. Well 460 comprises wall 461 having an interior surface 462, counter electrodes 464A and 464B and working electrode 474. Well 460 may, optionally, comprise a reference electrode (not shown). The exposed region of working electrode 474 is defined by boundary 470. Boundary 470 may abut counter electrodes 464A and 464B and may abut interior surface 462. Alternatively, boundary 470 may extend under or over counter electrodes 464A and 464B. In some embodiments, boundary 470 extends beneath counter electrodes 464A and 464B and electrically isolates them from working electrode 474. Boundary 470 may be comprised of a material deposited on working electrode 474 and may or may not be comprised of the same material as working electrode 474. Boundary 470 may be a region in which material has been removed from working electrode 474. Boundary 470 may also comprise a region of working electrode 474 with different physical, chemical or compositional properties. Preferably, boundary 470 is composed of a dielectric material deposited on the surface of working electrode 474. Boundary 470 may be coplanar with working electrode 474 and may extend out from or into the surface of working electrode 474. Working electrode 474 may have assay domains as described above. In preferred embodiments, boundary 470 confines materials (e.g. liquids, assay reagents, and the like) on working electrode 474. Boundary 470 may also be used to aid in or direct the deposition of materials to working electrode 474, for example, by preventing spreading of liquids to surrounding regions of working electrode 470 or to counter electrodes 464A and 464B. Boundary 470 may also serve as indicia during measurements using the apparatus of the present invention. In a preferred embodiment: working electrode 474 is a conducting material, either self supporting or supported on another material; boundary 470 is a non-conducting material deposited on working electrode 474 that covers working electrode 474; counter electrodes 464A and 464B are deposited on boundary 470 and are electrically isolated from working electrode 474 by boundary 470; and wall 461 with interior surface 462 serves to define the outer boundaries of counter electrodes 464A and 464B and define the interior walls of well 460. In another embodiment, boundary 470 is deposited on working electrode 474 so that it does not extend over or under counter electrodes 464A and 464B. Well 460 has working electrode 474 with assay domains 476, as described above for wells 300, 330 and 360. In another embodiment, assay domains 476 on working electrode 474 are defined by additional boundaries as described above for well 400.

FIG. 4D illustrates well 480, another embodiment of well 158. Well 480 comprises wall 482 with interior surface 484, counter electrodes 488A and 488B, boundary 492 and working electrode 494. Well 480 may, optionally, comprise a reference electrode (not shown). Regions 499A and 499B of working electrode 494 are defined by boundaries 498A and 498B. Boundaries 498A and 498B may be comprised of a material deposited on working electrode 494 or may be comprised on the same material as working electrode 494. Boundaries 498A and 498B may be regions in which material has been removed from working electrode 494. Boundaries 498A and 498B may also comprise regions of working electrode 494 with different physical, chemical or compositional properties. For example, boundaries 498A and 498B may be hydrophilic or hydrophobic, have high or low surface area, and/or an area of high or low conductivity. Preferably, boundaries 498A and 498B are composed of non-conducting or dielectric materials deposited on the surface of working electrode 494 and may provide a physical boundary. Boundaries 498A and 498B may be coplanar with working electrode 494 and may extend out from or into the surface of working electrode 494. Exposed working electrode regions 499A and 499B may comprise assay domains as described above. In preferred embodiments, boundaries 498A and 498B confine materials (e.g. liquids, assay reagents, and the like) on working electrode 494. Boundaries 498A and 498B may also be used to aid in or direct the deposition of materials to interior regions 499A and 499B, for example, by preventing spreading of liquids deposited to surrounding regions of working electrode 494 or to counter electrodes 488A and 488B. Boundaries 498A and 498B may also serve as an indicia during measurements using the apparatus of the present invention.

FIG. 4E illustrates well 4900, another embodiment of well 158. Well 4900 comprises wall 4902 with interior surface 4903, counter electrodes 4904A and 4904B, gaps 4906A and 4906B (the gaps preferably being dielectric surfaces separating working electrode 4910 from counter electrodes 4904A and 4904B) and barrier 4908 with a plurality of holes 4912 that expose working electrode 4910. Well 4900 may, optionally, comprise a reference electrode (not shown). In a preferred embodiment, boundary 4908 may be a dielectric material that provides a boundary that can confine small volumes of fluid to the exposed regions of the electrode (e.g., so as to allow the controlled immobilization of reagents onto defined assay domains on working electrode 4910). Working electrode 4910 may have assay reagents immobilized on its surface in regions where plurality of holes 4912 in boundary 4908 expose working electrode 4910. Boundary 4908 may also be used to aid in or direct the deposition of materials to working electrode 4910 where holes 4912 expose working electrode 4910.

5.1.2 Electrodes

One aspect of the invention relates to improved electrode compositions and surfaces and assay modules comprising these electrode compositions and surfaces. Electrodes in the present invention are preferably comprised of a conductive material. The electrode may comprise a metal such as gold, silver, platinum, nickel, steel, iridium, copper, aluminum, a conductive alloy, or the like. They may also comprise oxide coated metals (e.g. aluminum oxide coated aluminum). According to one embodiment, the working and counter electrodes are not the same material (e.g. metal counter electrode and carbon working electrode). Preferably, electrodes are comprised of carbon-based materials such as carbon, carbon black, graphitic carbon, carbon nanotubes, carbon fibrils, graphite, carbon fibers and mixtures thereof. Preferably, the electrodes comprise elemental carbon (e.g., graphitic, carbon black, carbon nanotubes, etc.). Advantageously, they may be comprised of conducting carbon-polymer composites, conducting particles dispersed in a matrix (e.g. carbon inks, carbon pastes, metal inks), and/or conducting polymers. One preferred embodiment of the invention is an assay module, preferably a multi-well plate, having electrodes (e.g., working and/or counter electrodes) that comprise carbon, preferably carbon layers, more preferably screen-printed layers of carbon inks. Some useful carbon inks include materials produced by Acheson Colloids Co. (e.g., Acheson 440B, 423ss, PF407A, PF407C, PM-003A, 30D071, 435A, Electrodag 505SS, and Aquadag™), E. I. Du Pont de Nemours and Co. (e.g., Dupont 7105, 7101, 7102, 7103, 7144, 7082, 7861D, and CB050), Conductive Compounds Inc (e.g., C-100), and Ercon Inc. (e.g., G-451).

Electrodes may also be comprised of semiconducting materials (e.g. silicon, germanium) or semi-conducting films such as indium tin oxide (ITO), antimony tin oxide (ATO) and the like. Electrodes may also be comprised of mixtures of materials containing conducting composites, inks, pastes, polymer blends, metal/non-metal composites and the like. Such mixtures may include conductive or semi-conductive materials mixed with non-conductive materials. Preferably, electrode materials are substantially free of silicone-based materials. Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication (e.g., chemical etching, photopatterning of a resist material, microlithographic techniques, etc.).

The terms "carbon fibrils", "carbon nanotubes", single wall nanotubes (SWNT), multiwall nanotubes (MWNT), "graphitic nanotubes", "graphitic fibrils", "carbon tubules", "fibrils" and "buckeytubes", all of which terms may be used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). The terms "fibrils" and "carbon fibrils" are used throughout this application to include this broad class of carbon-based materials.

Individual carbon fibrils as disclosed in U.S. Pat. Nos. 4,663,230; 5,165,909; and 5,171,560 are particularly advantageous. They may have diameters that range from about 3.5 nm to 70 nm, and length greater than $10^2$ times the diameter, an outer region of multiple, essentially continuous, layers of ordered carbon atoms and a distinct inner core region. Simply for illustrative purposes, a typical diameter for a carbon fibril may be approximately between about 7 and 25 nm, and a typical range of lengths may be 1000 nm to 10,000 nm. Carbon fibrils may also have a single layer of carbon atoms and diameters in the range of 1 nm-2 nm.

Carbon materials can be made to form aggregates. For example, as disclosed in U.S. Pat. No. 5,110,693, and references cited therein, two or more individual carbon fibrils may form microscopic aggregates of entangled fibrils. These aggregates can have dimensions ranging from 5 nm to several cm. Simply for illustrative purposes, one type of microscopic aggregate ("cotton candy or CC") resembles a spindle or rod of entangled fibers with a diameter that may range from 5 nm to 20,000 nm with a length that may range from 100 nm to 1 mm. Again for illustrative purposes, another type of microscopic aggregate of fibrils ("birds nest, or BN") can be roughly spherical with a diameter that may range from 0.1 um to 1000 um. Larger aggregates of each type (CC and/or BN) or mixtures of each can be formed (vide infra).

Fibrils that can be used in the present invention include but are not limited to individual fibrils, aggregates of one or more fibrils, suspensions of one or more fibrils, dispersions of fibrils, mixtures of fibrils with other materials (e.g., oils, paraffins, waxes, polymers, gels, plastics, adhesives, epoxies, teflon, metals, organic liquids, organic solids, inorganic solids, acids, bases, ceramics, glasses, rubbers, elastomers, biological molecules and media, etc.) as well as combinations thereof. One preferred embodiment of the invention relates to a multi-well plate comprising a substrate comprising a carbon nanotube-containing composite, wherein the surface of the substrate is etched to expose the carbon nanotubes, thereby forming one or more working electrodes.

Electrodes may be self supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support may be rigid or flexible, flat or deformed, transparent, translucent, opaque or reflective. Preferably, the support comprises a flat sheet of plastic such as acetate, polycarbonate, polypropylene, polyester (e.g., Mylar), polyimide (e.g., Kapton), or polystyrene. According to one embodiment, the material comprises polystyrene blended with High Impact Polystyrene (HIPS) to reduce the brittleness of the material. Preferably, between 4 and 16 wt % HIPS is blended with the polystyrene, more preferably between about 8 and 12 wt %. Electrode materials may be applied to a support by a variety of coating and deposition processes known in the art such as painting, spray-coating, screen-printing, ink-jet printing, laser printing, spin-coating, evaporative coating, chemical vapor deposition, laminating, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Yet another embodiment involves the combination of a counter-electrode comprising a chemically etched metal (e.g., steel) or die-cut aluminized film and a screen-printed working electrode.

Electrodes may be supported by another conducting material. Advantageously, conducting carbon electrodes may be in contact with conducting metal pastes. Preferably, electrodes are (or are capable of being) derivatized or modified, for example, to immobilize assay reagents such as binding reagents on electrodes. One may attach, e.g., antibodies, fragments of antibodies, proteins, enzymes, enzyme substrates, inhibitors, cofactors, antigens, haptens, lipoproteins, liposaccharides, bacteria, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chemical functional groups, chelating agents, linkers etc. Reagents may be immobilized on the electrodes by a variety of methods including passive adsorption, specific binding and/or through the formation of covalent bonds to functional groups present on the surface of the electrode.

Electrodes may be modified by chemical or mechanical treatment to improve the immobilization of reagents. The surface may be treated to introduce functional groups for immobilization of reagents or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate reagent immobilization, change the wetting properties of the electrode, increase surface area, increase the binding capacity for the immobilization of reagents or the binding of analytes, and/or alter the kinetics of electrochemical reactions at the electrode. In some applications, however, it may be preferable to use untreated electrodes. For example, we have found that it is advantageous to etch carbon ink electrodes prior to adsorbing binding reagents (e.g., avidin, streptavidin or antibodies) when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays may also be carried out on unetched carbon ink electrodes despite the presence of polymeric binders in the ink. In fact, in some applications requiring high sensitivity or low-non specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100 are used to facilitate spreading of capture reagents onto unetched screen-printed electrodes (i.e., so as to allow the immobilization of the capture reagents), the solutions containing the capture reagents are allowed to dry onto the electrode surface. It has been found that this drying step greatly improves the efficiency and reproducibility of the immobilization process.

Electrodes can be derivatized with chemical functional groups that can be used to attach other materials to them. Materials may be attached covalently to these functional groups, or they may be adsorbed non-covalently to derivatized or underivatized electrodes.

Electrodes may be prepared with chemical functional groups attached covalently to their surface. These chemical functional groups include but are not limited to COOH, OH, $NH_2$, activated carboxyls (e.g., N-hydroxy succinimide (NHS)-esters), poly-(ethylene glycols), thiols, alkyl ($(CH_2)_n$) groups, and/or combinations thereof). Certain chemical functional groups (e.g., COOH, OH, $NH_2$, SH, activated carboxyls) may be used to couple reagents to electrodes. For further reference to useful immobilization and bioconjugation techniques see G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

A reagent that can be used in an ECL assay can be attached to electrodes by covalent bonds (e.g., reaction with an NHS-ester), by reaction with an appropriate linker (vide supra), by non-specific binding, and/or by a combination thereof.

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $Ru^{III}(bpy)_3$ derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic, Tetronic, and Span).

Materials used in electrodes may be treated with surfactants to reduce non-specific binding. For example, electrodes may be treated with surfactants and/or detergents that are well known to one of ordinary skill in the art (for example, the Tween series, Triton, Span, Brij). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA) or immunoglobulin G (IgG). One may adsorb or covalently attach an assay reagent on an electrode and subsequently treat the electrode with a blocking agent so as to block remaining unoccupied sites on the surface.

In preferred embodiments, it may be desirable to immobilize (by either covalent or non-covalent means) biomolecules or other media to carbon-containing materials, e.g., carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components (e.g., organelles or membrane fragments), cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers etc. A plurality of species may be co-adsorbed to form a mixed layer on the surface of an electrode.

Electrodes used in the multi-well assay plates of the invention are typically non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

Electrodes used in assay modules of the invention are advantageously able to induce luminescence from luminescent species. It is preferable that electrodes are comprised of materials that are compatible with biological media, impervious to the reagents typically encountered in luminescence measurements, and robust.

A working electrode may have one or more of the properties described above generally for electrodes. Preferably materials for working electrodes are materials able to induce electrochemiluminescence from Ruthenium-tris-bipyridine in the presence of tertiary alkyl amines (such as tripropyl amine). Examples of such preferred materials include platinum, gold, ITO, carbon, carbon-polymer composites, and conductive polymers. In one embodiment, the working electrode is made of a continuous conducting sheet or a film of one or more conducting materials. This sheet or film may be extruded, pressed or molded, and can be self supporting. In a preferred embodiment, the working electrode is made of a carbon-polymer composite. The composite may be comprised of conducting carbon particles (e.g., carbon fibrils, carbon black, graphitic carbon) dispersed in a matrix (e.g., a polymer such as EVA, polystyrene, polyethylene, ABS). The working electrode may additionally comprise other conducting materials, for example, a conducting metal ink may be printed on the conducting composite.

In another embodiment, the working electrode is made of a conducting material deposited and/or patterned on a substrate (e.g., by printing, painting, coating, spin-coating, evaporation, chemical vapor deposition, electrolytic deposition, electroless deposition, photolithography and other electronics microfabrication techniques, etc.). In a preferred embodiment, the working electrode comprises a conductive carbon ink printed on a polymeric support (e.g., by ink-jet printing, laser printing, or, most preferably, by screen-printing). The working electrode may be a continuous film, it may be one or more discrete regions (e.g., patterns), or it may be a plurality of connected regions. The working electrode may additionally comprise other conducting materials, for example, a carbon ink overlayer may be deposited over a conducting metal ink (e.g., a silver ink) underlayer, the underlayer being used to increase the conductivity of the film. It may be beneficial to print or deposit the overlayer in multiple layers so as to ensure that the underlayer is completely covered so that the underlayer doesn't interfere with subsequent processing steps or with ECL measurements (e.g., a preferred electrode material comprises two layers, preferably three layers, of carbon ink over a layer of silver ink, the layers most preferably being deposited by screen printing). Alternatively, one or two layers of carbon may be used. For electrodes comprising one or more printed carbon ink layers over a printed silver ink layer, the silver layer has a thickness of, preferably, 2.5 microns to 25 microns, more preferably, 4-7 microns (or, alternatively, a thickness that produces a resistance of, preferably less than 2 ohms/square or, more preferably, 0.05-0.2 ohms/square) and the combined carbon layers have a thickness of, preferably, 2.5-75 microns or, more preferably, 6-25 microns (or, alternatively, a thickness that produces a resistance of, preferably less than 100 ohms/square or, more preferably, less than 30 ohms/square or, most preferably 20-30 ohms/square).

A counter electrode may have one or more of the properties described above generally for electrodes and for working electrodes. In one embodiment, the counter electrode is made of a continuous conducting sheet or a film of one or more conducting materials. This sheet or film may be extruded, pressed or molded, and can be self supporting. In a preferred embodiment, the counter electrode is made of a carbon-polymer composite. The composite may be comprised of conducting carbon particles (e.g., carbon fibrils, carbon black, graphitic carbon) dispersed in a matrix (e.g., a polymer such as EVA, polystyrene, polyethylene, ABS). The counter electrode may additionally comprise other conducting materials, for example, a conducting metal ink may be printed on the conducting composite.

In another embodiment, the counter electrode comprises a metal coating, film or foil. One preferred embodiment of the invention is a multi-well plate having wells containing (preferably in two or more wells of the plate) working electrodes that comprise carbon (preferably carbon ink or carbon particles, e.g., carbon nanotubes, dispersed in a matrix) and counter electrodes comprising a metal coating, film or sheet or foil (preferably, comprising aluminum, stainless steel, nickel or silver). A foil counterelectrode may be self-supporting or may be supported on another material. It may also additionally comprise an adhesive material, a non-conducting layer and/or a backing material. The foil may have holes, advantageously in a pattern that corresponds to the pattern of wells in industry standard multi-well assay plates. Holes may be punched, drilled, burned, laser drilled, machined, etched or otherwise introduced by removing material from a continuous film, or, the film many be generated (e.g., molded) to incorporate holes. In a preferred embodiment, the counter electrode is formed from a plastic sheet or support that is coated on one side with an aluminum film or foil and coated on the opposite side with an adhesive layer, preferably, having a removable backing strip.

In another embodiment, the counter electrode is made of a conducting material deposited and/or patterned on a substrate (as described above for the working electrode). In a preferred embodiment, the counter electrode comprises a conducting carbon ink printed on a polymeric support. The counter electrode may be a continuous film, it may be one or more discrete regions (e.g., patterns), or it may be a plurality of connected regions. The counter electrode may additionally comprise other conducting materials, for example, a conducting metal ink (e.g., a silver ink) may be printed on the substrate and may be in contact with the conducting ink of the counter electrode.

An unexpected feature of the instrumentation of the invention is its ability to conduct precise, accurate and reproducible electrode induced luminescent assays, particularly electrochemiluminescent assays, without the use of an independent reference electrode and potentiostat (i.e., without using a three electrode configuration: working, counter and reference). In a two electrode system (working and counter electrode) any potential applied across the working and counter electrodes is distributed, at least in part, over the two electrode/solution interfaces. The undefined nature of the potential at the surface of the counter electrode leads directly to uncertainty in the potential at the working electrode. This problem may be solved by using a counter electrode with a stable interfacial potential that is defined by a redox couple in solution or, preferably, by a redox couple confined to the surface of the electrode (such a counter electrode is sometimes termed a "counter/reference electrode"). Some examples of useful "counter/reference electrode" materials include metal/metal halide couples such as silver/silver chloride; metal/metal oxide couples such as silver/silver oxide, nickel/nickel oxide and zinc/zinc oxide; and metal oxides with allowing for multiple metal oxidation states such as manganese oxide. For optimal performance, these "counter/reference electrodes" should have a sufficiently high concentration of accessible redox species so as to prevent polarization of the electrode during the course of an ECL measurement.

Surprisingly, we have observed excellent performance and precision (e.g., coefficients of variation of <10%, more preferably <5%, even more preferably 2% and most preferably <1%) in ECL measurements using two electrode configurations and counter electrodes that are not typically considered useful "counter/reference electrodes", for example: aluminum (presumably with a native oxide layer) and various forms of carbon (including composites containing carbon black, graphite and/or carbon fibrils). Without being bound by theory, we believe this unanticipated performance has been achieved by i) maintaining a consistent and reproducible process for the manufacture of ECL multi-well assay plates; ii) maintaining a relatively consistent chemical environment during induction of ECL and/or iii) selection of appropriate voltage or current waveforms. In general, under the high current conditions typically used to generate ECL, the interfacial potential at the counter electrode is determined by the reduction potential for water at that electrode; as long as the electrode surface and chemical environment remain relatively consistent the interfacial potential can be highly reproducible. The voltage/current waveforms used to induce ECL, preferably, involve the i) application of voltage or current sufficient to induce ECL and ii) the maintenance of ECL until the ECL intensity decays (presumably due to consumption of ECL coreactant or destruction of assay components on the electrode surface). Under these conditions, a plot of ECL vs. time has the form of a peak. Such waveforms are tolerant of some inconsistency in working electrode and counter electrode potential, solution resistance and the like; these variations tend to shift the start and end of the ECL peak but have a much smaller effect on the total integrated light signal under the peak. An especially preferred voltage/current waveform is a voltage ramp beginning at a voltage less than that required to induce ECL and ending at a potential high enough to allow decay of the ECL signal to under 10% of the peak intensity.

Surprisingly, we have also found that we can attain excellent performance and precision (e.g., coefficients of variation of <10%, more preferably <5%, even more preferably 2% and most preferably <1%) in ECL measurements using two electrode systems despite using counter electrodes having exposed geometric surface areas that are equal or less than the exposed geometric surface area of the working electrode. Such excellent performance is attained even when using the unconventional counter electrode materials described above. By contrast, in standard electrochemical assays it is considered highly advantageous to have larger counter electrodes than working electrodes to ensure that the current is not limited by chemical or mass transport processes at the counter electrode. Reducing the surface area of the counter electrode gives certain advantages in the design of multi-well assay plates for ECL assays; by reducing the counter electrode area it is possible to increase the area of the active working electrode and thereby the kinetics of reactions occurring at the surface of the electrode, the binding capacity of assays using binding reagents immobilized on the working electrode and/ or the number of assay domains that may be patterned on a given working electrode. In preferred embodiments of the multi-well plates of the invention, the ratio of the geometric surface areas of the working and counter electrodes is greater than 1, greater than 2, greater than 5, greater than 10, greater than 50 or, most preferably, greater than 100.

While in many applications it is advantageous to have an electrode surface area that occupies a large fraction of an assay region (for reasons described above), in other applications it may be advantageous to have small exposed working electrode surfaces (preferably less than 4 $mm^2$, more preferably less than 1 $mm^2$, even more preferably less than 0.1 $mm^2$ and most preferably less than 0.01 $mm^2$). For example, small working electrode surfaces may in some cases lead to higher sensitivity and lower non-specific signals. For example, in a binding assay conducted using a binding reagent immobilized on the working electrode, the signal from a labeled binding partner of the binding reagent should be roughly independent of the area of the electrode (assuming the binding capacity of the electrode is sufficient to bind all the labeled binding partner and the binding reaction is allowed to proceed to completion). Non-specific signals, e.g., due to non-specific binding, should be roughly linearly dependent on electrode area. Under such conditions, reducing electrode area may lead to an improvement in the ratio of specific to non-specific signal. According to one embodiment of multi-well assay plates of the invention, the well bottoms comprise working electrodes and the ratio of working electrode surface to the surface area of the bottom of the well (or, alternatively, to dielectric surfaces on the bottom of the well) is less than 1 to 5, preferably 1 to 10, more preferably 1 to 30.

Despite the excellent performance we have observed with two electrode systems, some specialized applications may require multi-well assay plates having independent reference electrodes so as to allow control of the working electrode potentials with a potentiostat. Reference electrodes may be made using the materials and methods described above for working and counter electrodes. Preferably the reference electrode has a stable interfacial potential that is defined by a redox couple confined to the surface of the electrode; examples of materials having this property include metal/metal halide couples such as silver/silver chloride; metal/metal oxide couples such as silver/silver oxide, nickel/nickel oxide and zinc/zinc oxide; and metal oxides with allowing for multiple metal oxidation states such as manganese oxide. Many reference electrode materials have surface potentials that are dependent on their chemical environment (e.g., on the pH or concentration of halide ions). If necessary, reference electrodes may be protected from variations in the chemical environment by coating the electrode with a film (e.g., a hydrophilic polymeric film) that provides for a well defined chemical environment (e.g., controlled concentrations of hydrogen ions or halide ions) directly on the surface of the electrode but also allows for the passage of ions in and out of the film. It may be advantageous to cover a substantial portion of these polymer films with an ion impermeable film so as to balance the requirement for ion flow in and out of the polymer film with the requirement that the chemical environment in the film remain substantially unaffected by contact with a sample or reagent solution (see, e.g., U.S. Pat. Nos. 5,384,031 and 4,933,048).

The electrodes and power sources of the invention may be directly connected or may be connected via a conductive lead or pathway, preferably formed of a conductive matrix such as a metal, a conductive carbon-containing material or composite, a conductive polymer or an electrolytic solution. One embodiment of the invention relates to assay modules comprising electrodes connected to electrical power sources via electrolytic solutions (e.g., so called "floating electrodes"), such electrodes being, preferably, adapted for inducing electrode induced luminescence (most preferably, electrochemiluminescence). By way of example, in one embodiment of the well of a multi-well assay plate pictured in FIG. 4E, counter electrodes 4904A and 4904B may be adapted to be independently connected to the two poles of a source of electrical energy. In the use of this embodiment, the application of a potential across electrodes 4904A and 4904B is used to induce an electrical potential in electrode 4910 and, preferably, to induce luminescence (most preferably, electrochemiluminescence) from luminescent labels at electrode 4910.

5.1.3 Dielectrics

The assay modules of the present invention may use dielectric inks, films or other electrically insulating materials (hereinafter referred to as dielectrics). Dielectrics in the present invention may be used to prevent electrical connectivity between electrodes, to define patterned regions, to adhere materials together (i.e., as adhesives), to support materials, to define assay domains, as masks, as indicia and/or to contain assay reagents and other fluids. Dielectrics are non-conducting and advantageously non-porous (i.e., do not permit transmission of materials) and resistant to dissolving or degrading in the presence of media encountered in an electrode induced luminescence measurement. The dielectrics in the present invention may be liquids, gels, solids or materials dispersed in a matrix. They may be deposited in uncured form and cured to become solid. They may be inks, solid films, tapes or sheets. Materials used for dielectrics include polymers, photoresists, solder masks, plastics, adhesives, gels, glasses, non-conducting inks, non-conducting pastes, ceramics, papers, elastomers, silicones, thermoplastics. Preferably, dielectric materials of the invention are substantially free of silicones. Examples of non-conducting inks include UV curable dielectrics such as materials produced by Acheson Colloids Co. (e.g., Acheson 451SS, 452SS, PF-021, PD-039, ML25251, ML25240, ML25265, and Electrodag 38DJB16 clear), Nazdar Inc. (SPL 4000 series of half tone inks) and E. I. du Pont de Nemours and Co. (e.g., Dupont: 5018, 3571, and 5017).

Dielectrics of the present invention may be applied by a variety of means, for example, printing, spraying, laminating, or may be affixed with adhesives, glues, solvents or by use of mechanical fasteners. Patterns and/or holes in dielectric layers may be formed by molding processes (i.e., during fabrication of the layer), by selective etching and/or by a cutting process such as die cutting or laser drilling. Dielectrics may be deposited and/or etched in patterns through the use of established photolithographic techniques (e.g., techniques used in the semiconductor electronics industry) and/or by patterned deposition using an evaporative or CVD process (e.g., by deposition through a mask). In a preferred embodiment, a dielectric ink is deposited on a substrate by printing (e.g., ink jet printing, laser printing or, more preferably, screen printing) and, optionally, UV cured. Preferably, the screen printed dielectric is UV curable allowing for improved edge definition than solvent based dielectrics. In another preferred embodiment, a non-conducting polymeric film is affixed to a support using an adhesive.

When using a dielectric ink printed on or adjacent an electrode to confine fluids to regions of the electrode surface, the dielectric film preferably has a thickness of 0.5-100 micrometers, or more preferably 2-30 micrometers, or most preferably 8-12 micrometers and also, preferably, has a sharply defined edge with steep walls.

5.1.4 Plate Tops

The invention includes plate tops and assembled plates comprising a plate top and, preferably, a plate bottom defining well bottoms having one or more electrode surfaces, most preferably having one or more working electrode surfaces and, optionally, one or more counter electrode surfaces. Preferably, the plate top is a structure with holes, wherein the structure may be combined with a plate bottom to form a multi-well plate, the walls of the wells of the plate being at least partially defined by the inside surfaces of the holes through the plate top. The holes through the plate top may be a variety of shapes (e.g., round, oval, square, rectangular, triangular, star shaped, etc.). The holes may be of various sizes. They can also have irregular dimensions within a hole (e.g., the hole may become more narrow or more wide at different depths). For example, the hole may be shaped like a cone, becoming more narrow at the bottom so as to optimize the collection of light emitted from the well bottom. The plate top may also have structures or indicia thereon that aid in identifying the plate top, distinguishing the plate top from other configurations of plate top, or in aligning and handling the plate top. Advantageously, the dimensions and structure of the plate top are preferably in accordance with, or at least compatible with, industry standards for the footprints and shapes of assay plates.

The plate top may be made from conducting or non-conducting materials. Preferably, the majority of the plate top is a unitary molded structure made from rigid thermoplastic material such as polyethylene, acetate, polycarbonate, polypropylene, polyester (e.g., Mylar), polyimide (e.g., Kapton), or polystyrene. Preferably, the support comprises a flat sheet of plastic. According to one embodiment, the material comprises polystyrene blended with High Impact Polystyrene (HIPS) to reduce the brittleness of the material. Preferably, between 4 and 16 wt % HIPS is blended with the polystyrene, more preferably between about 8 and 12 wt %. Optimally, this unitary structure is formed of (or, alternatively, coated with) inexpensive material that is generally impervious to reactants, can withstand modest levels of heat and light and is, preferably, resistant to the adsorption of biomolecules. Preferably, the plate top is substantially free of silicones. Plate tops may be clear or translucent. Different colored materials may be used to improve the results of certain ECL measurement processes.

It is preferable that the plate top comprise a material that does not transmit light so as to prevent cross-talk between wells. A highly reflective metallic coating or constituent material may provide an especially reflective interior surface for each of the wells so as to increase the efficiency with which light can be transmitted to photodetectors. An opaque white plastic material such as a plastic filled with light scattering particles (e.g., lead oxide, alumina, silica or, preferably, titanium dioxide particles) may provide an interior surface for the wells that is highly light scattering thereby improving light gathering efficiency. In one embodiment, preferred plate tops comprise plastics (e.g., well walls) comprising such light scattering particles at a concentration of from 4-20 wt %, preferably 6-20%, more preferably 6-15%, even more preferably 6-12%, and most preferred approximately 9% or 10%. In an alternate preferred embodiment, the plate top comprises an opaque, preferably non-reflective, black material to prevent the reflection or scattering of ECL-generated light from different locations within a well and to prevent reflective interference during ECL test measurements. In general, when imaging light emitted from a well (e.g., when using a camera to produce an image of light emitted from the well) it is advantageous that the interior surface of the well (e.g., as defined by a plate top) comprise an absorptive (e.g., black) preferably non-scattering material since the detection of scattered light will reduce the fidelity of the image. In general, when detecting light in a non-imaging mode (e.g., when a single light detector is used to detect all the light emitted from a well) it is advantageous that the interior surface of the well comprise a reflective or highly scattering material so as to prevent the loss of light due to adsorption of light at the well walls and to maximize the collection of light at the detector.

Yet another aspect of the invention relates to improved materials for use in the assay modules (e.g., plate tops, cassette parts, etc.) of the invention, particularly assay modules used in luminescence assays. More specifically, the inventors have discovered improved materials for use in forming assay module components such as plate tops, which result in less background luminescence.

As described above, $TiO_2$ can be added to plate tops to provide a highly light scattering surface that increases the efficiency of light collection from the wells and prevents cross-talk between wells. One drawback of the use of $TiO_2$ plates is a relatively long-lived luminescence (on the order of minutes) when the plate is exposed to UV or fluorescent light prior to insertion into the instrument. This light intensity decays exponentially and thus, produces an undesirable time dependent background intensity signal. It is believed that the titanium dioxide is the source of this light. One explanation (although speculative) for the cause of this light emission is that upon excitation with band gap light, a photogenerated electron hole is produced in the $TiO_2$. The electron hole reacts with water to produce a hydroxyl radical. When the hydroxyl radical reacts with the conduction band electron of the $TiO_2$, light is generated.

To overcome this problem, a "wait before the read" time is preferably used during the plate read cycle and/or optical filters are used to reduce the effect. Upon further investigation, however, applicants discovered that the proper choice of $TiO_2$ (more specifically $TiO_2$ made by certain methods) greatly reduced the background luminescence and eliminated the need for optical filters in the instrument. More specifically, the use of $TiO_2$ having a luminescence reducing coating allows the wait time prior to measurement to be reduced to less than 2 minutes, preferably less than 1 minute, more preferably less than 50 seconds, even more preferably less than 40 seconds, even more preferably less than 30 seconds, and most preferably less than about 10 seconds without the use of optical filters. It should be noted that the wait time depends on the algorithm for data processing as well as the signal levels characteristic of a given assay. More sophisticated algorithms may be employed to further reduce the waiting time caused by the decaying luminescence of the $TiO_2$ (e.g., second order or exponential fitting of the background signals).

Titanium dioxide exists in three different crystal forms: Rutile (most common); Anatase (available, but less common); and Brookite (rare). In addition, most commercially available $TiO_2$ undergoes surface treatment during manufacture. There are two types of surface treatment: organic and inorganic. The $TiO_2$ may undergo either or both processes during manufacturing. The organic treatment is used to lower the surface energy of the $TiO_2$ particle so it will disperse well in polymers. Without an organic treatment, the hydrophilic $TiO_2$ will not disperse, but remains aggregated. Common organic surface treatments for $TiO_2$ are treatments with polyol (low molecular weight polyethylene glycol), silicone and polydimethyl siloxane. The inorganic surface treatment provides durability to the white pigment by preventing free radical breakdown by UV light. Common inorganic treatments include phosphate, alumina, zirconia and silica. Alumina and zirconia are the preferred organic treatments for protection from free radical damage.

Applicants have discovered that the use of inorganic surface treated $TiO_2$ as an additive to an assay module component such as a plate top results in reduced background luminescence. Thus, one embodiment of the invention relates to an assay module component comprising $TiO_2$ which had been subjected to inorganic treatment. Preferably, the inorganic treatment is selected from phosphate, alumina, zirconia and silica; even more preferably alumina and/or zirconia; and most preferably alumina. Thus, according to one preferred embodiment, the $TiO_2$ comprises an inorganic coating, preferably an alumina coating. Unintentional luminescence may also be reduced by using filters, shorter waveforms, and/or more sophisticated data processing algorithms. For example, optical filters may be chosen that transmit the wavelength of the desired ECL signal (preferably, from 500-800 nm, more preferably, from 550-650 nm) and absorb luminescence from the plate top (preferably, light having a wavelength less than 500 nm). Alternatively, ECL is induced using voltage waveforms that produce short but intense bursts of ECL (e.g., ramp waveforms having slopes of >1 V/s) so as to minimize the integrated background luminescence during the ECL measurement. Alternatively, a data processing algorithm is used to subtract background luminescence. For example, the background luminescence is measured prior to an ECL measurement. ECL is measured and the background luminescence is subtracted. If the decay characteristics of the background luminescence is known or measured, the value of background luminescence used in the correction can be adjusted for the time between the measurement of background luminescence and the measurement of ECL (e.g., by modeling the background luminescence as an exponential decay with a time constant or by using a linear approximation of an exponential decay).

FIG. 2E illustrates a plate top 280 according to a preferred embodiment of the present invention. Plate top 280 comprises a plate top body 281, a top surface 282, well wall 285, and well inner surface 286. Plate top 280 has one or more holes 284 defined by top surface 282 and inner surface 286. Plate top 280 is preferably has light absorptive/reflecting/scattering properties as described above. Holes 284 are, preferably, configured as described above. Plate top 280 also has one or more corner recesses 287 that provide identifying physical indicia for plate top 280. In particular, corner recesses 287 facilitate the alignment and handling of plate top 280 and assist in distinguishing plate top 280 from other plates having different configurations of recessed areas along their respective peripheries. Advantageously, the dimensions and structure of plate top body 281 are preferably in accordance with, or at least compatible with, industry standards for the footprints and shapes of similar types of assay plates. Plate top 280, preferably, also comprises indicia 283 that may be used to identify a particular hole 284.

FIG. 2F shows another embodiment of plate top 280. Plate top 290 illustrates a plate top with a plurality of holes 291. In a preferred embodiment, holes 291 in plate top 290 have the cross sectional shape of a square. In an alternate embodiment, holes 291 have the cross sectional shape of a circle, and decrease in diameter as they move away from the top of the plate. In FIG. 2F, plate top 280 has three hundred eighty four (384) holes 291, arranged in a 2 dimensional array of rows and columns. FIG. 2G shows another embodiment of plate top 280. Plate top 295 illustrates a plate top with an array of holes 297. In a preferred embodiment, the holes 297 in plate top 295 have the cross sectional shape of a circle. In an alternate embodiment, holes 297 have the cross sectional shape of a square. In FIG. 2G, plate top 295 has 1536 holes.

The invention also includes assay module tops and assembled assay modules comprising an assay module top and a plate bottom or assay module substrate. The assay module top may be a plate top (as described above). The assay module top may have, e.g., holes, channels, and/or wells that when mated to a plate bottom or assay module substrate define wells and/or chambers, such wells and/or chambers preferably comprising one or more electrodes (and/or assay domains) provided by the plate bottom or assay module substrate. The assay module top may have additional channels, tubes or other microfluidics so as to allow the flow of samples into, out of and/or between wells, flow cells and chambers of an assay module.

5.1.5 Electrode/Contact Configurations

Another aspect of the invention relates to novel electrode and/or contact configurations. According to the invention, the shape, composition, placement/location, configuration, pattern, thickness, surface properties and many other characteristics of the electrodes and contacts are optimized to result in improved methods and systems.

Optimizing the configuration of electrodes allows for: (i) higher density assay arrays, (ii) the reduction of the variation in voltage across a plurality of wells and/or assay domains; (iii) the division of an assay module into independently addressable portions (e.g., allowing for independently addressable sectors of jointly addressable wells on a multi-well assay plate); and/or (iv) ease of manufacture.

Optimizing the configuration of contacts (e.g., electrical contacts on the bottom of an assay module substrate and/or assay plate bottom) allows for: (i) reducing the number of necessary electrical connectors; (ii) reducing the variation in voltage across a plurality of wells and/or assay domains; (iii) controlling any flexing or bending of the well bottom during contacting; (iv) the division of an assay module into independently addressable portions (e.g., allowing for independently addressable sectors of jointly addressable wells on a multi-well assay plate); and/or (iv) ease of manufacture.

One embodiment of the invention relates to a multi-well plate comprising a plate top having a plurality of rows of openings and a plate bottom having first electrode strips (preferably working electrode strips) and second electrode strips (preferably counter electrode strips) patterned thereon, wherein the plate top is affixed on the substrate thereby forming a plurality of rows of wells from the openings, wherein the bottom of each well comprises an exposed portion of at least one first electrode strip and two exposed edge portions of the second electrode strips. More specifically, referring to FIG. 10A, working electrode strips 1052 and counter electrode strips 1054 are arranged on a plate bottom so that when the plate bottom is adjoined to the plate top, the working electrode strip is centered within each well, with a portion of two adjacent counter electrodes on each side.

Another embodiment of the invention relates to a multi-well plate comprising a plate top having a plurality of rows of openings and a substrate, wherein the plate top is placed on the substrate thereby forming a plurality of well rows from the plurality of openings and well bottoms, the well bottoms comprising a center portion of a working electrode strip and a portion from two counter electrode strips on each side of the portion of the working electrode strip. Preferably, the well rows are aligned with the working electrode strips and the counter electrode strips, wherein each of the plurality of well rows comprises: (i) a first well comprising a first well bottom including an exposed portion of a first working electrode strip (preferably centered within the well), a first edge portion including an exposed portion of a first counter electrode strip and a second edge portion including an exposed portion of a second counter electrode strip and (ii) at least a second well comprising a second well bottom including an exposed portion of the first working electrode strip (preferably centered), a first edge portion including an exposed portion of the first counter electrode strip and a second edge portion including an exposed portion of the second counter electrode strip. See, FIGS. 10A and 16A.

Another aspect of the invention relates to an assay module preferably having wells and/or chambers, most preferably a multi-well plate, comprising a substrate having a first side and a second side, the substrate comprising a plurality of first electrode surfaces (preferably working electrode surfaces) and, preferably, a plurality of second electrode surfaces (preferably counter electrode surfaces) on the first side and one or more conductive contacts on the second side, wherein two or more, preferably all or substantially all, of the plurality of wells and/or chambers each comprise one or more working electrode surfaces and one or more counter electrode surfaces.

One embodiment of the invention relates to a multi-well plate, wherein the plate substrate includes one or more conductive contacts adapted to: (a) distribute voltage, applied to the conductive contacts, uniformly throughout the plurality of wells, preferably distribute voltage such that any voltage variation is less than 0.5 volts, more preferably less than 0.1 volts, even more preferably less than 0.01 volts; (b) distribute voltage uniformly throughout the plurality of wells such that the variation of the sum of the effective resistance from the contacts to the counter electrode and the effective resistance from the contacts to working electrode for the plurality of wells is less than 10 ohms, preferably less than 5 ohms, more preferably less than 1 ohms, and most preferred constant; and/or (c) distribute voltage uniformly throughout the plurality of wells such that the variation of $V_c$ minus $V_w$ for the plurality of wells is less than 0.5 volts, preferably the variation of Vc–Vw is less than 0.1 volt, most preferably less than 50 mvolts, where Vc and Vw are defined as the voltage at the counter electrode and the voltage at the working electrode, respectively.

Preferably, the plates comprise plate contacts adapted to uniformly distribute current and/or voltage to the wells. According to one embodiment, the plate substrate further comprises a bottom surface comprising at least one independent electrical contact surface that is electrically connected to each of the plurality of independently addressable sectors of jointly addressable wells. The plate or plate substrate may further comprise one or more common (to more than one sector) electrical contact surfaces located on a surface of the plate, preferably, on the bottom of the plate substrate (e.g., there may be one or more common electrical contact surfaces that are connected to a counter electrode surface that is common to the entire plate). Advantageously, the electrical contact locations are positioned on the bottom surface between the plurality of wells such that the apparatus contacts contact the plate between the wells. According to one embodiment, the bottom surface comprises between 2 and 10 electrical contact surfaces per sector, even more preferably the bottom surface comprises two, six or seven contact surfaces per sector.

According to one embodiment, the plate bottom or substrate comprises a bottom surface comprising a plurality of electrical contacts or contact locations, preferably an array of electrical contact locations arranged in a 2×3 array.

The term "contact locations" is used herein to refer to the actual locations of the assay plate where the electrical connectors from the apparatus contact the plate. The term "contacts" or "contact surfaces" is intended to refer to the conductive surfaces on the plate bottom which are contacted with the electrical connections or electrical connectors. The "contact locations" are located within the "contact surfaces". The area of the "contact surface" can be significantly larger than that of the "contact locations". For example, referring to FIG. 10A, a plate bottom is illustrated showing working contacts 1072 (which are electrically connected to working electrodes 1052 via conductive through-holes 1062) and counter contacts 1074 (which are electrically connected to counter electrodes 1054 via conductive through-holes 1064). This figure shows an embodiment where the elongated counter contact surface 1074 is larger, yet encompasses the locations which are contacted by the counter electrical connector of the apparatus (e.g., the preferred counter electrode contact locations 3470 as shown in FIG. 34B).

Preferably, each of the electrical contact locations is positioned between 0.1 and 1 inches away from each adjacent electrical contact location, more preferably between 0.2 to 0.8 inches, even more preferably 0.3 to 0.4 inches.

Preferably, contact surfaces on the bottom of the plate comprise contact locations that are located between wells of the plate so that contacting the contact locations with an electrical connector does not distort the bottom surface of a well. FIG. 34A, shows (with respect to a fully assembled multi-well plate 3400 shown having wells 3405 arranged in a standard 96 well plate configuration) preferred contact locations on the plate bottom of plate 3400. Plate 3400 has an array, preferably a 2×3 array, of square sectors or regions 3410 (the division into sectors represented by dotted lines), wherein each sector comprises one or more electrical contact locations 3420 (represented by X's) and 3430 (represented by *'s) on a bottom surface of the plate bottom, the contact locations being located between wells on plate 3400. The contact locations on each sector are, preferably, arranged in a 2×3 array. Electrical contact locations 3420 are, preferably, connected to working electrodes; electrical contact locations 3430 are, preferably, connected to counter electrodes. The electrical contacts locations are located at at least one, preferably at least two, more preferably at least four and most preferably all, of the following locations, the locations being defined by coordinates (X, Y) measured (inches, ±0.250", preferably ±0.125") from the left and top edges, respectively, of the plate (viewing the plate from above, i.e., referring to FIG. 1, well A1 being the closest to the top left corner).

(i) one or more (preferably two or more, more preferably three or more and most preferably all) of first sector locations: (0.743, 0.620), (1.097, 0.620), (1.451, 0.620), (0.743, 1.329), (1.097, 1.329), (1.451, 1.329), most preferably, one or more working electrode contact locations selected from (0.743, 0.620), (1.451, 0.620), (0.743, 1.329), and (1.451, 1.329) and/or one or more counter electrode contact locations selected from (1.097, 0.620), and (1.097, 1.329);

(ii) one or more (preferably two or more, more preferably three or more and most preferably all) of second sector locations: (2.161, 0.620), (2.515, 0.620), (2.869, 0.620), (2.161, 1.329), (2.515, 1.329), (2.869, 1.329), most preferably, one or more working electrode contact locations selected from (2.161, 0.620), (2.869, 0.620), (2.161, 1.329), and (2.869, 1.329) and/or one or more counter electrode contact locations selected from (2.515, 0.620), and (2.515, 1.329);

(iii) one or more (preferably two or more, more preferably three or more and most preferably all) of third sector locations: (3.579, 0.620), (3.933, 0.620), (4.287, 0.620), (3.579, 1.329), (3.933, 1.329), (4.287, 1.329), most preferably, one or more working electrode contact locations selected from (3.579, 0.620), (4.287, 0.620), (3.579, 1.329), and (4.287, 1.329) and/or one or more counter electrode contact locations selected from (3.933, 0.620), and (3.933, 1.329);

(iv) one or more (preferably two or more, more preferably three or more and most preferably all) of fourth sector locations: (0.743, 2.038), (1.097, 2.038), (1.451, 2.038), (0.743, 2.747), (1.097, 2.747), (1.451, 2.747), most preferably, one or more working electrode contact locations selected from (0.743, 2.038), (1.451, 2.038), (0.743, 2.747), and (1.451, 2.747) and/or one or more counter electrode contact locations selected from (1.097, 2.038), and (1.097, 2.747);

(v) one or more (preferably two or more, more preferably three or more and most preferably all) of fifth sector locations: (2.161, 2.038), (2.515, 2.038), (2.869, 2.038), (2.161, 2.747), (2.515, 2.747), (2.869, 2.747), most preferably, one or more working electrode contact locations selected from (2.161, 2.038), (2.869, 2.038), (2.161, 2.747), and (2.869, 2.747) and/or one or more counter electrode contact locations selected from (2.515, 2.038), and (2.515, 2.747); and (vi) one or more (preferably two or more, more preferably three or more and most preferably all) of sixth sector locations: (3.579, 2.038), (3.933, 2.038), (4.287, 2.038), (3.579, 2.747), (3.933, 2.747), (4.287, 2.747), most preferably, one or more working electrode contact locations selected from (3.579, 2.038), (4.287, 2.038), (3.579, 2.747), and (4.287, 2.747) and/or one or more counter electrode contact locations selected from (3.933, 2.038), and (3.933, 2.747).

The pattern of contact locations described above is illustrated in FIG. 34A in relation to a 96-well plate, however, it is not limited to use with 96-well plates and may be applied to plates or plate bottoms of many plate formats including 1, 2, 6, 24, 384, 1536, 6144 and 9600-well plates. Preferably, the contact locations are located in the regions between the wells of a fully assembled plate.

The preferred locations of contact locations may also be specified in relation to the location of wells in a fully assembled plate. A preferred embodiment relates to a 96 well plate having electrodes and electrical contact surfaces. Referring to FIG. 1, the 96 well plate comprises rows (designated with the letters A through H) and columns of wells (designated with the numbers 1-12). The plate preferably comprises one or more, preferably two or more, more preferably all, of the following sectors (as shown in FIG. 34A):

a first sector comprising wells A1 through A4, B1 through B4, C1 through C4, and D1 though D4;

a second sector comprising wells A5 through A8, B5 through B8, C5 through C8, and D5 though D8;

a third sector comprising wells A9 through A12, B9 through B12, C9 through C12, and D9 through D12;

a fourth sector comprising wells E1 through E4, F1 through F4, G1 through G4, and H1 though H4;

a fifth sector comprising wells E5 through E8, F5 through F8, G5 through G8, and H5 though H8; and a sixth sector comprising wells E9 through E12, F9 through F1, G9 through G12, and H9 though H12.

Each of the designations refers to a region of the plate defined by the row and column. For example, A1 refers to the well in row A and column 1. We use the following notation herein to refer to the region between wells: "well1-well2". For example, the term "A1-B2" is used herein to refer to the region between well A1 (row A, column 1) and B2 (row B, column 2). The term "A1 through A4" is used to refer to the region including wells A1, A2, A3 and A4, including the space in-between.

According to one preferred embodiment of the invention, the sector comprises one or more electrical contact locations or contact surfaces on the plate bottom at one or more, preferably two or more, more preferably four or more and most preferred six of the following sector locations (by reference to FIGS. 1 and 34A):

(i) one or more, more preferably two or more and most preferred six, of first sector locations: A1-B2; A2-B3; A3-B4; C1-D2; C2-D3; C3-D4, most preferably, one or more working electrode contact locations selected from A1-B2, A3-B4, C1-D2 and C3-D4 and/or one or more counter electrode contact locations selected from A2-B3 and C2-D3;

(ii) one or more, more preferably two or more and most preferred six, of second sector locations: A5-B6; A6-B7; A7-B8; C5-D6; C6-D7; C7-D8, most preferably, one or more working electrode contact locations selected from A5-B6, A7-B8, C5-D6 and C7-D8 and/or one or more counter electrode contact locations selected from A6-B7 and C6-D7;

(iii) one or more, more preferably two or more and most preferred six, of third sector locations: A9-B10; A10-B11; A11-B12; C9-D10; C10-D11; C11-D12, most preferably, one or more working electrode contact locations selected from A9-B10, A11-B12, C9-D10 and C11-D12 and/or one or more counter electrode contact locations selected from A10-B11 and C10-D11;

(iv) one or more, more preferably two or more and most preferred six, of fourth sector locations: E1-F2; E2-F3; E3-F4; G1-H2; G2-H3; G3-H4, most preferably, one or more working electrode contact locations selected from E1-F2, E3-F4, G1-H2 and G3-H4 and/or one or more counter electrode contact locations selected from E2-F3 and G2-H3;

(v) one or more, more preferably two or more and most preferred six, of fifth sector locations: E5-F6; E6-F7; E7-F8; G5-H6; G6-H7; G7-H8, most preferably, one or more working electrode contact locations selected from E5-F6, E7-F8, G5-H6 and G7-H8 and/or one or more counter electrode contact locations selected from E6-F7 and G6-H7; and (vi) one or more, more preferably two or more and most preferred six, of sixth sector locations: E9-F10; E10-F11; E11-F12; G9-H10; G10-H11; G11-H12, most preferably, one or more working electrode contact locations selected from E9-F10; E11-F12; G9-H10 and G11-H12 and/or one or more counter electrode contact locations selected from E10-F11 and G10-H11.

By analogy, preferred contact location(s) on a 384-well plate or plate bottom for use with a 384 well plate may be defined in relationship to the wells of a 384-well plate having a standard configuration of wells in rows A-P and columns 1-24. In one embodiment, the plate, preferably, comprises one or more, preferably two or more, more preferably all, of the following sectors:

a first sector comprising wells A1 through A8, B1 through B8, C1 through C8, D1 though D8, E1 through E8, F1 through F8, G1 through G8, and H1 though H8;

a second sector comprising wells A9 through A16, B9 through B16, C9 through C16, D9 though D16, E9 through E16, F9 through F16, G9 through G16, and H9 though H16;

a third sector comprising wells A17 through A24, B17 through B24, C17 through C24, D17 though D24, E17 through E24, F17 through F24, G17 through G24, and H17 though H24;

a fourth sector comprising wells I1 through I8, J1 through J8, K1 through K8, L1 though L8, M1 through M8, N1 through N8, O1 through O8 and P1 through P8;

a fifth sector comprising wells I9 through I16, J9 through J16, K9 through K16, L9 though L16, M9 through M16, N9 through N16, O9 through O16 and P9 through P16; and a sixth sector comprising wells I17 through I24, J17 through J24, K17 through K24, L17 though L24, M17 through M24, N17 through N24, O17 through O24 and P17 through P24.

Preferably, each plate sector comprises one or more electrical contact locations at one or more, preferably two or more, more preferably four or more and most preferred six, of the following locations:
- (i) one or more, preferably two or more, more preferably four or more and most preferred all, of first sector locations: B2-C3; B4-C5; B6-C7; F2-G3; F4-G5; F6-G7, most preferably, one or more working electrode contact locations selected from B2-C3, B6-C7, F2-G3 and F6-G7 and/or one or more counter electrode contact locations selected from B4-C5 and F4-G5;
- (ii) one or more, preferably two or more, more preferably four or more and most preferred all, of second sector locations: B10-C11; B12-C13; B14-C15; F10-G11; F12-G13; F14-G15, most preferably, one or more working electrode contact locations selected from B10-C11, B 14-C15, F10-G11 and F14-G15 and/or one or more counter electrode contact locations selected from B12-C13 and F10-G11;
- (iii) one or more, preferably two or more, more preferably four or more and most preferred all, of third sector locations: B18-C19; B20-C21; B22-C23; F18-G19; F20-G21; F22-G23, most preferably, one or more working electrode contact locations selected from B18-C19, B22-C23, F18-G19 and F22-G23 and/or one or more counter electrode contact locations selected from B20-C21 and F20-G21;
- (iv) one or more, preferably two or more, more preferably four or more and most preferred all, of fourth sector locations: J2-K3; J4-K5; J6-K7; N2-O3; N4-O5; N6-O7, most preferably, one or more working electrode contact locations selected from J2-K3, J6-K7, N2-O3 and N6-O7 and/or one or more counter electrode contact locations selected from J4-K5 and N4-O5;
- (v) one or more, preferably two or more, more preferably four or more and most preferred all, of fifth sector locations: J10-K11; J12-K13; J14-K15; N10-O11; N12-O13; N14-O15, most preferably, one or more working electrode contact locations selected from J10-K11, J14-K15, N10-O11 and N14-O15 and/or one or more counter electrode contact locations selected from J12-K13 and J14-K15; and
- (vi) one or more, preferably two or more, more preferably four or more and most preferred all, of sixth sector locations: J18-K19; J20-K21; J22-K23; N18-O19; N20-O21; N22-O23, most preferably, one or more working electrode contact locations selected from J18-K19, J22-K23, N18-O19 and N22-O23 and/or one or more counter electrode contact locations selected from J20-K21 and N20-O21.

FIG. 34B, another embodiment of the invention, shows (with respect to a fully assembled multi-well plate 3450 shown having wells 3455 arranged in a standard 96 well plate configuration) preferred contact locations on the plate bottom of plate 3450, the plate having a different arrangement of sectors than plate 3400. Plate 3450 has an array, preferably a 1×12 array, of columnar sectors or regions 3460 (the division into sectors represented by dotted lines), wherein each sector comprises one or more electrical contact locations 3480 (represented by X's) and 3470 (represented by *'s) on a bottom surface of the plate bottom, the contact locations being located between wells on plate 3450. The contact locations on each sector are, preferably, arranged in a 7×1 array. Electrical contact locations 3480 are, preferably connected to working electrodes; electrical contact locations 3470 are, preferably, connected to counter electrodes. The electrical contacts are located at at least one, preferably at least two, more preferably at least four and most preferably all, of the following locations, the locations being defined by coordinates (X, Y) measured (inches, ±0.250", preferably ±0.125") from the left and top edges, respectively, of the plate (viewing the plate from above, i.e., referring to FIG. 1, well A1 being the closest to the top left corner):
- (i) one or more (preferably two or more, more preferably three or more and most preferably all) of first sector locations: (0.566, 0.620), (0.566, 0.975), (0.566, 1.329), (0.566, 1.684), (0.566, 2.038), (0.566, 2.393), (0.566, 2.747), most preferably, one or more working electrode contact locations selected from (0.566, 0.620), (0.566, 1.329), (0.566, 2.038) and (0.566, 2.747) and/or one or more counter electrode contact locations selected from (0.566, 0.975), (0.566, 1.684) and (0.566, 2.393);
- (ii) one or more (preferably two or more, more preferably three or more and most preferably all) of second sector locations: (0.920, 0.620), (0.920, 0.975), (0.920, 1.329), (0.920, 1.684), (0.920, 2.038), (0.920, 2.393), (0.920, 2.747), most preferably, one or more working electrode contact locations selected from (0.920, 0.620), (0.920, 1.329), (0.920, 2.038) and (0.920, 2.747) and/or one or more counter electrode contact locations selected from (0.920, 0.975), (0.920, 1.684) and (0.920, 2.393);
- (iii) one or more (preferably two or more, more preferably three or more and most preferably all) of third sector locations: (1.275, 0.620), (1.275, 0.975), (1.275, 1.329), (1.275, 1.684), (1.275, 2.038), (1.275, 2.393), (1.275, 2.747), most preferably, one or more working electrode contact locations selected from (1.275, 0.620), (1.275, 1.329), (1.275, 2.038) and (1.275, 2.747) and/or one or more counter electrode contact locations selected from (1.275, 0.975), (1.275, 1.684) and (1.275, 2.393);
- (iv) one or more (preferably two or more, more preferably three or more and most preferably all) of fourth sector locations: (1.629, 0.620), (1.629, 0.975), (1.629, 1.329), (1.629, 1.684), (1.629, 2.038), (1.629, 2.393), (1.629, 2.747), most preferably, one or more working electrode contact locations selected from (1.629, 0.620), (1.629, 1.329), (1.629, 2.038) and (1.629, 2.747) and/or one or more counter electrode contact locations selected from (1.629, 0.975), (1.629, 1.684) and (1.629, 2.393);
- (v) one or more (preferably two or more, more preferably three or more and most preferably all) of fifth sector locations: (1.983, 0.620), (1.983, 0.975), (1.983, 1.329), (1.983, 1.684), (1.983, 2.038), (1.983, 2.393), (1.983, 2.747), most preferably, one or more working electrode contact locations selected from (1.983, 0.620), (1.983, 1.329), (1.983, 2.038) and (1.983, 2.747) and/or one or more counter electrode contact locations selected from (1.983, 0.975), (1.983, 1.684) and (1.983, 2.393);
- (vi) one or more (preferably two or more, more preferably three or more and most preferably all) of sixth sector locations: (2.338, 0.620), (2.338, 0.975), (2.338, 1.329), (2.338, 1.684), (2.338, 2.038), (2.338, 2.393), (2.338, 2.747), most preferably, one or more working electrode contact locations selected from (2.338, 0.620), (2.338, 1.329), (2.338, 2.038) and (2.338, 2.747) and/or one or more counter electrode contact locations selected from (2.338, 0.975), (2.338, 1.684) and (2.338, 2.393);
- (vii) one or more (preferably two or more, more preferably three or more and most preferably all) of seventh sector locations: (2.692, 0.620), (2.692, 0.975), (2.692, 1.329), (2.692, 1.684), (2.692, 2.038), (2.692, 2.393), (2.692, 2.747), most preferably, one or more working electrode contact locations selected from (2.692, 0.620), (2.692, 1.329), (2.692, 2.038) and (2.692, 2.747) and/or one or more counter electrode contact locations selected from (2.692, 0.975), (2.692, 1.684) and (2.692, 2.393);

(viii) one or more (preferably two or more, more preferably three or more and most preferably all) of eighth sector locations: (3.046, 0.620), (3.046, 0.975), (3.046, 1.329), (3.046, 1.684), (3.046, 2.038), (3.046, 2.393), (3.046, 2.747), most preferably, one or more working electrode contact locations selected from (3.046, 0.620), (3.046, 1.329), (3.046, 2.038) and (3.046, 2.747) and/or one or more counter electrode contact locations selected from (3.046, 0.975), (3.046, 1.684) and (3.046, 2.393);

(ix) one or more (preferably two or more, more preferably three or more and most preferably all) of ninth sector locations: (3.400, 0.620), (3.400, 0.975), (3.400, 1.329), (3.400, 1.684), (3.400, 2.038), (3.400, 2.393), (3.400, 2.747), most preferably, one or more working electrode contact locations selected from (3.400, 0.620), (3.400, 1.329), (3.400, 2.038) and (3.400, 2.747) and/or one or more counter electrode contact locations selected from (3.400, 0.975), (3.400, 1.684) and (3.400, 2.393);

(x) one or more (preferably two or more, more preferably three or more and most preferably all) of tenth sector locations: (3.755, 0.620), (3.755, 0.975), (3.755, 1.329), (3.755, 1.684), (3.755, 2.038), (3.755, 2.393), (3.755, 2.747), most preferably, one or more working electrode contact locations selected from (3.755, 0.620), (3.755, 1.329), (3.755, 2.038) and (3.755, 2.747) and/or one or more counter electrode contact locations selected from (3.755, 0.975), (3.755, 1.684) and (3.755, 2.393);

(xi) one or more (preferably two or more, more preferably three or more and most preferably all) of eleventh sector locations: (4.109, 0.620), (4.109, 0.975), (4.109, 1.329), (4.109, 1.684), (4.109, 2.038), (4.109, 2.393), (4.109, 2.747), most preferably, one or more working electrode contact locations selected from (4.109, 0.620), (4.109, 1.329), (4.109, 2.038) and (4.109, 2.747) and/or one or more counter electrode contact locations selected from (4.109, 0.975), (4.109, 1.684) and (4.109, 2.393); and (xii) one or more (preferably two or more, more preferably three or more and most preferably all) of twelfth sector locations: (4.463, 0.620), (4.463, 0.975), (4.463, 1.329), (4.463, 1.684), (4.463, 2.038), (4.463, 2.393), (4.463, 2.747), most preferably, one or more working electrode contact locations selected from (4.463, 0.620), (4.463, 1.329), (4.463, 2.038) and (4.463, 2.747) and/or one or more counter electrode contact locations selected from (4.463, 0.975), (4.463, 1.684) and (4.463, 2.393).

The contact locations of a 96-well plate or plate bottom having a 1×12 array of sectors may also be defined in relationship to the position of the wells in the fully assembled plate. Preferably, at least one and, most preferably, all of the sectors have one or more (preferably two or more, more preferably three or more and most preferably all) contact locations selected from: An-Bn, Bn-Cn, Cn-Dn, Dn-En, En-Fn, Fn-Gn and Gn-Hn where n is the number designating the plate column defining the sector (by reference to FIG. 1), and most preferably has at least one working contact location selected from An-Bn, Cn-Dn, En-Fn, and Gn-Hn and at least one counter contact location selected from Bn-Cn, Dn-En and Fn-Gn.

According to preferred embodiments of the invention, the above-identified plate bottoms having the 2×3 or 1×12 array of sectors and contact locations defined on said sectors further comprise a plate top having a plurality of openings forming a plurality of wells aligned with the electrodes.

The invention also relates to an apparatus configured to measure luminescence from a multi-well plate having the above-identified contact configuration. More specifically, comprising electrical connectors to contact the plate bottom at the above-identified contact locations. The invention also relates to methods of performing assays comprising the step of contacting the assay plate at the above-identified contact locations.

According to one embodiment, the apparatus comprises a plurality of electrical connectors, wherein the plurality of electrical connectors is configured to contact the bottom surface, preferably between the wells. Preferably, the plurality of electrical connectors comprises one or more working connectors (i.e., the electrical connector which contacts the plate to electrically connect the source of electrical energy to the working electrodes) and one or more counter connectors (i.e., the electrical connectors which contact the plate to electrically connect the source of electrical energy to the counter electrodes).

Preferably, each sector is contacted by the plurality of electrical connectors at six locations, more preferably a 2×3 array of locations as defined above.

Another preferred embodiment of the invention relates to an apparatus comprising a light detector adapted to measure luminescence emitted from the plurality of wells and a plurality of electrical connectors, wherein the plurality of electrical connectors are configured to contact the bottom surface of a multi-well plate, preferably of a 384 well plate at the above-described contact locations.

Another aspect of the invention relates to plate bottom (and corresponding multi-well plates) having a plurality of electrodes on a first surface and a plurality of "contact sectors" on a second surface. The term "contact sector" is used herein to refer to independently addressable regions or sectors of contacts. FIG. 11A illustrates an example of a contact sector 1170 comprising a working contact surface 1172 and a counter electrode surface 1174.

Accordingly, another embodiment of the invention relates to a multi-well plate bottom and/or multi-well plate comprising:

(a) a substrate having a top surface and a bottom surface;
(b) a plurality of patterned working electrodes on the top surface;
(c) a plurality of patterned counter electrodes on the top surface, each of the patterned counter electrodes being associated with corresponding patterned working electrodes; and
(d) two or more independently addressable contact sectors on the bottom surface, each of the contact sectors corresponding to an electrode sector comprising one or more of the plurality of patterned working electrodes and one or more of the plurality of patterned counter electrodes on the top surface and including a plurality of conductive contact surfaces.

Preferably, the plurality of conductive contact surfaces include:

(i) a first conductive contact surface located within a first contact region, the first conductive contact surface being electrically connected to the one or more corresponding patterned working electrodes on the top surface; and
(ii) a second conductive contact surface located within a second contact region, the second conductive contact surface being electrically connected to the one or more corresponding patterned counter electrodes on the top surface;
wherein the first conductive contact surface and the second conductive contact surface are electrically isolated from each other.

Preferably, the two or more sectors comprise at least six sectors, more preferably six sectors in a 2×3 array of equal size sectors.

According to a preferred embodiment, the substrate further comprises: (i) first conductive through-holes electrically connecting the first conductive contact surface on the bottom surface with the one or more corresponding patterned working electrodes on the top surface and (ii) second conductive through-holes electrically connecting the second conductive contact surface to the one or more corresponding patterned counter electrodes on the top surface. Preferably, the first contact region has a U-shaped configuration and the second contact region has a T-shaped configuration, wherein the U-shaped configuration is mated with the T-shaped configuration within the sector. See FIGS. 11A and 12A. Table I (below) gives, preferred locations of said U-shaped first contact region and said T-shaped second contact region as defined with relation to the positions of wells in a fully assembled 96-well plate (having the standard configuration of rows A through H and columns 1 through 12) and a fully assembled 384-well plate (having the standard configuration of rows A through P and columns 1 through 24). The table describes the contact regions by dividing them into segments that are roughly aligned with lines, the endpoints of the lines being defined in relation ship to wells on the plates.

Referring to FIGS. 11A and 12A, preferred embodiments include 96-well plates or 384-well plates having a standard configuration of wells (or plate bottoms for said 96-well or 384-well plates), the multi-well plates (or plate bottoms) comprising:

a substrate having a top surface and a bottom surface;
a plurality of patterned working electrodes on the top surface;
a plurality of patterned counter electrodes on the top surface, each of the patterned counter electrodes being associated with corresponding patterned working electrodes; and
one or more, preferably six, independently addressable contact sectors on the bottom surface (e.g., one or more, preferably all, of the contact sectors as listed in Table I), each of the contact sectors corresponding to an electrode sector comprising one or more of the plurality of patterned working electrodes on the top surface and one or more of the plurality of patterned counter electrodes on the top surface, the one or more independently addressable contact sectors including a plurality of conductive contact surfaces;

preferably, wherein the plurality of conductive contact surfaces for a given contact sector include:
(i) a first conductive contact surface located within a first contact region, the first contact region having a U-shaped configuration and comprising segments aligned as defined in Table I, wherein the first conductive contact surface is electrically connected (preferably, via one or, more preferably, a plurality of conductive through-holes through said substrate, the through-holes, preferably, being located within the area defined by said first contact region) to the one or more corresponding patterned working electrodes on the top surface; and
(ii) a second conductive contact surface located within a second contact region, the second contact region having a T-shaped configuration and comprising segments as defined in Table I, wherein the second conductive contact surface is electrically connected (preferably, via one or, more preferably, a plurality of conductive through-holes through said substrate, the through-holes, preferably, being located within the area defined by said second contact region) to the one or more corresponding patterned counter electrodes on the top surface;
wherein the first conductive contact surface and the second conductive contact surface are electrically isolated from each other.

Other embodiments of the invention would include rotating any one of the above-identified U and/or T configurations in any one or more of the above sectors. For example, rotating either the U and/or the T 90 degrees, 180 degrees or the like.

TABLE I

| Contact Sector | Contact Region | Preferred Location of Contact Region (describing the contact regions as comprising segments roughly aligned with the following lines) | |
|---|---|---|---|
| | | Plate is 96-Well Plate | Plate is 384-Well Plate |
| 1 | First | A1-B2 to D1-D2, A3-B4 to D3-D4 and D1 to D4 | B2-C3 to H2-H3, B6-C7 to H6-H7 and H1 to H8 |
| | Second | A1 to A4 and A2-A3 to C2-D3 | A1 to A8 and A4-A5 to F4-G5 |
| 2 | First | A5-B6 to D5-D6, A7-B8 to D7-D8 and D5 to D8 | B10-C11 to H10-H11, B14-C15 to H14-H15 and H9 to H16 |
| | Second | A5 to A8 and A6-A7 to C6-D7 | A9 to A16 and A12-A13 to F12-G13 |
| 3 | First | A9-B10 to D9-D10, A11-B12 to D11-D12 and D9 to D12 | B18-C19 to H18-H19, B22-C23 to H22-H23 and H17 to H24 |
| | Second | A9 to A12 and A10-A11 to C10-D11 | A17 to A24 and A20-A21 to F20-G21 |
| 4 | First | G1-H2 to E1-E2, G3-H4 to E3-E4 and E1 to E4 | N2-O3 to I2-I3, N6-O7 to I6-I7 and I1 to I8 |
| | Second | H1 to H4 and H2-H3 to E2-F3 | P1 to P8 and P4-P5 to J4-K5 |
| 5 | First | G5-H6 to E5-E6, G7-H8 to E7-E8 and E5 to E8 | N10-O11 to I10-I11, N14-O15 to I14-I15 and I9 to I16 |
| | Second | H5 to H8 and H6-H7 to E6-F7 | P9 to P16 and P12-P13 to J12-K13 |
| 6 | First | G9-H10 to E9-E10, G11-H12 to E11-E12 and E9 to E12 | N18-O19 to I18-I19, N22-O23 to I22-I23 and I17 to I24 |
| | Second | H9 to H12 and H10-H11 to E10-F11 | P17 to P24 and P20-P21 to J20-K21 |

Table I. Table of Preferred Locations of Contact Regions on Bottom of Plate Bottom. Contact regions are described as comprising segments roughly aligned with lines on the plate bottom, the endpoints of the lines being defined by relationship to the position of the wells of the plate. The notation A1 refers to well A1. The notation A1-B2 refers to the region midway between wells A1 and B2. The notation A2-A3 to C2-D3, therefore, refers to a line starting midway between wells A2 and A3 and ending midway between wells C2 and D3.

Referring again to FIGS. 11A and 12A, another embodiment of the invention relates to a multi-well plate bottom or assay substrate and/or an assay module containing said plate bottom or assay substrate (preferably, a multi-well plate bottom and/or a multi-well plate containing said plate bottom), said plate bottom or assay substrate comprising:
- (a) a substrate divided into a 2×3 array of sectors, the substrate having a top surface and a bottom surface, each sector having an array of assay regions defined by columns and rows;
- (b) one or more patterned working electrodes on the top surface within each sector, each sector comprising elongated working electrodes being aligned with the array columns;
- (c) one or more patterned counter electrodes on the top surface within each sector, each sector comprising elongated counter electrodes being aligned with the array columns and being electrically isolated from and located between the elongated working electrodes; and
- (d) one or more contacts on the bottom surface of each sector.

Preferably, each assay region defines a surface of a well or chamber in the fully assembled assay module. Most preferably, the array of assay regions corresponds to the configuration of wells in a standard 96-well plate or a standard 384-well and the elongated counter electrodes comprise widened electrode areas adjacent and between the assay regions (the narrow regions match the resistance of the working electrode areas while the widened areas ensure that the surface of the counter electrodes are exposed in wells of the plate) and/or the elongated counter electrodes are electrically connected with an elongated connector perpendicular and adjacent one end of each elongated counter electrode within the sector. Preferably, each assay region overlaps a portion of at least two elongated counter electrodes and a portion of one elongated working electrode.

One embodiment of the invention relates to an assay module or assay module element (preferably a multi-well plate or multi-well plate bottom) comprising:
- (a) a substrate having a top surface and a bottom surface;
- (b) a plurality of working electrodes (preferably patterned) on the top surface;
- (c) a plurality of counter electrodes (preferably patterned) on the top surface, each of the counter electrodes being associated with corresponding working electrodes; and
- (d) two or more independently addressable sectors, each sector having two or more independently addressable contacts on the bottom surface, each of the contacts corresponding to one or more electrodes within assay regions or well regions (e.g., the surface of the substrate which forms part of the well bottom after attaching the plate top) within one of the sectors.

Preferably, the sectors include at least six, preferably at least twelve linear sectors. Preferably each sector comprises a row or column of wells. According to a preferred embodiment, the sectors comprise a 1×12 array of equal size linear sectors, wherein each sector corresponds to a row of wells.

Preferably, the substrate further comprises: (i) first conductive through-holes electrically connecting the working contact surfaces on the bottom surface with the one or more corresponding patterned working electrodes on the top surface and (ii) second conductive through-holes electrically connecting the counter contact surfaces to the one or more corresponding patterned counter electrodes on the top surface. Preferably, the one or more working contacts surfaces comprising one or more circular configurations and the one or more counter contact surfaces have an elongated configuration, said counter contact surfaces, preferably, being common to more than one, or more preferably, all of the sectors.

Another embodiment of the invention, shown in FIG. 10A, relates to multi-well plate or multi-well plate bottom comprising:
- (a) a substrate having a top surface and a bottom surface, the plate bottom having an array of regions corresponding to a standard 96-well plate configuration, the array comprising rows A, B, C, D, E, F, G, and H and columns 1, 2, 3, 4, 5, 6, 7, 8, 9, 10, 11 and 12;
- (b) a plurality of working electrodes (preferably patterned) on the top surface;
- (c) a plurality of counter electrodes (preferably patterned) on the top surface, each of the counter electrodes being associated with corresponding working electrodes; and
- (d) two or more independently addressable sectors, each sector having two or more independently addressable contacts on the bottom surface, the contacts corresponding to one or more electrodes within assay regions within one of the sectors.

wherein the contacts include first sector contacts comprising:
- (i) one or more working contacts located within one or more working contact regions at A1-B1, C1-D1, E1-F1 and G1-H1, the one or more working contacts being electrically connected to the one or more corresponding, preferably patterned, counter electrodes on the top surface; and
- (ii) one or more counter contacts located within one or more counter contact regions at B1-C1, D1-E1, and F1-G1, the counter contact surfaces being electrically connected to the one or more corresponding, preferably patterned, counter electrodes on the top surface;

wherein the one or more working contacts and the one or more counter contacts are electrically isolated from each other.

Preferably, the electrode surfaces are on the top surface of a plate bottom or substrate and the contacts are on the bottom surface, in which case the plate substrate advantageously further comprises one or more conductive through-holes (for example, a hole that is filled or coated with a conducting material) electrically connecting the one or more working electrode surfaces and the one or more counter electrode surfaces on the top side with the conductive contacts on the bottom side. Preferably, the plate substrate comprises two or more conductive through-holes, more preferably 6 or more, even more preferably 12 or more and most preferred 24 or more conductive through-holes.

Thus, another embodiment of the invention relates to a multi-well plate having a plurality of wells comprising a substrate having a top surface and a bottom surface, the top surface comprising a plurality of electrodes and the bottom surface comprises one or more electrical contacts, wherein the substrate further includes one or more conductive through-holes electrically connecting the one or more electrical contacts with the electrodes. Preferably, the one or more conductive through-holes are located between and/or adjacent the wells rather than directly beneath the wells to reduce the likelihood of detrimental leakage.

Preferably, the substrate includes one or more redundant conductive through-holes electrically connected to each of the working electrode surfaces and the counter electrode surfaces. That is, the working electrodes and/or counter electrodes are electrically connected to the plate contacts via two or more through-holes per electrode. Even though a single through-hole may be sufficient to electrically connect an electrode to an electrical contact, providing redundant through-holes allows for more uniform distribution of voltage or current.

Another embodiment of the invention relates to a multi-well plate having a standard 96-well plate configuration, the array comprising one or more, preferably two or more, more preferably all, of the following sectors:

a first sector comprising wells A1 through A4, B1 through B4, C1 through C4, and D1 though D4;
a second sector comprising wells A5 through A8, B5 through B8, C5 through C8, and D5 though D8;
a third sector comprising wells A9 through A12, B9 through B12, C9 through C12, and D9 through D12;
a fourth sector comprising wells E1 through E4, F1 through F4, G1 through G4, and H1 though H4;
a fifth sector comprising wells E5 through E8, F5 through F8, G5 through G8, and H5 though H8; and
a sixth sector comprising wells E9 through E12, F9 through F1, G9 through G12, and H9 though H12;
the top surface comprising a plurality of electrodes and each sector comprising one or more sector electrodes;
the bottom surface comprising one or more independently addressable contact sectors on the bottom surface and each of the contact sectors corresponding to the sector electrodes in a sector of the plate;
wherein the sectors each further include one or more conductive through-holes electrically connecting the one or more contact sectors with the corresponding sector electrodes, each of the one or more conductive through-holes being located between the wells and/or adjacent the wells.

Preferably, each sector comprises two, more preferably three, even more preferably four and most preferred at least eight through-holes. Preferably, each sector comprises eight through-holes in a 2×4 array. According to one preferred embodiment, the through-holes comprise through-hole pairs.

According to one preferred embodiment, the through-holes comprise:
(i) two or more, preferably three or more, more preferably all of first sector through-holes comprising four through-holes along sector edge adjacent A1-A4 and four through-holes at C1-D1; C2-D2; C3-D3 and C4-D4;
(ii) two or more, preferably three or more, more preferably all of second sector through-holes comprising four through-holes along sector edge adjacent A5-A8 and four through-holes at C5-D5; C6-D6; C7-D7 and C8-D8;
(iii) two or more, preferably three or more, more preferably all of third sector through-holes comprising four through-holes along sector edge adjacent A9-A12 and four through-holes at C9-D9; C10-D10; C11-D11 and C12-D12;
(iv) two or more, preferably three or more, more preferably all of fourth sector through-holes comprising four through-holes along sector edge adjacent H1-H4 and four through-holes at E1-F1; E2-F2; E3-F3 and E4-F4;
(v) two or more, preferably three or more, more preferably all of fifth sector through-holes comprising four through-holes along sector edge adjacent H5-H8 and four through-holes at E5-F5; E6-F6; E7-F7 and E8-F8; and
(vi) two or more, preferably three or more, more preferably all of sixth sector through-holes comprising four through-holes along sector edge adjacent H9-H12 and four through-holes at E9-F9; E10-F10; E11-F11 and E12-F12.

Preferably, each of the sector through-holes located within the first conductive region of the sectors electrically connects one or more contacts on the bottom surface to one or more working electrodes on the top surface and/or each of the sector through-holes located within the second conductive region of the sectors electrically connects one or more contacts on the bottom surface to one or more counter electrodes on the top surface.

Yet another embodiment of the invention relates to a multi-well plate having a standard 384-well plate configuration, the array comprising rows A through P and columns 1 through 24, the array comprising one or more, preferably two or more, more preferably four or more and most preferred six of the following:

a first sector comprising wells A1 through A8, B1 through B8, C1 through C8, D1 though D8, E1 through E8, F1 through F8, G1 through G8, and H1 though H8;
a second sector comprising wells A9 through A16, B9 through B16, C9 through C16, D9 though D16, E9 through E16, F9 through F16, G9 through G16, and H9 though H16;
a third sector comprising wells A17 through A24, B17 through B24, C17 through C24, D17 though D24, E17 through E24, F17 through F24, G17 through G24, and H17 though H24;
a fourth sector comprising wells I1 through I8, J1 through J8, K1 through K8, L1 though L8, M1 through M8, N1 through N8, O1 through O8 and P1 through P8;
a fifth sector comprising wells I9 through I16, J9 through J16, K9 through K16, L9 though L16, M9 through M16, N9 through N16, O9 through O16 and P9 through P16; and
a sixth sector comprising wells I17 through I24, J17 through J24, K17 through K24, L17 though L24, M17 through M24, N17 through N24, O17 through O24 and P17 through P24;
a top surface comprising a plurality of electrodes and each sector comprising one or more sector electrodes; and
a bottom surface comprising one or more independently addressable contact sectors on the bottom surface and each of the contact sectors corresponding to the sector electrodes;
wherein the sectors each further include one or more conductive through-holes electrically connecting the one or more contact sectors with the corresponding sector electrodes, the one or more conductive through-holes being located between the wells and/or adjacent to the wells.

Preferably, each sector comprises at least two, preferably at least three, more preferably at least four and even more preferably at least eight through-holes. According to a preferred embodiment, each sector comprises sixteen through-holes, preferably arranged in a 2×8 array. Preferably, the through-holes comprise through-hole pairs.

According to another preferred embodiment, the through-holes comprise:
(i) two or more, preferably three or more, more preferably all of first sector through-holes comprising four through-holes along sector edge adjacent A1-A8 and four through-holes along G1-H1 through G8-H8;
(ii) two or more, preferably three or more, more preferably all of second sector through-holes comprising four through-holes along sector edge adjacent A9-A16 and four through-holes along G9-H9 through G16-H16;
(iii) two or more, preferably three or more, more preferably all of third sector through-holes comprising four through-holes along sector edge adjacent A17-A24 and four through-holes along G17-H17 through G24-H24;

(iv) two or more, preferably three or more, more preferably all of fourth sector through-holes comprising four through-holes along sector edge adjacent P1-P8 and four through-holes along I1-J1 through I8-J8;

(v) two or more, preferably three or more, more preferably all of fifth sector through-holes comprising four through-holes along sector edge adjacent P9-P16 and four through-holes along I9-J9 through I16-J16; and (vi) two or more, preferably three or more, more preferably all of sixth sector through-holes comprising four through-holes along sector edge adjacent P-17 through P-24 and four through-holes along I17-J17 through I24-J24.jbjb 5.2 Embodiments of Multi-Well Assay Plates of the Invention In the following sections a variety of embodiments of assay modules, particularly multi-well assay plates of the invention are described. The figures will show plates having specific numbers and arrangements of wells, typically the figures show 96-well plates having a 12×8 array of wells. The description of the structure and the elements of the plates, however, are understood to be generic in the sense that they can apply or be readily adapted to a variety of assay modules including plates having any arbitrary number of wells in any arbitrary arrangement (e.g., any of the standard plate formats used in high-throughput screening).

5.2.1 Multi-Layer Electrode Plates

FIG. 5 shows an example of a multi-well assay plate of the invention. Multi-well assay plate 500 comprises a laminar structure comprising, in sequence, a first conductive layer 508, a dielectric layer 506, a second conductive layer 504 and a plate top 502. Holes 503 through plate top 502, holes 505 through second conductive layer 504, and holes 507 through dielectric layer 506 (the holes having interior surfaces 509, 510 and 512, respectively) are aligned so as to form a plurality of wells having well bottoms defined by first conductive layer 508 and well walls defined by the interior surfaces 509, 510 and 512. The cross-sectional shape of the holes in the plane of the laminar structure may be circular, square or any arbitrary shape. The interior walls of the holes may be perpendicular to the plane of the laminar structure so as to provide cylindrical wells or they may be shaped, e.g., to give conical or hemispherical wells. In one embodiment of the invention, the diameters of the holes 503, 505 and 507 are the same; in this embodiment, only the interior surfaces 510 of second conductive layer 504 are exposed to the volumes of the wells of the plate. Alternatively, the diameters of the holes 503 may be larger than the diameters of holes 505 and 507 so as to expose some of the top surface of conductive layer 504 to the volumes of the wells of the plate.

First conductive layer 508 is a material suitable for use as a counter electrode or, preferably, a working electrode in an ECL assay (see description of ECL electrodes above). In one embodiment it is a conductive sheet of material such as a metal sheet or foil (e.g., platinum or gold foil) or a sheet of conductive plastic. Preferably, it is a sheet of conductive plastic composite comprising carbon particles (e.g., carbon fibrils) dispersed in a polymeric matrix. In an alternate embodiment, conductive layer 508 is a film of a conductive material supported on a substrate. Suitable films include coatings such as conducting inks comprising conducting particles dispersed in a matrix (e.g., carbon or metal-based conducting inks) or metal or carbon films (e.g., metal or carbon films deposited on a substrate via evaporative or CVD processes or lamination). Suitable substrates include plastic sheet, glass and ceramic. Electrical contact to first conductive layer 508 can be made by contacting any exposed conductive surface, preferably, the bottom surface. Electrical contact to the top of first conductive layer 508 can be facilitated by extending the width and/or length of the layer beyond that of the other layers. In the embodiment where first conductive layer 508 comprises a conductive coating on a non-conductive substrate, electrical connection may be made to the bottom of the plate by incorporating through-holes through the non-conductive substrate. Such through-holes are, preferably, made conductive by inserting a conductive material such as a metal wire or by filling with a conductive material such as a metal-filled ink so as to provide a high conductivity path from the conductive coating to the bottom of the plate. According to another embodiment, the holes may be filled with carbon-filled ink. Typically, conductive layer 508 provides a fluid impermeable barrier and acts to contain fluid held within the wells. However, a porous conductive layer 508 may be, optionally, employed to conduct dot-blot assays and other assays that benefit from filtration of samples or reagents through the bottom of the plate and/or working electrode.

Dielectric layer 506 is an electrically insulating material and prevents conductive layers 504 and 508 from coming into electrical contact. Suitable materials include sheets of non-conductive plastic, glass or ceramic, preferably comprising an adhesive coating on one or both sides so as to provide adhesive bonds to conductive layers 504 and/or 508 (e.g., single or double sided adhesive tape). In such dielectric layers, holes 507 may be formed by a molding process (i.e., during fabrication of the layer), by selective etching or, preferably, through a cutting process conducted prior to final assembly of the plate, e.g., by die cutting or laser drilling. Alternatively, dielectric layer 506 is an electrically insulating coating such as a dielectric ink, a polymeric film, a photoresist film, and/or a ceramic or glass film (e.g., ceramic or glass films deposited by evaporative or CVD processes). Holes 507 in such layers may be formed by cutting, by a selective etching of the coating (e.g., by photolithography or by etching in the presence of a physical mask) or by a patterned deposition of the coating via a process like screen printing, laser printing or ink jet printing or deposition through a mask.

Second conductive layer 504 is a material suitable for use as a working electrode or, preferably, a counter electrode in an ECL assay (see description of ECL electrodes above). Optionally, second conductive layer 504 may be omitted (e.g., when plate top 502 comprises an electrode material or when the apparatus used to analyze the plate is capable of supplying an electrode (e.g., in the form of one or more conductive probes). In one embodiment it is a conductive sheet of material such as a metal sheet or foil (e.g., aluminum, platinum or gold foil) or a sheet of conductive plastic (e.g., a sheet of conductive plastic composite comprising carbon particles dispersed in a polymeric matrix). In such conductive layers, holes 505 may be formed by a molding process (i.e., during fabrication of the layer), by selective etching or, preferably, through a cutting process conducted prior to final assembly of the plate, e.g., by die cutting or laser drilling. In an alternate embodiment, conductive layer 504 is a film of a conductive material supported on a substrate. Suitable films include coatings such as conducting inks comprising conducting particles dispersed in a matrix (e.g., carbon or metal-based conducting inks) or metal films (e.g., metal films such as aluminum, gold and platinum deposited on a substrate via evaporative or CVD processes). Suitable substrates include plastic sheet, glass and ceramic. Holes 505 in such layers may be formed by cutting, by selective etching of the coating (e.g., by photolithography or by etching in the presence of a physical mask) or by patterned deposition of the coating via a process like screen printing, laser printing or ink jet printing or deposition through a mask. In a preferred embodiment of the invention, dielectric layer 506 and second conducting layer 504 are both provided by the layers of a metal-coated adhesive tape (i.e., a laminar structure comprising a layer of adhesive adjacent to a non-conducting plastic sheet that is coated on the opposite side with a metallic film (preferably an evaporated film of aluminum). Preferably, holes 505 and 507 are simultaneously formed in such a tape by a cutting process such as die cutting or laser drilling prior to assembly of the plate. Electrical contact to second conductive layer 504 can be made by contacting any exposed conductive surface. Electrical contact to the top or bottom of second conductive layer 504 can be facilitated by extending the width and/or length of the layer beyond that of the plate top. Alternatively, openings through the other layers can be incorporated to provide for additional exposed surfaces of second conductive layer 504. Such openings can be through-holes made conductive by inserting a conductive material such as a metal wire or by filling with a conductive material such as a metal-filled ink so as to provide a high conductivity path from second conductive layer 504 to the bottom or top of the plate. Optionally, multi-well assay plate 500 comprises an additional conductive layer (not shown) that comprises a material suitable for use as a reference electrode. This reference electrode layer should be electrically isolated from the other conductive layers, e.g., through the use of additional dielectric layers as necessary.

Plate top 502 is a plate top as described earlier in the application. Preferably, it complies with industry standards for microplate dimensions and well number so as to be compatible with commercially available equipment for storing, moving and processing microplates. Plate top 502 is generally made of a non-conductive plastic. It may be made of a conducting material or coated with a conductive material (suitable for acting as a working electrode or, preferably, a counter electrode in an ECL assay) in which case, second conductive layer 504 may be omitted. Preferably, the bottom surface of plate top 502 comprises an adhesive coating so as to provide adhesive bonding to second conductive layer 504. In some alternate embodiments, plate top 502 is omitted.

In use, components 502, 504, 506 and 508 of plate 500 should be sealed against adjoining layers so as to prevent the leakage of fluids contained within the wells of plate 500. Sealing may be accomplished by physically holding the components together under pressure through the use of fasteners and/or clamps. Such fasteners and/or clamps may be integrated into plate 500 and/or they may be comprised in an external fixture. Alternatively, sealing may be accomplished through the use of adhesive coatings on the surfaces of the components. In some cases, the components may have inherently adhesive properties; for example, evaporated films, CVD films, cast polymer films, printed inks, etc. can be designed to adhere to the substrate on which they are deposited. Some of the seals may also be accomplished through a welding process such as ultrasonic welding or solvent welding (i.e., by applying a solvent that softens or partially dissolves one or both of the surfaces to be sealed together). The layers of the plate are, preferably, aligned so that the exposed area of conductive layer 508 is centered in the well and surrounded by the exposed area of conductive layer 504.

In operation, test samples are introduced into wells of plate 500. A source of electrical energy is connected across first and second conducting layers 508 and 504. Application of electrical energy across these connections leads to the application of an electrochemical potential across the test samples via the exposed surfaces of conducting layers 508 and 504. In the case of an ECL assay, it is preferable to apply electrical energy so as to generate ECL at or near the surface of conductive layer 508 (i.e., conductive layer 508 provides the working electrode and conductive layer 504 provides the counter electrode) so that light is generated near the center of the well.

Figure 7B:
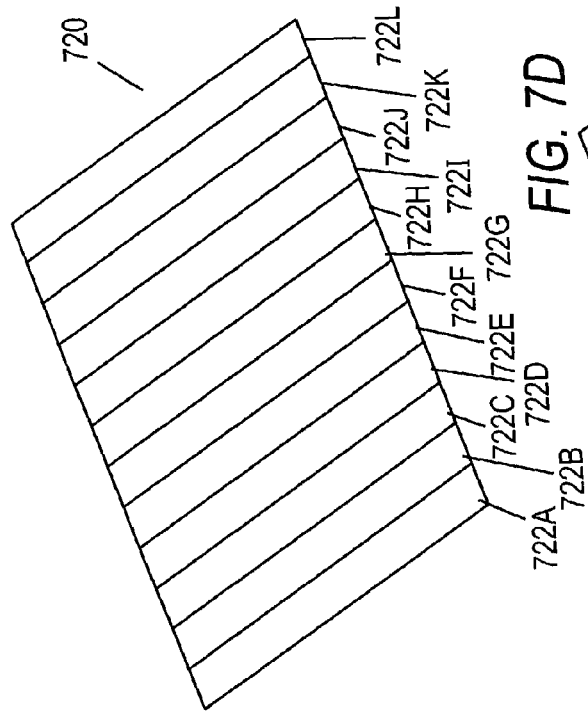
Figure 7D:
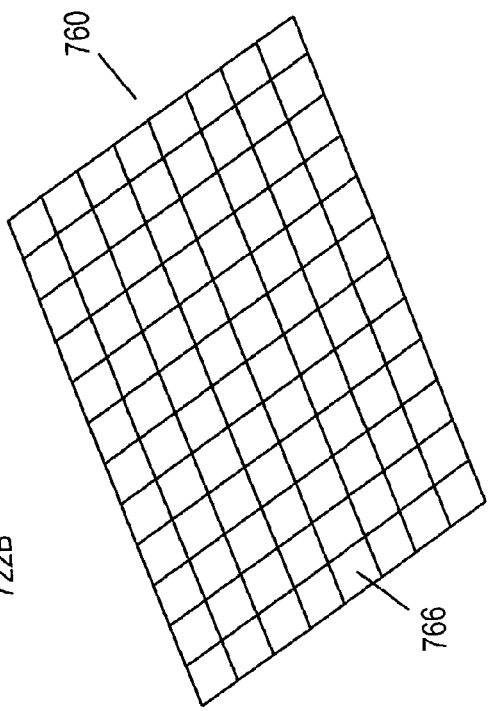
Figure 7A:
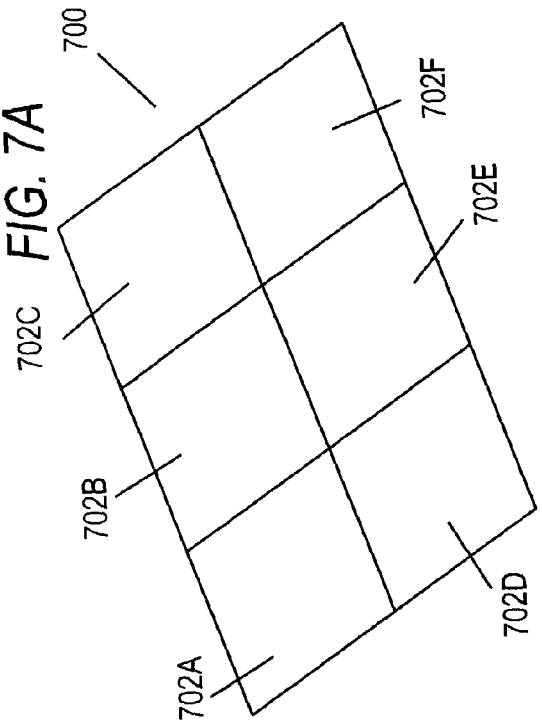
Figure 7C:
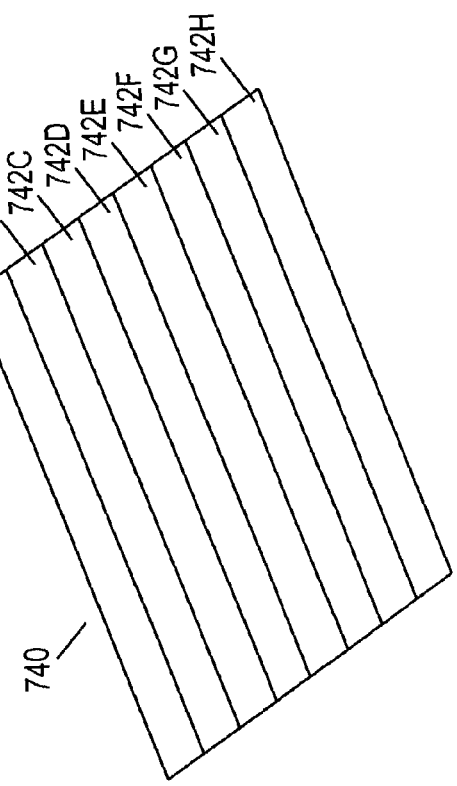

In some preferred embodiments, the plates are divided into individually addressable sectors of jointly addressable wells. Such sectoring may be accomplished by dividing conductive layers 504 and/or 508 into a plurality of individually addressable sections. FIG. 6A shows a second conductive layer 600 analogous to second conductive layer 504 described above except that the layer is sectioned into six square sections (602A-F) that are electrically isolated from each other. Applying a potential to, e.g., section 602A, will result in the potential being selectively applied to fluid in the plate sector defined by the wells in contact with section 602A. Such sectoring allows for the sequential induction and measurement of ECL from each sector in the plate. Some alternate sectioning schemes are illustrated in FIG. 6B (conductive layer 620 is sectioned into columnar sectors 622A through 622L) and FIG. 6C (conductive layer 640 is sectioned into individual well sectors 644). FIG. 7A shows a first conductive layer 700 analogous to first conductive layer 508 described above except that the layer is sectioned into six square sections (702A-F) that are electrically isolated from each other. Applying a potential to, e.g., section 702A, will result is the potential being selectively applied to fluid in the plate sector defined by the wells in contact with section 702A. Some alternate sectioning schemes are illustrated in FIG. 7B (conductive layer 720 is sectioned into columnar sectors 722 along the width of the plate), FIG. 7C (conductive layer 740 is sectioned into columnar sectors 742 along the length of the plate), and FIG. 7D (conductive layer 760 is sectioned into individual well sectors 766). In general, to divide plate 500 into independently addressable sectors, it is only required that one of conductive layers 504 and 508 of plate 500 be sectioned since electrical connections must be made to both conductive layers in contact with a specific well in order to complete an electrochemical circuit. In some embodiments, sectioning of both conductive layers 504 and 508 is used to maximize the number of individually addressable sectors while minimizing the number of electrical contacts. For example, a plate formed using first conductive layer 740 (as shown in FIG. 7C) with second conductive layer 620 (as shown in FIG. 6B) allows for the individual addressing of 96 wells while requiring only 20 electrical contacts. Sectioning of conductive layers 504 and/or 508 of plate 500 may be achieved by a variety of methods including cutting processes such as die cutting or drilling, selective etching, such as by photolithography or by etching through a mask, or by selective deposition.

5.2.2 Single Electrode Layer Plates

Sectioning of a conductive layer may be used to provide multiple independent electrodes within a given well. FIG. 16A shows another example of a multi-well assay plate of the invention. Multi-well assay plate 1600 is similar in structure to multi-well assay plate 500 from FIG. 5 except that it has a single conductive layer on a support, the conductive layer being sectioned so as to provide two or more independent electrodes (e.g., a counter and a working electrode) in a given well. Multi-well assay plate 1600 is a laminar structure comprising in sequence a plate top 1602, an adhesive layer 1604, a dielectric layer 1606, a conductive layer 1608 and a substrate 1610. Holes 1603 and 1605 through plate top 1602 and adhesive layer 1604, respectively, form a plurality of wells having well bottoms defined by dielectric layer 1606, conductive layer 1608 and/or substrate 1610. Conductive layer 1608 is sectioned into two electrically isolated sections, a working electrode section 1620 and a counter electrode section 1622. The sectioning is designed so that a fluid in a given well is exposed to surfaces of both sections. Element 1612 shows layers 1606, 1608, and 1610 aligned and stacked, in order from top to bottom—1606 (top), 1608 and 1610 (bottom)—so as to form a plate bottom with integrated electrodes.

Plate top 1602 is a plate top as described earlier in the application. Preferably, it complies with industry standards for microplate dimensions and well number so as to be Alternatively, dielectric 1606 may be a sheet of non-conductive plastic, glass or ceramic, preferably comprising an adhesive coating on one or both sides so as to provide adhesive bonds to adjoining layers. In such dielectric layers, holes 1607 may be formed by a molding process (i.e., during fabrication of the layer), by selective etching or, preferably, through a cutting process conducted prior to final assembly of the plate, e.g., by die cutting or laser drilling.

Conductive layer 1608 comprises materials suitable for use as counter electrodes or working electrodes in an ECL assay (see description of ECL electrodes above). Working electrode section 1620 and counter electrode section 1622 may comprise different materials (so as to optimize each for its function) or they may comprise the same materials (so as to simplify their formation, e.g., by printing both sections in one screen printing step). Preferably, conductive layer 1608 is a coating of a conductive material supported on a substrate 1610. Suitable films include coatings such as conducting inks that comprise conducting particles dispersed in a matrix (e.g., carbon or metal-based conducting inks) or metal films (e.g., metal films deposited on a substrate via evaporative or CVD processes). Formation of the patterned sections may be accomplished by selective patterned deposition of the film (e.g., by screen printing, laser printing, ink jet printing, evaporation through a mask, etc.) and/or by selective patterned etching of a contiguous film (e.g., by photolithographic and chemical etching protocols used in the semiconductor industry). Alternatively, sections 1620 and 1622 are sections cut, e.g., by die cutting, from a conductive sheet of material such as a metal sheet or foil (e.g., platinum, gold, steel, or aluminum foil) or a sheet of conductive plastic, such as a sheet of conductive plastic composite comprising carbon particles (e.g., carbon fibrils) dispersed in a polymeric compatible with commercially available equipment for storing, moving and processing microplates. Plate top 1602 is generally made of a non-conductive plastic. Adhesive 1604 is preferably an adhesive coating or adhesive tape suitable for sealing plate top 1602 to element 1612 and preferably forms fluid tight, high resistance seals. Adhesive 1604 is, preferably, a double sided adhesive tape. Optionally, adhesive 1604 may be omitted. In such case, plate top 1602 may be sealed to element 1612 via an adhesive coating on plate top 1602 or via other sealing techniques such as heat sealing, solvent welding, sonic welding or through the use of applied pressure by clamping. In some alternate embodiments, plate top 1602 is omitted.

Dielectric layer 1606 is an electrically insulating material and serves to define the regions of conductive layer 1608 that contact fluid in a well. In FIG. 16A, dielectric 1606 covers all of working electrode section 1620 that is exposed to the volume of a given well except for a region defined by holes 1607 in dielectric layer 1606. The boundaries formed by holes 1607 define a fluid containment region over working electrode 1620 that can be used to confine a small volume of fluid in contact with the exposed electrode but not in contact with the other exposed surfaces within the well. Such fluid containment regions may be used, advantageously, for selectively immobilizing a reagent on the active area of the working electrode in a well. Alternatively, dielectric layer 1606 may be omitted. Preferably, dielectric layer 1606 is an electrically insulating coating such as a dielectric ink, a polymeric film, a photoresist film, and/or a ceramic or glass film (e.g., ceramic or glass films deposited by evaporative or CVD processes). Holes 1607 in such layers may be formed by selective etching of the coating (e.g., by photolithography or by etching in the presence of a physical mask) or patterned deposition of the coating via a process like screen printing, laser printing or ink jet printing or deposition through a mask. Alternatively, dielectric 1606 may be a sheet of non-conductive plastic, glass or ceramic, preferably comprising an adhesive coating on one or both sides so as to provide adhesive bonds to adjoining layers. In such dielectric layers, holes 1607 may be formed by a molding process (i.e., during fabrication of the layer), by selective etching or, preferably, through a cutting process conducted prior to final assembly of the plate, e.g., by die cutting or laser drilling.

Conductive layer 1608 comprises materials suitable for use as counter electrodes or working electrodes in an ECL assay (see description of ECL electrodes above). Working electrode section 1620 and counter electrode section 1622 may comprise different materials (so as to optimize each for its function) or they may comprise the same materials (so as to simplify their formation, e.g., by printing both sections in one screen printing step). Preferably, conductive layer 1608 is a coating of a conductive material supported on a substrate 1610. Suitable films include coatings such as conducting inks that comprise conducting particles dispersed in a matrix (e.g., carbon or metal-based conducting inks) or metal films (e.g., metal films deposited on a substrate via evaporative or CVD processes). Formation of the patterned sections may be accomplised by selective patterned deposition of the film (e.g., by screen printing, laser printing, ink jet printing, evaporation through a mask, etc.) and/or by selective patterned etching of a contiguous film (e.g., by photolithographic and chemical etching protocols used in the semiconductor industry). Alternatively, sections 1620 and 1622 are sections cut, e.g., by die cutting, from a conductive sheet of material such as a metal sheet or foil (e.g., platinum, gold, steel, or aluminum foil) or a sheet of conductive plastic, such as a sheet of conductive plastic composite comprising carbon particles (e.g., carbon fibrils) dispersed in a polymeric matrix. Optionally, conductive layer 1608 comprises an additional section (not shown) that comprises a material suitable for use as a reference electrode.

Substrate 1610 is a non-conductive material such as plastic sheet, glass or ceramic. Electrical contact to electrode sections 1620 and 1622 may be made to any exposed surface. Electrical contact to the top of the electrode sections can be facilitated by extending the width and/or length of the sections (as well as that of substrate 1610) beyond that of plate top 1602. Alternatively, electrical connections may be made to the bottom of the plate by incorporating through-holes through substrate 1610. Such through-holes are, preferably, made conductive by inserting a conductive material such as a metal wire or by filling with a conductive material such as a metal-filled ink so as to provide a high conductivity path from the electrode sections to the bottom of the plate.

In use, components 1602, 1606 and 1608 of plate 1600 should be sealed against adjoining layers so as to prevent the leakage of fluids contained within the wells of plate 1600. Sealing may be accomplished by physically holding the components together under pressure through the use of fasteners and/or clamps. Such fasteners and/or clamps may be integrated into plate 1600 and/or they may be comprised in an external fixture. Alternatively, sealing may be accomplished through the use of adhesive coatings on the surfaces of the components (see discussion above in Section 5.1). Suitable adhesives include acrylic adhesives (3M 200 MP).

According to one embodiment, polypropylene plate tops are used. In order to attach the plate tops to the bottoms, it is preferably to use a low surface energy (LSE) adhesive. The only difference between the LSE adhesive and a non-LSE adhesive is the flow or "wet-out" characteristics. Non-LSE adhesives such as 3M 200 MP will not stick as well to surfaces characterized as having a low surface energy such as polypropylene. One suitable adhesive for use with polypropylene is a modified acrylic such as 3M 300LSE, which is designed specifically for low surface energy plastics.

In some cases, the components may have inherently adhesive properties; for example, evaporated films, CVD films, cast polymer films, printed inks, etc. can be designed to adhere to the substrate on which they are deposited. Some of the seals may also be accomplished through a welding process such as sonic welding or solvent welding (i.e., by applying a solvent that softens or partially dissolves one or both of the surfaces to be sealed together, contacting the two surfaces and then allowing the surfaces to re-harden to form a bond). The layers of the plate are, preferably, aligned so that the exposed area of section 1620 is centered in the well and surrounded on two sides by the exposed area of section 1622.

In operation, test samples are introduced into wells of plate 1600. A source of electrical energy is connected across working electrode section 1620 and counter electrode section 1622. Application of electrical energy across these connections leads to the application of an electrochemical potential across the test samples via the exposed surfaces of working electrode section 1620 and counter electrode section 1622.

In some preferred embodiments, the plates are divided into individually addressable sectors of jointly addressable wells. Such sectoring may be accomplished by further dividing working electrode section 1620 and/or counter electrode section 1622 into a plurality of individually addressable sections. FIG. 16B shows a conductive layer 1640 having a working electrode section 1642 and counter electrode section 1644. Conductive layer 1640 is analogous to conductive layer 1608 described above except that working electrode section 1642 is further divided into 12 subsections (1642A-L) that are electrically isolated from each other. Applying a potential to, e.g., subsection 1642A, will result in the potential being selectively applied to fluid in the plate sector defined by the wells in contact with subsection 1642A. An alternate sectioning scheme is illustrated in FIG. 16C (sectioning of working electrode section 1662 and counter electrode section 1664 of conductive layer 1660 into six square sectors). In general, to divide plate 1600 into independently addressable sectors, it is only required that one of working electrode section 1620 and counter electrode section 1622 be further sectioned since electrical connections must be made to both conductive layers in contact with a specific well in order to complete an electrochemical circuit. In some embodiments, the patterning of the sections is simplified by subsectioning both working electrode section 1620 and counter electrode section 1622.

5.2.3 Specific Embodiments of Multi-Layer Electrode Plates

Another aspect of the invention relates to assay plates, preferably multi-well plates, wherein one or more electrode surfaces are formed using conductive foils or conductive films or layers which are adjoined to form the assay plate.

One embodiment of the invention relates to a multi-well assay plate for conducting assays comprising:

(a) a first electrically conductive layer, preferably partitioned into two or more electrically isolated sectors;
(b) an insulating layer having a plurality of insulating layer openings;
(c) a second electrically conductive layer on the insulating layer, the second electrically conductive layer having a plurality of second electrically conductive layer openings, the second layer preferably being partitioned into two or more electrically isolated sectors; and
(d) a plate top having a plurality of plate top openings;
wherein the insulating layer is between the first electrically conductive layer and the plate top and wherein the insulating layer openings, the second electrically conductive layer openings and the plate top openings are aligned forming a plurality of wells.

According to another embodiment, the first conductive layer comprises a substrate comprising partitioned electrically conductive surfaces. Preferably, the layer is "partitioned" to correspond or align with a plate sector.

According to another embodiment, the first conductive layer comprises a substrate comprising an electrically conductive surface and the second layer comprises a partitioned conductive film on the insulating layer having a plurality of conductive film openings.

Preferably, the first conductive layer comprises a fibril composite with a bottom coated with or painted with a conductive metal, preferably silver.

A still further embodiment relates to a multi-well plate for conducting assays (preferably electrode induced luminescence, more preferably electrochemiluminescence assays) comprising:

(a) an electrically conductive layer;
(b) an insulating layer having a plurality of insulating layer openings;
(c) a conductive film on the insulating layer having a plurality of conductive film openings, the conductive film being partitioned into two or more electrically isolated sectors; and
(d) a plate top having a plurality of plate top openings;

wherein the insulating layer is between the electrically conductive layer and plate top and the insulating layer openings and the plate top openings are aligned forming wells for conducting the assays.

Another aspect relates to a multi-well plate for conducting assays (preferably electrode induced luminescence, more preferably electrochemiluminescence assays) comprising:

(a) an electrically conductive layer partitioned into two or more electrically isolated sectors;
(b) an insulating layer having a plurality of insulating layer openings;
(c) a conductive film on the insulating layer having a plurality of conductive film openings, the conductive film being partitioned into two or more electrically isolated sectors; and
(d) a plate top having a plurality of plate top openings;
wherein the insulating layer is between the electrically conductive layer and plate top and the insulating layer openings and the plate top openings are aligned forming wells for conducting the assays.

FIG. 8B shows an exploded view of multi-well assay plate 830, an embodiment of plate 500 (shown in FIG. 5) that comprises additional adaptations allowing for convenient electrical connections to the conductive layers of the plate. FIG. 8C shows a stylized cross-sectional view of two wells 842A and 842B of plate 830. Plate 830 comprises a laminar structure comprising, in sequence, plate top 832, adhesive layer 844, conductive tape layer 852B, conductive layer 858, and conductive tape layer 852A. Conductive tape layers 852A and 852B are provided by folding conductive tape 848 around conductive layer 858 at fold 854. Holes 834, 846, and 856 through plate top 832, adhesive layer 844, and conductive tape layer 852B, respectively, are aligned so as to form a plurality of wells having well bottoms defined by conductive layer 858. A plurality of holes 850 through conductive tape layer 852A allow for electrical contact to conductive layer 858 from the bottom of plate 830. After folding of conductive tape 848, holes 850 are, preferably, aligned with regions between the wells of plate 830. For example, FIG. 8C shows a cross-sectional view of two wells (842A and 842B) of plate 830. Hole 853 through conductive tape layer 852A exposes the bottom surface of conductive layer 858 to provide electrical contact 872. Contact 872 is located on the region of conductive layer 858 between wells 842A and 842B; this arrangement allows an electrical connection to be made to contact 872 without distorting or disturbing the surface of conductive layer 858 exposed to wells 842A or 842B.

Plate top 830 is a plate top analogous to plate top 502 in FIG. 5. Adhesive layer 844 is an adhesive suitable for forming a fluid-tight seal between plate top 502 and conductive tape layer 852B. Adhesive layer 844 may be an adhesive coating applied, e.g., by spray coating, onto plate top 502 or conductive tape layer 852B. In a preferred embodiment, adhesive layer 844 is a double sided adhesive tape (i.e. a plastic film coated on both sides with adhesive). Holes 846 are preferably formed by a cutting process such as laser drilling or die cutting. Conductive tape 848 is preferably a laminar structure comprising conductive film 864, dielectric film 866 and adhesive film 868. Conductive film 864 is a material suitable for use as a working electrode or, preferably, a counter electrode in an ECL assay (see for example the description of the analogous second conductive layer 504 in FIG. 5). Optionally, conductive film 864 may be omitted (e.g., when plate top 832 comprises an electrode material or when the apparatus used to analyze the plate is capable of supplying an electrode (e.g., in the form of one or more conductive probes). Conductive film 864 is preferably of sufficient conductivity so that, during use of the plate in an assay, a potential applied to conductive film 864 in conductive tape layer 852A will be evenly distributed over the surface of conductive film 864 in conductive tape layer 852B. Dielectric film 866 is an electrically insulating film suitable for preventing electrical contact between conductive film 864 and conductive layer 858. Adhesive film 868 is an adhesive suitable for forming a fluid-tight seal between dielectric film 866 and conductive layer 858. Optionally, adhesive film 868 provides for electrical isolation of conductive film 864 and conductive layer 858; dielectric film 866 may then be omitted. In one embodiment, conductive tape 848 is an electrically insulating plastic film coated on one side with an adhesive coating and on the other side with a conductive coating such as an evaporated metal film, preferably composed of aluminum. Holes 850 and 856 are preferably formed by a cutting process such as laser drilling or die cutting.

Conductive layer 858 is a material suitable for use as a counter electrode, or preferably a working electrode in an electrode induced luminescence assay (see for example the description of the analogous first conductive layers 508 in FIG. 5 and 700, 720, 740 and 760 in FIG. 7). Preferably, conductive layer 858 is a composite comprising carbon particles, most preferably carbon fibrils, distributed in a polymeric matrix. It is preferably sectioned into 12 electrically isolated columnar sections corresponding to a column of wells in plate 830. Holes 850 in conductive tape layer 852A expose the bottom surface of conducting layer 858. It is desirable that a potential applied to the bottom of conductive layer 858 leads to an even distribution of potential over the regions of the top surface of conductive layer 858 that form the bottom of the wells in plate 830. Such even distribution of potential may be achieved by providing multiple evenly-distributed sites for making electrical connection to conductive layer 858. For example, holes 850 are arranged are arranged in a 4×12 array so as to expose the bottom of conductive layer 858 in the regions centered between the first and second wells, the third and fourth wells, the fifth and sixth wells, and the seventh and eighth wells of the columns of wells of plate 830. Even distribution of potential is also aided by the conductivity of conductive layer 858. When a material of only moderate conductivity is used, e.g., a composite of carbon particles distributed in a matrix, it is advantageous that conductive layer 858 comprise a highly conductive coating on the bottom of the layer so as to better distribute potential across the surface of the layer. Preferred highly conductive coatings include metal films (e.g., evaporated, electro-deposited or electroless-deposited films) and metal-containing paints (e.g., silver paint). Suitable silver paints include materials available from E. I. du Pont de Nemours and Co. (e.g., Dupont 5000, 5007, 5008, 5021, 5025, 5028, 5031, and 5089), Acheson Colloids Co. (e.g., Acheson PD-020, 479SS, 478SS, 725A, PF-007, EL-010, 820C, and Electrodag 506SS), and Conductive Compounds Inc. (e.g., AG-410 and AG-500).

In operation, test samples are introduced into wells of plate 830. A source of electrical energy is connected to conducting film 864 and one or more sections of conductive layer 858. Preferably, the connection to conducting film 864 is made by contacting conductive tape layer 852A on the bottom of the plate. Preferably, the connection to the one or more sections of conductive layer 858 is made by contacting the bottom of conductive layer 858 via holes 850 in conductive tape layer 852A. Application of electrical energy across these connections leads to the application of an electrochemical potential across the test samples via the exposed surfaces of conducting film 864 and conductive layer 858 (the application of electrochemical potential being confined to wells in sectors contacting the one or more sections of conductive layer 858). In the case of an ECL assay, it is preferable to apply electrical energy so as to generate ECL at or near the surface of conductive layer 858 (i.e., conductive layer 858 provides the working electrode) so that light is generated near the center of the well.

FIG. 8B shows a multi-well assay plate with an 8×12 array of wells divided into columnar sectors via sectioning of conductive layer 858. It should be readily apparent that the design is readily adaptable to plates having different numbers of wells, different arrangements of wells or different arrangements of sectors (e.g., see discussion of 1536 plate below). FIG. 8A shows an alternative sectoring scheme. Multi-well assay plate 800 comprises a laminar structure comprising, in sequence, plate top 804, adhesive layer 806, conductive tape 810 providing conductive tape layer 814B, and conductive layer 820. Conductive tape 810 is folded at fold 818 to provide conductive tape layer 814A adjacent to conductive layer 820 (and on the opposite side of conductive layer 820 from conductive tape layer 814B). The components of plate 800 are analogous to those described for plate 830 except: i) conductive layer 820 is sectioned into six square sections (corresponding in a 96-well plate to six sectors each having a 4×4 array of wells) and ii) the arrangement of holes 812 through conductive tape layer 814A is optimized for this arrangement of sectors. Holes 812 are arranged in a 4×6 array with each hole centered between the first and second well and between the third and fourth well in each major diagonal defined by each 4×4 sector of wells. Plates analogous to plates 800 but having different number of wells, e.g., 384, 1536, or 9600 wells can be made by substituting the desired arrangement of holes, preferably using an industrial standard, in plate top 802, adhesive layer 806 and conductive plate layer 814B.

Yet another embodiment of the invention relates to a 1536-well plate wherein the counter electrode (e.g., see, counter electrode conductive tape 810 of FIG. 8A) wraps around working electrode(s) (e.g., see, working electrode conductive layer 820 of FIG. 8A) with access holes for working electrode contacts to pass through the counter electrode wrap and make contact with working electrodes (or contacts for the working electrodes). Preferably, four working electrode contacts contact the plate bottom (through the holes in the counter electrode wrap) and are arranged in a square to evenly distribute current across the working electrode area (e.g., see sectored working electrode surfaces 820 in FIG. 8A). Preferably, two counter electrode contacts make contact with the counter electrode sheet so as to provide redundancy and protection from a single dirty contact region or connector.

Yet another embodiment relates to a multi-well plate formed by stacking the conductive and dielectric layers and then drilling holes through the multi-layer composite thereby forming wells, preferably wells having walls comprising counterelectrode and/or working electrode surfaces. For example, referring to FIG. 5, a multi-well plate (preferably a 1536 or higher well plate) is formed using a first conductive layer 508, a dielectric layer 506, a second conductive layer 504 and a plate top 502, wherein one or more of the layer do not have holes (e.g., holes 502, 505 and/or 507). After the layers are bonded together, holes 502, 505 and/or 507 may be formed by drilling holes through the respective layers with a laser or the like thereby forming a multi-well plate where each well comprises a working electrode surface (e.g., exposed first conductive layer 508 forming the well bottom) and a counterelectrode surface (e.g., exposed second conductive layer forming part of the well wall).

5.2.4 Specific Embodiments of Plates Having Conductive Plate Tops

Another aspect of the invention relates to multi-well plates having a plate top coating with a conductive surface (e.g., a painted plate top). The painted plate top can then be affixed to a substrate having a working electrode surface whereby the conductive surfaces of the plate top may advantageously provide a counter electrode surface.

One embodiment relates to a multi-well plate comprising:
(a) an electrically conductive layer;
(b) an insulating layer having a plurality of insulating layer openings; and
(c) a plate top comprising an electrically conductive surface, the plate top having a plurality of plate top openings;
wherein the insulating layer is between the electrically conductive layer and the plate top and the insulating layer openings and the plate top openings are aligned forming wells for conducting assays.

Another embodiment relates to multi-well plate comprising:
(a) a substrate surface having a plurality of electrodes patterned thereon;
(b) an insulating layer having a plurality of insulating layer openings; and
(c) a plate top comprising an electrically conductive surface, the plate top having a plurality of plate top openings;
wherein the insulating layer is between the substrate surface and the plate top and the insulating layer openings and the plate top openings are aligned forming plate openings over one or more of the plurality of electrodes thereby forming wells.

A still further embodiment relates to a multi-well plate comprising:
(a) an electrically conductive layer partitioned into two or more electrically isolated sectors;
(b) an insulating layer having a plurality of insulating layer openings; and
(c) a plate top comprising an electrically conductive surface, the plate top having a plurality of plate top openings;
wherein the insulating layer is between the electrically conductive layer and the plate top and the insulating layer openings and the plate top openings are aligned forming wells.

Yet another embodiment relates to a multi-well plate comprising:
(a) an electrically conductive layer;
(b) an insulating layer having a plurality of insulating layer openings; and
(c) a plate top comprising an electrically conductive surface partitioned into two or more electrically isolated sectors, the plate top having a plurality of plate top openings;
wherein the insulating layer is between the electrically conductive layer and the plate top and the insulating layer openings and the plate top openings are aligned forming wells.

In certain embodiments of plate 800 (or 830) (FIGS. 8A and 8B), conductive tape 810 (or 848) may be omitted. In these embodiments, plate top 802 (or 832) comprises a conductive material suitable for use as a working electrode or, preferably, a counter electrode in an ECL assay. Plate top 802 (or 848) may be made of a conducting material such as metal or a carbon-containing plastic composite. Alternatively, conductivity is achieved via a conductive coating such as a metal film (e.g., an evaporated, electrodeposited or electroless deposited metal film) or a metal-containing paint such as a silver paint. Sectoring of the plates into individually addressed sectors of jointly addressable wells can be achieved by sectioning conductive layer 820 (or 858) and/or plate top 802 (or 832) into electrically isolated sections. The plate top may be sectioned by division into individual pieces or by patterning of a conductive coating on a contiguous piece.

In operation, test samples are introduced into wells of plate 800 (or 830). A source of electrical energy is connected to plate top 802 (or 832) and one or more sections of conductive layer 820 (or 858). Preferably, the connection to plate top 802 (or 832) is made by contacting the side of the plate. Preferably, the connections to the one or more sections of conductive layer 820 (or 858) are made by contacting the bottom of the plate. Application of electrical energy across these connections leads to the application of an electrochemical potential across the test samples via the exposed surfaces of plate top 802 (or 832) and conductive layer 820 (or 858) (the application of electrochemical potential being confined to wells in sectors contacting the one or more sections of conductive layer 820 or 858). In the case of an ECL assay, it is preferable to apply electrical energy so as to generate ECL at or near the surface of conductive layer 820 or 858 (i.e., conductive layer 820 or 858 provides the working electrode) so that light is generated near the center of the well.

5.2.5 Multi-Layer Electrode Plates Having Conductive Through-Holes

FIG. 9A shows an exploded view of multi-well assay plate 930, an embodiment of multi-well assay plate 500 from FIG. 5 that comprises additional adaptations allowing for convenient electrical connections to the conductive layers of the plate. FIG. 9B shows a stylized cross-sectional view of three wells 942A, 942B and 942C of the same plate. Plate 930 comprises a laminar structure comprising, in sequence, plate top 932, adhesive layer 944, second conductive layer 948, dielectric layer 950, first conductive layer 958, substrate layer 959 and contact layer 960. Holes 934, 946, 949 and 956 through plate top 932, adhesive layer 944, second conductive layer 948 and dielectric layer 950, respectively, are aligned so as to form a plurality of wells having well bottoms defined by first conductive layer 958. Conductive through-holes 962 through substrate 959 provide a conductive path between first conductive layer 958 and the portion of contact layer 960 that define electrical contacts 963 (963A being, preferably, working contacts and 963B being, preferably, counter contacts). Conductive through-holes 964 and 966 through substrate 959 and dielectric layer 950, respectively, provide a conductive path between second conductive layer 948 and the portion of contact layer 960 that define electrical contacts 965. Electrical connection to conductive layers 948 and 958 can, therefore be made from the bottom of the plate by contacting electrical contacts 965 and 963, respectively. Element 970 (FIG. 9A) shows layers 960, 959, 958, 950 and 948 aligned and stacked, in order from top to bottom—948 (top), 950, 958, 959, and 960 (bottom)—so as to form a plate bottom with integrated electrodes.

Plate top 932 is a plate top analogous to plate top 502 in FIG. 5. Adhesive layer 944 is an adhesive suitable for forming a fluid-tight seal between plate top 932 and second conductive layer 948. Adhesive layer 944 may be an adhesive coating applied, e.g., by spray coating, onto plate top 932 or second conductive layer 948. In a preferred embodiment, adhesive layer 944 is a double sided adhesive tape (i.e., a plastic film coated on both sides with adhesive). Holes 946 are preferably formed by a cutting process such as laser drilling or die cutting. Optionally, adhesive 944 may be omitted (when second conductive layer 948 or plate top 932 have adhesive properties or when sealing is accomplished without the use of adhesives, e.g., by clamping, heat sealing, sonic welding, solvent welding, etc.). Alternatively, both plate top 932 and adhesive 944 may be omitted. Second conductive layer 948 is a material suitable for use as a working electrode, or preferably a counter electrode in an ECL assay (see for example the description of the analogous second conductive layer 504 in FIG. 5). Preferably, it is a conductive coating such as a carbon ink and may be formed by a printing process such as ink jet printing, laser printing, or, most preferably, screen printing. Second conductive layer 948 is preferably of sufficient conductivity so that, during use of the plate in an assay, an electrical potential applied to second conductive layer 948 will be evenly distributed over its surface. To attain suitably high conductivity with a moderately conductive electrode material such as a carbon ink, it may be advantageous that second conductive layer 948 comprise two layers: i) a highly conductive underlayer such as a silver paint and ii) an electrode material overlayer such as carbon ink. When forming such layers, e.g., by a two step printing process, it is beneficial that the overlayer be thick enough and of suitable dimensions to ensure that a sample in wells 932 is not exposed to the underlayer material. Dielectric layer 956 is an electrically insulating film suitable for preventing electrical contact between conductive layers 948 and 958. Preferably, dielectric layer 956 is comprises dielectric ink and is formed by a printing process such as screen printing and, optionally, UV curing.

First conductive layer 958 is a material suitable for use as a counter electrode, or preferably a working electrode in an ECL assay (see for example the description of the analogous first conductive layers 508 in FIG. 5 and 700, 720, 740 and 760 in FIG. 7). Preferably, first conductive layer 958 comprises a conductive coating such as a carbon ink and may optionally comprise a highly conductive underlayer, such as silver ink, to better distribute electrical potential across the layer during the course of an assay. Such one or two layer coatings may be formed by printing processes such as screen printing and are preferably designed so as to ensure that samples in wells 932 do not contact the underlayer. First conductive layer 958 is sectioned into 12 electrically isolated columnar sections corresponding to a column of wells in plate 930; such sectioning may be achieved via patterned printing, e.g., by screen printing. Substrate 959 is a non-conducting material such as a non-conducting plastic sheet. Through-holes 962 and 964 in substrate 959 are, preferably, made by a cutting process such as die cutting or laser drilling. Through-holes 962 are filled with a conductive material to provide an electrical connection between electrical contacts 963 and first conductive layer 958. Through-holes 964 and 966 are filled with conductive material to provide an electrical connection between contacts 965 and second conductive layer 948 (holes 964 and 966 are located in the regions between the sections of first conductive layer 958 so as to ensure that that they are electrically isolated from first conductive layer 958). Through-holes 962, 964 and 966 are preferably filled with conductive material during the formation of conductive layers 960, 958 and/or 948, e.g., during the screen printing of a conductive ink on a substrate, excess ink is forced into holes in the substrate so as to fill the holes with the conductive ink. Contact layer 965 is a conductive material such as a conductive ink. Preferably it is a screen printed silver paint with a screen printed carbon ink overlayer to prevent corrosion of the silver. We have also found that the presence of exposed silver appears to negatively influence the plasma treatment of surfaces (even on the opposite side of the plate); therefore, when plasma treatment is used to modify a surface of the assay plate it is particularly advantageous that there be no exposed silver.

In operation, test samples are introduced into wells of plate 930. A source of electrical energy is connected to second conducting layer 948 and one or more sections of conductive layer 958 (via electrical contacts 965 and one or more of electrical contacts 963, respectively). Application of electrical energy across these connections leads to the application of an electrochemical potential across the test samples via the exposed surfaces of conducting layers 948 and 958 (the application of electrochemical potential being confined to wells in sectors contacting the one or more sections of conductive layer 958). In the case of an ECL assay, it is preferable to apply electrical energy so as to generate ECL at or near the surface of conductive layer 958 (i.e., conductive layer 958 provides the working electrode) so that light is generated near the center of the well.

5.2.6 Single-Layer Electrode Plates Having Conductive Through-Holes

Another aspect of the invention relates to multi-well plates having one or more printed electrodes. Thus, one embodiment of the invention relates to a multi-well plate comprising:

(a) a substrate surface;
(b) one or more working electrodes on the substrate surface;
(c) one or more counter electrodes on the substrate surface; and
(d) a plate top having plate top openings;
wherein the plate top openings are positioned on the substrate surface so as to form a plurality of wells having at least one working electrode and at least one counter electrode.

Preferably, the electrodes are printed, most preferably screen printed, onto substrate. Preferably, the electrodes comprise carbon ink.

Another embodiment relates to a multi-well plate having a plurality of wells comprising a first electrode surface formed by applying two or more conductive layers comprising carbon.

Preferably, three or more layers of carbon are formed. Preferably, a patterned working electrode surface is formed by applying a first layer of carbon and a second layer of carbon, wherein the area of one layer of carbon is greater than the area of the other layer of carbon.

Preferably, the wells comprise a working electrode surface formed by applying one or more layers of carbon onto a conductive layer comprising silver. Preferably, the one or more layers of carbon completely cover the conductive layer.

FIGS. 10A and 10B show another embodiment of the multi-well assay plate of the invention. Multi-well assay plate 1000, is similar to multi-well assay plate 1600 from FIG. 16A but comprises additional adaptations allowing for convenient electrical connections to the conductive layers of the plate. Multi-well assay plate 1000 is a laminar structure comprising, in sequence, a plate top 1020, an adhesive layer 1030, a dielectric layer 1040, a conductive layer 1050, a substrate layer 1060 and a contact layer 1070. Holes 1022 and 1032 through plate top 1020 and adhesive layer 1030, respectively, are aligned so as to form a plurality of wells 1002 having well bottoms defined by dielectric layer 1040, conductive layer 1050 and/or substrate layer 1060 and well walls defined by the interior surfaces of holes 1022 and 1032. Through-holes 1062 and 1064 through substrate layer 1060 provide an electrical path between elements of conductive layer 1050 and elements of contact layer 1070. Element 1080 shows layers 1070, 1060, 1050 and 1040 aligned and stacked, in order from top to bottom—1040 (top), 1050, 1060, and 1070 (bottom)— so as to form a plate bottom with integrated electrodes.

Plate top 1020 is a plate top analogous to plate top 502 in FIG. 5. Adhesive layer 1030 is an adhesive suitable for forming a fluid-tight seal between plate top 1020 and dielectric layer 1040, conductive layer 1050 and/or substrate layer 1060. Adhesive layer 1030 may be an adhesive coating applied, e.g., by spray coating, onto plate top 1020. In a preferred embodiment, adhesive layer 1030 is a double sided adhesive tape (i.e., a plastic film coated on both sides with adhesive). Holes 1032 are preferably formed by a cutting process such as laser drilling or die cutting. Optionally, adhesive 1030 may be omitted (e.g., when the adjoining layers have adhesive properties or when sealing is accomplished without the use of adhesives, e.g., by clamping, heat sealing, sonic welding, solvent welding, etc.). Alternatively, both plate top 1020 and adhesive layer 1030 may be omitted.

Conductive layer 1050 comprises materials suitable for use as working electrodes and/or counter electrodes in an ECL assay and is supported on substrate 1060, a non-conductive substrate such as a plastic sheet or film. Preferably, conductive layer 1050 is a conductive coating such as a carbon ink and may be formed by a printing process such as screen printing. Conductive layer 1050 is sectioned, e.g., by screen printing in a defined pattern, into 12 electrically isolated working electrode sections 1052 and 13 electrically connected counter electrode sections 1054. As shown in the figure, the sectioning is designed so that fluid in a given well will be in contact with at least one working electrode section and at least one counter electrode section. The working electrode sections may have a different composition than the counter electrode sections so as to optimize the performance of the electrodes or they may comprise the same materials so as to minimize the complexity of manufacturing, e.g., to reduce the number of printing steps. Preferably, they both comprise a carbon ink overlayer over a silver ink underlayer; the carbon ink providing the active electrode surface and the silver ink providing sufficient conductivity so that, during use of the plate in an assay, electrical potential is evenly distributed throughout a particular section. When forming such layers, e.g., by a two step printing process, it is beneficial that the overlayer be of slightly larger dimensions than the underlayer and that it be of suitable thickness to ensure that a sample in wells 1002 is not exposed to the underlayer material. It may be beneficial to print or deposit the overlayer in multiple layers so as to ensure that the underlayer is completely covered so that the underlayer does not interfere with subsequent processing steps or with ECL measurements (e.g., a preferred electrode material comprises three layers of carbon ink over a layer of silver ink, the layers most preferably being deposited by screen printing). Dielectric layer 1040 is an electrically insulating film, preferably formed from a dielectric ink by a printing process such as screen printing. Dielectric layer 1040 is patterned so as to define the surfaces of conductive layer 1050 that contact fluids in wells 1002 (i.e., the surfaces that are not covered). Holes 1042 in dielectric layer 1040 define fluid containment regions on the working electrode sections 1052 of conductive layer 1050. In such fluid containment regions, the dielectric layer acts as a barrier that can be used to confine small volumes of fluids over the working electrode. Optionally, dielectric layer 1040 may be omitted.

Contact layer 1070 is a conductive layer that allows for electrical connection of the multi-well assay plate to an external source of electrical energy. The contact layer is sectioned in a series of working electrode contacts 1072 and counter electrode contacts 1074 to allow independent connection to specific sections of electrodes 1052 and 1054. The contact layers are, preferably, formed by printing, most preferably screen printing, a silver ink under layer (to provide high conductivity) followed by a carbon ink overlayer (to prevent corrosion of the silver ink and prevent any deleterious effects by the exposed silver on a subsequent plasma processing step). Holes 1062 and 1064 in substrate 1060 are, preferably, made by a cutting process such as die cutting or laser drilling. Holes 1062 are filled with a conductive material to provide an electrical connection between working electrode contacts 1072 and working electrode sections 1052. Holes 1064 are filled with conductive material to provide an electrical connection between counter electrode contacts 1074 and counter electrode sections 1054. Holes 1062 and 1064 are preferably filled with conductive material during the formation of conductive layer 1050 or contact layer 1070, e.g., during the printing of a conductive ink on a substrate, excess ink is forced into holes in the substrate so as to fill the holes with the conductive ink.

In operation, test samples are introduced into wells of plate 1000. A source of electrical energy is connected across one or more working electrode sections 1052 and one or more counter electrode sections 1054 (via one or more of working electrode contacts 1072 and one or more of counter electrode contacts 1074, respectively). Application of electrical energy across these connections leads to the application of an electrochemical potential across the test samples via the exposed surfaces of electrode sections 1052 and 1054 (the application of electrochemical potential being confined to wells in sectors contacting working electrode and counter electrode sections that are in electrical connection to the source of electrical energy).

Plate 1000 as shown in FIGS. 10A and 10B is a 96-well plate divided into 12 independently addressable sectors of 8 wells (i.e. 12 columns of 8 wells). The structure shown in FIGS. 10A and 10B is readily modified so as to be applicable to plates having different numbers of wells, different arrangements of wells and/or different arrangements of independently addressable sectors.

FIGS. 11A and 12A show two alternative embodiments. FIG. 11A shows a multi-well assay plate 1100 that is analogous in structure and function to plate 1000 except that the components are configured so as to divide the plate into six independently addressable square sectors each having a 4×4 array of wells. Element 1180 shows layers 1140, 1150, 1160 and 1170 aligned and stacked, in order from top to bottom, 1140 (top), 1150, 1160 and 1170 (bottom). FIG. 12A shows a multi-well assay plate 1200 that is analogous in structure and function to plate 1100 except that the components are configured so as to provide 384 wells in a 24×16 array. Element 1280 shows layers 1240, 1250, 1260 and 1270 aligned and stacked, in order from top to bottom, 1240 (top), 1250, 1260 and 1270 (bottom).

The electrode patterns illustrated in details C of FIGS. 11A and 12A (i.e., the patterns used for conductive layers 1150 and 1250, respectively) illustrate some useful concepts in the design of suitable electrode patterns. In general, the electrode material should be of sufficient conductivity that potential drops along the surface of the electrodes are small relative to the potential drops between opposing electrodes. By proper electrode design it is possible, although not required, to make additional compensations for these small potential drops along the surface of the electrode. FIG. 12A shows the division of conductive layer 1250 into i) electrodes 1254 that, preferably, provide the counter electrode surface within wells of the plate and ii) electrodes 1252 that, preferably, provide the working electrodes within wells of the plate. The electrodes are divided into electrode strips that run the length of a given plate sector. Each full-width strip of electrode 1252 is matched with two half-width strips of electrode 1254 so that the overall electrical resistance along the length of the sector is evenly matched between the opposing electrodes. The opposing electrodes are contacted at opposite ends of the sector so the overall resistance in the leads to any particular well should be a constant value. Any potential drop due to this resistance should therefore be constant and should not cause variability between wells. Similarly, the resistance in electrodes 1152 and 1154 as shown in FIG. 11A are matched along the length of the sector; in this case the resistance matching is accomplished by patterning electrodes 1154 so that the length of the electrodes comprises wide regions (to maximize electrode surface area within the wells) alternating with narrow regions (to help match the overall resistance of along the length of electrodes 1154 with that of electrodes 1152).

5.2.7 Specific Embodiments of Plates Having Wells Divided into a Plurality of Assay Domains In some embodiments of the invention, the active area of the working electrode in a well of a multi-well assay plate is divided into a plurality of assay domains. For example, a working electrode used in an ECL binding assay may have immobilized on distinct regions of its surface a plurality of different binding reagents so as to form a plurality of distinct binding domains differing in their affinity for analytes of interest. Wells having such electrodes allow a number of different analytes to be measured concurrently in the same sample in the same well (e.g., by imaging the light emitted from the well and correlating the amount of each analyte of interest to the light emitted from an assay domain specific for that analyte). A patterned dielectric may be used to facilitate the division of the working electrode area in a well into one or more assay domains; the assay domains are defined by one or more holes in a dielectric layer covering the working electrode. The dielectric layer providing a barrier that can confine small volumes of fluid to the assay domains formed by the regions of exposed working electrode (also referred herein as fluid containment regions). The use of dielectric layers to form such assay domains is described in more detail in the description of FIG. 4. Microdispensing of fluids onto selected fluid containment regions allows for the selective immobilization of reagents in specific fluid containment regions or the confinement of certain steps of an assay to specific fluid containment regions.

FIGS. 13, 14 and 15 show examples of multi-well assay plates of the invention that have a plurality of fluid containment regions in each well. FIG. 13A shows multi-well assay plate 1300, a plate analogous to multi-well assay plate 500 (as shown in FIG. 5) except that the pattern of holes 1312 through dielectric layer 1306 has been modified to define a plurality of fluid containment regions over the working electrode surface (i.e., first conductive layer 1308). FIG. 13B shows multi-well assay plate 1350, a plate analogous to multi-well assay plate 500 (as shown in FIG. 5) except that the pattern of holes 1360 in second conductive layer 1354 and the pattern of holes 1362 in dielectric layer 1356 has been modified to define a plurality of fluid containment regions over the working electrode surface (i.e., first conductive layer 1358). The modifications of FIGS. 13A and 13B can also by analogy be introduced into the specific embodiments of the invention described by FIGS. 8, 9, 10, 11 and 12. FIG. 14 shows a multi-well assay plate 1400, a plate analogous to multi-well assay plate 1600 (as shown in FIG. 16) except that the pattern of holes through dielectric layer 1406 has been modified to define a plurality of fluid containment regions 1407 over the working electrode surface (i.e., working electrode section 1422). Element 1412 shows layers 1406, 1408 and 1410 aligned and stacked, in order from top to bottom, 1406 (top), 1408 and 1410 (bottom). The modification of FIG. 14 can also by analogy be introduced into the specific embodiments of the invention described by FIGS. 10-12. FIG. 14 does not show sectoring or conductive contacts, however, such sectoring and/or conductive contacts may be introduced as described above, e.g., by analogy to FIG. 10 and/or 11. FIG. 15 shows, multi-well assay plate 1500, an embodiment of the invention that is particularly well suited for genomic or proteomic analysis. Multi-well assay plate 1500 is an adaptation of plate 1300 having only six independently addressable square wells. The size of the wells is chosen so as to optimize the efficiency of the imaging of luminescence generated from the wells by the imaging instrument (as described below). Multi-well assay plate 1500 is a laminar structure comprising, in sequence, plate top 1520, adhesive layer 1530, conductive tape layer 1514B, dielectric layer 1540, conductive layer 1552, substrate 1560, contact layer 1572 and conductive tape layer 1514A. Element 1580 shows layers 1572, 1560, 1552 and 1540 aligned and stacked, in order from top to bottom, 1540 (top), 1552, 1560, 1572 (bottom). Conductive tape layers 1514A and 1514B are provided by folding conductive tape 1510 around element 1580 at fold 1516 (by analogy to FIG. 8A). Holes 1522, 1532 and 1518 are aligned so as to form a plurality of wells having well bottoms defined by element 1580. Through-holes 1562 through substrate 1560 provide an electrical path between conductive layer 1552 and contact layer 1572. Through holes 1512 through conductive tape layer 1514A provide access to contact layer 1572 (and, therefore a way to contact conductive layer 1552). Plate top 1520 is analogous to plate top 1020 from FIG. 10 except for the specific arrangement of wells. Adhesive layer 1530 is an adhesive analogous to adhesive layer 1030 in FIG. 10 and may be omitted. Conductive tape 1510 is analogous to conductive tape 810 as described in FIG. 8A. Substrate 1560, conductive layer 1552, dielectric layer 1540 and contact layer 1572 are similar in composition and preparation to substrate 1060, conductive layer 1050, dielectric layer 1040 and contact layer 1072 as described for FIG. 10. Conductive layer 1552 is sectioned into 6 square sections so as to divide plate 1500 into 6 independently addressable sectors (each having one well). Holes 1542 through dielectric layer 1540, define a large number (preferably 10-50,000, more preferably 100-10,000; 256 are shown in the figure) of fluid containment regions in each well. Binding reagents such as specific nucleic acid sequences or specific proteins can be selectively introduced and or immobilized into specific fluid containment regions by selectively microdispensing the binding reagents into the specific fluid containment regions.

While the figures illustrating embodiments of the plates of the invention have shown specific patterns for number, shape and distribution of wells, sectors and fluid containment regions/assay domains, it should be clear that the designs are adaptable so as to allow for a wide variation in these parameters.

5.3 Apparatus for Reading Multi-Well Assay Plates

Another aspect of the invention relates to an apparatus for measuring luminescence, preferably electrode induced luminescence, more preferably electrochemiluminescence, from a multi-well assay plate having a plurality of wells or a single-well plate having a plurality of assay domains within a single well. Although the apparatus is configured for electrode induced luminescence, such an apparatus can also be additionally configured to other luminescence assays such as chemiluminescence and/or fluorescence assays.

Preferably, the apparatus is adapted to measure light from at least a portion of the plurality of wells. Preferably, the portion comprises one or more, more preferably two or more, even more preferably four or more and most preferred eight or more, and, preferably, less then all, of the wells of the plate.

The apparatus may comprise a source of electrical energy for generating luminescence within at least a portion of the plurality of wells, preferably the source of electrical energy is applied as an electrical voltage or current to the portion of the plurality of wells. Preferably, the portion comprises one or more, more preferably two or more, even more preferably four or more and most preferred eight or more, and preferably less then all, of the wells of the plate. The source of electrical energy may include a power cable, power source, power generator, battery or other energy storage media or the like. Preferably, the source of electrical energy includes an electrical subsystem (for example, a current source, voltage source, or current and/or voltage waveform generator) capable of providing current and/or voltage to one or more of the plurality of wells. It is understood that the term "source of electrical energy" includes devices and apparatuses which require that such source be connected to an external power supply (e.g., a wall socket). According to one preferred embodiment, the source of electrical energy is capable of delivering a potential to the working electrode relative to the counter electrode of from 0 to +8 Volts DC. Preferably, the source of electrical energy has a voltage resolution less than or equal to 50 mV, preferably 20 mV, even more preferably 10 mV and most preferred 5 mV. According to another preferred embodiment, the source of electrical energy is capable of generating voltage waveforms consisting of ramps (constant dV/dt).

The apparatus may also include a support or plate holder adapted to hold the multi-well assay plate. Preferably, the support comprises a carrier (e.g., a drawer) adapted to carry the plate into and/or through the apparatus, preferably into and/or through a light tight enclosure within the apparatus.

According to another embodiment, the apparatus further comprises a motion control subsystem (preferably comprising one or more computers, linear actuators or translation tables having one, two, three or more axis of motion, and/or motors for driving the motion) for moving plates in and out of the apparatus and for correctly aligning the plate with light detectors and/or electrical contacts within the apparatus. Preferably, the motion control subsystem provides independent control of at least four stepper motors. Preferably, the motion control subsystem is capable of independently controlling the maximum plate carrier velocity. Moreover, the motion control subsystem preferably allows for controlled acceleration for each motion axis and/or provides integration of a plate position encoder on each motion axis and/or is adapted to allow the plate position of each axis to be verified using a position encoder. Preferably, the motion control subsystem provides for stall detection using a position encoder. The plate motion control subsystem preferably (i) has a movement resolution less than or equal to 0.01 inches, preferably less than or equal to 0.005 inches, even more preferably less than or equal to 0.001 inches, (ii) is capable of providing continuous motion of at least 1 inch per second, preferably at least 5 inches per second and/or (iii) is capable of placing the plate within a circular tolerance zone within within 0.01 inches, more preferably within 0.005 inches and even more preferably within 0.001 inches.

In one embodiment of the invention, the apparatus includes one or more electrical connectors (optionally included as part of a plate contact subsystem) adapted to connect the source of electrical energy to the wells and/or plate support. Preferably, the connectors are adapted to contact the bottom of the multi-well plate. Preferably, the apparatus comprises two or more electrical connectors, more preferably between 3 and 20 electrical connectors, even more preferably comprises six electrical connectors. The electrical connectors may be incorporated within a plate holder so that electrical connection to the plate is achieved by placing the plate in the plate holder or the electrical connectors may be in separate components. Alternately, some electrical connectors may be incorporated within the plate holder and some may be included in separate components.

According to one preferred embodiment, the apparatus comprises a 2×3 array of electrical connectors, preferably the 2×3 array comprises four working electrical connectors and two counter electrical connectors. According to another preferred embodiment, the apparatus comprises seven electrical connectors, preferably a linear array of seven electrical connectors, most preferably a linear array of four working electrical connectors and three counter electrical connectors. In another embodiment, one or more electrical connectors (preferably two or more, more preferably between 3 and 20) are incorporated within a plate holder so that electrical connection to the plate is achieved by placing the plate in the plate holder.

Preferably, the electrical connectors and/or plate contact subsystem are adapted to make contact to the bottom of an assay plate. Optionally, at least one electrical contact is made to the top or side of the plate. Preferably the upward movement of a plate due to force of the electrical contacts and/or plate contact subsystem is less than 0.010 inches. According to another embodiment, the plate contact subsystem has a minimum step resolution of at least 0.004 inches.

The emitted luminescence is preferably measured to determine, for example, the presence or absence or amount of analyte of interest in one or more samples. The apparatus may comprise a light detector for measuring the luminescence within at least a portion of the plurality of wells. Alternatively, the apparatus may comprise a structure (e.g., a slot or the like) for inserting or adjoining a suitable light detector such as film. Such an apparatus would include all the other components of the system, but the user would add the light detector. Preferably, such an apparatus would be adapted to be suitably mated with one or more light detectors.

One preferred embodiment of the invention incorporates a light detector for measuring emitted luminescence from at least a portion of the plurality of wells. Preferably, the apparatus includes both a light detector and a source of electrical energy for generating luminescence, more preferably electrochemiluminescence, within the plurality of wells and a light detector for measuring emitted luminescence. Advantageously, such an apparatus may also include the electrical connectors adapted to connect the source of electrical energy to the wells.

One aspect of the invention relates to apparatus capable of measuring luminescence and/or generating luminescence in sectors. For example, the apparatus may induce luminescence and/or measure emitted luminescence in less than the entire plate and/or less than all of the wells on the plate. The term "sector" as used herein is defined as independently addressable sectors of jointly addressable wells. Preferably, a "sector" comprises one or more wells, two or more wells, less than all the wells, and/or less than 50% of the wells.

Thus, one embodiment of the invention relates to an apparatus for measuring luminescence from a multi-well assay plate having a plurality of independently addressable sectors of jointly addressable wells.

According to one embodiment, the apparatus includes one or more electrical connectors adapted to connect the source of electrical energy to the independently addressable sectors. Preferably, the apparatus also includes a plate holder for holding the plate and the electrical connectors and the plate holder are adapted to move relative to one another to allow for sequentially contacting the sectors. In an alternate embodiment, one or more electrical connectors (preferably between 3 and 20) are incorporated within the plate holder so that electrical connection to one or more sectors of the plate is achieved by placing the plate in the plate holder.

According to one embodiment, the apparatus comprises a plate holder adapted to hold the plate onto a measuring platform or a detection location (e.g., where the luminescence is induced and/or detected) during the detection step and a plurality of electrical connectors adapted to contact the plate, thereby providing electrical energy to the wells. Preferably, the electrical connectors contact the bottom surface of the plate. Advantageously, the contacting occurs between the wells, preferably by pushing against the well walls, i.e., where the plate is most rigid.

The apparatus may include a plate holder adapted to hold the plate onto a measuring platform during the measuring. This is advantageous when the electrical connectors contact the plate bottom since the holder may be configured to hold the plate down and/or to prevent the contacts from lifting the plate. This is important, for example, when an imaging system is employed to image the luminescence from the wells. If the connectors were allowed to lift or otherwise move the plate, the image may be distorted.

According to another embodiment, the apparatus comprises a light detector and a support adapted to hold the multi-well assay plate, wherein the light detector and the support are adapted to move relative to one another to allow for sequentially measuring the sectors.

Another aspect of the invention involves the use of an imaging system to image emitted luminescence. Preferably, the apparatus further comprises a computer image analyzer. According to one preferred embodiment, the computer has software for subtracting background light and/or eliminating cosmic ray induced artifacts and/or any defects in the photodetector.

One embodiment of the invention relates to an apparatus for measuring luminescence from a multi-well assay plate having a plurality of wells comprising:
 (a) an imaging system comprising a camera, the imaging system adapted to image at least a portion of the plurality of wells and thereby measure the luminescence; and
 (b) a source of energy for generating luminescence within at least a portion of the plurality of wells, the source of electrical energy applied as an electrical voltage or current to the portion of the plurality of wells.

Another relates to an apparatus for measuring luminescence from a multi-well assay plate having a plurality of wells comprising:
 (a) an imaging system comprising a camera, the imaging system adapted to image at least a portion of the plurality of wells and thereby measure the luminescence; and
 (b) a source of electrical energy adapted to provide electrical energy to the plurality of wells in sectors.

Another embodiment of the invention relates to an apparatus for measuring luminescence from a multi-well assay plate having a plurality of wells comprising:
 (a) an imaging system comprising a camera, the imaging system adapted to image the plurality of wells in sectors and thereby measure the luminescence in sectors; and
 (b) a source of electrical energy, the source of electrical energy applied as an electrical voltage or current to the portion of the plurality of wells.

Accordingly, the invention includes an apparatus for measuring luminescence from a multi-well assay plate having a plurality of wells comprising an imaging system comprising a camera, the imaging system adapted to image at least a portion of the plurality of wells of the multi-well assay plate. Preferably, the apparatus further comprises a support adapted to hold the multi-well assay plate in a detection position where the camera can image the portion. Advantageously, the camera and/or the support are adapted to image the plurality of wells in sectors and thereby measure the luminescence. Preferably, the apparatus further comprises a camera mounting system for positioning the camera and/or any associated optics (e.g., lenses). Preferably, the camera mounting system maintains the camera imaging surface of an imaging system and/or the associated optics perpendicular to the multi-well plate within plus or minus 5 degrees, more preferably within plus or minus 3 degrees, even more preferably within plus or minus 2 degrees and most preferably within plus or minus 1 degree.

Providing an apparatus, method and plate, which enables the luminescence to be measured in sectors, allows for greater light collection efficiency. Accordingly, one preferred embodiment of the invention relates to an apparatus comprising an imaging system adapted to simultaneously image emitted luminescence from at least two of the plurality of wells, wherein the imaging collects a cone of luminescence having a cone full angle of at least 10 degrees, preferably at least 15, more preferably at least 20, even more preferably at least 25, and most preferred at least 30 degrees.

According to another embodiment, the apparatus further comprises a support adapted to hold the multi-well assay plate in a detection position and/or electrical connectors adapted to connect the multi-well assay plate to the source. Preferably, the apparatus is adapted to connect the electrical connectors to a plurality of sectors and/or image the plurality of sectors sequentially.

Another aspect of the invention relates to an apparatus or method, which employ an array of light detectors, preferably an array of discrete light detectors such as an array of photodiodes.

Thus, one embodiment of the invention relates to an apparatus for measuring luminescence from a multi-well assay plate having a plurality of wells comprising:
(a) an array of light detectors adapted to detect light from at least a portion of the multi-well assay plate, preferably in sectors; and/or
(b) a source of electrical energy for providing electrical energy to the multi-well plate, preferably in sectors;
wherein the apparatus preferably induces and/or measures the luminescence in sectors.

Another embodiment relates to an apparatus further comprising:
(a) a support adapted to hold the multi-well assay plate in a detection position; and/or
(b) electrical connectors adapted to connect the sector of the multi-well plate to the source;
    wherein the apparatus is preferably adapted to connect the electrical connectors to the plurality of sectors and/or detect luminescence from the plurality of sectors sequentially.

Preferably, wherein the apparatus is adapted to allow the array of light detectors to move relative the support so as to allow for alignment of each sector with the array of detectors.

According to a preferred embodiment, the apparatus comprises one detector per well per sector. Preferably, the array of light detectors is adapted to be aligned with an array of wells. For example, referring to FIG. 1, a linear array of eight appropriately sized photodiodes could be aligned with a row of wells. Preferably the light detector array is a linear array, which can be linearly scanned across the plate.

According to another embodiment, the apparatus is adapted to use modules (preferably plates) where the working electrode and/or the counter electrode on the module is replaced with one or more probes provided by the apparatus, preferably an array of working electrode probes and/or counter electrode probes, which are inserted into the wells to provide electrical energy to the wells. A single probe could be aligned and arranged so as to provide electrical energy to one well of a multi-well plate at a time or an array of probes could be used to provide electrical energy to a plurality of wells (e.g., the array could be used to provide electrical energy to one group of wells and then be moved to provide electrical energy to a different group of wells). Preferably, the probes comprise one or more fiber optic probes coated in an electrode material so as to function both as electrodes (preferably a counter electrode) and conduits for conveying light generated in wells to one or more light detectors in the apparatus.

According to one preferred embodiment, the apparatus further comprises one or more robotic and/or computer systems adapted to perform one or more of the following functions: (i) moving assay modules; (ii) shaking the assay modules (and assay contents therein); (iii) storing plates (e.g., refrigeration unit); (iv) liquid or reagent handling (e.g., mixing reagents); and (v) reagent delivery (e.g., dispensing reagents into wells, etc.).

FIG. 17 illustrates an embodiment of the apparatus of the present invention. Reader 1700 comprises a cover (or case) 1702, a light tight enclosure 1704 with one or more doors and/or apertures 1714, a photodetector 1706, optics 1708, multi-well assay plate 1710, plate alignment mechanism 1712, plate transport mechanism 1716, bar code reader 1718, electronics 1720, current/voltage source 1722, plate electrical connector 1724, computer 1726, power supply 1728, data and network connections 1730, indicators 1732, reagent handler 1734, one or more plate stackers 1736, robotics 1738, and plate carrier 1740. Preferably, the majority of cover 1702 is a molded structure made from rigid plastic materials such as polyurethanes, structural foams, ABS, polystyrenes, polypropylene, polycarbonates and the like. Cover 1702 may also incorporate metals (e.g., aluminum, brass, steel), composites (e.g. carbon fiber composites, polymer composites), and/or carbon based materials. Cover 1702 may also be painted; conductive paints (e.g., paints containing metal flake) may be used to reduce electromagnetic interference (i.e., as EMI shielding). The cover, preferably, functions to enclose, support and protect certain elements of the reader. The cover may incorporate vents or other openings and may also include one or more fans for cooling the instrument and/or for maintaining the circulation of air through the instrument. In a preferred embodiment the cover provides separate intake and exhaust vents for cooling photodetector 1706.

Light tight enclosure 1704 is a sealed compartment designed to prevent the entrance or exit of light. Preferably, the majority of light tight enclosure 1704 is comprised of a rigid material such as steel or aluminum. In a preferred embodiment, light tight enclosure 1704 is comprised of aluminum sheet metal. Light tight enclosure 1704 may also incorporate non-rigid or compliant materials. In a preferred embodiment, light tight enclosure 1704 contains a compliant closed cell foam gasket that acts as a seal to prevent passage of light. Light tight enclosure 1704 has one or more doors and/or apertures 1714 and through which multi-well assay plates of the invention may pass during operation of the reader. Aperture 1714 incorporates a door that opens to allow transport of multi-well assay plates into and out of the reader. The door opens and closes by sliding along a tongue and groove configuration at the junction between the door and aperture 1714. The tongue and groove configuration provides a tortuous path that reduces transmission of light. The movement of the door or aperture 1714 is mechanically driven by a linear actuator that is controlled by computer 1726 and electronics 1720. Light tight enclosure 1704 is joined to optics 1708, or if optics 1708 are omitted, to photodetector 1706. Enclosure 1704 provides a compliant coupling between optics 1708 (or photodetector 1706) that allows focusing of the emitted light onto the photodetector (e.g., by focusing a lens) without disrupting the light tight enclosure. This compliant coupling may include one or more baffles, light tight seals or light tight flexible housings. In a preferred embodiment, the flexible coupling is a slipping light tight seal comprised of a silicone gasket or layer. According to another preferred embodiment, the coupling comprises flexible, light-tight bellows (preferably made of neoprene) at the lens-light tight enclosure interface. The bellows allows easier focusing and motion of the lens while still providing a light tight seal. Light tight enclosure 1704 can be dismantled without disturbing the optics 1708 and/or photodetector 1706. The walls of the light tight enclosure are preferably black to reduce reflection of light. Preferably, the light tight enclosure is adapted to provide at least a degree of external light rejection so that a change in ambient light level from 500 lux to 0 lux does not increase the apparent coefficient of variation in background signal by more than 20%, more preferably by more than 15%, even more preferably by more than 10% and most preferred by more than 5%.

Photodetector 1706 primarily measures the light emitted from multi-well assay plates during the conduct of electrochemiluminescent assays in reader 1700. Photodetector 1706 is preferably one or more photodetectors that measure the intensity of light or one or more photodetectors that image the emitted light. Examples of photodetectors include cameras, photodiodes, avalanche photodiodes, CCD chips, CCD cameras, photomultiplier tubes, CMOS detectors, film, phosphorescent materials, and intensifiers. Photodetectors may be cooled to decrease background signals. In a preferred embodiment, photodetector 1706 is an array of photodiodes. In another preferred embodiment, photodetector 1706 is a charge coupled device (CCD) camera. Photodetector 1706 is connected to computer 1726 and electronics 1720. Photodetector 1706 may be joined to optics 1708 and/or to light tight enclosure 1704. Photodetector 1706 may also incorporate control electronics, connectors and high speed cables for efficient transfer of images to electronics 1720 and computer 1726. The active surface of photodetector 1706 (or the imaging surface when photodetector 1706 is an imaging detector such as a CMOS or CCD chip) is preferably matched to the size of the object (e.g., individual well, multi-well assay plate sector or multi-well assay plate) being imaged so as to balance the requirements for light capturing efficiency and the spatial resolution of the recorded image with the cost and size of the detector (and associated optics). Preferably, the area of the active surface or imaging surface of the photodetector is 25% to 200% of the area being detected or imaged or more preferably between 50% and 100%. In a preferred embodiment of an imaging detector adapted to image a standard multi-well assay plate in six square sectors, the area of the imaging detector (e.g., a CCD or CMOS chip) is between 0.95 sq. in. and 2.0 sq. in. or more preferably between 0.95 and 1.2 sq. in. In an alternate embodiment, a smaller imaging detector may be used without significant loss in light capturing efficiency or resolution by including a tapered fiber optic bundle in optics 1708. For example, optics 1708 may include a combination of a lens, preferably a telecentric lens, that projects an image having an area of preferably between 25% and 100% (more preferably, between 50% and 100%) of the area being imaged and a tapered fiber optic bundle to reduce this image to the size of the imaging detector.

Optics 1708 generally collect light emitted from multi-well assay plate 1710 and focus that light on photodetector 1706. Optics 1708 may include, for example, elements that transmit, scatter, block, filter, modify, diffract, refract, and/or reflect light. Optics 1708 may also include physical/mechanical elements that provide structural support or couple the optical elements to other elements of reader 1700. Examples of elements include lenses, prisms, filters, splitters, mirrors, optical fibers, optical couplers, optical epoxies and adhesives, windows, modulators, optical coatings and the like. In a preferred embodiment, optics 1708 comprises a telecentric lens to achieve uniform collection of light over a large area (which may otherwise be imaged in a distorted manner by optics using non-telecentric lenses). The diameter of the lens (especially the front lens element of a multi-element lens) is, preferably, matched to the size of the object (e.g., multi-well assay plate sector) being imaged so as to balance the requirements for minimal distortion and maximal light capturing efficiency with the cost of the lens. In a preferred embodiment of the lens adapted to image a standard multi-well assay plate in six square sectors, the diameter of the lens or the first lens element in a compound lens is between 3.0" and 5.0" or more preferably between 3.5" and 4.5" or most preferably between 3.9" and 4.3". The lens, preferably, has a light capture efficiency of greater than 2% or more preferably, greater than 5% for hemispherical radiation from point sources in the object plane. The full cone angle for accepted light from the object plane is, preferably greater than 10%, more preferably greater than 15%, even more preferably greater than 20%, even more preferably greater than 25% or, most preferably, greater than 30%. In another embodiment, optics 1708 comprises one or more optical fibers or an optical fiber array. In another preferred embodiment, optics 1708 comprise a window and/or a filter and do not focus light on photodetector 1706. In another embodiment, optics 1708 comprise a lens and fiber optic bundle (e.g. a tapered fiber optic bundle). Optics 1708 may comprise a compliant coupling that allows focusing without disrupting the light tight properties of the connection between optics 1708 and light tight enclosure 1704. Optics 1708 may optionally include filters designed to maximize the collection of a desired luminescent signal relative to background light. In a preferred embodiment, optics 1708 includes filters designed to selectively pass the luminescence generated from transition metal labels, particularly ruthenium-tris-bipyridine labels. Preferably, the optics in such a system would block light the majority of light with a wavelength greater than 800 nm (or, more preferably, 750 nm) and optionally light with a wavelength less than 500 nm (or, more preferably, 550 nm). The filter elements may, optionally, be removable or replaceable. According to one preferred embodiment, the filter has a band pass characteristic with a long wavelength cutoff (50% transmission) of 750 nm+/−25 nm and a short wavelength cutoff less than 550 nm and/or has an average pass band transmission greater than 80%. According to another embodiment, the apparatus comprises a filter covering the light detector(s) (e.g., a dichroic, interference and/or absorbance filter). For example, the light detector may be an array of light detectors comprising an array of silicon photodiodes covered by filters (e.g., dichroic, interference and/or absorbance filters).

Plate transport mechanism 1716 moves multi-well assay plates into, within and out of reader 1700. Plate transport mechanism 1716 comprises a plate carrier 1740 that holds the multi-well assay plates during transport, one or more linear translation stages that move the plate carrier 1740, one or more magnetizable (preferably, reversibly magnetizable) tabs, sensors, and a variety of mechanisms that align and/or hold the multi-well assay plate to the carrier. Plate transport mechanism 1716 is primarily composed of metal and plastic. In one embodiment, plate transport mechanism 1716 moves plates 1710 from plate stacker 1736 through aperture 1714 into light tight enclosure 1704 and visa versa. In an example of operation, one or more multi-well assay plates are loaded into plate stacker 1736. Under computer control, plate transport mechanism 1716 and an elevator in plate stacker 1736 are moved to the home position, which is verified by sensors. Plate transport mechanism 1716 is translated out of light tight enclosure 1704 through aperture 1714 into plate stacker 1736. The movement of plate transport mechanism 1716 brings plate carrier 1740 into contact with elements that retract a spring loaded rear slider and rotates a spring loaded positioning element located on plate carrier 1740, readying plate carrier 1740 to receive a multi-well assay plate. An elevator in plate stacker 1736, driven by a motor, raises the stack of plates. A spring loaded latch in stacker 1736 is opened by a solenoid, allowing the elevator in plate stacker 1736 to lower the stack of plates until one plate 1710 (on the bottom of the stack) has passed through the latch. The spring loaded latch then closes, and the stacker continues to lower the plate 1710 until plate 1710 is placed in the plate carrier 1740 of plate transport mechanism 1716. A sensor, preferably an infrared sensor, verifies that plate 1710 is on plate carrier 1740. As the plate transport mechanism 1716 moves plate carrier 1740 out of plate stacker 1736, the spring loaded positioning element releases and pushes plate 1710 to register it against one side of plate carrier 1740. The spring loaded rear slider also releases, covers part of the rear lip of plate 1710 and pushes plate 1710 against another side of plate carrier 1740. Optionally, plate transport mechanism 1716 retracts plate carrier 1740, which actuates a pin that holds plate 1710 tightly to the plate carrier 1740 such that upward vertical force applied to the bottom of plate 1710 (for example, in an attempt to make good electrical contact with electrical connector 1724) does not move the plate. Plate transport mechanism 1716 moves plate carrier 1740 through aperture 1714 into light tight enclosure 1704. Aperture 1714 closes and plate transport mechanism 1716 translates plate 1710 to bar code reader 1718, which identifies plate 1710. Plate 1710 is translated until the first sector of plate 1710 is aligned with optics 1708 and plate electrical connector 1724. After one or more electrochemiluminescent assay measurements are conducted, plate transport mechanism 1716 then removes plate 1710 from light tight enclosure 1704 by using a similar set of steps that may be conducted in a different order. In another embodiment, individual plates 1710 are placed in plate carrier 1740 (for example, manually or by robotics 1738). The motion of plate carrier 1740 is accomplished by one or more linear actuators. In one embodiment, the actuators are driven with a stepper motor in an open loop configuration. The plate is moved to specific locations when computer 1726 instructs the stepper motor to move a specified number of steps. In another embodiment, the motion of plate carrier 1740 in plate transport mechanism 1716 is driven by DC motors using a closed feedback loop controlled by computer 1726.

The movement and position of plate 1710 in plate carrier 1740 is verified by plate alignment mechanism 1712. Plate alignment mechanism 1712 uses one or more sensors to verify certain positions of plate carrier 1740 and/or to set a reference point for its position. The sensors can be, for example, mechanical sensors, optical sensors, electrical sensors, magnetic sensors or other sensors known for sensing position of an object accurately. In a preferred embodiment, plate alignment mechanism 1712 incorporates a Hall effect sensor that senses one or more magnetizable (preferably, reversibly magnetizable) tabs (made, for example, from magnetizable steel) on plate carrier 1740 or on one or more axis of plate transport mechanism 1716 (the tab being sensed when it travels in between the Hall sensor and a magnet mounted opposite the Hall sensor, thus blocking the effect of the magnet on the sensor). The tab and Hall sensor may be used to detect when plate transport mechanism 1716 is in the "home" position and may thus be used to determine the true position of plate transport mechanism 1716. In another preferred embodiment, plate alignment mechanism incorporates an infrared sensor that senses the interruption of light between an infrared light source and an infrared light detector when plate 1710 and/or plate carrier 1740 interrupt the path of the infrared light. Plate alignment mechanism 1712 may also include a sensor that verifies that the stepper motor has conducted a specified number of steps and/or to verify that the stepper motor has not stalled. In a preferred embodiment, this sensor comprises an optical encoder. In another preferred embodiment, plate alignment mechanism 1712 incorporates a pressure switch to detect the corner chamfer of a plate (e.g., the chamfers on the top and bottom left corners of plate top 932 in FIG. 9A). The presence or absence of the chamfer determines the orientation of the plate in plate carrier 1740. If the sensor determines that the plate is in the incorrect orientation, computer 1726 may instruct the instrument to stop the run, skip the plate or, more preferably, to read the plate but to transpose the data so as to correct for the mis-orientation (thus preventing costly delays or loss of precious samples).

Bar code reader 1718 is used in the reader 1700 to identify specific multi-well assay plates. The bar code reader is preferably a fixed position laser bar code scanner, for example, an Opticon Series NLB 9625/9645. Electronics 1720 participate in the operation, controlling, and monitoring of one or more electronic and/or mechanical elements in reader 1700. Electronics 1720 may comprise a variety of components typically encountered in devices, for example, wires, circuits, computer chips, memory, logic, analog electronics, shielding, controllers, transformers, I/O devices, and the like. Current/voltage source 1722 is an electrical circuit capable of generating defined voltage waveforms and/or defined current waveforms. Current/voltage source 1722 is connected to electronics 1720, computer 1726 and plate electrical connector 1724. In one embodiment of the invention, current/voltage source 1722 includes a potentiostat. The potentiostat is advantageous for reading plates that include independent reference electrodes and allows the potentials at the working and/or counter electrodes to be referenced relative to the potential at the reference electrode.

Plate electrical connector 1724 makes contact with multi-well assay plate 1710 to allow the application of current and/or voltage waveforms by current/voltage source 1722. Plate electrical connector 1724 comprises one or more connectors, electrical connections, a linear actuator and, optionally, a support. In a preferred embodiment, the connectors are spring loaded to improve electrical contact with plate 1710. Connectors may be made of any suitable material that has a conducting outer surface. Preferably, they are sufficiently durable to withstand repeatedly making contact with plates. Typically, the connectors are comprised of a hard metal or metal alloy coated with a highly conducting metal film (e.g. gold or silver). In a preferred embodiment, connectors include a waffle-point contact head comprised of gold plated nickel/silver, spring loaded on a gold plated stainless steel spring in a nickel/silver receptacle, for example, connectors offered by Interconnect Devices, Inc. (GSS-18.3.8-G). In an alternative embodiment, connectors are comprised of a compliant material coated with a highly conducting material. The support for the connectors may be comprised of any material that can support the connectors when the connectors are pushed against plates. In a preferred embodiment, the support in plate electrical connector 1724 is comprised of a circuit board, preferably with traces that electrically connect the connectors to current/voltage source 1722 and/or electronics 1720. Plate electrical connector 1724 may include a sensor (in a preferred embodiment, a Hall sensor) that verifies the home position. Plate electrical connector 1724 may also incorporate a thermal sensor (e.g., a thermister, a thermocouple, a platinum RTD), which in a preferred embodiment, is spring loaded on the support of plate electrical connector 1724. In one embodiment, the thermal sensor makes contact with a multi-well assay plate 1710 to measure its temperature. The linear actuator in plate electrical connector 1724 pushes the connectors (and optionally the support) into plate 1710 to make electrical connections.

Advantageously, the apparatus includes a temperature sensor or thermometer adapted to measure the temperature of a plate. Preferably, the temperature sensor or thermal sensor can detect the well temperature within 5° C., more preferably within 3° C., even more preferably within 1° C. and most preferred within 0.25° C. Even more preferably, the temperature sensor can reach steady state within ten seconds, preferably within five seconds, even more preferably within three seconds. The sensor may be a contact sensor (e.g., a thermister, a thermocouple, or a platinum RTD). Alternatively it may be a non-contact sensor such as an IR sensor. In a preferred embodiment, the apparatus comprises one or more non-contact temperature sensors and the apparatus is adapted to be able to measure the temperature of various locations on the plate (e.g., through the use of multiple sensors and/or by moving the plate relative to the sensors). In another preferred embodiment, the apparatus further comprises a computer adapted to receive the signal from a temperature sensor, report the temperature to the user and, preferably, adjust the measured luminescence signals to account for the effects of temperature on luminescent signals, electrochemiluminescent signals, and/or other reactions occurring during the conduct of an assay. The computer, preferably, further comprises memory for saving data and/or calibration curves from calibration measurements conducted at a variety of temperatures and software for using said data and/or calibration curves to normalize test data against variations in temperature. According to another embodiment, the apparatus also comprises a temperature controller to control the temperature within the well. According to yet another embodiment, the apparatus is adapted to reject or otherwise flag an assay plate (e.g., with an indication of a software error or warning or the like) if the temperature detected is outside a specified range.

Computer 1726 participates in the operation, controlling, managing of data, and monitoring of reader 1700 and/or other peripheral devices. It is preferably comprised of a computer, a display, user input devices, data storage devices, I/O devices, networking devices, ethernet connections, modems, optical connections, software and the like. Power supply 1728 supplies electrical power to reader 1700 and/or other devices. Data and network connections 1730 may comprise connections, hardware, buses and the like. Data and network connections 1730 may be, for example, RS-232 ports, USB ports, PCMCIA cards, PCI boards, ethernet cards, modems and the like. Indicators 1732 provide information on the operation and/or status of reader 1700 and may be, for example, lights, gauges, audible devices or devices that send and/or receive signal to/from computer 1726.

Reagent handler 1734 is one or more devices that add or remove reagents to multi-well assay plates. In a preferred embodiment, reagent handler 1734 is a pipetting station. Robotics 1738 may comprise one or more electromechanical devices that transport, incubate and/or mix multi-well assay plates and the contents of their wells. Plate stacker 1736 comprises one or more containers for holding one or more multi-well assay plates and, advantageously, electrical and/or mechanical systems for moving plates. Plate stackers may also comprise mechanisms such as latches, positioning elements, sliders, grabbers, push arms, etc., that can be used to control the movement and position of plates. Plate stackers may have features that aid in the alignment and/or orientation of plates. Many plate stackers are known in the art.

In the use of reader 1700, one or more multi-well assay plates containing assay reagents in one or more wells are loaded into the input stack of plate stacker 1736. (All of the following steps are under control of computer 1726 and electronics 1720.) Plate stacker 1736 and plate transport mechanism 1716 move a multi-well assay plate 1710 from the input stack of plate stacker 1736 into plate carrier 1740, transport plate 1710 through input aperture 1714 and into light tight enclosure 1704 as described above. Aperture 1714 closes and plate transport mechanism 1716 translates plate 1710 to bar code reader 1718, which identifies plate 1710. Plate 1710 is translated until the first sector of plate 1710 is aligned with optics 1708 and plate electrical connector 1724. Photodetector 1706 acquires and, preferably, stores a background image and sends data to computer 1726. Plate electrical connector 1724 pushes against multi-well assay plate 1710 to bring the contacts of electrical connector 1724 into electrical contact with the first sector of plate 1710. Photodetector 1706 begins to acquire an image and current/voltage source 1722 generates a waveform that is applied to plate 1710 by plate electrical connector 1724. After completion of the waveform and image, the data are transferred from photodetector 1706 and electronics 1720 to computer 1726 where they are processed. Plate electrical connector 1724 lowers away from plate 1710 to break electrical contact; a sensor verifies when plate electrical connector 1724 is fully lowered. Plate transport mechanism 1716 translates plate 1710 so that the next sector (if another sector is to be measured) becomes aligned with optics 1708 and plate electrical connector 1724 and the process of making contact and acquiring a measurement are repeated. Reader 1700 continues to repeat these steps until all desired measurements have been completed. Alternatively, more than one sector may be contacted, fired and/or read at a time. In another alternate embodiment, the entire plate is fired and read at the same time. After the final measurement, plate electrical connector 1724 is lowered and output aperture 1714 is opened. Plate transport mechanism 1716 translates plate 1710 out of light tight enclosure 1704 through output aperture 1714 and into the output stack of plate stacker 1736. The movement of plate transport mechanism 1716 brings plate carrier 1740 into contact with elements that retract a spring loaded rear slider and rotates a spring loaded positioning element located on plate carrier 1740, readying plate 1710 to be removed from plate carrier 1740. Plate transport mechanism 1716 and plate stacker 1736 move plate 1710 from plate carrier 1740 to the output stack of output stacker 1736. A sensor, preferably an infrared sensor, verifies that plate 1710 is out of plate carrier 1740. Plate transport mechanism 1716 translates plate carrier 1740 out of plate stacker 1736, through output aperture 1714 into light tight enclosure 1704 and into home position. If desired, the process repeats to read another plate.

In another embodiment of the use of reader 1700, robotics 1738 are used to introduce plates into the input stack of plate stacker 1736. When measurements from a given multi-well assay plate are complete, it is returned to plate stacker 1736 and removed by robotics 1738.

In some embodiments of reader 1700, one or more of cover 1702, optics 1708, multi-well assay plate 1710, bar code reader 1718, data and network connections 1730, indicators 1732, reagent handler 1734, plate stacker 1736 and/or robotics 1738 may be omitted. In another embodiment of reader 1700, bar code reader 1718 is replaced with another device for identifying plates, for example, a scanner, a camera, a magnetic strip reader, or the like. In another embodiment of reader 1700, one or more components such as computer 1726, power supply 1728, data and network connections 1730, reagent handler 1734, plate stacker 1736 and/or robotics 1738 are positioned inside cover 1702.

In another embodiment of reader 1700, a plurality of light tight enclosures 1704, photodetectors 1706, optics 1708, plate alignment mechanisms 1712, plate transport mechanisms 1716, bar code readers 1718, electronics 1720, current/voltage sources 1722, plate electrical connectors 1724, plate stacker 1736 and/or robotics 1738 are combined within a single reader to provide additional capabilities such as improved speed, throughput and efficiency.

FIG. 18 shows a preferred embodiment of reader 1700 in which selected elements of reader 1800 are illustrated. Reader 1800 illustrates a light tight enclosure 1804, photodetector 1806, optics 1808, plate transport mechanism 1816, plate electronics 1820, input plate stacker 1836A, output plate stacker 1836B, input plate stack 1837A, output plate stack 1837B, and output door and/or aperture 1814B. Preferably photodetector 1806 comprises a cooled CCD camera and optics 1808 comprise a telecentric lens. Plate stacks 1837A and 1837B can preferably hold between 1 and 50 96-well plates and between 1 and 75 384-well plates.

FIG. 19 illustrates selected elements of another embodiment of reader 1700. Light tight enclosure 1904 is coupled to optics 1908, which comprise a lens and a filter (e.g., a filter designed to selectively pass luminescence from ruthenium-tris-bipyridine labels). Optics 1908 is coupled to photodetector 1906 which, preferably, comprises a CCD chip 1907. Door and/or aperture 1914 is present as part of light tight enclosure 1904. Plate 1910, with sectors 1910A, 1910B, and 1910C, is held in plate carrier 1940 attached to plate transport mechanism 1916. Plate electrical connector 1924 moves plate electrical connector contacts 1925 up and down to make and break contact, respectively, with contact surfaces in a sector of plate 1910. In the position illustrated in FIG. 19, connector contacts 1925 are in electrical contact with sector 1910A of plate 1910. Plate transport mechanism 1916, together with plate alignment mechanism (not illustrated) have aligned plate 1910, and in particular, sector 1910A appropriately with optics 1908, plate electrical connector 1924 and plate electrical connector contacts 1925. In another embodiment, plate electrical connector contacts 1925 are not in contact with plate 1910, and plate transport mechanism 1916 can translate plate 1910 such that another sector (e.g., sector 1910B or 1910C) are aligned with optics 1908 and plate electrical connector 1924 and plate electrical connector contacts 1925. Plate carrier 1940, preferably, holds plate 1910 such that plate 1910 resists the upward force exerted by plate electrical connector allowing plate electrical connector contacts 1925 to apply sufficient pressure to plate contacts on plate 1910 to achieve electrical contact with low contact resistance. In a preferred embodiment, this contact resistance is less than 10 ohms. In another preferred embodiment, the contact resistance is less than 10 ohms, preferably less than 5 ohms, more preferably less than 2 ohms, even more preferably less than 1 ohm and most preferred less than 0.5 ohms.

FIG. 20 illustrates selected elements of another embodiment of reader 1700. Photodetector 2056 with imaging element 2057 is coupled to optics 2058 comprising a telecentric lens and a filter element 2059. Multi-well assay plate 2042, with sectors 2042A, 2042B, 2042C, 2042D, 2042E and 2042F is held by plate carrier 2040 attached to plate transport mechanism 2047 (shown in part). In FIG. 20, optics 2058 collect an image of sector 2042A and focus that image onto imaging element 2057 of photodetector 2056. In a preferred embodiment, sector 2042A has an area equivalent to $\frac{1}{6}$ the area of a standard 96-well microplate and optics 2058 and imaging element 2057 have dimensions appropriate for imaging such a sector. In an especially preferred embodiment, optics 2058 is a telecentric lens with a diameter of approximately 4.1" and imaging element 2057 is a CCD chip with dimensions of approximately 1 inch by 1 inch. Preferably, optics 2058 collect light from sector 2042A uniformly and with reasonable efficiency. Plate transport mechanism 2047 can translate plate 2042 such that another sector (e.g. sector 2042B, etc.) is aligned with optics 1908.

In another embodiment of FIG. 17, reader 1700 comprises a cover 1702, a light tight enclosure 1704 with a door and/or aperture 1714, a photodetector 1706, optics 1708, multi-well assay plate 1710, plate alignment mechanism 1712, plate transport mechanism 1716, electronics 1720, current/voltage source 1722, plate electrical connector 1724, computer 1726, power supply 1728, data and network connections 1730, indicators 1732, reagent handler 1734, one or more plate stacker 1736, plate carrier 1740 and robotics 1738.

Photodetector 1706 is preferably an array of photodiodes, and more preferably, a linear array of eight photodiodes spaced to align with the eight wells in a row of wells in a 96-well plate. Photodetector 1706 further comprises a circuit board on which the photodiodes are mounted. The photodiodes of photodetector 1706 preferably have a conductive shield (most preferably made of brass) to reduce EMI. The photodiode printed circuit board preferably resides in metal case (e.g., an aluminum case) to reduce EMI. Optics 1708 preferably comprise an optical filter and/or optical coating, and a thin shield to reduce optical crosstalk and the measurement of background or non-specific light signals. In a preferred embodiment, the light detector is an array of light detectors comprising an array of photodiodes covered by dichroic, interference and/or absorbance filters (the filters, preferably, being designed to exclude infra red light, most preferably light with a wave length greater than 750 nm and, optionally, light with a wave length shorter than 550 nm).

During a measurement, photodetector 1706 and optics 1708 are in close proximity to multi-well assay plate 1710.

Light tight enclosure 1704 is a sealed compartment designed to prevent the entrance or exit of light. Aperture 1714 incorporates a door that opens to allow transport of multi-well assay plates into and out of the light tight enclosure. The door opens and closes by sliding along a tongue and groove configuration at the junction between the door and aperture 1714 that provides a tortuous path that reduces transmission of light. The movement of the door in aperture 1714 is mechanically driven by an actuator (e.g., a linear actuator and/or a belt driven by a motor such as a stepper motor) that is controlled by computer 1726 and electronics 1720. The door in aperture 1714 can also be activated by pressing a touch button. Light tight enclosure 1704 encloses photodetector 1706, plate carrier 1740, plate 1710 and the connector contacts of electrical contact mechanism 1724. The walls of the light tight enclosure are preferably black to reduce reflection of light.

Plate transport mechanism 1716 moves multi-well assay plates within the reader 1700. Plate transport mechanism comprises a plate carrier 1740 that holds the multi-well assay plates during transport, a linear translation stage that move the plate carrier 1740, one or more magnetizable (preferably, reversibly magnetizable) tabs, sensors, and a variety of mechanisms that align and/or hold the multi-well assay plate to the carrier. Plate transport mechanism 1716 translates plate carrier 1740 along a single axis within light tight enclosure 1704. Plate 1710 is translated so that a sector of plate 1710 can be aligned with photodetector 1706 and plate electrical connector 1724. The motion of plate carrier 1740 is accomplished by an actuator (e.g., a linear actuator and or a belt driven by a motor such as a stepper motor) located outside the light tight enclosure 1704. In one embodiment, the actuators are driven with a stepper motor in an open loop configuration. The plate is moved to specific locations when computer 1726 instructs the stepper motor to move a specified number of steps. In another embodiment, the motion of plate carrier 1740 in plate transport mechanism 1716 is driven by DC motors using a closed feedback loop controlled by computer 1726. Individual plates 1710 are placed in plate carrier 1740 (for example, manually or by robotics 1738).

The movement and position of plate 1710 in plate carrier 1740 is verified by plate alignment mechanism 1712. Plate alignment mechanism 1712 incorporates a Hall effect sensor that verifies certain positions of plate carrier 1740 and/or sets a reference point for its position (i.e., by sensing one or more magnetizable (preferably, reversibly magnetizable) tabs (made, for example, from magnetizable steel) on plate carrier 1740 or on one or more axis of plate transport mechanism 1716 (the tab being sensed when it travels in between the Hall sensor and a magnet mounted opposite the Hall sensor, thus blocking the effect of the magnet on the sensor). Alternatively, plate alignment mechanism 1712 incorporates an infrared sensor that senses the interruption of light between an infrared light source and an infrared light detector when plate 1710 and/or plate carrier 1740 interrupt the path of the infrared light. Plate alignment mechanism 1712 may also include a sensor that verifies that the stepper motor has conducted a specified number of steps and/or to verify that the stepper motor has not stalled. In a preferred embodiment, this sensor comprises an optical encoder. In a preferred embodiment, plate alignment mechanism 1712 incorporates a pressure switch to detect the corner chamfer of a plate (e.g., the chamfers on the top and bottom left corners of plate top 932 in FIG. 9A). The presence or absence of the chamfer determines the orientation of the plate in plate carrier 1740. If the sensor determines that the plate is in the incorrect orientation, computer 1726 may instruct the instrument to stop the run, skip the plate or, more preferably, to read the plate but to transpose the data so as to correct for the mis-orientation (thus preventing costly delays or loss of precious samples).

Electronics 1720 participate in the operation, controlling, and monitoring of one or more electronic and/or mechanical elements in reader 1700. Electronics 1720 may comprise a variety of components typically encountered in devices, for example, wires, circuits, computer chips, memory, logic, analog electronics, shielding, controllers, transformers, I/O devices, and the like. Current/voltage source 1722 is an electrical circuit capable of generating defined voltage waveforms and/or defined current waveforms. Current/voltage source 1722 is connected to electronics 1720, computer 1726 and plate electrical connector 1724. In one embodiment of the invention, current/voltage source 1722 includes a potentiostat. The potentiostat is advantageous for reading plates that include independent reference electrodes and allows the potentials at the working and/or counter electrodes to be referenced relative to the potential at the reference electrode.

Plate electrical connector 1724 makes contact with multi-well assay plate 1710 to allow the application of current and/or voltage waveforms by current/voltage source 1722. Plate electrical connector 1724, preferably, comprises one or more connector contacts, electrical connections, a linear actuator and, optionally, a support. In a preferred embodiment, the connector contacts are spring loaded to improve electrical contact with plate 1710. Connector contacts may be made of any suitable material that has a conducting outer surface. Preferably, they are sufficiently durable to withstand repeatedly making contact with plates. Typically, connector contacts are comprised of a hard metal or metal alloy coated with a highly conducting metal film (e.g. gold or silver). In a preferred embodiment, connector contacts are a waffle-point contact head comprised of gold plated nickel/silver, spring loaded on a gold plated stainless steel spring in a nickel/silver receptacle, for example, contacts offered by Interconnect Devices, Inc. (GSS-18.3.8-G). In an alternative embodiment, connector contacts are comprised of a compliant material coated with a highly conducting material. The support for the connector contacts may be comprised of any material that can support the connector contacts when the contacts are pushed against plates. In a preferred embodiment, the support in plate electrical connector 1724 is comprised of a circuit board, preferably with traces that electrically connect the contacts to current/voltage source 1722 and/or electronics 1720. Plate electrical connector may include a sensor (in a preferred embodiment, a Hall sensor) that verifies the home position. Plate electrical connector 1724 may also incorporate a thermal sensor (e.g., a thermister, a thermocouple, a platinum RTD), which in a preferred embodiment, is spring loaded on the support of plate electrical connector 1724. In one embodiment, the thermal sensor makes contact with a multi-well assay plate 1710 to measure its temperature. The linear actuator in plate electrical connector 1724 pushes the connector contacts (and optionally the support) into plate 1710 to make electrical connections. In a preferred embodiment, plate electrical connector 1724 has seven electrical connector contacts arranged in a line. In this embodiment between one and six working connector contacts may contact contact surfaces connected to working electrodes on plate 1710 and between one and six counter connector contacts may contact contact surfaces connected to the counter electrodes on plate 1710.

Advantageously, the apparatus includes a temperature sensor or thermometer adapted to measure the temperature of a plate. Preferably, the temperature sensor or thermal sensor can detect the well temperature within 5° C., more preferably within 2° C., even more preferably within 1° C. and most preferably within 0.25° C. Even more preferably, the temperature sensor can reach steady state within ten seconds, preferably within five seconds, even more preferably within three seconds. The sensor may be a contact sensor (e.g., a thermister, a thermocouple, or a platinum RTD). Alternatively it may be a non-contact sensor such as an IR sensor. In a preferred embodiment, the apparatus comprises one or more non-contact temperature sensors and the apparatus is adapted to be able to measure the temperature of various locations on the plate (e.g., through the use of multiple sensors and/or by moving the plate relative to the sensors). In another preferred embodiment, the apparatus further comprises a computer adapted to receive the signal from a temperature sensor, report the temperature to the user and, preferably, adjust the measured luminescence signals to account for the effects of temperature on luminescent signals, electrochemiluminescent signals, and/or other reactions occurring during the conduct of an assay. The computer, preferably, further comprises memory for saving data and/or calibration curves from calibration measurements conducted at a variety of temperatures and software for using said data and/or calibration curves to normalize test data against variations in temperature. According to another embodiment, the apparatus also comprises a temperature controller to control the temperature within the well.

In operation, case 1702 is opened and aperture 1714 is opened, either by computer 1726 or by pressing a touch button located on case 1702. A multi-well assay plate is loaded into plate carrier 1740 which resides within light tight enclosure 1704, and aperture 1714 is closed. Under control of computer 1726, plate transport mechanism translates multi-well assay plate 1710 until the first sector of plate 1710 is aligned with the photodiode array of photodetector 1706 and with the contacts of plate electrical connector 1724. Photodiode array of photodetector 1706 is held in close proximity to the upper surface of plate 1710 to improve the efficiency of optical collection and to reduce optical crosstalk between wells. Plate electrical connector 1724 pushes the connector contacts into plate 1710 to create an electrical connection. Current/voltage source 1722 generates a waveform that is applied to plate 1710 via plate electrical connector 1724. Photodetector 1706 measures the light emitted from the active sector in plate 1710. Each of the eight photodiodes in photodetector 1706 are located about a well in a row of wells in the multi-well assay plate and the light recorded on a particular photodiode is identified as the light collected from a particular well. Preferably, there is also software correction to compensate for the expected amount of crosstalk due to light from a well hitting a light detector aligned with a different well. Signal collected by photodetector 1706 is sent to computer 1726. After the measurement is complete, plate electrical connector 1724 retracts the connector contacts from plate 1710, and plate transport mechanism 1716 translates plate 1710 so that the next sector is aligned with plate electrical connector 1724 and with the photodiode array of photodetector 1706. Contact with plate 1710 is resumed, and excitation/detection of light occurs again. This cycle is repeated until all desired measurements are completed. At the completion of measurements for a given plate 1710, plate transport mechanism 1716 translates plate carrier 1740 until plate 1710 is aligned with the door in aperture 1714. Aperture 1714 opens and plate 1710 is removed.

FIG. 21 illustrates selected elements of an embodiment of FIG. 17. Photodetector 2106 comprises an array of photodiodes 2107 and a circuit board 2105. Photodiode array 2107 comprises eight photodiodes arranged in a line. Plate carrier 2140, attached to plate transport mechanism 2116, holds plate 2110. Plate 2110, a multi-well assay plate of the invention, has 12 sectors 2110A-L. In FIG. 21, sector 2110A of plate 2110 is positioned below photodiode array 2107. Plate 2110 has 96 wells; each sector contains 8 wells arranged in a line. The photodiode array 2107 is configured such that each of the eight wells in a sector of plate 2110 can be located directly below a unique photodiode in photodiode array 2107. The top of a sector of plate 2110 is held in close proximity to photodiode array 2107 to improve the efficiency of light collection and to reduce optical crosstalk between wells. In FIG. 21, multi-well assay plate 2110 is also positioned so that the contacts for sector 2110A are aligned with connector contacts 2125 of plate electrical connector 2124. In operation, plate electrical connector 2124 pushes connector contacts 2125 into the back side of sector 2110A of plate 2110 to establish electrical contact. Plate carrier 2140, preferably, holds plate 2110 to resist the upward force imposed by plate electrical connector 2124. If plate electrical connector 2124 has connector contacts 2125 retracted from plate 2110, plate transport mechanism 2116 can translate plate carrier 2140 so that another sector (e.g., sector 2110B) becomes aligned with plate electrical connector 2124, connector contacts 2125 and the photodiodes 2107 of photodetector 2106.

FIG. 22 illustrates selected elements of an embodiment of FIG. 17. Light tight enclosure 2204 houses photodetector 2207, plate 2210, plate carrier 2240, a plurality of connector contacts 2205 of plate electrical connector 2224 and shield 2208. Photodetector 2207 comprises an array of photodiodes, with individual photodiodes 2207A, 2207B, 2207C, 2207D, 2207E, 2207F, 2207G, and 2207H. The shield 2208 is attached to photodetector 2207 to prevent electromagnetic interference. The shield 2208 is preferably made of a conductive material such a metal, most preferably brass. Plate 2210 comprises 96 individual wells; FIG. 22 shows eight wells, 2210A, 2210B, 2210C, 2210D, 2210E, 2210F, 2210G, and 221 OH that comprise one sector of plate 2210. Plate 2210 is held by carrier 2240. Plate electrical connector 2224 pushes connector contacts 2205 into the bottom of plate 2210 to establish electrical connections to one sector of plate 2210. Plate carrier 2240 positions plate 2210 so that the sector of plate 2210 is aligned with connector contacts 2205 and with photodetector 2207. The position of plate 2210 is such that well 2210A is aligned directly with photodiode 2207A; well 2210B is aligned with photodiode 2207B, and so on. Connector contacts 2205 are lined up with the bottom of the wells to contact seven walls between the eight wells of a row. Light emitted from each well is collected primarily by its corresponding photodiode. Preferably, there is also software correction of the signal received by the photodiodes, the correction compensating for the expected amount of crosstalk due to light from a well hitting a light detector aligned with a different well.

FIG. 23 illustrates selected elements of a preferred embodiment of FIG. 17. Reader 2300 includes a chassis 2301, photodetector 2306, multiwell assay plate 2310, plate transport mechanism 2316, plate electrical connector 2324 and a plurality of connector contacts 2325. Photodetector 2306 preferably comprises a plurality of photodiodes, a photodetector circuit board, a shield and a metal cover (shown in FIG. 23). Other elements of reader 2300 are not shown in FIG. 23.

In further embodiments of FIG. 17, reader 1700 may measure the light emitted by light emitting substances other than electrochemiluminescent labels. For example, reader 1700 may be used for fluorescence assays, chemiluminescence assays, radioactive assays employing light emitting scintillants, bioluminescence assays, etc. It may also be used for absorbance and scattering based measurements. In one embodiment, optics 1708 further comprises one or more light sources and appropriate optical elements for stimulating and detecting fluorescent labels. In another embodiment, optics 1708 further comprises one or more light sources and appropriate optical elements for absorbance or scattering measurements. In another embodiment, reagent handler 1734, optics 1708 and photodetector 1706 further comprises appropriate reagent handling equipment for chemiluminescent or bioluminescent assays. For example, some chemiluminescent assays require measurement of chemiluminescence signals after a short and controlled time after addition of a chemiluminescent reagent, so it is advantageous to include within the apparatus plate washers and/or means for dispensing reagents in a controlled manner. Such dispensing means may include pipettes, syringes or other fluid dispensers adapted to deliver fluid to one well at a time or multiple wells at a time. In operation, a plate is introduced into the instrument, the plate is optionally washed by an integrated plate washer, a chemiluminescence reagent is optionally introduced by an integrated fluid dispenser and the chemiluminescence is monitored (optionally after incubating the plate for a controlled period of time after washing or introduction of reagents).

5.4 Methods of Measuring Luminescence

Another aspect of the invention relates to methods for measuring luminescence from an assay plate, preferably a multi-well assay plate having a plurality of wells. Preferably, the multi-well plate has a standard plate configuration such as a 96-well, 384-well plate, etc.

One preferred embodiment of the invention relates to methods of measuring luminescence using any of the apparatuses and/or assay plates described above.

The method comprises measuring luminescence, preferably electrode induced luminescence, more preferably electrochemiluminescence, emitted from the wells or assay domains. In the case of electrochemiluminescence, the method may also comprise providing electrical energy to the plurality of wells or assay domains or otherwise inducing luminescence. In the case of fluorescence, for example, the method may comprise inducing fluorescence by directing a light source onto an assay region. In the case of chemiluminescence, the method may comprise adding a chemical initiator to the assay region.

According to one embodiment, the method involves measuring the luminescence in sectors. According to another embodiment, the method includes providing electrical energy to the multi-well assay plate in sectors. As described above, measuring the plate in sectors provides improved luminescence collection efficiencies. Moreover, it allows for the use of a smaller imaging surface and/or the use of a smaller number of light detectors.

Accordingly, a preferred embodiment of the invention relates to a method for measuring luminescence from a multi-well assay plate having a plurality of independently addressable sectors of jointly addressable wells, the method comprising:
 (a) providing electrical energy to the multi-well assay plate; and
 (b) measuring luminescence from the multi-well assay plate in sectors.

Another embodiment relates to a method for measuring luminescence from a multi-well assay plate having a plurality of independently addressable sectors of jointly addressable wells, the method comprising:
 (a) providing an electrical connection to the multi-well assay plate in sectors; and
 (b) measuring luminescence from the multi-well assay plate in sectors.

Yet another embodiment relates to a method for measuring luminescence from a multi-well assay plate having a plurality of wells comprising:
 (a) providing electrical energy to a first sector of the plurality of wells;
 (b) measuring luminescence from the first sector of the plurality of wells;
 (c) providing electrical energy to a second sector of the plurality of wells; and
 (d) measuring luminescence from the second sector of the plurality of wells.

A still further embodiment of the invention relates to a method for measuring luminescence from a multi-well assay plate having a plurality of wells comprising:
 (a) measuring luminescence from a first sector of the plurality of wells; and
 (b) measuring luminescence from a second sector of the plurality of wells.

A still further embodiment relates to a method for measuring luminescence from a multi-well assay plate having a plurality of wells comprising:
 (a) providing electrical energy to a first sector of the plurality of wells; and
 (b) providing electrical energy to a second sector of the plurality of wells.

A still further embodiment relates to a method of conducting one or more assays using an apparatus for measuring luminescence from an assay plate, preferably a multi-well assay plate having an array of wells, comprising a substrate having a top surface and a bottom surface and the apparatus comprising a light detector adapted to measure luminescence emitted from the assay regions or assay wells, wherein the plate is held onto a measuring platform during the measuring luminescence and/or during the inducing the luminescence, particularly if the electrical connector contacts push up on the plate from the bottom. The term "held onto" is intended to refer to holding the plate down as electrical connectors are pressing against the plate. This is advantageous since even slight movement of the plate can alter the light detection or imaging. The plate can be "held down" from the bottom (e.g., magnetically), the top (e.g., securing devices come down into the plate edges) or the sides (e.g., the sides are clamped onto a support).

5.4.1 Imaging Methods

One embodiment of the invention relates to a method of conducting a luminescence assays employing imaging systems, preferably imaging systems comprising a camera. More specifically, an imaging system which images the luminescence emitted from the assay plate or multi-well plate.

One preferred embodiment of the invention relates to a method for measuring luminescence from a multi-well plate having a plurality of wells comprising simultaneously imaging emitted luminescence from at least two of the plurality of wells, wherein the imaging collects a cone of luminescence having a cone full angle of at least 10 degrees, preferably at least 15 degrees, more preferably at least 20 degrees, even more preferably at least 25 degrees and most preferably at least 30 degrees.

Another aspect of the invention relates to methods for measuring luminescence from a multi-well assay plate comprising the step of imaging the emitted luminescence in sectors.

One embodiment of the invention relates to a method for measuring luminescence from a multi-well assay plate having a plurality of wells comprising:
 (a) forming a first image of a first sector of the multi-well assay plate with an imaging system; and
 (b) forming a second image of a second sector of the multi-well assay plate.

Another embodiment method for measuring luminescence from a multi-well assay plate having a plurality of wells comprising:
 (a) aligning a first sector of the multi-well assay plate with an imaging system;
 (b) measuring luminescence from the first sector of the multi-well assay plate with the imaging system;
 (c) aligning a second sector of the multi-well assay plate with the imaging system; and
 (d) measuring luminescence from the second sector of the multi-well assay plate with the imaging system.

Another embodiment relates to a method for measuring luminescence from a multi-well assay plate having a plurality of wells comprising:
 (a) providing electrical energy to a first sector of the plurality of wells;
 (b) measuring luminescence from the first sector of the plurality of wells using an imaging system;
 (c) providing electrical energy to a second sector of the plurality of wells; and
 (d) measuring luminescence from the second sector of the plurality of wells using the imaging system.

Preferably, the method employing an imaging system employs an apparatus and/or an assay plate, preferably multi-well assay plate, as described above.

Another embodiment of the invention relates to a method comprising introducing approximately 25-300 micro liters of assay mixture into each of the plurality of wells and measuring the assay mixture from the wells, more preferably 75-200, more preferably 125-175, even more preferably approximately 150 micro liters of assay mixture into the wells of a 96 well plate. Another embodiment relates to introducing 20-60 micro liters of assay mixture, preferably 30-40 micro liters, and even more preferably approximately 35 micro liters, into each of the plurality of wells and measuring the assay mixture from the wells, preferably from the wells of a 384 well plate.

Another embodiment of the invention relates to a method of conducting one or more assays using an apparatus for measuring luminescence from a multi-well plate, the multi-well plate having a standard configuration of wells and comprising a substrate having a top surface and a bottom surface, and the apparatus comprising a light detector adapted to measure luminescence emitted from the plurality of wells, wherein the method comprises:

(a) contacting each sector of the bottom surface with a plurality of electrical connector contacts at one or more sector contact locations, wherein the plurality of electrical connector contacts contact the bottom surface between the wells; and (b) measuring emitted luminescence.

Preferably, the sector contact locations comprise one or more, preferably two or more, more preferably three or more, even more preferably four or more, and most preferably all of the following locations shown in FIG. 34A or 34B and as discussed above in relation to novel plate bottom configurations.

Preferably, the sector contact locations comprise one or more, preferably two or more, more preferably three or more, even more preferably four or more and most preferably all of the following locations shown in FIG. 34A or 34B and discussed above in relation to novel plate bottom configurations.

Another embodiment of the invention relates to a method of conducting one or more assays using an apparatus for measuring luminescence from a multi-well plate, the multi-well plate comprising a substrate having a top surface and a bottom surface, the multi-well plate having an array of wells corresponding to a standard 96-well plate configuration, the array comprising one or more preferably two or more, more preferably all, of the following:

a first sector comprising wells A1 through A4, B1 through B4, C1 through C4, and D1 though D4;

a second sector comprising wells A5 through A8, B5 through B8, C5 through C8, and D5 though D8;

a third sector comprising wells A9 through A12, B9 through B12, C9 through C12, and D9 through D12;

a fourth sector comprising wells E1 through E4, F1 through F4, G1 through G4, and H1 though H4;

a fifth sector comprising wells E5 through E8, F5 through F8, G5 through G8, and H5 though H8; and a sixth sector comprising wells E9 through E12, F9 through F1, G9 through G12, and H9 though H12 (each of the designations referring to a region of the well defined by the row and column);

the apparatus comprising a light detector adapted to measure luminescence emitted from the plurality of wells, wherein the method comprises:

(a) contacting each sector of the bottom surface with a plurality of electrical connector contacts at one or more sector contact locations, wherein the plurality of electrical connector contacts contact the bottom surface between the wells; and (b) measuring emitted luminescence.

According to a preferred embodiment of the invention, each sector is contacted by the plurality of electrical connector contacts at least two, preferably at least three, more preferably at least four, even more preferably at least five and most preferred at least six locations.

Preferably, each sector is contacted by a 2×3 array of locations.

According to another preferred embodiment, the sector contact locations comprise one or more of the following locations:

(i) two or more, preferably three or more, more preferably four or more, even more preferably five or more, and most preferred all of first sector locations: A1-B2; A2-B3; A3-B4; C1-D2; C2-D3; C3-D4;

(ii) two or more, preferably three or more, more preferably four or more, even more preferably five or more, and most preferred all of second sector locations: A5-B6; A6-B7; A7-B8; C5-D6; C6-D7; C7-D8;

(iii) two or more, preferably three or more, more preferably four or more, even more preferably five or more, and most preferred all of third sector locations: A9-B10; A10-B11; A11-B12; C9-D10; C10-D11; C11-D12;

(iv) two or more, preferably three or more, more preferably four or more, even more preferably five or more, and most preferred all of fourth sector locations: E1-F2; E2-F3; E3-F4; G1-H2; G2-H3; G3-H4;

(v) two or more, preferably three or more, more preferably four or more, even more preferably five or more, and most preferred all of fifth sector locations: E5-F6; E6-F7; E7-F8; G5-H6; G6-H7; G7-H8; and (vi) two or more, preferably three or more, more preferably four or more, even more preferably five or more, and most preferred all of sixth sector locations: E9-F10; E10-F11; E11-F12; G9-H10; G10-H11; G11-H12.

Another embodiment relates to a method of conducting one or more assays using an apparatus for measuring luminescence from a multi-well assay plate, the multi-well plate comprising a substrate having a top surface and a bottom surface, the multi-well plate having an array of wells corresponding to a standard 384-well plate configuration, the array comprising rows A through P and columns 1 through 24 (described above in relation to plate bottoms)

the apparatus comprising a plurality of electrical connector contacts, wherein the plurality of electrical connector contacts contact the bottom surface between wells, and a light detector adapted to measure luminescence emitted from the plurality of wells.

Preferably, each sector comprises one or more electrical contacts at one or more (preferably all) of the following locations:

(i) two or more, preferably three or more, more preferably four or more, even more preferably five or more, and most preferred all of first sector locations: B2-C3; B4-C5; B6-C7; F2-G3; F4-G5; F6-G7;

(ii) two or more, preferably three or more, more preferably four or more, even more preferably five or more, and most preferred all of second sector locations: B10-C11; B12-C13; B14-C15; F10-G11; F12-G13; F14-G15;

(iii) two or more, preferably three or more, more preferably four or more, even more preferably five or more, and most preferred all of third sector locations: B18-C19; B20-C21; B22-C23; F18-G19; F20-G21; F22-G23;

(iv) two or more, preferably three or more, more preferably four or more, even more preferably five or more, and most preferred all of fourth sector locations: J2-K3; J4-K5; J6-K7; N2-O3; N4-O5; N6-O7;

(v) two or more, preferably three or more, more preferably four or more, even more preferably five or more, and most preferred all of fifth sector locations: J10-K11; J12-K13; J14-K15; N10-O11; N12-O13; N14-O15; and (vii) two or more, preferably three or more, more preferably four or more, even more preferably five or more, and most preferred all of sixth sector locations: J18-K19; J20-K21; J22-K23; N18-O19; N20-O21; N22-O23.

5.4.2 Methods Employing Light Detector Arrays

Another aspect of the invention relates to methods for measuring luminescence using an array of light detectors comprising:
(a) providing electrical energy to a first sector of the plurality of wells;
(b) measuring luminescence from the first sector of the plurality of wells with an array of light detectors;
(c) providing electrical energy to a second sector of the plurality of wells; and
(d) measuring luminescence from the second sector with the array of light detectors.

Another embodiment includes a method for measuring luminescence from a multi-well assay plate having a plurality of wells comprising:
(a) providing electrical energy to a first sector of the plurality of wells;
(b) measuring luminescence from the first sector of the plurality of wells using an array of light detectors;
(c) providing electrical energy to a second sector of the plurality of wells; and
(d) measuring luminescence from the second sector of the plurality of wells using an array.

Yet another embodiment relates to a method comprising:
(a) providing electrical energy to a first sector of the multi-well assay plate;
(b) measuring luminescence from the first sector of the multi-well assay plate with an array of light detectors;
(c) aligning a second sector of the multi-well assay plate with the light detector; and
(d) measuring luminescence from the second sector of the multi-well assay plate with the array of light detectors.

Another embodiment includes a method for measuring luminescence from a multi-well assay plate having a plurality of wells comprising:
(a) providing electrical energy to a first sector of the multi-well assay plate;
(b) measuring luminescence from the first sector of the multi-well assay plate with an array of light detectors;
(c) aligning a second sector of the multi-well assay plate with the array of light detectors; and
(d) measuring luminescence from the second sector of the multi-well assay plate with the array of light detectors.

Another embodiment of the invention relates to methods of conducting one or more assays using an apparatus for measuring luminescence from a multi-well assay plate having a plurality of wells arranged in an array, the method comprising inducing and measuring the luminescence from the plurality of wells row by row or column by column.

Yet another embodiment relates to a method comprising contacting the multi-well plate bottom with at least one counter electrode connector contact and at least one working electrode connector contact to simultaneously induce luminescence in a row or column of wells, preferably at least two counter electrode connector contacts and at least two working electrode connector contacts, more preferably at least three counter electrode connector contacts and at least three working electrode connector contacts, and most preferred three counter electrode connector contacts and four working electrode connector contacts.

Preferably, the light detector comprises one or more photodiodes, more preferably an array of photodiodes.

Preferably, the measuring luminescence comprises measuring luminescence from each well using at least one light detector aligned with each well being measured.

Preferably, less than 2% of luminescence is cross-talk luminescence, more preferably less than 1%, even more preferably less than 0.5%, and most preferred less than 0.1%.

Another aspect of the invention relates to measuring luminescence from different plate formats using the same apparatus, particularly an apparatus having a fixed array of light detectors (e.g., a linear array of eight photodiodes). Using this aspect of the invention, an apparatus configured for one type of plate format (e.g., a 96-well plate) can be used with other plate formats (e.g., a 384-well plate) with little or no modification to the apparatus. For example, apparatuses have been described above as being adapted to read ECL from multi-well plates in the 96-well format wherein an array of eight photodiodes reads ECL emitted from each column of wells with each photodiode corresponding to a single well at each measurement step (i.e., each column comprises eight wells (8 rows×12 columns); the measurement of the plate is performed in twelve steps (one measurement/inducement step per column)).

Surprisingly, the same apparatus may be employed to read other plates such as 384-well plates, 96-well plates with 4-spot wells and other multi-spot plates with the same fixed array of light detectors, where the apparatus and/or plate is either configured as described above or with minor modifications to the instrument and/or plate design.

One embodiment employs an apparatus having an array of light detectors such as an array of eight photodiodes where, without modifying the instrument, two or more alternative plate formats can be measured. Preferably, the apparatus is adapted to measure an assay plate wherein the number of times the array of light detectors is shifted to the next row or column of wells is less than the number of times ECL is induced (e.g., voltage is applied to the plate). For example, one method involves moving the light detector array (with respect to the plate) 12 times, wherein ECL is induced at least 24 times, preferably at least 48 times, more preferably at least 84 times and most preferred at least 120 times.

According to a still further embodiment of the invention, an apparatus having an array of light detectors is used to measure luminescence from multi-well plates wherein each well comprises a plurality of assay spots or assay domains (See, FIGS. 3A-3C). More specifically, for example, a plate having a plurality of assay domains within each well (e.g., 4-spot plate, FIG. 3A) can be made to work in an apparatus having a single row of photodiodes (thus a single photodiode per well per column). This plate type could be a standard 96 well plate top with 4 independently addressable spots for measuring 4 different analytes in each well. Since the 4 spot well plate requires that 4 spots be fired in sequence in a single fluid volume, the working electrode is preferably sectioned into four separate, addressable leads that are electrically isolated from one another. A single counter electrode could be connected together across each row of plates as in the standard plate, i.e., a small portion of counter electrode on opposite edges of the well bottom (See, FIG. 3A, counter electrodes 306A and B).

For example, such an apparatus can be used to measure a 96-well plate wherein each well comprises four discrete spots ("a 4-spot 96-well plate") in addition to measuring a single spot 96-well plate. Since each photodiode in the array corresponds to a single well during each step of the measurement scan, the photodiode would not be capable of measuring the 4 spots simultaneously. Therefore, the 4 spots per well are preferably fired sequentially. This may be achieved by indexing the plate using smaller distances than the size of the wells. That is, modifying the plate bottom to include independently addressable contacts and leads for each working electrode of each spot. Thus, for each single column of wells of the 96-well plate, the corresponding bottom would have four working electrode contacts for each spot of the 4-spot wells.

Referring to FIG. 38, well 3810 comprises four assay domains on four independently addressable working electrode surfaces 3811, 3812, 3813 and 3814, which are electrically connected to four independently addressable working electrode contacts 3820, 3821, 3822 and 3823 via working electrode connections 3824, 3825, 3826 and 3827. Working electrode contacts 3820, 3821, 3822 and 3823 are each contacted by the apparatus (e.g., at locations "x"). Portions (e.g., portion 3860) of the working electrode connections within well 3810 are preferably covered with dielectric (not shown) so that the only exposed electrode surface within well 3810 when the working electrode contact (e.g., working electrode contact 3820) is contacted is the corresponding working electrode surface (e.g., working electrode surface 3812). Working electrode contacts 3820, 3821, 3822 and 3823 are also preferably electrically connected to four working electrodes within one or more adjacent wells (not shown) via working electrode connectors 3840, 3841, 3842 and 3843. Thus, referring to FIG. 34B, two adjacent wells on each side of a contact location "x" can both be addressed using a single set of four contacts. By using multiple contacts "x" as shown in FIG. 34B, all eight wells of a column can be similarly contacted so as to allow four (or more) spots within the wells to be sequentially fired and thus sequentially measured with a single linear array of eight light detectors. Counter electrode 3850 is preferably contacted by the apparatus at four locations (*) and is preferably electrically connected to well 3810 via counter electrode connections 3851A and/or 3851B to exposed counter electrode surfaces 3854A and/or 3854B and/or counter electrode 3850 may be partially exposed within well 3810 (e.g., exposed counter electrode surface 3855).

Counter electrode 3850 may also be electrically connected to one or more adjacent wells up to an entire column wells (not shown) via counter electrode connections 3851A and/or 3851B (e.g., counter electrodes 3851A and/or 3851B may extend along an entire column of wells). Thus, referring to FIG. 34B, three counter electrode contact locations (*) can be electrically connected to eight wells via electrical connections 3851A and/or 3851B and/or via exposed portions within wells (e.g., 3855).

Preferably, working electrode contacts 3820, 3821, 3822 and 3823 and counter electrode contact(s) 3850 are on the bottom of a multi-well plate. According to a preferred embodiment, such bottom contacts are electrically connected to the working electrode 3811, 3812, 3813 and 3814 and counter electrode surfaces 3854A, 3854B and 3855 via connective through holes, preferably located at locations such as "x" and "*" and the working electrode connections and/or counter electrode connections are on the same plate surface as the corresponding working and counter electrode surfaces with well 3810. Alternatively, the working and counter electrode connections can be on the bottom surface and the conductive through hole located beneath the corresponding working and counter electrode surfaces. According to another embodiment, the working electrode connections and/or counter electrode connections are within one or more patterned intermediate layers (not shown) located between the contact layer and the electrode surface layer. The intermediate layer(s) would provide electrically isolated conductive paths from the working electrode and/or counter electrode contacts to the corresponding working electrode and counter electrode surfaces. The use of an intermediate layer to provide conductive paths would allow for higher density arrays of spots within each well since the electrical connections would not be limited to a two-dimensional configuration.

Using a plate such as that shown in FIG. 38, the electrical connectors of the apparatus would contact the plate bottom at the four different contact locations (e.g., four steps vs. one step) per column of wells while the array of photodiodes remained above that column of wells. Referring to FIG. 34B, for example, the single working electrical contact locations 3480 (represented by X's) shown in the figure would be replaced with four spaced working electrical contact locations per column of wells (e.g., working electrode contacts 3820, 3821, 3822 and 3823 of FIG. 38). Each contact/inducement step would result in a voltage being applied to one spot per well. The corresponding photodiode for each well would measure ECL from that spot. Then the second set of contacts would be contacted by the connectors to induce ECL at the second spot and the same photodiode would measure ECL from the second spot, then the third set of contacts and finally the fourth. Throughout the scan of the 4 spots of a single column of wells, the bottom contacts connect to different spots as the column of wells would remain under the array of photodiodes. The different spots under a single photodiode are induced to emit ECL sequentially thereby allowing a single photodiode to distinguish and measure luminescence from more then one spot. After the fourth spot is induced to emit ECL and the emitted ECL measured, the array of photodiodes is then shifted to the next column of 4-spot wells and the process is repeated for each column.

Thus, the only modifications needed to convert the system adapted for reading single-spot 96-well plates to 4-spot 96-well plates is to modify the electrical contacts on the plate bottoms and change the measurement scan of the plate from a 12 step scan to a 48 step scan (4 spots×12 columns) wherein each step involves contacting the plate bottom 48 times instead of 12 times, while the array of photodiodes is shifted with respect to the plate only 12 times. As a result, the same apparatus having the same fixed array of light detectors can be employed to measure ECL from a different plate format. The same methodology can be employed to measure a 7-spot 96-well plate (e.g., 7 spots×12 columns=84 step scan; 12 spots×12 columns=144 steps, etc.).

Thus, one preferred embodiment involves forming independently addressable working electrodes (and/or counter electrodes) within a single "sector" (e.g., column of wells) thereby allowing each spot or well beneath a given photodiode to be measured sequentially.

According to another embodiment, the same array of light detectors can be used to measure ECL from a 384-well plate. For example, referring to FIG. 2F, a single linear array of photodiodes adapted for measuring ECL from a column of wells of a 96-well plate would cover two columns of wells (e.g., columns 1 and 2) in a 384-well plate. Thus, a single photodiode would be used to measure luminescence from each of wells A1, A2, B1 and B2 (a 384 well plate has rows A-P and columns 1-24) by sequentially applying a voltage to each well and a second photodiode would (simultaneously with the first photodiode) measure luminescence from each of wells C1, C2, D1 and D2 by sequentially applying a voltage to each well, etc. The sequential application of voltage to each well under the individual photodiode can be achieved by using different electrical contacts for each well (e.g., an array of 16 connectors to provide voltage to each of the 16 wells beneath the array of eight photodiodes where the connectors apply a voltage to only one well per photodiode at a time) or by using modified bottom contacts as described above with respect to the 4-spot 96-well plate or by the methods described further below.

According to another embodiment, alternative assay domains or wells within a column are induced to emit electrochemiluminescence and measured. One preferred embodiment employs 384-well plates wherein each column of wells would have alternating counter or working electrodes. For example, referring again to FIG. 2F, the counter (or working) electrode in wells A1, C1, E1, G1, I1, K1, M1, O1 would all be connected electrically, and the counter (or working) electrode in wells B1, D1, F1, H1, J1, L1, P1 would be connected to each other electrically. The corresponding working (or counter) electrode would preferably be common to all of these wells. First, the A1 group of wells would be excited by connecting to that counter electrode and the working electrode. The plate would then be shifted by half the spacing of the 384 well plate (2.25 mm) such that when the contacts were raised to the plate, they would connect to the working electrode and the counter electrode connected to the B1 bank of wells, but not the A1 group of wells. Thus the second half of the column would be excited and the light measured by the 8 photodiodes, completing the read of the column. The remaining 23 columns of the plate would be read in the same way. Thus, the plate would be shifted to allow the A2 groups of wells to be measured, and shifted again to allow the B2 group of wells, etc. Preferably, it is the plate that is shifting within the apparatus. Alternatively, the electrical connectors contacting the plate contacts can shift. The alternating connection to the counter electrodes can be realized either by modifying the screen printing to include the counter electrode on one side of each well bottom in an alternating fashion, or by modifying the dielectric layer to selectively cover the counter electrode in an alternating fashion.

For example, referring to FIG. 2B, if counter electrode 226B is covered by dielectric in every other well in a row of wells (and counter electrode 226A is covered by dielectric in the wells of that row where counter electrode 226B is not covered), then (step 1) applying voltage to the bottom contact corresponding to working electrode 230 (where the working electrodes for the column of wells are electrically connected) and to the bottom contact corresponding to counter electrode 226B (where the counter electrodes for the column of wells are electrically connected, but were only exposed in alternating wells) would only result in ECL in alternating wells. Then (step 2) the contacts connected to working electrodes 230 and counter electrode 226A would be contacted to induce ECL in the other set of alternating wells of the same column. This approach would not require fundamental modification to the instrument, as it would run both plate types with the same mechanical design.

Preferably, the software controlling the instrument is modified to induce luminescence and/or read luminescence greater than 12 times (preferably at least 48 times, more preferably at least 84 times and most preferred at least 120 times) rather than the 12 times required for the standard 96-well multi-array plate using a single linear array of light detectors.

According to another embodiment, a similar, but preferable approach could be implemented for using different plate formats (e.g., 96 and 384 well plates) with relatively simple electronic modifications to the instrument. In this case, a switch may be added to the wiring that applies voltage to the contacts in the instrument (i.e., to the contacts or connectors that contact the plate bottom). In the unmodified apparatus described above, the voltage sweep is applied to redundant contacts (e.g., see FIG. 34B wherein multiple redundant connectors contact redundant contact surfaces on the plate bottom for a single column of wells of a 96-well plate). Thus, without repositioning the contacts, but instead selectively applying voltages to a subset of the contacts, it is possible independently addressable plate contacts to first excite the A1, C1, etc group of wells centered under the photodiodes. Then, using appropriate software control, the voltage may be switched such that it was applied across a different set of contact pins, which would contact other separately addressable plate contacts on the back of the plate connected to the B1, D1, etc. group of wells, without requiring any motion of the plate.

As another example, as described above, these 4 different electrodes could be addressable by indexing the plate in small steps such that the same contact points connect to different working electrode leads on the bottom of the plate. Preferably, a switching mechanism is integrated into the apparatus electronics that provide the connection to the existing contact mechanism, such that the plate would remain completely stationary and the four spots would be fired in sequence. According to another embodiment, the electrical mechanisms to provide switching are field upgradeable or are provided in a different version of the instrument. The plates and instrument are preferably designed such that the standard 96 well plates could still be run on the instrument. The software controlling the instrument is preferably modified to accommodate the changes in ECL excitation sequence required and allow the user to specify what plate type is being used. The contact height and plate top would preferably remain exactly the same in this case.

The multi-spot or multi-well embodiments described above can be generalized beyond the specific example of 4 spots to any number of spots or wells, where the number of addressable spots is limited by the printing resolution of the screen-printing used to fabricate the independently addressable electrodes. Alternative manufacturing techniques (microfabrication and lithography) could be employed to increase the number of addressable spots beyond what is possible in screen-printing.

Using different plate formats in the same apparatus may require other minor adjustments. For example, different plates may have different plate heights (e.g., the 384 well plate may be shorter than the 96 well format). Preferably, a spacer would be used to elevate the shorter 384-well plate to the photodiodes and/or the contact height would be adjusted to the correct position (if the instrument is adapted for 96-well plates). Alternatively, instead of elevating the height of the contacts and including a spacer, a full height plate top could be used with the 384-well format. This plate top would have the same height as the 96 well plate top (preferably, the volumes of wells of the 384 are maintained by raising the well bottom to compensate for the elevated height of the plate walls).

Using these embodiments, the excited regions may be somewhat off-center relative to the photodiode which may compromise the light collection and/or cross talk between photodiodes, as compared to measurements using the standard 96 well format. This is preferably compensated for by the user and/or by the software of the system. Alternatively, the array of light detectors and/or plate may be shifted with respect to each other to align the well to be induced with the corresponding photodiode. For example, the instrument may preferably be further modified to include the ability to offset the position of the plate (e.g., 384 well plate) in the orthogonal direction, for example, to the standard translation in the non-modified reader (i.e., along the columns of wells) to center each well under its photodiode perfectly to optimize the light collection and cross talk between sectors.

A still further embodiment of the invention relates to the use of the above-described approaches in an apparatus having an imaging device rather than an array of light detectors. For example, sequentially firing spots or wells under an imager could provide for a higher density of spots or wells for a given level of image resolution. If an imager cannot differentiate light emitted from a group of four tightly packed spots, sequentially firing the spots would allow the user to differentiate between the spots. Thus, the above-identified approaches can also be applied to an apparatus having an imaging system instead of an array of light detectors.

According to yet another embodiment, the apparatus having an array of light detectors could be modified to include an array of 16 photodiodes matched to the size and spacing of the 384-well plate such that all 16 wells in each column could be excited simultaneously. This approach would have the advantage of reducing the read time compared to the other approaches by a factor of 2. In this case, the plate bottom would be designed in the same concept as the non-modified 96-well plate, with no alternation between wells in the application of voltages. Thus, another embodiment of the invention relates to an apparatus having an array of light detectors wherein the number of light detectors in the array corresponds to the number of wells and/or spots in the column or row being measured.

5.4.3 Assays Methods

The assay plates and instrumentation of the invention are useful for carrying out a wide variety of established assay formats, e.g., assays based on the measurement of photoluminescence, Scintillation Proximity Assay (SPA), chemiluminescence, measurement of electrochemical voltage and/or current or, preferably, an electrode-induced luminescence, most preferably, electrochemiluminescence. For examples of methods for conducting ECL assays, the reader is directed towards U.S. Pat. Nos. 5,591,581; 5,641,623; 5,643,713; 5,705,402; 6,066,448; 6,165,708; 6,207,369; and 6,214,552 and Published PCT Applications WO87/06706 and WO98/12539, these references hereby incorporated by reference. Assays may be directed to, but are not limited to, the measurement of the quantity of an analyte; the measurement of a property of a sample (e.g., temperature, luminescence, electrochemical activity, color, turbidity, etc.); the measurement of a chemical, biochemical and/or biological activity (e.g., an enzymatic activity); the measurement of a kinetic or thermodynamic parameter (e.g., the rate or equilibrium constant for a reaction), etc.

The embodiments of the invention can be used to test a variety of samples which may contain an analyte or activity of interest. Such samples may be in solid, emulsion, suspension, liquid, or gas form. They may be, but are not limited to, samples containing or derived from, for example, cells (live or dead) and cell-derived products, cell fragments, cell fractions, cell lysates, unfractionated cell lysates, organelles, organs, animal parts, animal by-products, cell membranes, cell culture supernatants (including supernatants from antibody producing organisms such as hybridomas), immortalized cells, waste or drinking water, food, beverages, pharmaceutical compositions, blood, serum, plasma, hair, sweat, urine, feces, tissue, biopsies, structural biological components, skeletal components (e.g., bone, ligaments, tendons), separated and/or fractionated skeletal components, hair, fur, feathers, hair fractions and/or separations, skin, skin fractions, dermis, endodermis, effluent, separated and/or fractionated samples, unfractionated samples, separated and/or fractionated liquids, saliva, mucous, oils, plants, plant parts, plant by-products, sewage, environmental samples, dust, swipes, absorbent materials, gels, organic solvents, chemicals, chemical solutions, soil, minerals, mineral deposits, water supply, water sources, filtered residue from fluids (gas and/or liquids), solids, gases, or air. The sample may further comprise, for example, water, organic solvents (e.g., acetonitrile, dimethyl sulfoxide, dimethyl formamide, n-methyl-pyrrolidone or alcohols) or mixtures thereof. Analytes and/or other samples that may be measured include, but are not limited to, whole cells, cell surface antigens, cell nucleus/nuclei, nuclear fractions, subcellular particles (e.g., organelles or membrane fragments), membranes, solubilized membranes, membranes fractions, nuclear membranes, nuclear membrane fractions, lipids, lipids with proteins, lipids with sugars, lipid bilayers, micelles, septa, monolayers, separating materials, barriers, dialysis membranes, permeable membranes, nonpermeable membranes, cell membranes, organelle membranes, viruses, prions, eukaryotic cells, prokaryotic cells, immunological cells, fungus, yeast, dust mites or fragments thereof, viroids, antibodies, antibody fragments, antigens, haptens, fatty acids, nucleic acids (and synthetic analogs), proteins (and synthetic analogs), lipoproteins, cytoskeleton, protein complexes, polysaccharides, inhibitors, cofactors, haptens, cell receptors, receptor ligands, lipopolysaccharides, glycoproteins, peptides, polypeptides, cAMP, EGF, kinases, enzymes, enzyme substrates, enzyme products, second messengers, cell signaling factors and/or components, second messenger signaling factors and/or components, cellular metabolites, hormones, endocrine factors, paracrine factors, autocrine factors, immunological factors, cytokines, pharmacological agents, drugs, therapeutic drugs, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample.

Activities that may be measured include, but are not limited to, the activities of phosphorylases, phosphatases, esterases, trans-glutaminases, nucleic acid damaging activities, transferases, oxidases, reductases, dehydrogenases, glycosidases, ribosomes, protein processing enzymes (e.g., proteases, kinases, protein phophatases, ubiquitin-protein ligases, etc.), nucleic acid processing enzymes (e.g., polymerases, nucleases, integrases, ligases, helicases, telomerases, etc.), cellular receptor activation, second messenger system activation, etc.

In one embodiment of the invention, a sample potentially containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured so as to measure the quantity of the substance. In another embodiment of the invention, a sample containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured so as to measure the presence of substances, chemical activities or biological activities that affect the production of the signal from the substance (e.g., the presence, production and/or consumption of ECL coreactants, hydrogen ions, luminescence quenchers, chemiluminescence triggers, etc.). In other embodiments of the invention, luminescent, chemiluminescent and/or redox-active substances (preferably an ECL-active substances) are used as labels to allow the monitoring of assay reagents such as enzyme substrates or binding reagents. Assays formats for measuring analytes through the use of labeled binding reagents specific for the analyte include homogeneous and heterogeneous methods.

Preferred assay formats employ solid-phase supports so as to couple the measurement of an analyte or activity to the separation of labeled reagents into solution-phase and solid phase supported portions. Examples include solid-phase binding assays that measure the formation of a complex of a material and its specific binding partner (one of the pair being immobilized, or capable of being immobilized, on the solid phase support), the formation of sandwich complexes (including a capture reagent that is immobilized, or capable of being immobilized, on the solid phase support), the competition of two competitors for a binding partner (the binding partner or one of the competitors being immobilized, or capable of being immobilized, on the solid phase support), the enzymatic or chemical cleavage of a label (or labeled material) from a reagent that is immobilized, or capable of being immobilized on a solid phase support and the enzymatic or chemical attachment of a label (or labeled material) to a reagent that is immobilized or capable of being immobilized on a solid-phase support. The term "capable of being immobilized" is used herein to refer to reagents that may participate in reactions in solution and subsequently be captured on a solid phase during or prior to the detection step. For example, the reagent may be captured using a specific binding partner of the reagent that is immobilized on the solid phase. Alternatively, the reagent is linked to a capture moiety and a specific binding partner of the capture moiety is immobilized on the solid phase. Examples of useful capture moiety-binding partner pairs include biotin-streptavidin (or avidin), antibody-hapten, receptor-ligand, nucleic acid—complementary nucleic acid, etc.

In assays carried out on solid-phase supports, the amount of analyte or activity is, preferably, determined by measuring the amount of label on the solid phase support and/or in solution, measurements typically being conducted via a surface selective technique, a solution selective technique, or after separation of the two phases. Most preferably, the solid phase support in the embodiments described above is a working electrode of an assay plate or within a well of an assay plate of the invention; this arrangement allows for surface selective electrochemiluminescent excitation and measurement of labels on the solid phase support. Alternatively, the solid phase support may be a surface sufficiently distant from a working electrode so that the working electrode only measures labels in the solution phase.

In assays carried out on solid-phase supports, the amount of analyte or activity is, preferably, determined by measuring the amount of label on the solid phase support and/or in solution, measurements typically being conducted via a surface selective technique, a solution selective technique, or after separation of the two phases. More preferably, the solid phase support in the embodiments described above is a working electrode of an assay plate or within a well of an assay plate of the invention; this arrangement allows for surface selective excitation of electrode-induced luminescence (most preferably electrochemiluminescence) and measurement of labels on the solid phase support. Alternatively, the solid phase support may be a surface sufficiently distant from a working electrode so that the working electrode only induces luminescence from labels in the solution phase.

In one embodiment of the invention, a reagent labeled with a luminescent, chemiluminescent and/or redox-active label (preferably an ECL label) is measured by a method comprising the steps of i) introducing the sample to an assay plate or one or more wells of an assay plate of the invention; ii) contacting the labeled reagent with a binding reagent; ii) forming a binding complex comprising the binding reagent and the labeled reagent; iii) inducing the labeled reagent to produce an electrochemical or luminescent signal (preferably, electrochemiluminescence) and iv) measuring the signal so as to measure the labeled reagent. Preferably, the binding reagent is immobilized or capable of being immobilized on a solid phase support, the solid phase support, most preferably being a working electrode in an assay plate or a well of an assay plate of the invention. The method may also comprise the step of immobilizing the binding reagent on the solid phase support and/or working electrode.

The present invention also relates to methods of measuring an analyte in a sample comprising the steps of i) contacting the sample with a labeled detection reagent and optionally a capture reagent, the detection and binding reagents having specific binding affinity for the analyte; ii) forming a binding complex comprising the binding reagent, the analyte and, optionally, the capture reagent; iii) inducing the labeled detection reagent to produce an electrochemical or luminescent signal (preferably, electrochemiluminescence) and iv) measuring the signal so as to measure the analyte in the sample. Preferably, the capture reagent is immobilized or capable of being immobilized on a solid phase support, the solid phase support, most preferably, being a working electrode in an assay plate or a well of an assay plate of the invention. The method may also comprise the step of immobilizing the capture reagent on the solid phase support and/or working electrode.

The present invention also relates to methods of measuring an analyte in a sample comprising the steps of i) contacting the sample with an analog of the analyte and a binding reagent, one of said analog and said binding reagent having a label, wherein said analyte and said analog compete for binding to said binding reagent; ii) inducing said label to produce an electrochemical or luminescent signal (preferably, electrochemiluminescence) and iii) measuring the signal so as to measure the analyte in the sample. Preferably, the binding reagent (if the analog of the analyte has the label) or the analog of the analyte (if the binding reagent has the label) is immobilized or capable of being immobilized on a solid phase support, the solid phase support, most preferably, being a working electrode in an assay plate or a well of an assay plate of the invention. The method may also comprise the step of immobilizing the detection reagent or the analog of the analyte on the solid phase support and/or working electrode.

Another aspect of the invention relates to methods and systems for performing chemiluminescence assays wherein a chemiluminescent label is induced to emit luminescence by introducing a trigger, which reacts with the label to form chemiluminescence. See, U.S. Pat. No. 5,798,083 to Massey et al., hereby incorporated by reference. Preferably, the trigger (such as hydrogen peroxide) is generated by application of electrochemical energy at the working electrode. See, U.S. Pat. No. 5,770,459 to Massey et al., hereby incorporated by reference. The generation of the trigger by the application of electrochemical energy allows for the timed and/or sequential inducement of chemiluminescence in, for example, the sectors or wells of the assay module.

When chemiluminescence measurements are performed, Applicants have found it advantageous to adapt the way the background luminescence is subtracted (e.g., how the instrument subtracts a background image). Typically, when performing an ECL measurement, a background image with the plate positioned under the camera or light detector is taken prior to applying any voltage and the resulting background image is then subtracted from the image taken while the ECL stimulating voltage is applied. For the chemiluminescence measurements, this approach can be disadvantageous if there is chemiluminescence being emitted from the wells during the background read time. However, several different approaches can be used to overcome this problem. According to one embodiment, the apparatus is adapted to take the background image or measure the background luminescence before the plate is brought inside the light tight enclosure (e.g., take an image of the interior of the light tight enclosure to determine the level of background prior to introducing the plate into the enclosure). According to another embodiment, the apparatus is adapted to take a background image after introduction of the plate while the plate is inside the light tight enclosure, but far from the imaged region (i.e., not under the lens or light detector) so that any chemiluminescence emitted from the plate does not interfere with the background measurement. According to yet another embodiment, the apparatus is adapted to characterize the background of a given instrument and subtract those values from the processed chemiluminescence data, rather than directly subtracting a background image before processing for each chemiluminescence measurement (e.g., provide an "estimated background" for a given instrument and use that value for each chemiluminescence measurement).

Yet another aspect of the invention relates to methods for determining the rate of a reaction or the time course of reaction using the assay modules or devices of the invention. See, U.S. Pat. No. 5,527,710 to Nacamulli et al. issued Jun. 18, 1996, hereby incorporated by reference.

Surprisingly, after an assay electrode is used in an ECL assay wherein the electrode is exposed to electrochemical energy to generate ECL, the ability of the electrode to induce ECL in a subsequent assay is reduced, but not eliminated. Particularly, if the voltage is kept at a minimum (e.g., close to the minimum required to induce ECL) and/or the duration of time the voltage is applied to induce ECL is minimized, any damage to the electrodes is minimized or eliminated thereby allowing the electrodes to be used multiple times. One embodiment of using the electrodes more than once relates to a method for determining the time course of a reaction in which at least one reactant is converted to one or more products, the method comprising:
(a) forming a composition containing the reactant and a luminescent label, wherein
    (i) the reactant reacts to form a reaction product;
    (ii) the luminescent label is capable of being induced to emit a luminescence signal, wherein the luminescence signal emitted by the luminescent label is affected by the reaction; and
    (iii) the luminescence signal emitted changes as the reaction progresses; and
(b) detecting emitted luminescence, preferably at selected time intervals, to determine the time course of the reaction.

Preferably, a component of the complex (e.g., the reactant or a second reaction partner) is immobilized on an electrode so that said complex is formed on the electrode. Preferably, the method further comprises exposing the composition to electrical energy at selected time intervals and/or measuring the luminescence signal during the selected time intervals to determine the time course of the reaction.

Preferably, the label is an electrochemiluminescent label.

Preferably, the method further comprises calculating the time course of the reaction from the luminescent signals detected in step (b).

Another embodiment of the invention relates to a method for determining the time course of a binding reaction comprising:
(a) forming a composition containing a reactant, a reaction partner and a luminescent label, wherein:
    (i) the reactant and the reaction partner bind to form a complex;
    (ii) the luminescent label is capable of being induced to emit a luminescence signal; and
    (iii) the luminescent label is attached to the reaction partner; and
(b) detecting emitted luminescence, preferably at selected time intervals, to determine the time course of the reaction.

Preferably, the method further comprises exposing the composition to electrical energy at selected time intervals and/or measuring the luminescence signal at the selected time intervals to determine the time course of the binding reaction.

Preferably, the reaction partner is an antibody and the reactant is an antigen.

According to one preferred embodiment, the reaction partner is attached to the luminescent label via a covalent bond or via a biotin-streptavidin binding interaction.

Another embodiment relates to a method for determining the time course of an enzymatic reaction comprising:
(a) forming a composition containing an enzyme, an enzyme substrate and a luminescent label, wherein:
    (i) the enzyme catalyzes the reaction of the substrate to form a reaction product;
    (ii) the luminescent label is capable of being induced to emit a luminescence signal and the luminescence signal emitted from the luminescent label varies with the concentration of the substrate or the reaction product; and
    (iii) the intensity of the luminescence signal emitted changes as the reaction progresses; and
(b) detecting emitted luminescence, preferably at selected time intervals, to determine the time course of the reaction.

Preferably, the method further comprises exposing the composition to electrical energy at selected time intervals and/or measuring the luminescence signal at the selected intervals to determine the time course of the reaction.

Preferably, the enzyme substrate is a cofactor, more preferably NADH.

Preferably, the reaction product is a cofactor, more preferably NADH.

Another preferred embodiment relates to a method for determining the time course of a reaction in a composition containing a luminescent label wherein the composition is exposed to electrical energy at selected time intervals during said reaction to induce the label to emit an electrochemiluminescent signal and the electrochemiluminescent signal is measured during said selected time intervals to determine the time course of reaction.

According to one preferred embodiment, the reaction is a reaction of a reactant with a reaction partner to form a reaction product. Preferably, the intensity of the luminescence signal relates to the concentration of the reactant, the reaction partner or the reaction product.

Preferably, the reaction is a specific binding reaction of a reactant with the reaction partner.

Preferably, the reaction is an enzyme catalyzed reaction. Preferably, the reaction is of a reactant to form a reaction product and the concentration of said reactant affects said electrochemiluminescent process.

A wide variety of materials have been shown to emit electrode induced luminescence, particularly electrochemiluminescence, and may be used with the methods, plates, kits, systems and instruments of the invention. In preferred electrochemiluminescence systems, ECL-active materials and/or labels are regenerated after the emission of electrochemiluminescence and, during an electrochemiluminescence experiment, may be repeatedly excited to an excited state and/or induced to emit luminescence. For example, one class of ECL-active materials are believed to function via a mechanism that includes the steps of i) oxidation of the material; ii) reduction of the oxidized material by a strong reducing agent so as to produce the material in an excited state and iii) emission of a photon from the excited state so as to regenerate the ECL-active material. Preferably, the difference in redox potentials between the ECL-active material and the strong reducing agent is sufficient so that the energy released by step (ii) is equal to or greater than the energy of the photon. In an analogous mechanism, steps (i) and (ii) may be replaced by i) reduction of the material and ii) oxidation of the reduced material by a strong oxidizing agent. In some especially preferred systems, the mechanism is believed to further comprises the step of oxidizing an ECL coreactant so as to form the strong reducing agent or, analogously, reducing an ECL coreactant to form the strong oxidizing agent.

Preferred luminescent materials and labels include luminescent organometallic complexes of Ru, Os and Re. Some especially useful materials are polypyridyl complexes of ruthenium and osmium, in particular, complexes having the structure $ML^1L^2L^3$ where M is ruthenium or osmium, and $L^1$, $L^2$ and $L^3$ each are bipyridine, phenanthroline, substituted bipyridine and/or substituted phenanthroline. We have found that the inclusion of substituted bipyridines or phenanthrolines presenting substituents comprising negatively charged groups, preferably sulfate groups and most preferably sulfonate groups (as described in copending U.S. patent application Ser. No. 09/896,974, entitled "ECL Labels Having Improved Non-Specific Binding Properties, Methods of Using and Kits Containing the Same" filed on Jun. 29, 2001, the disclosure hereby incorporated by reference) are especially preferred due to their resistance to non-specific binding, in particular to electrodes comprising carbon, carbon particles, carbon fibrils, carbon composites, carbon fibril composites and/or carbon inks.

Yet another aspect of the invention relates to methods of reusing the assay modules of the invention. More specifically, a method of using an assay module a second (or third, etc.) time wherein any decrease in signal (e.g., ECL) emitted by the previously used module is compensated and/or calibrated for in determining the presence or amount of analyte of interest. For example, surprisingly, after an assay electrode is used in an electrochemiluminescence assay wherein the electrode is exposed to electrochemical energy to generate ECL, the ability of the electrode to induce ECL in a subsequent assay is reduced, but not eliminated. Accordingly, one embodiment relates to using an assay module to perform a first assay (preferably an electrochemiluminescence assay) and then using the assay module to perform a second assay (preferably an electrochemiluminescence assay), wherein any decrease in signal generated by the used assay module is compensated and/or calibrated for in performing the second assay. According to one embodiment, the second assay described above is a second reading (preferably an electrochemiluminescence assay) of the same assay in order to generate better statistical analysis of the results or to confirm the initial assay determination.

Yet another aspect of the invention relates to methods of refurbishing and/or reconstructing the assay modules after a first use. More specifically, methods of reconstituting the electrode surface with binding reagents to enable the performance of subsequent assays. One embodiment comprises removing the used biological reagents from the electrode surface (e.g., cleaning the electrode surface) and reapplying biological reagents to the electrode surface. Another embodiment relates to reapplying a refurbishing layer (e.g., a carbon layer on a carbon electrode) over the used biological reagents and then applying new biological reagents to the refurbishing layer.

The step of removing the used biological reagents can be performed by a variety of methods including washing with solutions such as (i) water, (ii) bleach, (iii) water with surfactant/detergent, (iv) acid solutions, (v) base solutions, (vi) organic solvents (e.g., alcohol, ethanol, methanol, DMSO, acetone, etc.) where the solvent is preferably chosen not to dissolve the material used in the module (e.g., carbon/polymer ink electrodes and polystyrene or polypropylene plate) but instead to denature biological materials on the electrode surface, (vii) hydrogen peroxide, (viii) reducing agents (e.g., chemical reduction) on the carbon surface, (ix) chemical cleaning reaction that will "etch" organic material, (x) electrochemical reduction of cleaned/washed carbon surface, (xi) electrochemically active solution where applying a voltage to the electrodes during washing will cause the "cleaning" action—preferably including the step of monitoring the electrical properties (current/voltage) to determine the effect of cleaning, (xii) using elevated temperature solutions to speed the washing, (xiii) multiple washes (e.g., wash 3 times with 200 ul per well to achieve better cleaning than a single wash—where the number of wash cycles varies between 2-10 and the volume varies from 25 to 350 ul (e.g., using standard microplate washing protocols and equipment)), and (xiv) combinations of any of these approaches.

The step of removing the used biological reagent and/or otherwise refurbishing the surface can also be performed using non-liquid/solution approaches such as (i) plasma etching, (ii) plasma deposition of material, (iii) corona treatment, (iv) exposure to ozone, (v) ion or electron bombardment, (vi) irradiating the carbon surface, (vii) flame treatment of surface, (viii) baking the surface (to drive off material), (ix) baking the surface at reduced pressure, (x) annealing the carbon surface to reform/refurbish the electrode surface, (xi) combination of any solution wash as described above with subsequent nonsolution processing, and/or (xii) physical/mechanical treatment (e.g., sanding/polishing/rubbing, etc.).

Preferably, the refurbished assay module is tested to determine whether the refurbishing steps have been sufficient. For example, the electrical properties (current/voltage) of the refurbished electrode is tested or monitored to determine the effect of cleaning. Testing can also be performed visually using an optical microscope or using electron microscopy.

The step of coating the washed or otherwise refurbished electrode surface (preferably carbon electrode surface) with capture reagent can be performed by (i) microdeposition with or without drying of the deposited reagent, (ii) coating biological molecules from solution, (iii) using any of the coating approaches described above after the electrode has already been coated and used once, and/or (iv) electrochemical/chemical/physical/mechanical or any other deposition of any conductive material onto the surface.

5.5 Systems

Another aspect of the invention relates to a system for conducting a luminescence assay, preferably an electrode induced luminescence assay, more preferably a electrochemiluminescence assay, comprising an apparatus, preferably as described above, for inducing and measuring luminescence and a multi-well plate containing an electrode induced luminescence reagent, preferably an electrochemiluminescence reagent.

Another embodiment relates to a system comprising the apparatus, a multi-well plate and an electrode induced luminescence reagent, preferably an electrochemiluminescence reagent.

Yet another embodiment relates to a system comprising the apparatus as described above for measuring luminescence and an assay plate, preferably a multi-well assay plate.

Yet another embodiment relates to a system comprising the apparatus for inducing and measuring luminescence and an assay plate, preferably a multi-well assay plate as described above.

A still further embodiment comprises an apparatus and an assay plate, preferably a multi-well assay plate, containing an electrode induced luminescence reagent, preferably an electrochemiluminescence label.

A still further embodiment comprises the apparatus and one or more robotic devices and/or systems configured to performing one or more of the following functions: (a) moving the plates into, within and out of the apparatus, (b) storing the plates (e.g., refrigeration unit), (c) liquid or reagent handling device (e.g., adapted to mix reagents and/or introduce reagents into wells), (d) assay plate shaker (e.g., for mixing reagents and/or for increasing reaction rates), (e) plate washer (e.g., for washing plates and/or performing assay wash steps (e.g., well aspirator)). Such robotic devices and/or systems may be integrated into the apparatus and/or linked as separate components.

According to a preferred embodiment, the apparatus or system incorporates (or adjoined to or adjacent to or robotically linked or coupled to), for example, one or more of the following devices: plate sealer (e.g., Zymark), plate washer (e.g., TECAN, BioTek), reagent dispensor and/or automated pipetting station and/or liquid handling station (e.g., Zymark, Labsystems, Beckman, TECAN), incubator (e.g., Zymark), plate shaker (e.g., Zymark), compound library or sample storage and/or compound and/or sample retrieval module.

According to a preferred embodiment, one or more of these devices are coupled to the apparatus of the invention via a robotic assembly such that the entire assay process can be performed automatically. According to an alternate embodiment, multi-well plates are manually moved between the apparatus and various devices by manually moving stacks of plates.

A particularly preferred embodiment relates to the integration of the apparatus of the invention to a high-throughput assembly. Preferably, the high-throughput assembly comprises one or more of the following devices, preferably in series (either by placement or by coupling with a robotic assembly): compound library storage, reagent dispensor and/or automated pippetting station and/or liquid handling station, incubation and/or shaker station, washer (optional), and the apparatus of the invention. The system may also comprise a waste disposal module for disposal of the assay module after the assay is performed.

5.6 Kits

Another aspect of the invention relates to kits for use in conducting assays, preferably luminescence assays, more preferably electrode induced luminescence assays, and most preferably electrochemiluminescence assays, comprising an assay module, preferably an assay plate, more preferably a multi-well assay plate, and at least one assay component selected from the group consisting of binding reagents, enzymes, enzyme substrates and other reagents useful in carrying out an assay. Examples include, but are not limited to, whole cells, cell surface antigens, subcellular particles (e.g., organelles or membrane fragments), viruses, prions, dust mites or fragments thereof, viroids, antibodies, antigens, haptens, fatty acids, nucleic acids (and synthetic analogs), proteins (and synthetic analogs), lipoproteins, polysaccharides, lipopolysaccharides, glycoproteins, peptides, polypeptides, enzymes (e.g., phosphorylases, phosphatases, esterases, trans-glutaminases, transferases, oxidases, reductases, dehydrogenases, glycosidases, protein processing enzymes (e.g., proteases, kinases, protein phophatases, ubiquitin-protein ligases, etc.), nucleic acid processing enzymes (e.g., polymerases, nucleases, integrases, ligases, helicases, telomerases, etc.)), enzyme substrates (e.g., substrates of the enzymes listed above), second messengers, cellular metabolites, hormones, pharmacological agents, tranquilizers, barbiturates, alkaloids, steroids, vitamins, amino acids, sugars, lectins, recombinant or derived proteins, biotin, avidin, streptavidin, luminescent labels (preferably electrochemiluminescent labels), electrochemiluminescence coreactants, pH buffers, blocking agents, preservatives, stabilizing agents, detergents, dessicants, hygroscopic agents, etc. Such assay reagents may be unlabeled or labeled (preferably with a luminescent label, most preferably with an electrochemiluminescent label). One embodiment of the invention includes a kit for use in conducting assays, preferably luminescence assays, more preferably electrode induced luminescence assays, and most preferably electrochemiluminescence assays, comprising an assay module, preferably an assay plate, more preferably a multi-well assay plate, and at least one assay component selected from the group consisting of: (a) at least one luminescent label (preferably electrochemiluminescent label); (b) at least one electrochemiluminescence coreactant); (c) one or more binding reagents; (d) a pH buffer; (e) one or more blocking reagents; (f) preservatives; (g) stabilizing agents; (h) enzymes; (i) detergents; (j) desiccants and (k) hygroscopic agents.

Preferably, the kit comprises the assay module, preferably an assay plate, and the assay component(s) in one or more, preferably two or more, more preferably three or more containers.

Preferably, the assay module is a multi-well plate is adapted for use in conducting the electrode induced luminescence assays (preferably electrochemiluminescence assays) in sectors.

According to one embodiment, the kit comprises one or more of the assay components in one or more plate wells, preferably in dry form.

According to one embodiment, the assay components are in separate containers. According to another embodiment, the kit includes a container comprising binding reagents and stabilizing agents. According to another embodiment, the well reagents may include binding reagents, stabilizing agents. Preferably, the kits do not contain any liquids in the wells.

One preferred embodiment relates to a kit for use in conducting electrode induced luminescence assays (preferably electrochemiluminescence assays) comprising an assay plate, preferably a multi-well assay plate, and at least one assay component selected from the group consisting of at least one luminescent label (preferably electrochemiluminescent label) and at least one electrochemiluminescence coreactant).

Another embodiment relates to a kit comprising a multi-well plate and at least one electrode induced luminescent label (preferably electrochemiluminescent label) and/or at least one bioreagent and/or at least one blocking reagent (e.g., BSA).

According to one preferred embodiment, the kit comprises at least one bioreagent, preferably immobilized on the plate surface selected from: antibodies, fragments of antibodies, proteins, enzymes, enzyme substrates, inhibitors, cofactors, antigens, haptens, lipoproteins, liposaccharides, cells, subcellular components, cell receptors, viruses, nucleic acids, antigens, lipids, glycoproteins, carbohydrates, peptides, amino acids, hormones, protein-binding ligands, pharmacological agents, luminescent labels (preferably ECL labels) or combinations thereof.

Preferably, the kit includes immobilized reagents comprise proteins, nucleic acids, or combinations thereof.

According to another embodiment, the kit also comprises an assay diluent (e.g., a reagent into which a reagent is diluted for optimum assay performance).

According to one preferred embodiment, the plurality of wells includes at least two different bioreagents. For example, a well may include two or more assay domains, wherein two or more assay domains have different bioreagent Preferably, the kit comprises at least one electrochemiluminescence coreactant and/or at least one electrode induced luminescence label (preferably electrochemiluminescent label).

According to another embodiment, the kit is adapted for multiple assays. Preferably, the kit further comprises an additional assay reagent for use in an additional assay, the additional assay selected from the group consisting of a radioactive assays, enzyme assays, chemical colorimetric assays, fluorescence assays, chemiluminescence assays and combinations thereof.

According to another embodiment, the kit comprises two or more, preferably four or more, more preferably eight or more, more preferably 15 or more and most preferably 25 or more assay modules or plates. According to a preferred embodiment, the kit is contained in a resealable bag or container (e.g., zip-lock opening).

Preferably, the bag or container is substantially impermeable to water. According to one preferred embodiment, the bag is a foil, preferably an aluminized foil.

The packaging may be translucent, transparent or opaque. Preferably, the plates are packaged in aluminum lined plastic containers or bags containing a dry or inert atmosphere (e.g., the bags may be sealed under an atmosphere of nitrogen or argon or the bags may contain a desiccant). According to another embodiment, the containers are vacuum sealed.

Preferably, the container contains 1 plate. According to another embodiment, the container contains ten plates. According to another embodiment, the container includes between 10 and 100 plates.

Preferably, the assay modules or plates are sterile and/or substantially free of dust and other contaminants.

Preferably, the assay modules are also substantially sterile.

According to one embodiment, the kit is manufactured (at least in part) and/or packaged in a "clean room" environment. Preferably, the kit is manufactured (at least in part) and/or packaged in a Class 100,000 clean room having <100,000 particles (the clean room particle count using a 0.5 micron particle count number) per cubic foot (or 3.53 million particles per cubic meter).

Preferably, the contaminant particle counts (particles less than 0.5 microns) of the kit is less than 60 million per square meter, more preferably 30 million per square meter, even more preferably less than 20 million, even more preferably less than 15 million and most preferably less than 10 million.

Preferably, any contaminating non-volatile residue is less than 0.50 g/meter$^2$, more preferably less than 0.25 g/meter$^2$, even more preferably less than 0.15 g/meter$^2$ and most preferably less than 0.10 g/meter$^2$.

Preferably the contaminant ion concentration is less than 50 ppm, more preferably less than 20 ppm, even more preferably less than 10 ppm, even more preferably less than 5 ppm, and most preferably less than 1 ppm.

Another aspect of the invention relates to novel approaches for stabilizing various biological/chemical species coated onto assay electrodes or assay modules or the like, preferably onto the electrodes of the multi-well plates of the invention. For example, multi-well plates or kits may be manufactured for a range of applications. The plates may be uncoated or pre-coated with specific reagents. Typically, the reagents coated onto the plate enable specific binding of some assay constituent to the plate surface. Once these reagents are coated onto the plates, there will usually be some time delay before the plates are used in an assay. Therefore, the stability of the reagent coating is critical. The reagent may become less biologically active or become inactive if it denatures or otherwise degrades. The approaches of stabilizing coatings described below can be applied to the different types of coatings and/or different assay modules (e.g., multi-well multi-spot plates, etc.) described throughout this specification.

One embodiment for stabilizing reagents on the plate surface involves application of a stabilizing solution to the plate and subsequent drying of this solution on the surface prior to, during or after the application of the biological reagents. Preferably, the stabilizing solution is a sugar containing, buffered solution. When dried, the solution leaves a coating of sugar that creates a desirable environment, which promotes stability of the biological activity of the immobilized reagents. Preferably, the resultant coated surface comprises between 1 to 100 μg/cm$^2$ of sugar. The amount of sugar present on the surface can be measured by re-hydrating the wells with an aqueous solution and measuring the amount of sugar that dissolves into the solution.

One embodiment employs a stabilizing solution comprising: (a) a buffer (e.g., ammonium phosphate, sodium phosphate, and/or potassium phosphate) and (b) a sugar. The sugar can be any one of the family of simple sugars including fructose, maltose, sucrose, glucose, trehelose, etc. Preferably, the sugar is sucrose.

According to another embodiment, the stabilizing solution further comprises a preservative (e.g., Kaython (a commercial preservative)). According to another embodiment, the stabilizing solution further comprises a surfactant, preferably a nonionic surfactant (e.g., Tween 20). According to yet another embodiment, the stabilizing solution further comprises the preservative and the surfactant. However, the stabilizing solution could optionally comprise the buffer and the sugar, without a preservative or surfactant.

According to a preferred embodiment, the stabilizing solution comprises: from 10 to 30 g/l ammonium dihydrogenphosphate; 1 to 2 g/l ammonium monobasic phosphate; 1 to 3 g/l Kaython (commercial preservative); 0.5 to 2 g/l Tween 20 (a commercial surfactant); and 10 to 30 g/l sucrose.

According a particularly preferred embodiment, the stabilizing solution comprises: 24.7 g/l ammonium dihydrogenphosphate; 1.5 g/l ammonium monobasic phosphate; 2 g/l Kaython (commercial preservative); 1 g/l Tween 20 (a commercial surfactant); and 20 g/l sucrose.

Preferably, the pH of the solution is adjusted to between 6.5 and 8.5, more preferably between 7.0 and 8.0, even more preferably between 7.4 and 7.8 and most preferably about 7.6.

Preferably, the pH is adjusted with either a simple acid or simple base, such as potassium hydroxide (base) or hydrogen chloride (acid).

The invention also relates to methods of applying the stabilizing solution. There are several ways to apply the stabilizing solution to the surface (e.g., electrode or plate) according to the invention. Typically, a capture reagent is microdispensed onto the working area(s) (e.g., assay spots, assay regions or assay domains) of the working electrode(s). After an incubation period, the wells are optionally washed and/or blocked with a blocking reagent. If the plates are not blocked, the stabilizing solution may be used to wash off unbound capture reagent, leaving a small amount of stabilizing solution to dry in the well. Typically, only a thin film of stabilizing solution is left in the well (e.g., quantities less than 5 ul are preferable for each well of a 96 well plate while quantities less than 2 ul are preferable for each well of a 384 well plate). According to another embodiment, the plates are blocked wherein the blocking solution is aspirated from the wells, and the remaining solution is washed away with the stabilizing solution. A small amount of stabilizing solution is left in the well to coat the biological reagents wherein both the capture reagents and the blocking reagents are stabilized by the stabilizing solution.

Another embodiment of the invention relates to a method of properly storing the assay modules of the invention. In order to maintain stability over long storage times, the plates should be dry. Several steps may be employed to ensure the dryness of the plates. First, most of the stabilizing solution is preferably removed at the end of the wash cycle. The remaining fluid is typically dried in ambient conditions for some period of time. Alternatively, the wells may be dried by blowing dry air into the wells for a period of time. According to one embodiment, the air is blown through individual tubes into each well of the plate. Alternatively, air can be sucked through tubes placed in each well causing the relatively dry air in the room to flow into the wells. Both approaches achieve similar drying of the wells. Another method of drying the plates is to place batches of plates that have been washed with stabilizing solution into a vacuum chamber. The remaining water evaporates in the vacuum leaving the plates dry. The drying of the stabilizing solution on the plates can be achieved in individual batches or as part of an automated plate-processing system.

After the plates are dried with the stabilizing solution, they are preferably packaged with desiccant packs to ensure that further drying may take place. The desiccant may also absorb any detrimental water vapor that penetrates the packaging material over the shelf life of the product. Preferably, high barrier materials are used for packaging to prevent the penetration of water vapor. Preferably, the atmosphere in the package is removed as the plates are vacuum-packed. Prior to vacuum-packaging, the package can be filled with an inert gas (e.g., nitrogen, argon) to displace the oxygen and water vapor from the package. According to one preferred embodiment, the plates are contained in a bag comprising polypropylene laminated to an aluminum foil (e.g., 0.35 mil aluminum foil) and containing a desiccant (e.g., preferably silica gel, more preferably about 3.5 grams silica gel desiccant with each packaged plate). The exact quantity of silica gel desiccant required depends on the permeability of the packaging material to water vapor, the residual water on the plate, and the desired shelf life of the product. In one preferred embodiment, between 1 and 2 grams or desiccant is used per plate. Preferably, the desiccant will change color after absorbing a threshold amount of water. The amount of desiccant required increases when multiple plates are packaged together, both because of the increased water remaining on the plates and because of the larger surface area of the packaging.

Another embodiment of the invention relates to novel methods of measuring the drying or dryness of an assay module by measuring the change in conductivity of the surface on which the reagents are immobilized. For example, the multi-well plates of the invention have integrated electrodes on the bottom of each well allowing for the measurement of the dryness of the plate bottoms in a way that is not possible with standard multi-well plates. The stabilizing solution that coats the well bottom and well walls is a conductive material and the conductivity of the solution depends on the concentration of water. Thus, as the solution forms a coating and dries, the conductivity decreases until it reaches a steady state. By measuring the conductivity from the working to counter electrode, it is possible to monitor the degree of dryness, serving as a quality control measurement for plate drying. A similar measurement can be performed after storage of the packaged plates to confirm that the packaging provided a good barrier to water and/or that the desiccant was sufficient to keep the plate dry. To ensure stability of the plates, the plates are dried until the conductivity is less than 30 µS (microsiemens), preferably less than 10 µS, more preferably less than 5 µS, and most preferably less than about 1 µS.

5.7 Adaptor for Non-Conforming Plate

Another aspect of the invention relates to plate adaptor designed and configured for use with an apparatus for conducting electrode induced luminescence assays (preferably electrochemiluminescence assays) using plates having contact surfaces not aligned with the electrical connectors of the apparatus. Thus, an adaptor is employed to allow for an adaptive electrical connection between the electrical connectors of the apparatus and the contact surfaces of the non-conforming plate.

One embodiment of the invention relates to a plate contact adapter for use in an apparatus for conducting assays in an assay plate, preferably multi-well assay plate having a plurality of wells, comprising a plurality of plate working contact surfaces and a plurality of plate counter contact surfaces for providing electrical energy to the plurality of wells, the apparatus including one or more working connectors and one or more counter connectors adapted to provide electrical energy to the plurality of wells, wherein the one or more working connectors and/or one or more counter connectors do not mate and/or are not aligned with the corresponding plate working contact surfaces and/or plate counter contact surfaces, the plate contact adapter comprising:

(a) a nonconductive substrate having at least a first adaptor surface and a second adaptor surface;
 (b) one or more working adaptor contact surfaces on the first adaptor surface configured to mate with the one or more working connectors of the apparatus;
 (c) one or more counter adaptor contact surfaces on the first adaptor surface configured to mate with one or more counter connectors of the apparatus;
 (d) one or more working adaptor contacts on the second adaptor surface electrically connected to the one or more working adaptor contact surfaces and configured to come into electrical contact with one or more of the plate working contact surfaces; and
 (e) one or more counter adaptor contacts on the second adaptor surface electrically-connected to the one or more counter adaptor contact surfaces and configured to come into electrical contact with one or more of the plate counter contact surfaces. Preferably, the plate adapter has dimensions roughly corresponding to a standard 96-well or 384-well plate and adapter contact surfaces at adapter contact locations that are located at at least one, preferably at least two, more preferably at least four and most preferably all, of the following locations on the first adapter surface, the locations being defined by coordinates (X, Y) measured (inches, ±0.250", preferably ±0.125") from the left and top edges, respectively, of the plate adapter (i) one or more (preferably two or more, more preferably three or more and most preferably all) of first sector locations: (0.743, 0.620), (1.097, 0.620), (1.451, 0.620), (0.743, 1.329), (1.097, 1.329), (1.451, 1.329), most preferably, one or more working adapter contact locations selected from (0.743, 0.620), (1.451, 0.620), (0.743, 1.329), and (1.451, 1.329) and/or one or more counter adapter contact locations selected from (1.097, 0.620), and (1.097, 1.329);

(ii) one or more (preferably two or more, more preferably three or more and most preferably all) of second sector locations: (2.161, 0.620), (2.515, 0.620), (2.869, 0.620), (2.161, 1.329), (2.515, 1.329), (2.869, 1.329), most preferably, one or more working adapter contact locations selected from (2.161, 0.620), (2.869, 0.620), (2.161, 1.329), and (2.869, 1.329) and/or one or more counter adapter contact locations selected from (2.515, 0.620), and (2.515, 1.329);

(iii) one or more (preferably two or more, more preferably three or more and most preferably all) of third sector locations: (3.579, 0.620), (3.933, 0.620), (4.287, 0.620), (3.579, 1.329), (3.933, 1.329), (4.287, 1.329), most preferably, one or more working adapter contact locations selected from (3.579, 0.620), (4.287, 0.620), (3.579, 1.329), and (4.287, 1.329) and/or one or more counter adapter contact locations selected from (3.933, 0.620), and (3.933, 1.329);

(iv) one or more (preferably two or more, more preferably three or more and most preferably all) of fourth sector locations: (0.743, 2.038), (1.097, 2.038), (1.451, 2.038), (0.743, 2.747), (1.097, 2.747), (1.451, 2.747), most preferably, one or more working adapter contact locations selected from (0.743, 2.038), (1.451, 2.038), (0.743, 2.747), and (1.451, 2.747) and/or one or more counter adapter contact locations selected from (1.097, 2.038), and (1.097, 2.747);

(v) one or more (preferably two or more, more preferably three or more and most preferably all) of fifth sector locations: (2.161, 2.038), (2.515, 2.038), (2.869, 2.038), (2.161, 2.747), (2.515, 2.747), (2.869, 2.747), most preferably, one or more working adapter contact locations selected from (2.161, 2.038), (2.869, 2.038), (2.161, 2.747), and (2.869, 2.747) and/or one or more counter adapter contact locations selected from (2.515, 2.038), and (2.515, 2.747); and (vi) one or more (preferably two or more, more preferably three or more and most preferably all) of sixth sector locations: (3.579, 2.038), (3.933, 2.038), (4.287, 2.038), (3.579, 2.747), (3.933, 2.747), (4.287, 2.747), most preferably, one or more working adapter contact locations selected from (3.579, 2.038), (4.287, 2.038), (3.579, 2.747), and (4.287, 2.747) and/or one or more counter adapter contact locations selected from (3.933, 2.038), and (3.933, 2.747).

Preferably, the adapter comprises a first layer comprising one or more adapter contact surfaces, a second layer comprising one or more adapter contacts and an insulating layer(s) in between. Preferably, the insulating layer(s) includes one or more conductive pathways electrically connecting the one or more adapter contact surfaces with the one more adapter contacts. According to one preferred embodiment the adapter comprises an adhesive on the surface having the adaptor contacts so that the adapter can be affixed to a plate bottom. According to another embodiment, the adaptor clamps onto the plate. According to yet another embodiment, the adapter is configured to connect to the electrical connectors of the apparatus.

Another embodiment of the invention relates to a method for measuring luminescence from a multi-well assay plate having a plurality of wells comprising providing electrical energy to the multi-well assay plate using an adapter.

Another embodiment relates to an apparatus comprising the adapter.

Yet another embodiment relates to a multi-well plate with an adapter affixed thereto or in contact therewith.

5.8 Method of Re-Focusing Wells

Another aspect of the invention relates to a method of conducting one or more assays using an apparatus for measuring luminescence from a multi-well assay plate having a plurality of wells, the apparatus comprising a source of energy for generating luminescence within the plurality of wells and a camera for measuring luminescence emitted from the plurality of wells, the method comprising optimizing the measuring by adjusting the camera focus thereby optimizing the method of conducting the one or more assays in the apparatus. Preferably, the optimizing comprises adjusting a lens and/or adjusting the distance between the wells and the camera. Such methods, for example, allow for the use of plates having different dimensions (i.e., the distances between the imaging or detecting surface and the emitting surface varies) and/or different volumes of fluid within the wells and/or different sample compositions (e.g., having different optical properties).

Preferably, the apparatus is adapted to allow for re-focusing to allow for the detection of the presence of a lid or cover and the subsequent compensation for the effect of that lid or cover on the image of the plate bottom. Additionally, the re-focusing would allow the detection of the amount of fluid in the well (or a change in the index of refraction of the fluid in the well) and subsequent refocusing on the plate bottom.

5.9 Method of Rearranging the Electrical Contacts or Electrical Connectors

Another aspect of the invention relates to methods of conducting one or more assays using multi-well plates having different contact surface configurations. That is, a method comprising re-configuring or rearranging the electrical connectors of the apparatus to properly align and contact the contact surfaces of the plate. Such methods allow for greater flexibility in plate selection. Such methods also allow for the future use of future plates having new contact configurations.

One embodiment of the invention relates to a method of conducting one or more assays using an apparatus for measuring luminescence from a multi-well assay plate having a plurality of wells and two or more plate contact surfaces electrically connected to the plurality of wells, the apparatus comprising a source of energy for generating luminescence within the plurality of wells, a camera for measuring luminescence emitted from the plurality of wells and one or more electrical connectors for contacting the multi-well plate thereby providing energy to the wells, the method comprising arranging and/or reconfiguring the one or more electrical connectors of the apparatus to align with the plate contact surfaces.

Another embodiment of the invention relates to a method where a first set of electrical connectors is replaced with a second set having a different configuration. Thus, another aspect of the invention relates to an apparatus adapted to provide for such re-configuration or re-positioning of the electrical contacts and/or replacement of a first set of electrical contacts with a second set having a different configuration.

5.10 Computer Implemented Control/Interface System

CCD Implementation

Figure 35A:
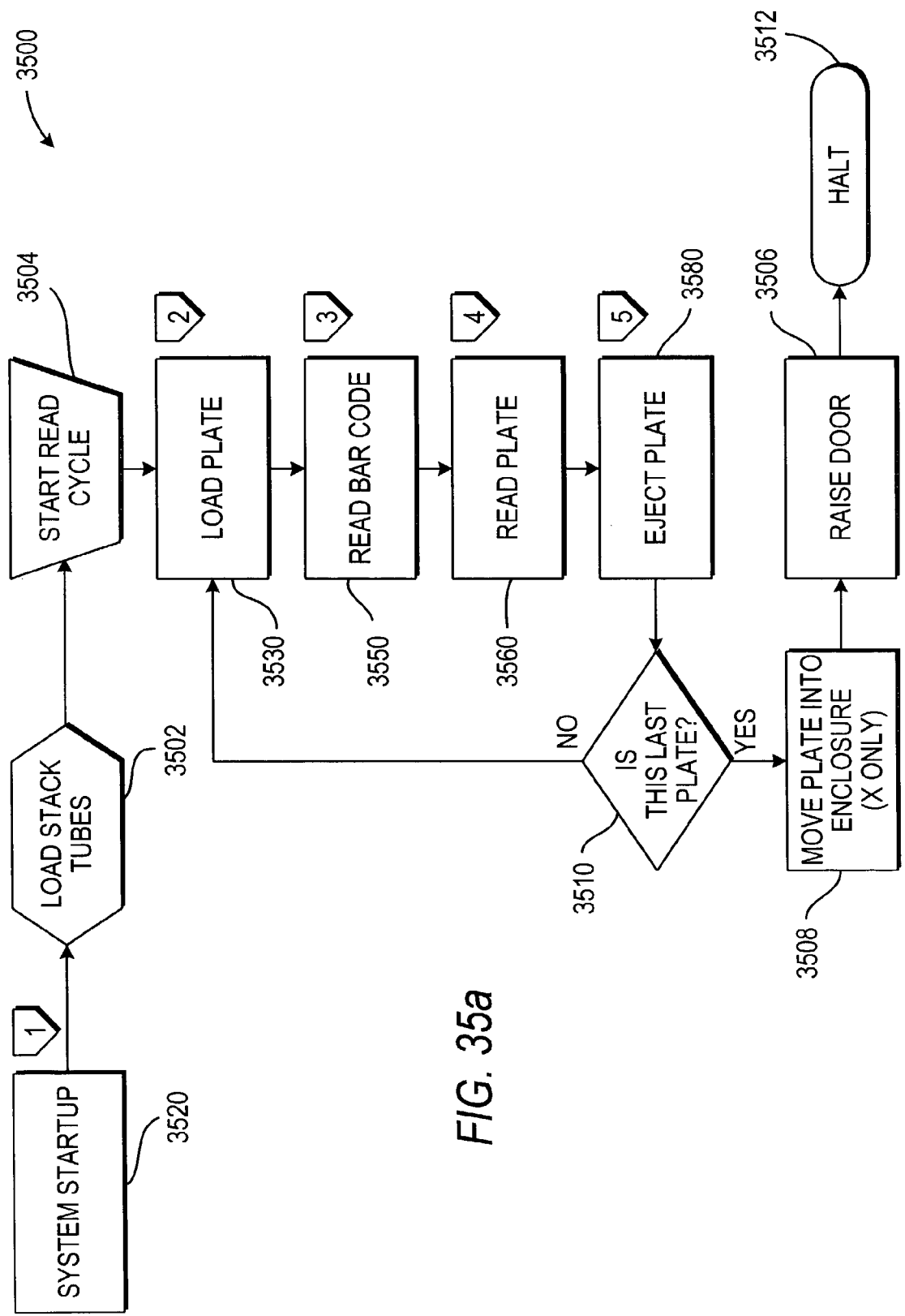

FIG. 35a depicts a top level block diagram for one embodiment of an automated/computerized process for carrying out the ECL-based assays on a representative diagnostic device as described herein. It should be understood that any one of, or all of, the steps depicted in the process flow diagram in FIG. 35a and any related figures may be implemented by a general purpose computer system or by a specially designed/outfitted computer system. A typical computer system would consist of at least one processor and at least one memory coupled to the processor. In one embodiment, the process flow depicted in FIG. 35a and the related figures may be embodied in a set of instructions that can be executed by a processor. In such an embodiment, the set of instructions for performing ECL-based assays on an instrument coupled to a computer may be stored in a computer readable storage medium including, for example, any magnetic medium, any optical medium, any magneto-optical medium, and the like. The computer readable storage medium may be accessed: in a local fashion such as, for example, by direct access to read only memory (ROM) or by loading the storage medium containing the executable instructions into an appropriate reading device locally coupled to the computer system; or in a remote fashion such as, for example, by downloading the set of instructions from a device remotely coupled to the computer system. A device remotely coupled to the computer system may, for example, include a server networked to the computer system, a remote storage device or dedicated network appliance, a digital transmission device (e.g., satellite, microwave, infrared and/or radio broadcast) or the like.

Figure 35B:
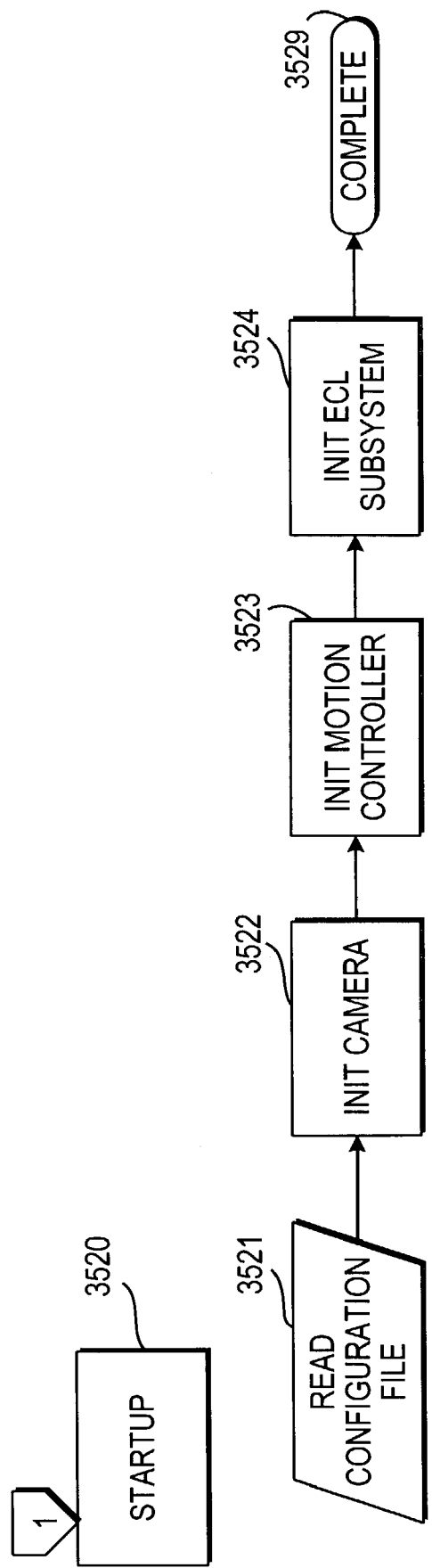

At step 3520 at least a portion of the set of instructions is loaded into a memory coupled to the processor for execution by the processor. FIG. 35b is a more detailed block diagram illustrating the operations carried out at step 3520. In one embodiment, initialization of the instructions may include reading a configuration file 3521 that contains information related to the configuration of the instrument such as, for example, information related to the specific camera, information related to the motion control system, information related to the ECL electronics/subsystem, and the like. Camera specific information may include, for example, camera type (CCD, CMOS), parameters relating to the specific CCD chip, operating parameters (integration time, binning, gain settings, etc.), defect maps, filters, fixed focal length or variable focal length, and the like. Information related to the control system may include, for example, number and placement of motors, number and placement of position sensors, degrees of freedom, ranges of motion, velocity profile parameters, viable paths, the presence or absence of a robotic loading system (e.g., robotic system to load each plate or to load each stack tube, etc.), and the like. Information related to the ECL electronics/subsystem may include, for example, power source, range of waveforms that can be applied, number and position of electrical contacts, range of motion of electrical contacts, and the like. Once the configuration file is read 3521, the computer system may execute appropriate instructions to initialize the camera and related subsystems 3522, initialize the motion controller and related subsystems, initialize the ECL electronics and/or related subsystems and initialize any other systems or subsystems which may be defined in the configuration file read at 3521.

Figure 35C:
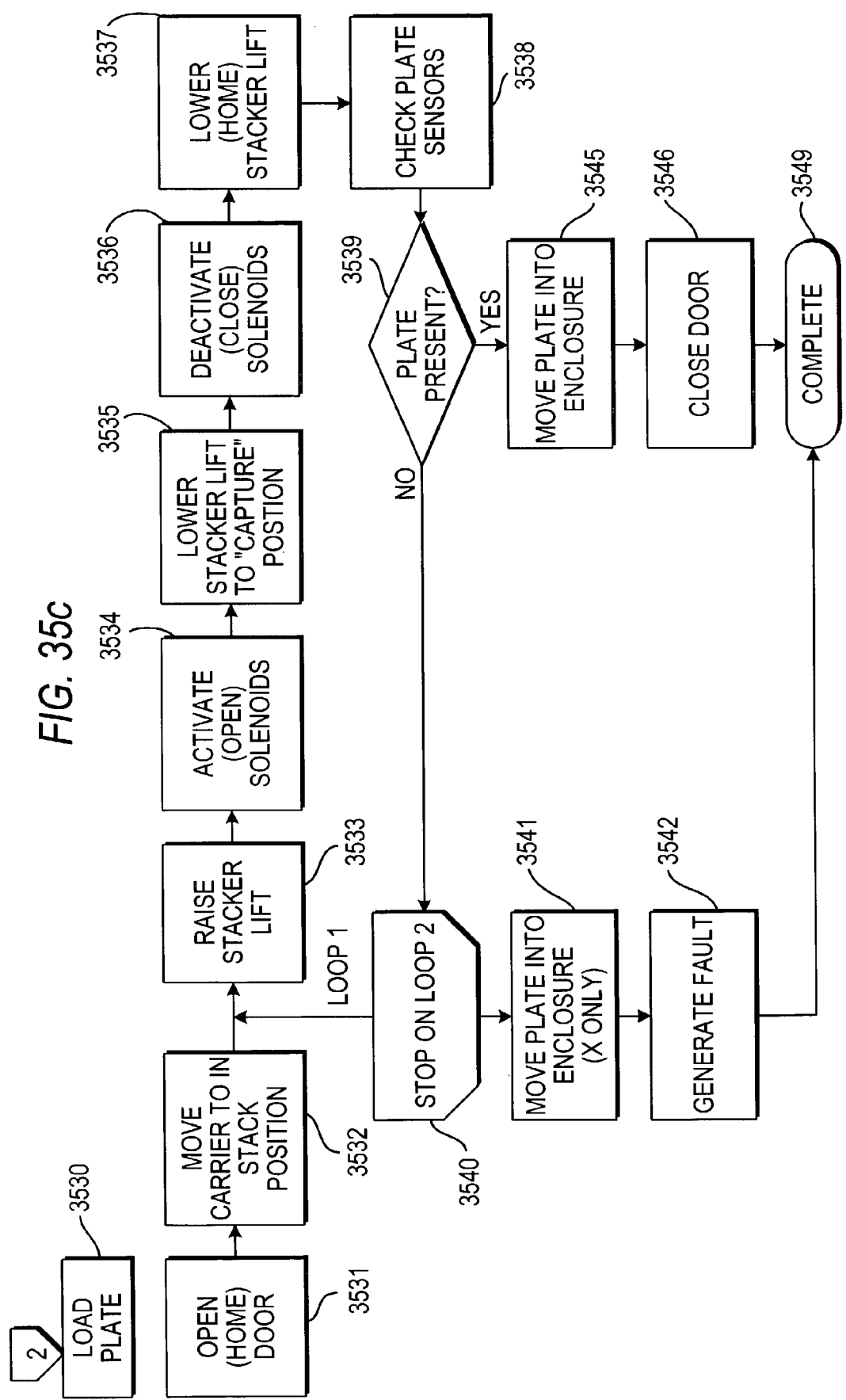

At step 3502, the stack tubes are loaded into their respective receptacles. Loading of the stack tubes may occur in an entirely automated fashion, in an entirely manual fashion, or in any combination thereof. For example, in an entirely automated fashion, a computer system coupled to a robotic manipulation system could contain instructions for directing the robotic manipulation system to load/unload the stack tubes. Of course it should be understood that the computer system coupled to the robotic manipulation system could be the same computer system coupled to the diagnostic device or could be a separate computer system dedicated to controlling the robotic manipulation system. At step 3530 an instruction is issued to the motion control system to load a plate onto the plate carrier. FIG. 35c is a more detailed block diagram illustrating the operations carried out at step 3530. At step 3531 the computer system carries out the instructions directing the appropriate subsystems to open the enclosure's door 3531 and move the plate carrier into position 3532, 3533 for receiving a plate from the stack tube containing the plates to be analyzed. Once the plate carrier is in position for receiving a plate, the computer carries out the instructions 3534, 3535 directing the appropriate subsystems to release a plate from the stack tube onto the plate carrier. At steps 3536, 3537 the appropriate subsystems are directed to engage the plate retention mechanism on the stack tube and move the plate carrier into position for subsequent transport into the enclosure of the diagnostic device. In one embodiment, as depicted in FIG. 35c, mechanical latches may be actuated by solenoids to release/retain 3534/3536 the plates from/in the stack tube. In a preferred embodiment, sensors would indicate whether or not a plate has been successfully loaded onto the plate carrier 3538. If the sensors indicate to the computer system that a plate is present, instructions directing the appropriate subsystems to move the plate carrier into the enclosure 3545 and close the enclosure's door 3546 are executed. If however, the sensors indicate that a plate has not been loaded onto the plate carrier, alternate instructions are executed directing the appropriate subsystems to execute the instructions for implementing steps 3533 through 3539 once again. At step 3539 if it is determined that a plate is still not present, the computer first determines whether this operation has been attempted before and if so 3540 executes an alternate set of instructions directing the appropriate subsystems to move the plate carrier back into the enclosure 3541 and generate a fault 3542, terminating the process 3549. Of course it should be understood that FIG. 35c depicts one illustrative embodiment where an attempt to load a plate onto the plate carrier is made only twice and that the number of attempts made to load a plate could vary from as little as once to as many times as is specified; the number of attempts could be a fixed number prescribed in the set of instructions or it could be a variable number either prescribed by the configuration file loaded at 3521 or by the user/operator.

Figure 35D:
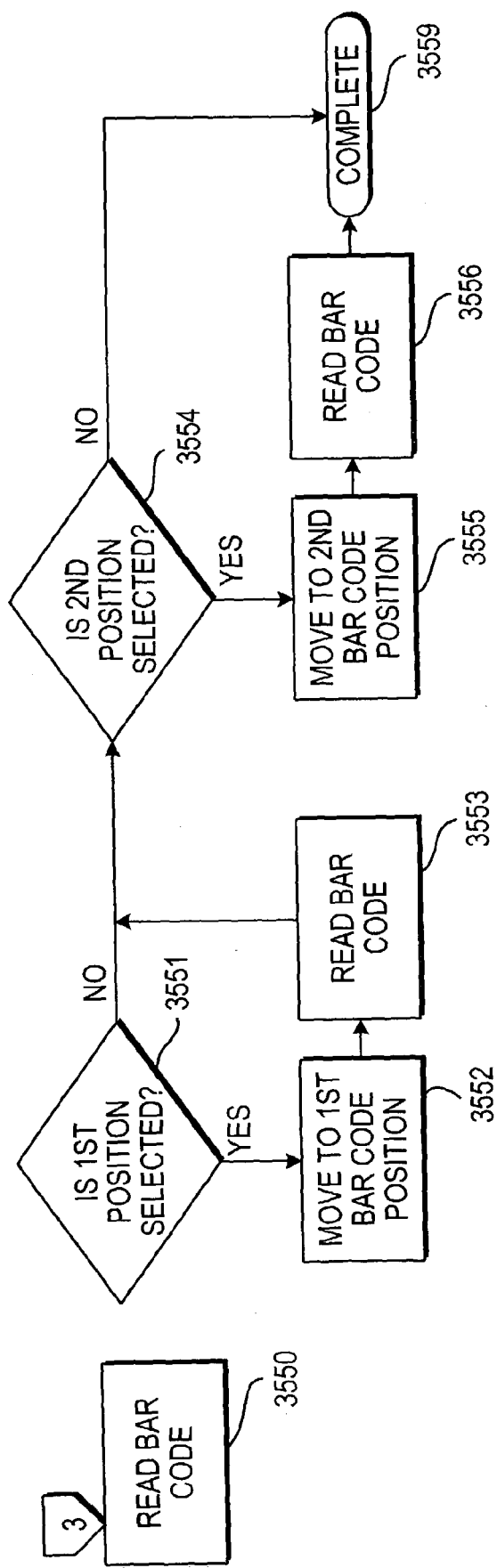

Next, after a plate has been loaded onto the plate carrier at 3530, a bar code 3730-3733, 3740-3743 as depicted in FIG. 37 for one illustrative embodiment, is read from the plate 3550. FIG. 35d is a more detailed block diagram illustrating the operations carried out at step 3550. At step 3551 the computer system determines whether a first position, e.g., 3730 is occupied by bar code information. In one embodiment, the user/operator can specify the number and placement of bar codes on the plate, for example, through a user input device such as a mouse, keyboard, data file, and the like. In another embodiment, the first position 3730 itself could contain encoded information indicating the number and placement of any bar codes. In such an embodiment, the computer system could, for example, execute instructions which direct it to always read the first position and use the information from the first position to determine the number and placement of other bar coded information. If the first position contains bar code information, the computer system would instruct the appropriate subsystems to move the plate carrier to the first bar code reading position 3552 and read 3553 the bar code information 3730. This process could then repeat 3554-3556 for any number of subsequent bar code positions 3730-3733, 3740-3743 occupied by bar code information until all bar codes specified have been read. It is important to note that FIG. 35*d* illustrates only one possible embodiment where two bar codes are possible and that any number of bar codes (see e.g., FIG. 37) may in practice be utilized limited only by physical constraints (e.g., readable areas of the plate, number of bar codes that can be placed on the readable areas of the plate, etc.).

In a preferred embodiment, the system can use a software design pattern known as a "chain of responsibility" to allow microtiter plates to be processed based on bar codes. The diagnostic device may be configured to read and interpret bar codes on microtiter plates. Bar codes may have a multitude of information encoded in them in a multitude of various formats. The chain of responsibility pattern allows the computer system to read and interpret many different formats. Some formats may have been specified at the time of manufacture or assembly of the diagnostic device while others may be specified at some later point in time while still others may be specified by various parties.

For instance, in one example the manufacturer of the diagnostic device may have specified certain requirements and/or limitations for the number and types of assays, the type of microtiter plates, the number of wells, the number of spots within wells, the number, type, composition and/or placement of electrodes, and the like, that the particular device can handle. In another example the manufacturer of the microtiter plates, or a portion of the microtiter plates (e.g., the microtiter plate without the plate bottom, the plate bottom with integral electrodes, etc.), which may or may not be the same as the manufacturer of the diagnostic device itself, may also have certain requirements/limitations that it has specified for proper handling and use of its plates (e.g., materials used, processes used in fabricating electrodes, etc.).

In still another example the party responsible for immobilizing certain reagents on the electrode, which may or may not be the same party as either the microtiter plate or diagnostic device manufacturer, may have specified further its own requirements/limitations for proper use and handling of the microtiter plates it has processed with its reagents (e.g., temperature, moisture, light/UV exposure, shelf life, storage requirements, which wells contain controls (positive and/or negative), known calibrators with specific concentrations, unknown samples, and the like). In yet another example, the party performing assays may wish to apply bar codes to the plates in order to track which compounds have dispensed into which wells.

Use of a chain of responsibility approach allows new formats to be introduced at any time and by any party. A party wishing to place a bar code upon the microtiter plate may do so by simply providing a component, a bar code interpreter, which may be added to the system without the need for existing code to be re-written or modified. Each bar code interpreter could be a self-contained component that implements a generic interface for parsing and decoding a particular bar code format. When a bar code is read, the computer system executes instructions which assigns the task of identifying an appropriate bar code interpreter to another set of instructions which constructs a list of the available bar code interpreters, and asks the first interpreter to decode the bar code.

In one embodiment, if the first interpreter understands the encoding, it parses and decodes the information on the bar code; if the interpreter does not recognize the format, it passes the bar code on to the next interpreter on the list. In this way, each interpreter is given a chance to process the bar code. In another embodiment, the computer system could pass the encoded information to each interpreter, either in parallel or in successive fashion, and await a response as to whether the interpreter recognizes the format. If a new format is introduced, the system need only be configured with a new interpreter to handle the new format. Other interpreters in the chain will ignore the new format and either instruct the computer system that it does not recognize the format or pass it on to the next interpreter in the chain until the proper interpreter for the format is found.

Figure 35E:
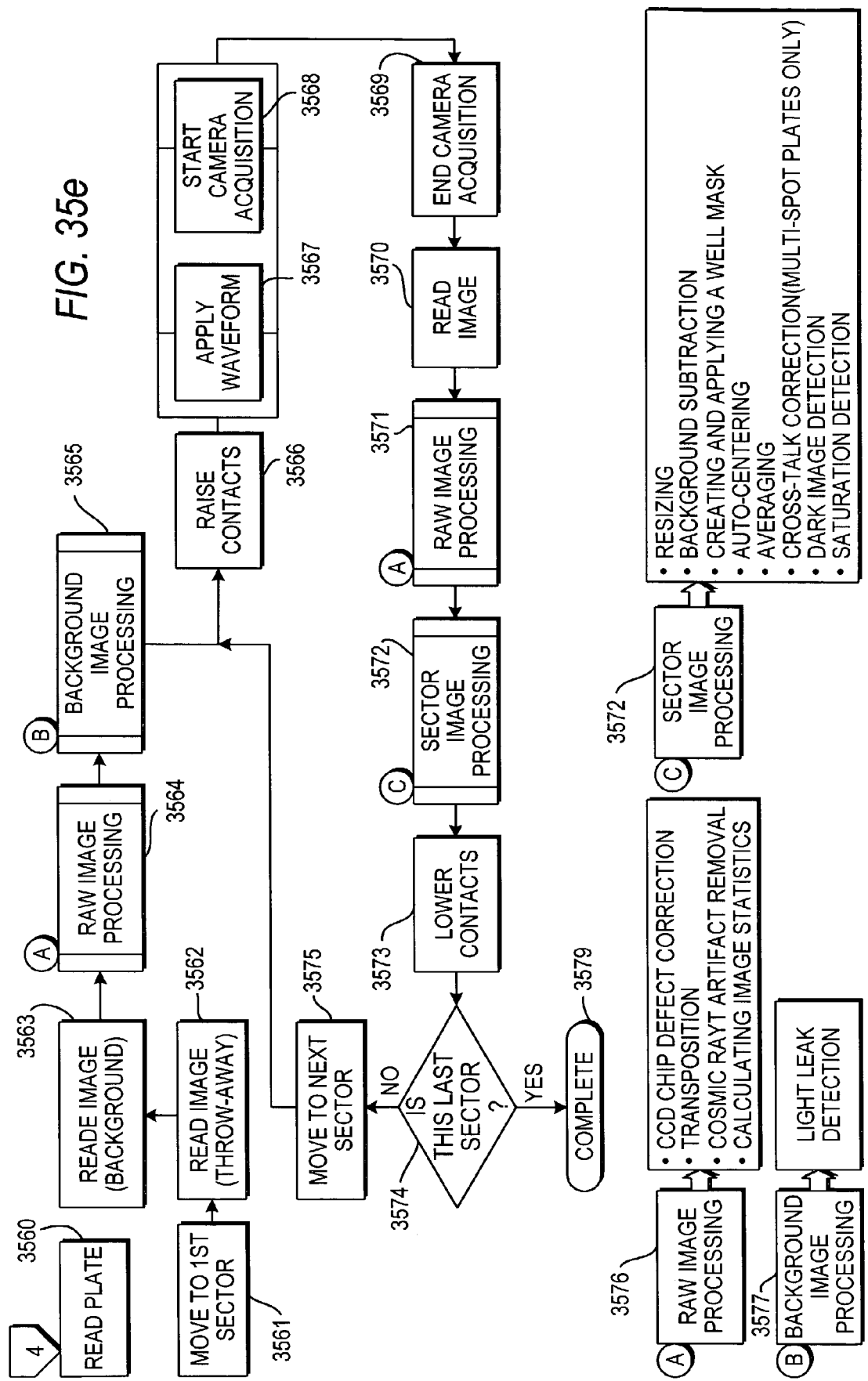

Once the bar code information has been read at 3550 instructions are executed which direct the appropriate subsystems to "read" the plate 3560. FIG. 35*e* is a more detailed block diagram illustrating the operations carried out at step 3560. At step 3561 instructions are executed which direct the appropriate subsystems to move the plate carrier into position to read the first sector. Once in position for reading of the first sector, instructions are executed which direct the appropriate subsystems to read a background image 3562, 3563. At step 3564 instructions are executed to perform raw image processing on the background image taken at 3563. Step 3564 could include, for example, execution of instructions and application of certain algorithms to perform CCD chip defect correction, transposition (if necessary), cosmic ray artifact removal and calculation of image statistics 3576 (image processing is discussed in greater detail below).

After the image taken at 3563 has undergone raw image processing, the background image processing step 3565 is performed in order to determine whether a light leak condition exists 3577. If there is not a determination of a light leak condition the process continues to step 3566 where the appropriate subsystems are directed to raise the electrical contacts 3566, apply the appropriate waveform 3567 and begin the camera acquisition procedure 3568. As depicted in FIG. 35*e*, steps 3567 and 3568 are conducted substantially in parallel; i.e., in a substantially simultaneous manner. After the camera acquisition procedure has terminated at 3569 the image acquired is read at 3570 and subjected to raw image processing 3571, which could include one or more of CCD chip defect correction, transposition, cosmic ray artifact removal and calculation of image statistics 3576.

Next, the image processed at 3571 is passed to a sector image processing procedure 3572. In one embodiment, step 3572 could include one or more of resizing, background subtraction, creation and application of a well mask, auto-centering, averaging, cross-talk correction, dark image detection and saturation detection. The appropriate subsystems are then directed to lower the electrical contacts 3573. If there are any remaining sectors to be read 3574 the appropriate subsystems are directed to move the plate carrier to the next sector 3575 and this process continues until all of the sectors on the plate have been read 3579. Of course it should be understood that steps 3571 and 3572 need not be conducted in a real time manner but instead may be performed in an off-line mode; e.g., the diagnostic device can read all the sectors on an individual plate, all the plate in a stack tube or any number of plates, and store the images for subsequent image processing. In this manner of operation, one embodiment could allow a user to initiate the image processing by executing an image processing routine or another embodiment could allow image processing to be automatically scheduled to occur at a predetermined time, after a predefined number of plates/sectors have been read, or any combination thereof.

Figure 35F:
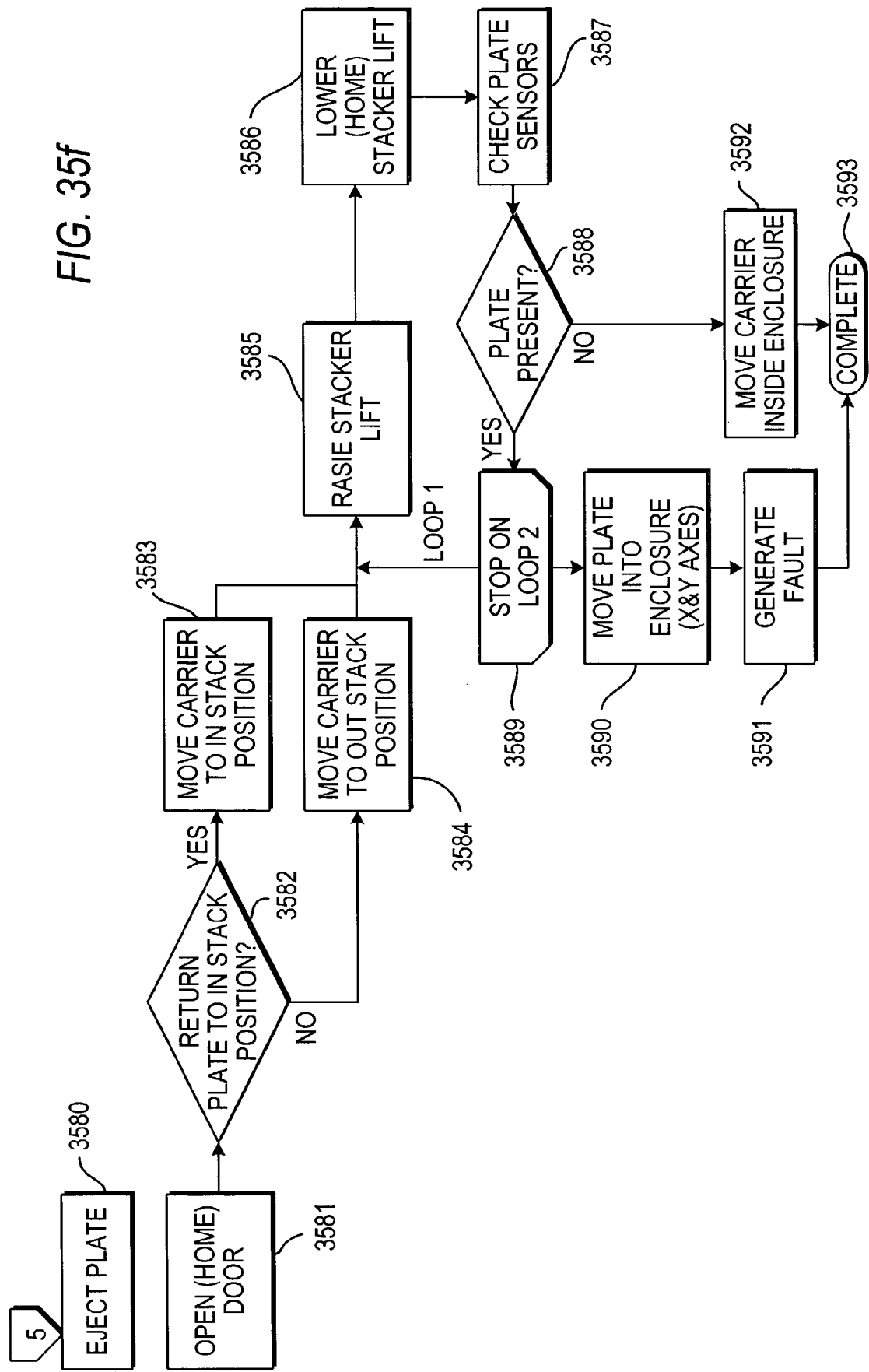

After the entire plate has been read instructions are executed that direct the appropriate subsystems to eject the plate 3580. FIG. 35f is a more detailed block diagram illustrating the operations carried out at step 3580. In response to directions to eject the plate from the enclosure, the appropriate subsystems open the enclosure's door 3581. Next, it is determined whether or not the plate is to be returned to the in-stack position (e.g., running the device with a robotic manipulation system) and if so, the appropriate subsystems are directed to move the plate carrier to the "in-stack" position. If it is determined that the plate is not to be returned to the in-stack position, the appropriate subsystems are directed to move the plate carrier to the "out-stack" position. In either case, whether positioned at the in-stack position or the out-stack position, the appropriate subsystems are directed to raise the plate carrier, or raise the stacker lift, so that the plate is placed into the appropriate receptacle. The stacker lift is then lowered 3586 and in a preferred embodiment a determination is made as to whether or not the plate has been successfully ejected from the plate carrier 3587, 3588. If the plate has not been successfully ejected, steps 3585 through 3588 are repeated for as many times as specified or until the plate has been ejected. While FIG. 35f depicts an iterative process for steps 3585 through 3588 which is performed only twice, it should be understood that this process can be carried out for any number of iterations. Once the iteration count has exceeded the allowable amount 3589, the appropriate subsystems are directed to move the plate carrier into the enclosure 3590 and generate a fault 3591. If the plate has been successfully ejected as determined at step 3588, the appropriate subsystems would be instructed to move the plate carrier into the enclosure 3592.

Photodiode Array Implementation

Figure 36A:
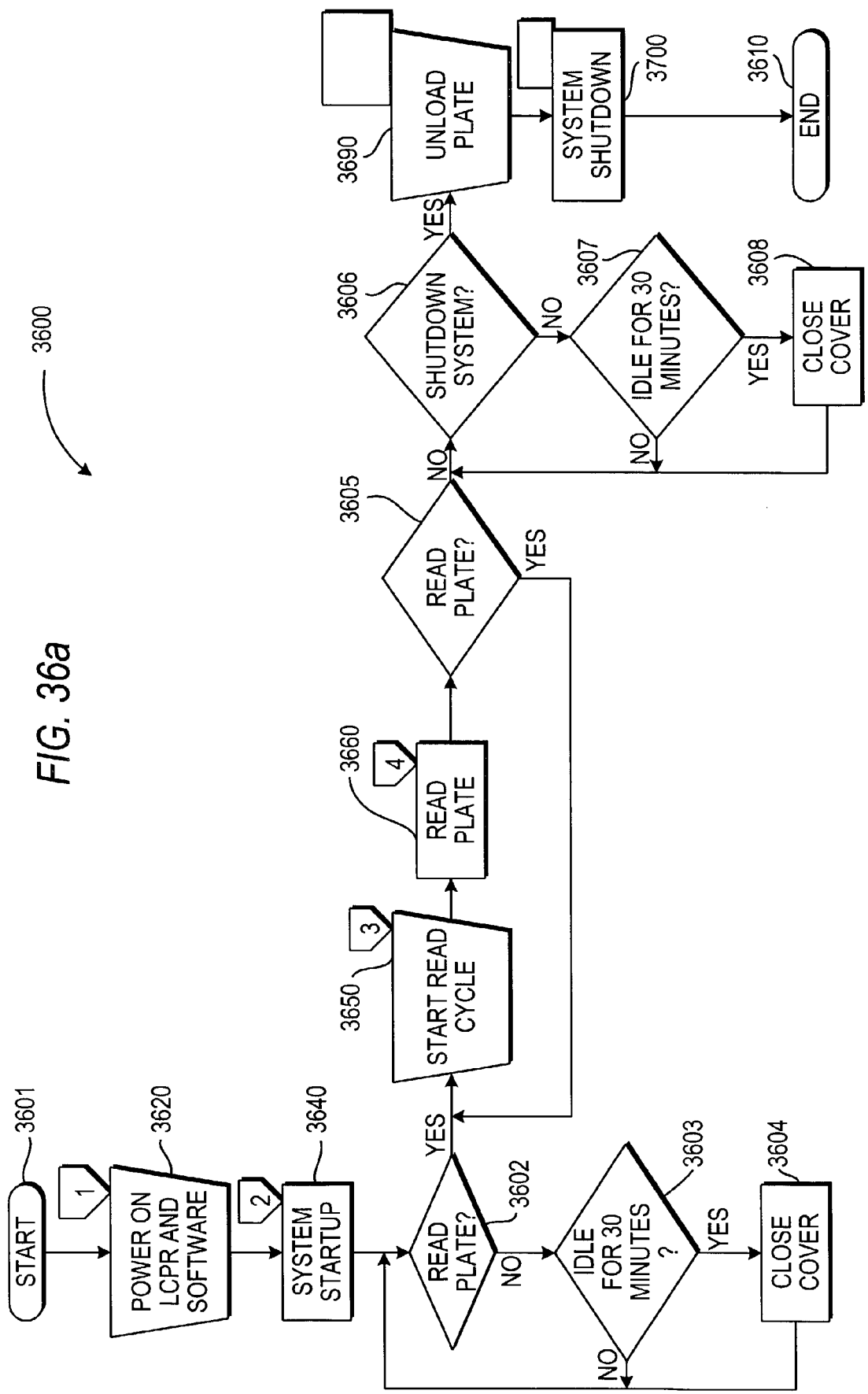

FIG. 36a depicts a top level block diagram for one embodiment of an automated/computerized process for carrying out the ECL-based assays on a representative diagnostic device that utilizes a photodiode array as described herein. It should be understood that any one of, or all of, the steps depicted in the process flow diagram in FIG. 36a and any related figures may be implemented by a general purpose computer system or by a specially designed/outfitted computer system. A typical computer system would consist of at least one processor and at least one memory coupled to the processor. In one embodiment, the process flow depicted in FIG. 36a and the related figures may be embodied in a set of instructions that can be executed by a processor. In such an embodiment, the set of instructions for performing ECL-based assays on an instrument coupled to a computer may be stored in a computer readable storage medium including, for example, any magnetic medium, any optical medium, any magneto-optical medium, and the like. The computer readable storage medium may be accessed: in a local fashion such as, for example, by direct access of read only memory (ROM) or by loading a storage medium containing the executable instructions into an appropriate reading device locally coupled to the computer system; or in a remote fashion such as, for example, by downloading the set of instructions from a device remotely coupled to the computer system. A device remotely coupled to the computer system may, for example, include a server networked to the computer system, a remote storage device or dedicated network appliance, a digital transmission device (e.g., satellite, microwave, infrared and/or radio broadcast) or the like.

Figure 36B:
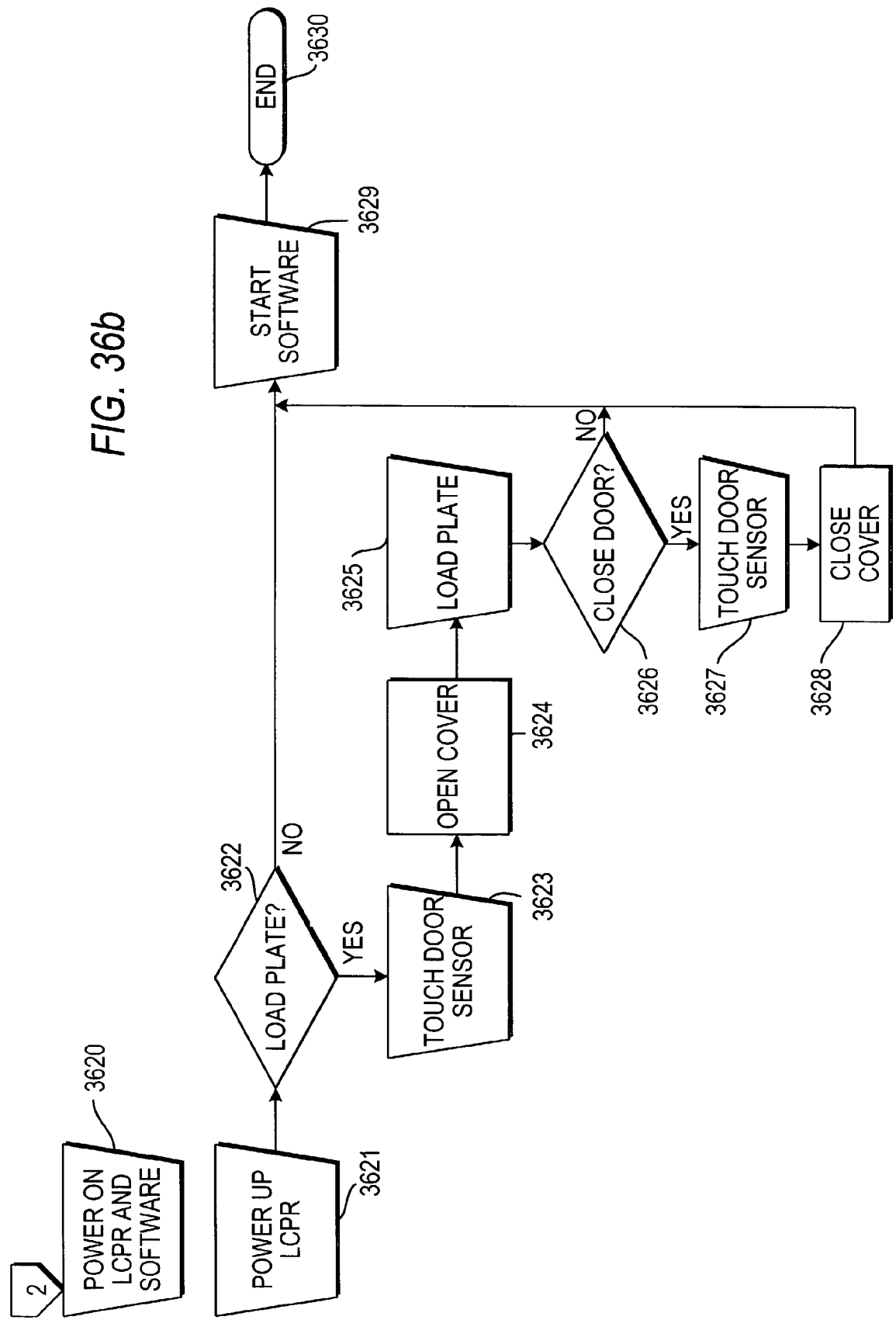

At step 3620 the diagnostic device is powered up and at least a portion of the set of executable instructions is loaded into a memory coupled to the processor for execution by the processor. FIG. 36b is a more detailed block diagram illustrating the operations carried out at step 3620. In one illustrative embodiment, the diagnostic device is initially powered up by a user/operator 3621 and the user/operator can elect to load a plate at this time 3622. If the user/operator wishes to load a plate, touching the door sensor 3623 activates the appropriate subsystems to open the unit's cover 3624. Once the cover has been opened, the user/operator can load a plate 3625 and close the door 3626 by touching the door sensor 3627. Touching the door sensor 3627 activates the appropriate subsystems to close the cover 3628. At this point the program/software can be started up 3629 by the user/operator to begin operation of the device.

Figure 36C:
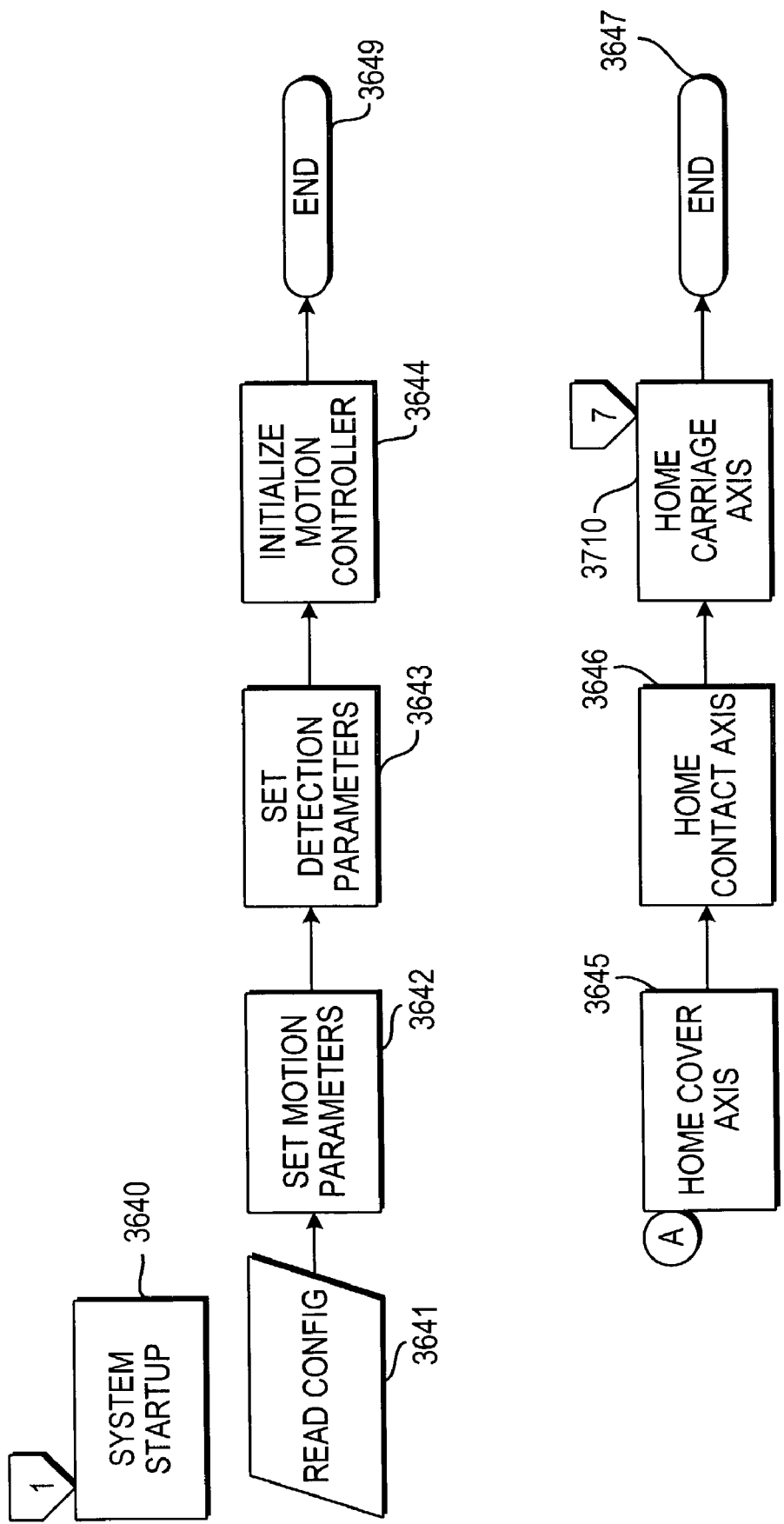
Figure 36D:
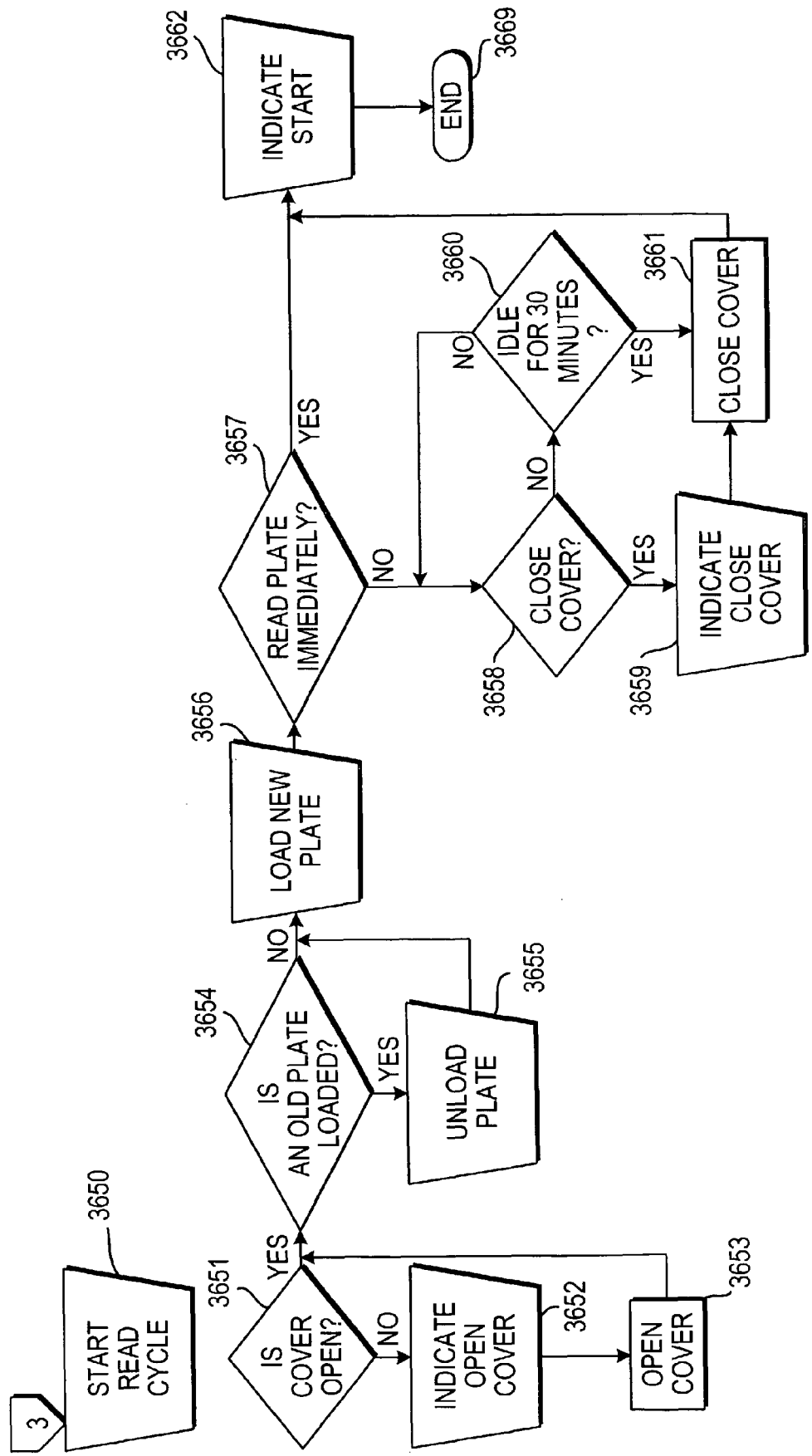
Figure 36E:
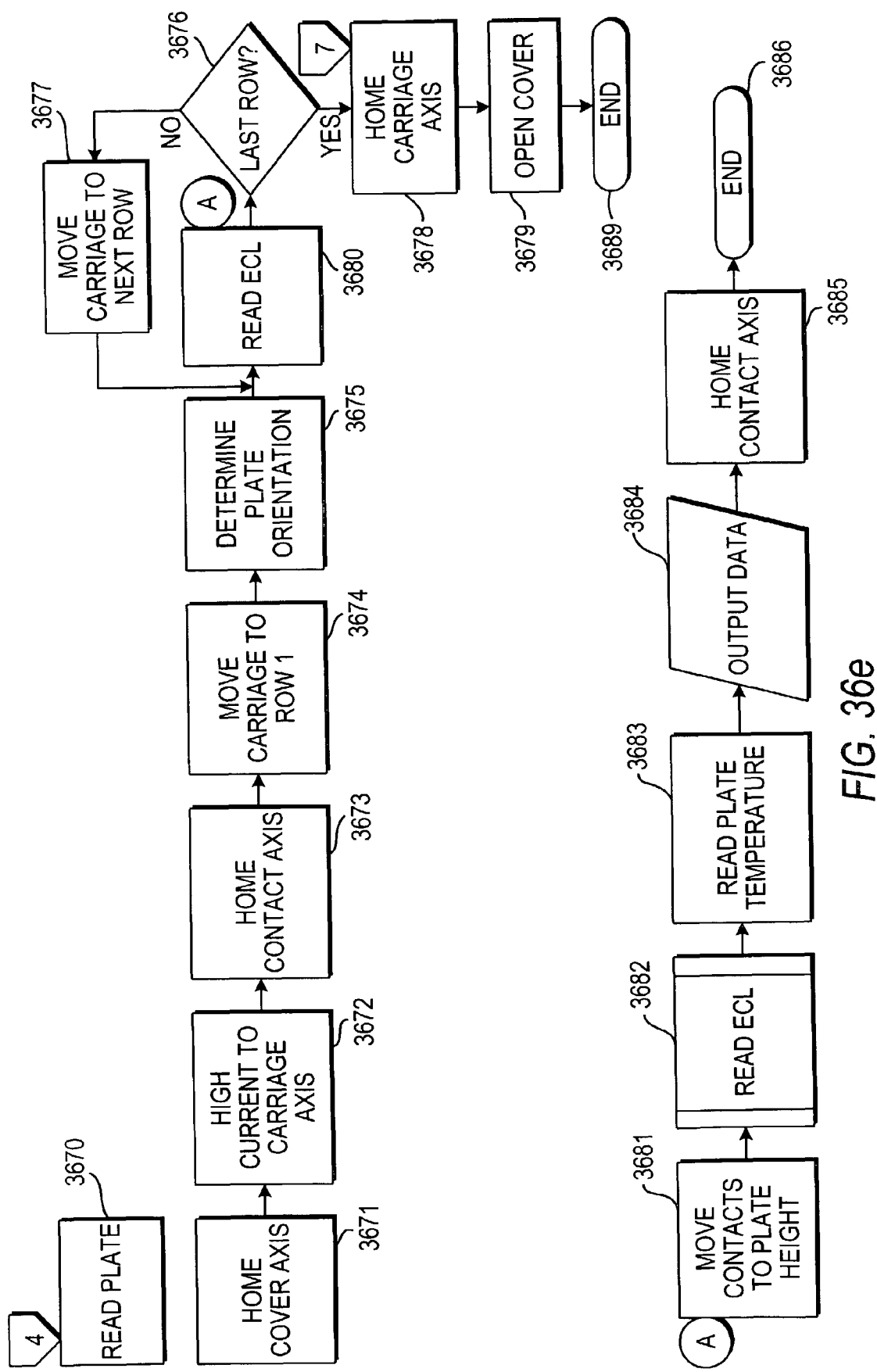
Figure 36F:
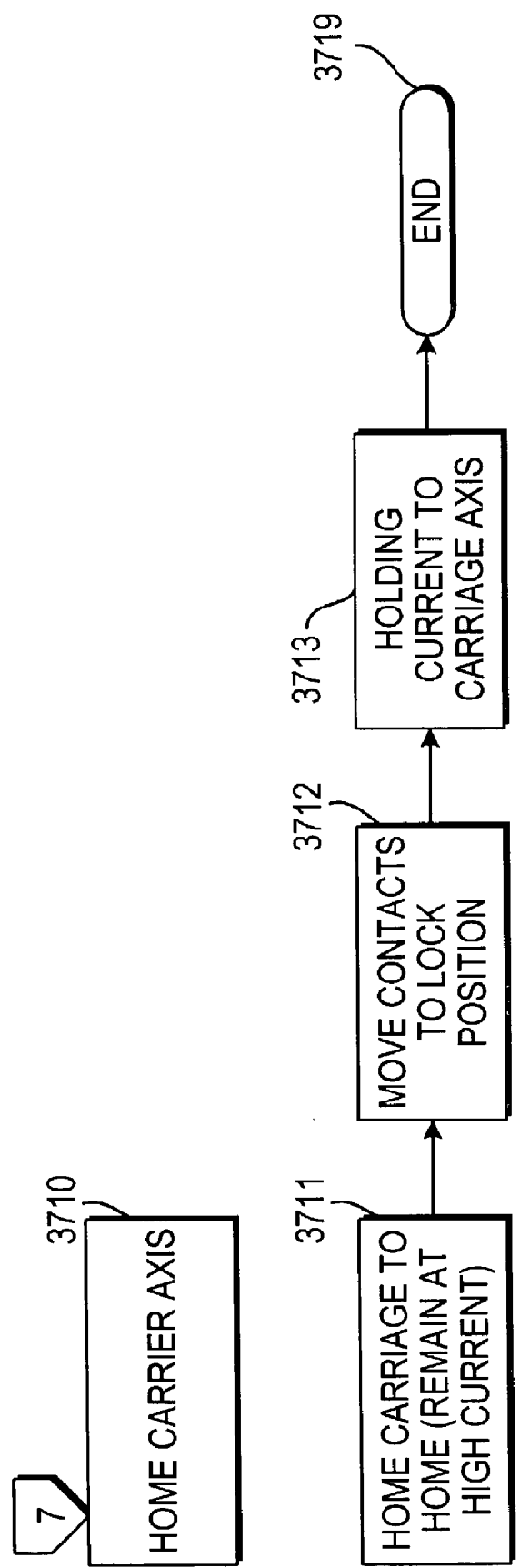

At step 3640 at least a portion of the set of instructions is loaded into a memory coupled to the processor for execution by the processor. FIG. 36c is a more detailed block diagram illustrating the operations carried out at step 3640. In one embodiment, initialization of the instructions may include reading a configuration file 3641 that contains information related to the configuration of the instrument such as, for example, information related to the specific photodiode sensors, information related to the motion control system, information related to the ECL electronics/subsystem, and the like. Photodiode specific information may include, for example, diode type, operating parameters, dynamic range, detection limits, filters, wavelength, and the like. Information related to the control system may include, for example, number and placement of motors, number and placement of position sensors, degrees of freedom, ranges of motion, viable paths, the presence or absence of a robotic loading system (e.g., robotic system to load each plate or to load each stack tube, etc.), and the like. Information related to the ECL electronics/subsystem may include, for example, power source, range of waveforms that can be applied, number and position of electrical contacts, range of motion of electrical contacts, and the like. Once the configuration file is read 3641, the computer system may execute appropriate instructions to set the appropriate motion parameters 3642, set the appropriate detection parameters 3643, initialize the motion controller and related subsystems 3644 (e.g., directing the appropriate subsystems to carry out "home" instructions for the cover axis 3645, contact axis 3646 and carriage axis 3710) and initialize any other systems or subsystems which may be defined in the configuration file read at 3641. FIG. 36f is a more detailed block diagram illustrating the operations carried out at step 3710. In one embodiment, homing the carriage axis 3710 might involve moving the carriage to the home position while remaining at high current 3711, moving the contacts to the lock position 3712 and holding the current to the carriage axis 3713.

At step 3602 the user/operator can indicate to the computer system that instructions should be executed to prepare for reading the plate 3650. FIG. 36d is a more detailed block diagram illustrating the operations carried out at step 3650. In one embodiment as show in FIG. 36d, preparation for reading a plate may include the steps of determining whether the cover is open 3651, and if not, allowing a user/operator to indicate that the cover should be opened 3652 (e.g., by pressing the door sensor as indicated at step 3623 of FIG. 36b) and executing instructions directing the appropriate subsystems to open the cover 3653. If the cover was determined to be open at 3651, the computer system could determine whether an "old plate" is present in the plate carrier 3654 and if so, the computer system may be programmed to prompt the user to unload the old plate 3655. Next a new plate could be loaded 3656 by the user/operator and a determination can be made as to whether the plate should be read immediately 3657 and if so the user/operator could indicate to the system that the plate should be read immediately 3662. In the embodiment depicted in FIG. 36*d*, as a safety precaution, the system could be programmed to determine whether the cover has been left open for more than a specified period of time (e.g., thirty (30) minutes) 3660 without any action by the user/operator, and if so execute instructions directing the appropriate subsystems to close the cover 3661.

Once an indication has been received that the plate should be read, e.g., the user could press a button on the device itself or could press a button displayed by the graphical user interface software, instructions would be executed directing the appropriate subsystems to read the plate 3660. FIG. 36*e* is a more detailed block diagram illustrating the operations carried out at step 3660. In the embodiment depicted in FIG. 36*e*, the computer system could execute instructions directing the appropriate subsystems to home the cover axis (i.e., close the cover) or ensure that it has been homed (i.e., closed) 3671, apply high current to the carriage axis 3672, home the contact axis (i.e., retract the electrical contacts or ensure that they have been retracted) 3673 and move the plate carrier, or carriage, to the first row to be read 3674. Prior to proceeding with the reading process, the plate orientation is determined 3675. At step 3680 instructions are executed directing the appropriate subsystems to read the plate by moving the electrical contacts to the proper plate height 3681 and reading the ECL signal 3682 from the row of wells under investigation. Next a plate temperature measurement is taken 3683 for use in temperature correction of the ECL signal and the acquired data is output to, for example, one or both an electronic file stored on a fixed disk storage device coupled to the computer system or a portable computer readable medium (e.g., floppy diskette, CD-ROM, DVD, magneto-optical storage medium, or the like). After the data has been acquired, instructions are executed directing the appropriate subsystems to home the contact axis (i.e., retract the electrical contacts) and a determination is made as to whether there are any remaining unread rows 3676. If the last row has not been read, the appropriate subsystems are directed to move the carriage to the next row 3677 for reading 3680. Once the last row has been read, the appropriate subsystems are directed to home the carriage axis (i.e., return the carriage to the plate loading/unloading position) 3678, as described in greater detail above with reference to FIG. 36*c*, step 3710, and open the cover 3679.

In one embodiment, this plate reading procedure 3650, 3660 can be continuously repeated 3605 for as many iterations as the user/operator specifies. If there are no more plates to be read, the user/operator may indicate that the system should be shutdown 3606. At this point, the user/operator can unload the plate 3690 and allow the system to be shutdown 3700. Again, the system could be programmed to sit idle for a certain predefined amount of time 3607 (e.g., thirty (30) minutes) before closing the cover, or ensuring that it is closed 3608.

It should be understood that the user/operator steps discussed above for one possible embodiment may be automated as well by, for example, utilizing robotic manipulation systems, and that the invention is not limited to requiring human intervention for loading/unloading plates, opening the cover, etc.

Image Processing

FIG. 35*a* depicts an illustrative process flow diagram for one embodiment where a CCD camera is used to acquire images of luminescence-based assays performed in one or more wells of a microplate. FIG. 35*e* depicts in greater detail the step of reading a plate as depicted in FIG. 35*a*. Generally, use of a CCD camera for image acquisition and/or analysis typically requires that certain factors be taken into account and that certain measures be taken to insure precision, accuracy and or integrity of the data. Typical factors include CCD chip defect correction, background image subtraction/correction, cosmic ray removal/correction, hardware binning, software binning, image transposition and various other factors known to those of ordinary skill in the art. Some of these factors are often times modified by the unique and/or particular application; e.g., background image subtraction/correction when imaging/analyzing celestial bodies from the earth may depend on certain variables that are different from imaging/analyzing celestial bodies from outer space. Consequently, and as discussed in greater detail below, the general factors affecting use of a CCD camera for imaging/analyzing image data of luminescence-based assays performed in one or more wells of a microplate must be considered in light of the variables associated with the particular application. Other factors which are not present in typical applications, whether modified or not, but instead are present only in the particular application of a CCD camera for image acquisition/analysis of luminescence-based assays performed in one or more wells of a microplate include, for example, creating and applying a well mask, image alignment/centering, averaging, cross-talk correction, dark image detection, saturation detection and other factors which may affect image acquisition/analysis.

In one embodiment, CCD camera defect correction can be based on a user-defined defect map. A defect map could simply be a text-based file which defines areas of the camera that are defective or nonfunctioning and that therefore would be excluded from image acquisition/analysis. For example, each defect could be defined as a specific pixel or a rectangular area on the full chip image with top-left and bottom-right coordinates. A defect map listing each CCD chip defect could, for example, be determined by analyzing a full chip image under both dark and illuminated conditions. In one embodiment, a defect map may consist of an initial defect map that was created at the time of manufacture of the CCD camera and a real-time defect map which is created and updated subsequent to CCD camera manufacture. This real-time defect map could, for example, be created upon initial camera installation and thereafter updated either at regularly scheduled intervals, including weekly, monthly, after a certain number of uses, each use of the camera, or at intervals that are arbitrarily specified or selected by the operator/user.

The defect maps could be stored in electronic format or in non-electronic format. Electronic format files could either be stored in the camera hardware, such as for example in the camera firmware, bios, memory registers, or the like, or in an electronic file stored on a machine-readable storage medium that is separate and distinct from the camera hardware. The separate and distinct electronic file could be a database file that is stored as part of the overall system or as and independent file that is used, for example, as a configuration file or initialization file. Alternatively, the defect map could be stored in a non-electronic file on traditional non-electronic media and manually entered into the system as part of the setup process or procedure. In embodiments where the defect maps are not stored in the camera hardware, the defect maps could include an identification entry/field that could enable assignment of the particular camera with a particular set of defect maps associated with that camera. Typically, since defect maps may be specified in full chip image coordinates, prior to any pre-processing, the defect correction is preferably the first operation performed on an image. In an illustrative embodiment, a computer could be programmed to conduct such image processing automatically.

Where defect correction must be utilized, as for instance when there is an associated defect correction map for a particular camera, correction could be achieved by, for example, substituting for each defective pixel value an average value of its neighboring pixels. Neighboring values may be selected from nearest neighbor pixels or from second nearest neighbor pixels if common defects include row or column defects. For example, if a defect is defined as a single pixel $I_{r,c}$, where r represents the pixel's row value and c represents the pixel's column value then the following second nearest neighbor formula could be applied:

$$I_{r,c} = \frac{I_{r-1,c-1} + I_{r-1,c+1} + I_{r+1,c-1} + I_{r+1,c+1}}{4}$$

Where a defect is not limited to a single pixel but instead may include an entire column or a portion of a column, then the following formula could be applied to obtain the corrected value for each pixel in the column or portion of the column:

$$I_{r,c} = \frac{I_{r,c-1} + I_{r,c+1}}{2}$$

Additionally, where a defect includes an entire row or portion of a row, then the following formula could be applied for each pixel in the row or portion of the row:

$$I_{r,c} = \frac{I_{r-1,c} + I_{r+1,c}}{2}$$

In the event that a defect includes more than a single adjacent row or column or portion of a single adjacent row or column, then the substitution value could be obtained through use of, for example, linear interpolation between its next closest adjacent neighbors.

An embodiment may also require another typical image processing/correction operation which could include, for example, image transposition and/or rotation, where for example the particular camera installation would result in an image that would not be naturally oriented for a user/operator. In this instance the image could be transposed and/or rotated to give the user a natural image orientation.

Another factor that typically is considered when using a CCD camera for image acquisition/analysis is the possibility that one or more pixels of the CCD camera may have been impinged upon by a cosmic ray; i.e., a cosmic ray hit. Cosmic rays can cause bright spots to occur on the sensor and therefore affect the resulting image acquisition/analysis. Cosmic ray hits occur randomly both in space and time. Therefore, in order to ensure proper image acquisition/analysis, it is advantageous to identify pixel values that may be considerably greater than the values observed in a local area of the CCD camera and make corrections as required. In one embodiment, a cosmic ray removal/correction algorithm could be employed that first identifies cosmic ray hits by finding pixels that are brighter then their neighbors, as may be defined by a threshold value (e.g. by using a gradient operation to identify large differences in the values of neighboring pixels), or by identifying pixels that are determined to be statistically significant outliers. A threshold value may be defined by, for example, a fixed, preset value, a fixed, user-specified value, a variable, preset value based on certain variables or a variable, user-specified value based on certain variables that are either predefined or defined by the user. For example, a threshold value may be defined as a factor to be applied to a particular pixel. Therefore, in one embodiment, it may be specified that if a pixel's value is four (4) times greater than each of its surrounding neighbor pixels, then it would be considered a cosmic ray hit. Alternatively, a cosmic ray hit may be identified by simply comparing a pixel's value with either its neighboring pixels in the same row or its neighboring pixels in the same column, as opposed to comparing the pixel's value with both its row-adjacent and column-adjacent pixels' values.

Once a pixel value has been identified as likely being the result of a cosmic ray hit, the pixel value could be replaced by an average value of the neighboring pixels. Such a cosmic ray removal/correction procedure could be applied repeatedly until an acceptable image results. Additionally, a background value, or offset, could be pre-subtracted from all pixels prior to performing the cosmic ray hit search.

For example, a procedure for identifying cosmic ray hits that compares either the row-adjacent or column-adjacent values could begin by a user specifying both a threshold value (T=4) and background, or offset value (O=7). Then, for all the pixels in the image the minimum value could be ascertained (M). Next, the pixel value offset could be computed using the following formula:

$$C=M-O$$

Next, for each image pixel $I_i$, the parameters $R_{i-1}$ and $R_{i+1}$, where "i" refers to either the row or column pixel, could be computed using the following formulas:

$$R_{i-1} = \frac{I_i - C}{I_{i-1} - C}$$

and $$R_{i+1} = \frac{I_i - C}{I_{i+1} - C}$$

Finally, if the parameters $R_{i-1}$ and $R_{i+1}$ are each greater than the threshold value T, the pixel value is likely the result of a cosmic ray hit. In addition, the cosmic ray removal/correction procedure could be used multiple times to remove/correct the cosmic ray hits that damage more than one pixel.

Still another factor that typically is considered when using a CCD camera for image acquisition/analysis is the use of hardware binning to improve detection limits of the CCD camera. For example, binning of CCD pixels in hardware can be used to reduce read noise per unit area. Read noise may include noise that results from the process of analog-to-digital (A/D) conversion of the analog signal, or the like. In one embodiment, larger binning could result in lower total electronic noise, and preferably larger binning is used until the electronic noise is driven down to a level where the read noise is less than the noise due to the dark current; dark current is typically unaffected by the binning choice. In one embodiment, where a CCD camera is used for acquiring/analyzing images of luminescence-based assays performed in one or more wells of a microplate, binning advantageously has the added benefit of faster readout time and reduced image data. Larger binning, however, also may result in reduced dynamic range; i.e., the detector could saturate at lower light levels. Binning may also affect the resolution of the images and therefore the level of binning that may be used in a particular application may be limited by that particular application's resolution requirements. In certain embodiments, typical binning settings could include, for example, 2×2, 4×4, 8×8, and the like, or no binning at all.

As discussed above, other factors that are not generally found in other uses of a CCD camera for acquiring/analyzing images of luminescence-based assays performed in one or more wells of a microplate, could be taken into consideration. For example, it may be desirable to ascertain the integrity of the light-tight enclosure by performing a light leak detection routine. Light leak detection could be performed by acquiring a background image and using the image statistics of the background image to determine whether the integrity of the light-tight enclosure has been compromised. In one embodiment the average intensity and standard deviation of the background image could be compared with user-defined light leak detection threshold values. For example, if either the average value or the standard deviation of the background image intensity is greater than the corresponding threshold value, then a light leak condition may exist. The light leak condition could, for example, be flagged for subsequent processing, a warning could be issued to the user/operator, operation could be terminated until a user/operator has taken corrective action or affirmatively indicated that operation should continue despite the light leak condition, etc. The light leak detection procedure could be carried out prior to performing defect correction and/or cosmic ray removal/correction, but preferably is performed only after the image has been processed to reduce the potential effects that defects and/or cosmic ray hits may have on identification of a light leak condition.

Another factor which could be taken into consideration relates to resizing of the image(s) acquired. In some embodiments, in order to make image processing independent of any hardware binning, and in some cases to reduce processing time, both the background and sector images could be resized to certain predefined sizes. For example, a predefined size could be 160×160 for a 96 well plate, 320×320 for a 384 well plate, 640×640 for a 1536, and 640×640 for multi-spot plates. Where resizing is used and where the original image size is greater than the predefined size, the resized image pixel value could be a sum of the sub-pixels, for example:

$$factor = \frac{original}{predefined}$$

and $$I_{new(r,c)} = \sum_{i,j=0}^{factor} I_{original(r \times factor+i, c \times factor+j)},$$

where original size > predefined size;

Alternatively, if the original image size is smaller than the predefined size, the resized image pixel value could be obtained by distributing the original image pixel value among N pixels of the resized image. In other words, to calculate the resized image pixel value, the original image could be unfolded iteratively by a factor of two (2) until the resized image equals the predefined size. For example, upon each iteration, the intermediate pixel value could be calculated based upon one quarter (¼) of the original pixel value and a weighted value for its neighboring pixel values. The original pixel could, for example be given a weight of nine sixteenths (9/16), the next row-adjacent pixel could be given a weight of three sixteenths (3/16), the next column-adjacent pixel could be given a weight of one sixteenth (1/16), and the diagonal-adjacent pixel could be given a weight of one sixteenth (1/16), for example:

$$factor = \frac{predefined}{original}$$

and $$N = factor^2$$

then, $$I_{intermediate\,(r,c)} = \frac{9}{16} \times \frac{1}{4} \times I_{original(\frac{r}{2},\frac{c}{2})} + \frac{3}{16} \times \frac{1}{4} \times I_{original(\frac{r}{2}-1,\frac{c}{2})} + \frac{3}{16} \times \frac{1}{4} \times I_{original(\frac{r}{2},\frac{c}{2}-1)} + \frac{1}{16} \times \frac{1}{4} \times I_{original(\frac{r}{2}-1,\frac{c}{2}-1)}$$

$$I_{intermediate\,(r+1,c)} = \frac{9}{16} \times \frac{1}{4} \times I_{original(\frac{r}{2},\frac{c}{2})} + \frac{3}{16} \times \frac{1}{4} \times I_{original(\frac{r}{2}+1,\frac{c}{2})} + \frac{3}{16} \times \frac{1}{4} \times I_{original(\frac{r}{2},\frac{c}{2}-1)} + \frac{1}{16} \times \frac{1}{4} \times I_{original(\frac{r}{2}+1,\frac{c}{2}-1)}$$

$$I_{intermediate\,(r,c+1)} = \frac{9}{16} \times \frac{1}{4} \times I_{original(\frac{r}{2},\frac{c}{2})} + \frac{3}{16} \times \frac{1}{4} \times I_{original(\frac{r}{2}-1,\frac{c}{2})} + \frac{3}{16} \times \frac{1}{4} \times I_{original(\frac{r}{2},\frac{c}{2}+1)} + \frac{1}{16} \times \frac{1}{4} \times I_{original(\frac{r}{2}-1,\frac{c}{2}+1)}$$

$$I_{intermediate\,(r+1,c+1)} = \frac{9}{16} \times \frac{1}{4} \times I_{original(\frac{r}{2},\frac{c}{2})} + \frac{3}{16} \times \frac{1}{4} \times I_{original(\frac{r}{2}+1,\frac{c}{2})} + \frac{3}{16} \times \frac{1}{4} \times I_{original(\frac{r}{2},\frac{c}{2}+1)} + \frac{1}{16} \times \frac{1}{4} \times I_{original(\frac{r}{2}+1,\frac{c}{2}+1)}$$

Yet another factor which could be taken into consideration relates to background subtraction. CCD cameras integrate thermally generated electrons as well as electrons that result from exposure to a light source. In one embodiment, a background image taken with the same settings as the luminescence based assay image can be subtracted in order to cancel the potentially adverse effects that thermally generated electrons may have on the acquisition/analysis of images from luminescence based assays. The subtraction of the background image can be accomplished by using a differencing operation to remove the contribution of the thermally generated electrons. This could simply be the subtraction of the background image array from the actual image array, for example:

$$I_{new(r,c)} = I_{original(r,c)} - I_{background(r,c)}$$

Still another factor which could be taken into consideration relates to creating and applying an image mask that corresponds to the particular microplate layout being imaged. In one embodiment, the image mask could be a binary matrix $M_{(r,c)}$ of the same size as the acquired image. The binary matrix could define pixels that are in optical registration with the wells of a microplate or with one or more spots within a well, with a value of one (1). In addition, where manufacturing defects introduce misalignments, the image mask could also be rotated relative to a certain coordinate on the microplate by adding offsets to the centers' coordinates. Once the image mask has been created, the image mask can by applied simply by multiplying the acquired image matrix and the binary image mask matrix.

In one embodiment, the user could be required to specify certain parameters in order to create the appropriate image mask for a particular microplate configuration. For example, a user could specify the following parameters to define the plate configuration: the plate type that defines the number of wells in the mask; well radius and well spacing that could be in absolute units or in units as a function of the predefined image size; well shape, such as circle, square, or the like; and the coordinates of the center mask in, for example, column (X) and row (Y) coordinates. For multi-spot plates the user could also be required to define the spacing between spots in the well, the arrangement of spots in the well, the size of the spots in the well, and the like. In another embodiment, one or more of the previously described parameters could be automatically specified by an indicator found on the plate itself, for example, through use of a bar-code label placed on the plate at the time of manufacture or at the time the reagents are applied.

In certain instances, another form of misalignment or error may be present as evidenced when the actual sector image does not perfectly align with the center of the entire image taken by the CCD camera. Such misalignment may be the result of, for example, mechanical changes in the instrument itself, mis-registration of the microplate beneath the CCD camera, and the like. In one embodiment, such misalignment may be taken into consideration by performing one or more of calibrating the instrument to set the coarse center position and angle after any mechanical change to the instrument and performing a fine adjustment on each sector. Calibration of the instrument may be performed by the user/operator or by service technicians and may be performed according to a predefined maintenance schedule, upon the occurrence of a certain maintenance event, after a predefined number of uses, or the like. This calibrated center could then be used to position the microplate beneath the CCD camera through the use of, for example, stepper motors.

In one embodiment, fine adjustment can be accomplished through a computer-implemented process that automatically performs a fine adjustment of the image mask alignment on every sector to compensate for any slight plate mis-registration. For example, an auto-centering algorithm could be used that calculates a correlation function $F(\Delta r, \Delta c, \Delta \theta)$, where $\Delta r$, $\Delta c$, and $\Delta \theta$ are positional and rotational offsets between the mask and image, to locate the actual center and rotation of the microplate sector. Proper calibration, as discussed above, would help to ensure that, starting at the calibrated position, the closest local maximum in the correlation function will be the true center. To find the maximum, the correlation function could be calculated for all possible $\Delta r$, $\Delta c$, and $\Delta \theta$, or alternatively, an iterative process can be used to locate the maximum by taking steps in $\Delta r$, $\Delta c$, and $\Delta \theta$ towards increasing values of $F(\Delta r, \Delta c, \Delta \theta)$.

In one embodiment the auto-centering algorithm could begin by using reduced-resolution images to get the initial aligned position, and then progress through several steps of higher resolution images to home in on the precisely aligned position. Such an approach could provide for rapid convergence to the optimally aligned position. For example, in a first step the auto-centering algorithm could begin with a low resolution image by binning the image four (4) fold, evaluate the correlation function $F(\Delta r, \Delta c, \Delta \theta)$ at values of $\Delta r$, $\Delta c$, $\Delta \theta$ that are offset by one pixel and angle increment, and then move to the position at which F is greatest. The process would then repeat until the maximum value of the correlation function is found, or until some predefined number of iterations has been carried out. In one embodiment, it could be specified that if the maximum is not found within the predefined number of iterations an error message could be displayed and/or the image could be checked for being dark. If the maximum is found then the corresponding center becomes the starting point for the next step, at which point the image would be unfolded by a factor of two (2) and the procedure is repeated until the initial (predefined) image size is reached.

In order to insure that a few very bright wells do not dominate the alignment calculation, in one embodiment, a normalizing function can be applied to the image to more evenly weight the bright and dim spots/wells. One example of such a normalizing function consists of taking the third root of all pixel values in the image.

Finally, the center that corresponds to the greatest value of $F(\Delta r, \Delta c, \Delta \theta)$ would be considered to be the true center. Additionally, the newly calculated center could be compared to the initial calibrated center and if it is determined that the new center is more than a predefined value, such as ½ of the well/spot spacing, a precautionary measure could be taken such as issuing a warning, halting operation of the instrument, or the like.

As discussed above, if the auto-centering algorithm cannot find the true center of the sector image within a certain predefined number of iterations, then another procedure can be used to determine if the image is actually dark. Alternatively, identification of a dark image could be accomplished prior to carrying out the steps outlined above for auto-centering. In one embodiment, dark image detection can be accomplished by comparing the result values with certain predefined baseline values. The baseline values can be empirically defined with reference to, for example, typical values of assay buffer results, plate type, and the like. For example, if the maximum result value of a sector is less than the baseline value then the image would be considered to be dark.

Still yet another factor that could be taken into consideration relates to cross-talk. Cross-talk occurs due to optical system imperfections such as, for example, when light from one well, or spot, diffracts, refracts, is multiply reflected or scattered ("bleeds") into a neighboring well, or onto a neighboring spot. In one embodiment, cross-talk can be empirically measured and a corrective matrix can be assembled and used to deconvolve the cross-talk. The cross-talk corrective matrix is the inverse of the cross-talk matrix between a well, or a spot, and its neighbors. Cross-talk correction can be applied to single spot and multispot applications, however, experience has shown that satisfactory performance can be achieved in single spot applications without cross-talk correction.

In addition to cross-talk correction, in certain embodiments it may be advantageous to provide for correction of collection efficiency variations that may be present across a well. In certain embodiments, the collection efficiency across a well may not be uniform. For example, light from regions near the edge of the well may not be as efficiently collected as from the region near the center of the well. In embodiments where multiple spots are located in a single well, for example, variation in collection efficiency could be more significant since it is possible that the same reaction located at a region near the edge of a well could appear to have a lower pixel value. In embodiments where only single spots are used in each well variations in collection efficiency may still be present since it could be possible that the same reaction located at a region near the edge of a plate could appear to have a lower pixel value. In one embodiment, such variations in collection efficiency could be corrected by, for example, calculating or empirically determining the efficiencies and using an appropriate scale factor to the initial reported pixel values measured.

Still further corrections may be necessary to account for thermal sensitivity/variation. It has generally been observed that luminescence-based assays may exhibit some thermal dependency/sensitivity. In one embodiment, it would be advantageous to control and/or measure the temperature and/or any variations in order to achieve optimal results. Temperature variations may exist, for example, across a microplate, in one or more localized portions of a microplate, within a single well, or the like. Measuring temperature and/or temperature variations may be accomplished by, for example, utilizing either a contact or non-contact temperature sensor. Contact temperature sensors may include thermistors, thermocouples, and the like and would be used to measure temperature of, for example, the bottom of the microplate in order to estimate the actual temperature of the reactants whereas non-contact temperature sensors may include infrared photometers, infrared spectrometers, lasers, and the like and would be used to take remote temperature readings of the reactants.

Thermal corrections may be applied by, for example, using empirical relations derived from data for a particular assay's and/or label's temperature dependence to determine the appropriate thermal correction factor which should be applied to a particular set of assay results. The thermal correction factor may be a single factor that is based on an average temperature for an entire microplate or may be a variable factor which could depend on, for example, the actual temperature within each well, the actual temperature of a single spot's reactants, the average temperature of a single sector, and the like.

In another embodiment, non-contact sensors for remotely detecting both the temperature of the reactants within one or more wells as well as remotely detecting the temperature at one or more locations on the microplate itself might be employed to better estimate the actual temperature of the reactants within a well. The plate could be moved into a position that would allow the temperature sensor to take a measurement, the plate could be held in a fixed position and the sensor moved into the measurement position, and/or the plate could be held in a fixed position and a scanning sensor could be used to take thermal measurements. A scanning sensor could include, for example, the use of a non-contact sensor such as a infrared spectrometer that uses adjustable mirrors to scan various location on the plate and within the wells.

In addition to the previously described image processing procedures, the use of a CCD camera may also allow for the analysis of the image to determine, for example, non-uniformity of the reaction, quality of the assay or image acquisition, and the like. In one embodiment, it would be possible to determine the percentage of pixels that are active to detect non-uniformity of the reaction which may indicate that there are problems with the plate and/or the reactants' preparation. In addition, image statistics within one or more wells (e.g., mean, variance, median) could provide some indication of the quality of the read.

According to another preferred embodiment, the apparatus is adapted to allow for image acquisition of the plate prior to inducing ECL to determine (a) the position of the plate (e.g., centering, location of spots, etc.), (b) the orientation of the plate (e.g., 180° orientation), (c) type of plate, (d) existence of plate cover or seal, (e) focus, (f) well sample volume, etc. Preferably, the apparatus further comprises a LED or other light source to allow image acquisition of the plate within the light tight enclosure, where the light source may be pulsed on to illuminate the plate only during this image acquisition and turned off for the subsequent measurement of the luminescence. According to a further embodiment, information gathered from the images acquired with the light on, prior to inducing ECL, is used as input for subsequent data processing (e.g., knowledge of the centering of the sector, plate orientation, and plate type).

FIG. 36a depicts an illustrative process flow diagram for one embodiment where one or more photodiodes are used to detect luminescence from luminescence-based assays performed in one or more wells of a microplate. FIG. 36e depicts in greater detail the step of reading luminescence as depicted in FIG. 36a. Preferably, the flow diagram further comprises the step of measuring the plate and/or sample temperature. Use of one or more photodiodes to detect luminescence from one or more wells of a microplate could require consideration of certain additional/modified factors, and implementation of certain additional/modified corrective measures, beyond those previously discussed with reference to CCD cameras. For example, background prediction and subtraction when using photodiode sensors varies since the luminescence data acquired using photodiode sensors is in the form of a waveform. Of course it should be understood that the mode of use of a CCD cameras, as discussed above, is not limited to integrating the ECL signal in the detection hardware itself but alternatively may be used in a mode where the CCD camera measures the ECL signal intensity as a function of time and integrate the signal in a programmable computer system programmed with the appropriate algorithm(s) and set of software instructions. In one embodiment, luminescence data is acquired both before and after activation of the luminescence-based assays in order to obtain background readings that represent the dark condition. The dark values are acquired before and after the activation of the luminescence-based assays to remove the effect of electronic drift, i.e., low frequency noise, and offset. An estimate of the dark signal can be generated using both measurements and a linear, quadratic or other model could be used to correct for any background light that may originate from, for example, the plate when a white microplate is used to increase collection efficiency (for example, due to phosphorescence). The dark signal estimate is subtracted from the measured signal and the resulting waveform is integrated in time to obtain the final reading. Alternatively, rather than integrating, a known temporal response function can be used to fit the measured response.

Alternatively, in another embodiment where the luminescence-based assay is, for example, an ECL assay, the activation waveform could be pulsed and the dark signal could be measured between one or more pulses. Such pulsing could, for example, improve the detection limits by more aptly removing low-frequency noise by essentially shifting the signal to a higher frequency.

5.11 Method of Selecting Biologically Active Compounds and Producing Novel Drugs Another aspect of the invention relates to improved methods and systems for selecting or identifying biologically active compounds and, optionally, incorporating such biologically active compounds into suitable carrier compositions in appropriate dosages. The invention includes the use of the multi-well plates, apparatuses, systems, kits and/or methods of the invention to screen for new drugs, preferably, by high-throughput screening (HTS), preferably involving screening of greater than 50, more preferably 100, more preferably 500, even more preferably 1,000, and most preferably 5,000.

According to a particularly preferred embodiment, the screening involves greater than 10,000, greater than 50,000, greater than 100,00, greater than 500,000 and/or greater than 1,000,000 compounds.

One embodiment of the invention relates to a method for selecting or identifying biologically active compounds from a library of compounds, said method comprising screening said library of compounds for biological or biochemical activity, wherein said screening includes assaying the library of compounds for the biological or biochemical activity, the assays being conducted using the plates and/or apparatus of the invention.

Preferably, the method further comprises identifying one or more active compounds.

Preferably, the method further comprises testing said one or more active compounds for bioavailability, toxicity and/or biological activity in vivo. According to one preferred embodiment, the testing comprises further screening using the plates and/or the apparatus of the invention.

Preferably, the method further comprises synthesizing analogues of said one or more active compounds. According to one preferred embodiment, the analogues are screened for bioavailability, biological activity and/or toxicity using the plates and/or apparatus of the invention.

According to a particularly preferred embodiment, the method further comprises formulating the one or more compounds into drugs for administrating to humans and/or animals. Preferably, the formulating comprises determining the suitable amount of the one or more active compounds in the drug and mixing the suitable amount with one or excipients or carriers. Preferably, the excipient comprises sugar and/or starch.

Another embodiment of the invention relates to a method of analyzing a complex mixture of biochemical substances to measure a plurality of binding components therein, comprising:
(a) introducing said mixture into a multi-well plate adapted for electrode induced luminescence assays (preferably electrochemiluminescence assays), said plate comprising a plurality of wells having a plurality of binding reagents therein;
(b) inducing one or more samples in said wells to luminesce; and
(c) measuring the luminescence from each of said wells.

Another embodiment of the invention relates to a method of analyzing the output of a combinatorial (biological and/or chemical) mixture to measure a plurality of binding components therein, comprising:
(a) introducing said mixture into a multi-well plate adapted for electrode induced luminescence (preferably electrochemiluminescence) assays, said plate comprising a plurality of wells having a plurality of binding reagents therein;
(b) inducing one or more samples in said wells to luminesce; and
(c) measuring the luminescence from each of said wells.

Another embodiment of the invention relates to a method for measuring a single biochemical substance in a sample in a multiplicity of simultaneous assays, comprising:
(a) introducing said sample into a multi-well plate adapted for electrode induced luminescence (preferably electrochemiluminescence) assays, said plate comprising a plurality of wells having a plurality of binding reagents therein;
(b) inducing one or more samples in said wells to luminesce; and
(c) measuring the luminescence from each of said wells.

A further embodiment of the invention relates to a method of drug discovery comprising:
(a) selecting a multiplicity of compounds for testing;
(b) screening said multiplicity of compounds for biological activity (using any one of the multi-well plates and/or apparatus described above) to find one or more biologically active compounds; and
(c) modifying said one or more biologically active compounds to reduce toxicity and/or enhance biological activity thereby forming one or more modified biologically active compounds.

Preferably, the method further comprises screening said modified biologically active compounds for biological activity and/or toxicity (using the multi-well plate and/or apparatus described above).

Preferably, the method further comprises determining the appropriate dosage of one or more of said modified biologically active compounds. Preferably, the method still further comprises incorporating such dosage into a suitable carrier such as sugar or starch to form a drug in solid (e.g., pill or tablet) or liquid form.

Advantageously, the methods, apparatus and/or assay plates or modules of the invention may be integrated into and/or used in a variety of screening and/or drug discovery methods. Such screening and/or drug discovery methods include those set forth in U.S. Pat. No. 5,565,325 to Blake; U.S. Pat. No. 5,593,135 to Chen et al.; U.S. Pat. No. 5,521,135 to Thastrup et al.; U.S. Pat. No. 5,684,711 to Agrafiotis et al.; U.S. Pat. No. 5,639,603 to Dower et al.; U.S. Pat. No. 5,569,588 to Ashby et al.; U.S. Pat. No. 5,541,061; U.S. Pat. No. 5,574,656; and U.S. Pat. No. 5,783,431 to Peterson et al.

According to another embodiment, the invention further comprises identifying adverse effects associated with the drug and storing information relating to the adverse effects in a database. See, U.S. Pat. No. 6,219,674 by Classen, hereby incorporated by reference.

Another aspect of the invention relates to improved biologically active compounds and/or drugs made using the inventive methods.

The following examples are illustrative of some of the apparatuses, plates, kits and methods falling within the scope of the present invention. They are, of course, not to be considered in any way limitative of the invention. Numerous changes and modification can be made with respect to the invention by one of ordinary skill in the art without undue experimentation.

6. EXAMPLES

6.1 Fabrication of Multi-Well Assay Plates Having Screen Printed Electrodes

Multi-layer plate bottoms were prepared by screen printing electrodes and electrical contacts on 0.007" thick Mylar polyester sheet. The Mylar sheet was first cut with a $CO_2$ laser so to form conductive through-holes (i.e., holes that were subsequently made conductive by filling with conductive ink) as well as to form alignment holes that were used to align the plate bottom with the plate top. Electrical contacts were formed on the bottom of the Mylar sheet by screen printing an appropriately patterned silver ink layer (Acheson 479ss) and a carbon ink overlayer (Acheson 407c). The carbon ink layer was dimensioned slightly larger (0.01 inches) than the silver ink layer to prevent exposure of the edge of the silver film. Working and counter electrodes were formed on the top of the Mylar film in a similar fashion except that three layers of carbon ink were used to ensure that no silver remained exposed. The conductive through-holes filled with conductive ink during these screen-printing steps. A dielectric ink was subsequently printed over the electrode layers so as to define the active exposed surface area of the working electrode. Typically, nine plate bottoms were simultaneously printed on an 18"×12" Mylar sheet. Typical registrational tolerances during the screen printing steps were +/−0.007-0.008 inches on the top side of the substrate and +/−0.010 inches on the bottom side. The separation between the printed counter and working electrode strips was kept at >0.010 inches to prevent the formation of short circuits. The working electrodes were conditioned for use in assays by treating the patterned plate bottoms for 5 min. with an oxygen plasma (2000 W, 200 mtorr) in a plasma chamber (Series B, Advanced Plasma Systems, St. Petersburg, Fla.) modified with large area flat electrodes.

Multi-well assay plates were assembled using the plate bottoms described above and injection molded plate tops. The dimensions of the plate tops met industry standards as established by the Society of Biomolecular Screening. The plate tops were either made of black plastic (polystyrene loaded with black pigment) or white plastic (polystyrene loaded with titanium dioxide). The bottom surfaces of the plate tops were contacted with die-cut double sided tape (1 mil PET coated on each side with 2 mil of acrylic pressure sensitive adhesive) so as to allow for sealing of the plate tops to the plate bottoms. The tape was cut to form holes that were slightly oversized relative to the holes in the plate tops. The plate bottoms were fixed (using the laser cut alignment holes) onto alignment pins on an X-Y table. The plate bottoms were optically aligned to the plate tops and then sealed together using a pneumatic press (400 pounds, 10 s). Alignment was carried out sufficiently accurately so that the exposed working electrodes were centered within the wells (+/−0.020 inches for 96-well plates and +/−0.015 inches for 384 well plates). These tolerances ensured that the exposed regions of the working electrodes were within the wells and that there were exposed counter electrode surfaces on both sides of the working electrode.

A variety of types of multi-well assay plates were prepared according to the procedure described above. A few specific plate designs are described in more detail below to allow for reference in subsequent examples. Plate A, a 96-well plate sectioned into 12 columnar sectors of 8 wells, was prepared using components and patterns as pictured in FIG. 10 and a white plate top. Plate B, a 96-well plate sectioned into 6 square sectors of 4×4 wells, was prepared using components and patterns as pictured in FIG. 11 and a black plate top. Plate C, a 96-well plate sectioned into 6 square sectors of 4×4 wells, was prepared using components and patterns as pictured in FIG. 14 (except that the electrodes and contacts are sectioned such as illustrated in FIG. 11 (Details A and C)) and a black plate top. The dielectric layer in Plate C is patterned so as to expose four isolated "fluid containment regions" on the working electrode surface within each well. Plate D was similar to Plate C except that the dielectric layer was patterned so as to expose 7 isolated "fluid containment regions" on the working electrode within each well. Plate E was similar to Plate C except that the dielectric layer was patterned so as to expose 10 isolated "fluid containment regions" on the working electrode within each well. Plate F, a 384-well plate sectioned into 6 square sectors of 8×8 wells, was prepared using components and patterns as pictured in FIG. 12 and a black plate top. In each of the FIGS. 10, 11, 12 and 14, details A, B, C and D show, respectively, the printed contact layer, the Mylar film with through-holes, the printed electrode layer and the printed dielectric layer.

6.2 Fabrication of Multi-Well Assay Plates Having Plate Bottoms Formed from Extruded Carbon-Polymer Composites This example describes the fabrication of an embodiment of multi-well assay plate 800 shown in FIG. 8A (referred to hereafter as Plate G). In this example, conductive layer 820 was a composite comprising carbon fibrils dispersed in ethylene—vinyl acetate (EVA) copolymer; conductive tape 810 was a conductive foil laminate (Lamart APS-25 having a 0.36 mil aluminum film on a 1 mil polyester (PET) substrate coated with a 1 mil layer of acrylic pressure sensitive adhesive and having a protecting backing to protect the adhesive during processing steps); adhesive layer 806 was a double-sided adhesive tape comprising a 1 mil polyester film (PET) coated on both sides with 2 mil of acrylic pressure sensitive adhesive and plate top 802 was an injection-molded black polystyrene plate top that conformed to the Society of Biomolecular Screening guidelines.

The carbon fibril—EVA composite was prepared as described in Published PCT Application WO98/12539 and extruded into a 0.010" thick sheet. The sheet was backed with an adhesive polyester liner and cut with a flat bed engraved die (the depth of the cuts were designed so as to leave the six square sections of the composite in correct orientation on a single piece of liner). The conductive tape was die cut using a rotary die and married to the top surface of the composite sheet. The exposed top surface of the composite sheet was conditioned for use in assays by treating the patterned plate bottoms for 5 min. with an oxygen plasma (2000 W, 200 mTorr) in a plasma chamber (Series B, Advanced Plasma Systems, St. Petersburg, Fla.) modified with large area flat electrodes. The plate bottom was attached to the plate top using a double sided adhesive before the bottom was painted with silver and the counter electrode was folded over. The liner was then removed from the back of the composite sheet, the back of the composite sheet was painted with silver paste and the conductive tape folded around and married to the back of the composite sheet to form the completed plate bottom. Two other plates were prepared using analogous protocols except: Plate H had a 16×24 arrangement of wells and Plate I was prepared using a 8×12 arrangement of wells, but had a white plate top and a fibril composite that was sectioned into 12 columnar sections as shown in FIG. 8B.

6.3 ECL Measurements

ECL was induced from multi-well assay plates and measured using one of two instrumental configurations. Plates that were sectioned into 12 columnar sectors of 8 wells (Plates A and H) were read on an instrument designed to make electrical contact to single columnar sectors. The sector in electrical contact with the instrument was aligned with an array of 8 photodiodes that were used to measure the ECL emitted from each well. A translation table was used to translate the plate under the array of photodiodes so as to allow all 12 sectors to be read. Plates that were sectioned into 6 square sectors (Plates B, C, D, E, F and G) were read on an instrument designed to make electrical contact to individual square sectors. The sector in electrical contact with the instrument was aligned with a telecentric lens (having a front element with a diameter of 4.1") coupled to a cooled CCD camera (VersArray: 1300F, Princeton Instruments) that was used to image ECL emitted from the sector. The camera employed a CCD chip with dimensions of roughly 2.6 cm×2.6 cm and having a 1340×1300 array of pixels. The pixel size was 0.02 mm×0.022 mm. An optical band pass filter in the optical path was used to select for light matching the emission profile of ruthenium-tris-bipyridine. A translation table was used to translate the plate under the telecentric lens so as to allow all 6 sectors to be read. Image analysis software was used to identify wells or assay domains within wells and to quantitate ECL from specific wells or domains. ECL from plates having screen printed carbon working electrodes was induced using a linear voltage scan from 2.5 V to 5.5 V over 3 seconds. ECL from plates having fibril-EVA composite electrodes was induced using a linear voltage scan from 2 V to 5 V over 3 seconds. ECL is reported as the total integrated light signal measured over the period of the voltage scan (after correcting for background light levels and detector offset). ECL signals measured on the two different instruments are not directly comparable.

6.4 ECL from Ruthenium-Tris-Bipyridine in Solution

Solutions containing varying concentrations of ruthenium (II)-tris-bipyridine dichloride were prepared in a buffer containing approximately 100 mM tripropylamine and 0.1% triton X-100 in 200 mM phosphate buffer, pH 7.5 (Origeng Assay Buffer, IGEN International). ECL from these solutions was measured (according to the procedures described in Example 6.3) in multi-well assay plates prepared according to Examples 6.1 and 6.2. The volume of solution in the wells was 100 uL for 96-well plates and 40 uL for 384 well plates. FIGS. 24 and 25 show the ECL signal as a function of the concentration of ruthenium-tris-bipyridine in a variety of different plate configurations. The plots show that the multi-well assay plates were suitable for the highly sensitive detection of ruthenium-tris-bipyridine in solution.

6.5 ECL Immunoassay Using Multi-Well Assay Plates

The following example illustrates the use of multi-well assays plates in ECL-based sandwich immunoassays. Plates prepared according to Examples 6.1 and 6.2 were coated with a capture antibody specific for an epitope on the analyte of interest. The coating was achieved by dispensing a solution containing the antibody onto the active working electrode surface of each well and allowing the solution to dry over the course of an hour. The volume of the solution was chosen so that the antibody solution would spread over the surface of the working electrode but would be confined to the surface of the working electrode (i.e., by the physical barrier provided by either the conductive tape layer or a printed dielectric layer). The concentration of antibody was chosen so as to provide a small excess of antibody relative to the amount present on a fully saturated working electrode surface. In some cases it was found that the deposition of antibody was more reproducible and/or efficient when a biotin-labeled antibody was used and when the biotin antibody was mixed with avidin prior to deposition on the working electrode surface. Alternatively, avidin could be adsorbed on the working electrode and the biotin-labeled antibody could be bound to the avidin layer in a subsequent step. After drying the antibody solution on the working electrode, the excess unbound antibody was removed (and uncoated surfaces blocked) by filling the wells with a solution containing 5% (w/v) bovine serum albumin (BSA) in phosphate buffered saline (PBS). The plates were incubated with the blocking solution overnight at 4° C. and then washed with PBS. In this step and in subsequent steps the volume of fluid in the well was sufficient to cover the entire bottom surface of the well, as opposed to being confined to the exposed surface of the working electrode. The assays were carried out by combining in the wells of the coated plates i) the samples and ii) a solution (a buffered electrolyte containing BSA, detergent and/or other blocking agents) containing a detection antibody (labeled by reacting with a sulfonated derivative of ruthenium-tris-bipyridine, NHS ester 1 shown below) that was specific for a second epitope on the analyte of interest. The label is described in copending U.S. patent application Ser. No. 09/896,974, entitled "ECL LABELS HAVING IMPROVED NON-SPECIFIC BINDING PROPERTIES, METHODS OF USING AND KITS CONTAINING THE SAME", filed on even date, the disclosure hereby incorporated by reference.

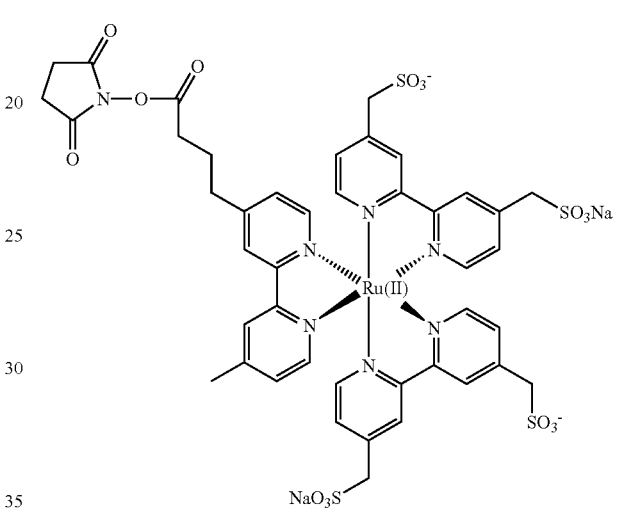

1

The plates were incubated for 1 h at room temperature (96 well plates were mixed using a plate shaker; the 384 plates were not mixed). The wells were washed with PBS. The wells were filled (100 uL in 96-well plates; 40 uL in 384-well plates) with tripropylamine-containing solution (ORIGEN Assay Buffer, IGEN International) and analyzed using ECL-detection as described in Example 6.3.

FIGS. 26 and 27 show ECL signal as a function of the concentration of prostrate specific antigen (PSA) in samples as measured on a variety of different plate configurations. The capture and detection antibodies were prepared by labeling the same antibodies as used in the Roche Elecsys PSA Assay Kit (Roche Diagnostics). FIG. 28 shows ECL signal as a function of the concentration of alpha-fetoprotein (AFP) as measured using an ECL immunoassay for AFP. The capture and detection antibodies were prepared by labeling the same antibodies as used in the Roche Elecsys AFP Assay Kit (Roche Diagnostics). The reported ECL signals are corrected for background signals as measured using samples that do not contain the analyte of interest.

6.6 Multi-Analyte Immunoassays in Multi-Well Assay Plates

Sandwich immunoassays for four different cytokines—interleukin 1β (IL-1β), interleukin 6 (IL-6), interferon γ (IFN-γ) and tumor necrosis factor α (TNF-α)—were carried out simultaneously in the wells of plates manufactured according to the design and procedure described for Plate C in Example 6.1, except that antibodies were adsorbed onto the surfaces of the working electrodes subsequent to the plasma treatment step and prior to attachment of the plate top. This plate design has a dielectric pattern printed over the working electrode in each well that exposes four "fluid containment regions" over each electrode. Four capture antibodies (each selective for one of the analytes of interest) were patterned into distinct assay domains by microdispensing solutions of the antibodies on the fluid containment regions within each well (one antibody per region) and allowing the antibodies to adsorb to the surface of the working electrode. Solutions (0.25 uL) containing the antibody (at a concentration of 32 ug/mL for IL-1β and TNF-α or 64 ug/mL for IL-6 and IFN-γ) and 0.1% BSA in phosphate buffered saline were dispensed onto the fluid containment regions using a solenoid valve controlled microdispensor (Biodot Dispensor, Cartesian Technologies) and allowed to evaporate to dryness. The volume of the antibodies was sufficient to spread over all of the exposed electrode surface within a fluid containment region but was small enough so that the fluid did not spread past the boundary formed by the dielectric layer. After drying the antibody solution on the working electrode, the plate tops were attached and the excess unbound antibody was removed (and uncoated surfaces blocked) by filling the wells with a solution containing 5% (w/v) bovine serum albumin (BSA) in phosphate buffered saline (PBS). The plates were incubated with the blocking solution overnight at 4° C. and then washed with PBS.

The assays were carried out by the steps of i) adding 0.02 mL of the sample to the well and incubating for 1 hour on a plate shaker; ii) washing the wells with PBS; iii) adding 0.02 mL of a solution containing 2,000 ng/mL each of four detection antibodies (labeled with NHS ester 1) against the four analytes of interest and incubating for 1 hour on a plate shaker; iv) washing with PBS; v) introducing 0.1 mL of a solution containing tripropylamine in phosphate buffer (ORIGEN Assay Buffer, IGEN International) and vi) measuring ECL as described in Example 6.3. The ECL emitted from the plates was imaged using a cooled CCD camera. The apparatus used image analysis software to identify the assay domains in the ECL image and to quantify the light emitted from each of the four assay domains in each well. FIG. 29 demonstrates that each of the analytes of interest can be independently measured in a single sample in a single well of a multi-well assay plate. The figures show ECL emitted from each assay domain as a function of the concentration of each analyte. The introduction of a specific analyte led to a linear increase in ECL with analyte concentration (relative to the background signal measured in the absence of any analyte) at assay domains having capture antibodies directed against that analyte, but did not affect the ECL at assay domains having antibodies directed against the other analytes. FIG. 30 shows an image of the ECL emitted from a sector of wells used to assay solutions containing mixtures of the four analytes. The highlighted well is annotated to show the arrangement of the four assay domains. That specific well was used to assay a sample having 250 pg/mL each of IL-1β and TNF-α and 8 pg/mL each of IL-6 and IFN-γ.

6.7 ECL-Based Nucleic Acid Hybridization Assays in Multi-Well Assay Plates

This example describes a nucleic acid hybridization assay carried out on a plate manufactured as described for Plate G in Example 6.2. The exposed surface of the working electrode in each well was coated by dispensing on the working electrode 1,500 nL of a solution containing avidin at a concentration of 1 mg/mL and allowing the solution to dry on the surface (the avidin was confined to the working electrode surface by the fluid barrier provided by the conductive tape). After drying the avidin solution on the working electrode, the excess unbound antibody was removed (and uncoated surfaces blocked) by filling the wells with a solution containing 5% (w/v) bovine serum albumin (BSA) in phosphate buffered saline (PBS). The plates were incubated with the blocking solution overnight at 4° C. and then washed with PBS.

Avidin-coated plates provide a convenient generic platform for the immobilization of biotin-labeled reagents. In this example, a biotin-labeled 28 nucleotide DNA probe sequence was immobilized on the plates by introducing to each well 0.05 mL of a 100 nM solution of the biotin-labeled probe, incubating the plate for 1 hour while shaking on a plate shaker and washing excess probe away with PBS. The immobilized probe was used to assay for samples containing a complementary DNA target sequence that was labeled at the 5' position with a derivative of ruthenium-tris-bipyridine (TAG Phosphoramidite, IGEN International). Varying amounts of the labeled target DNA sequence in a volume of 0.05 mL were introduced into the wells and allowed to hybridize at room temperature over a period of 1 hour while shaking the plate on a plate shaker. After washing the wells with PBS, the wells were filled with 0.1 mL of ORIGEN Assay Buffer (IGEN International) and analyzed as described in Example 6.3. FIG. 31 shows that the ECL signal (corrected for the background signal observed in the absence of the labeled target sequence) was linearly dependent on the concentration of the target sequence over a concentration range exceeding four orders of magnitude.

6.8 Use of Multi-Well Assay Plates and Luminescence Imaging Apparatus in Chemiluminescence-Based Assays This example describes a chemiluminescence-based binding assay carried out on a plate manufactured as described for Plate B in Example 6.2. In this example, the carbon ink working electrode of the plate is not used as an electrode but is only used as a high surface area solid phase support for binding reagents. The exposed surface of the working electrode in each well was coated by dispensing on the working electrode 2,500 nL of a solution containing avidin at a concentration of 1 mg/mL and allowing the solution to dry on the surface (the avidin was confined to the working electrode surface by the fluid barrier provided by the conductive tape). After drying the avidin solution on the working electrode, the excess unbound antibody was removed (and uncoated surfaces blocked) by filling the wells with a solution containing 5% (w/v) bovine serum albumin (BSA) in phosphate buffered saline (PBS). The plates were incubated with the blocking solution overnight at 4° C. and then washed with PBS.

The avidin-coated plates were used as a solid phase for assaying for a biotin labeled antibody. Samples containing varying amounts of a biotin-labeled mouse monoclonal IgG in 0.05 mL of 0.1% BSA/PBS were added to the wells. The plates were mixed on a plate shaker for 1 hour and then washed with PBS. The wells were then treated with 0.05 mL of a 1:10,000 dilution of a alkaline phosphatase labeled goat anti-mouse antibody (Sigma) diluted in 0.1% BSA in PBS. The plates were mixed on a plate shaker for 1 hour and then washed with PBS followed by a Tris based buffer. A solution containing a chemiluminescent alkaline phosphate substrate and a chemiluminescence enhancer (50 uL of Emerald II substrate and enhancer, Perkin Elmer) was added to the wells. The plate was allowed to incubate for 5-10 min to allow the chemiluminescent reaction to stabilize and was then imaged using the imaging plate reader described in Example 6.3 except that an electrical potential was not applied to the plates. FIG. 32 shows the chemiluminescence as a function of the concentration of biotin-labeled monoclonal antibody. The chemiluminescence was considerably more intense than that measured in an analogous experiment using avidin adsorbed on standard polystyrene plates; presumably, the assay on the carbon surface benefited from the high surface area and excellent adsorptive properties of the plasma-treated carbon surface.

6.9 ECL Measurements in 1536-Well Plates

The basic multi-well plate structure shown in FIG. 8A was adapted to a 1536-well plate format. The sectioned working electrode layer was made by screen printing, on a Mylar substrate, 6 square pads composed of carbon ink over silver ink. The conductive pads were connected to screen-printed electrical contacts on the back of the plate (also carbon ink over silver ink) through laser-cut through-holes in the Mylar substrate that filled with conductive material during the screen-printing steps. The counter electrode layer was made by patterning 2-ml thick aluminum foil using standard photolithographic techniques to produce a 48×32 array of square holes in the foil: i) the foil was coated with a layer of photoresist, ii) the photoresist was patterned by illumination through a patterned mask, iii) the photoresist was washed to reveal a pattern of exposed aluminum, iv) the aluminum was chemically etched to produce the array of holes and v) the remainder of the photoresist was removed. By analogy to FIG. 8A, the aluminum film was oversized relative to the plate so as to allow it to be folded around the working electrode layer. This oversized section of the aluminum foil had photolithographically defined holes so as to allow contact through the aluminum film to the working electrode contacts. The etched aluminum foil was then laminated on one side to a dielectric film having the same pattern of holes.

The plate was assembled as follows. Double sided adhesive tape having a laser-cut 48×32 array of square shaped holes (in the 1536-well pattern) was aligned and mated to the bottom of a 1536-well plate top with square wells (Greiner America). The remaining exposed side of the adhesive tape was then aligned and mated to the non-laminated side of the patterned aluminum foil. A second layer of double sided adhesive tape with a laser-cut 48×32 array of square holes was then aligned and mated to the laminated side of the aluminum foil. Finally, the remaining exposed side of the second layer of double sided adhesive was aligned and mated to a Mylar substrate so as to form a 1536-well plate with wells having walls defined by holes through the plate top, the laminated aluminum foil and the two layers of double sided adhesive, and having well bottoms defined by the working electrode pads. To complete the plate structure, a third layer of double sided adhesive tape (this layer having holes patterned in the same arrangement as the oversized section of the aluminum foil layer) was aligned and mated to the back of the screen-printed Mylar substrate. The oversized section of the laminated aluminum foil layer was folded back around the substrate and mated to this third layer of double sided adhesive tape so as to allow electrical contact to the aluminum foil as well as electrical contact (through the holes in the laminated aluminum foil and the third layer of double sided adhesive tape) to the patterned electrical contacts on the back of the substrate.

ECL was induced in and measured from the 1536-well plates was read on the instrument designed to make electrical contact to individual square sectors (as described in Example 6.3). Solutions containing varying concentrations of ruthenium(II)-tris-bipyridine dichloride in a TPA-containing buffer (ORIGEN Assay Buffer, IGEN International) were dispensed into wells of a plate (0.005 mL/well). ECL was induced by ramping the voltage applied to the working electrode from 2 to 4 volts over a period of 3 seconds. FIG. 33 shows the integrated electrochemiluminescence associated with each well as a function of the concentration of ruthenium (II)-tris-bipyridine dichloride in the well. Each point represents the average of values obtained from 32 wells of the plate. The expected linear dependence of ECL intensity with the concentration of ruthenium(II)-tris-bipyridine dichloride was observed (slope of log-log plot as determined by linear regression=1.06).

Section 6.10: Effect of Type of $TiO_2$ on Photochemically Induced Luminescence

The following forms of $TiO_2$ were tested to determine the effect of type of $TiO_2$ on photochemically induced luminescence. All grades are rutile except where noted:

| Grade | Source | Inorganic treatment | Organic treatment |
|---|---|---|---|
| R101 | DuPont | 1.7% alumina | 0.2% polyol |
| R102 | DuPont | 3.2% alumina | 0.25% polyol |
| R104 | DuPont | 1.7% alumina | 0.3% silicone |
| R105 | DuPont | 2.5% alumina, 3.0% silica | Yes, but undisclosed |
| R960 | DuPont | 3.5% alumina, 6.5% silica | none |
| RCL 6 | Millienium | Silica | Yes, but undisclosed |
| RCL 188 | Millienium | Phosphate | Yes, but undisclosed |
| Anatase | Millienium | Unknown | Unknown |

Experiment 1:

Procedure:

1. 0.6 grams of each type of $TiO_2$ in powder form were weighed out.
2. 3.4 grams of epoxy were weighed out and mixed by hand with the $TiO_2$ to give a final concentration of 15 weight percent $TiO_2$.
3. All the samples were then spotted onto an aluminum surface.
4. The surface was exposed to either UV or fluorescent light for several seconds and then placed in a reader with a CCD camera.
5. The luminescent intensity was read after 15 seconds.

Results: 15 wt. % $TiO_2$ in epoxy - 15 seconds after insertion into instrument

| | | Background corrected light intensity | |
|---|---|---|---|
| Grade | Source | UV light | Fluorescent |
| R101 | DuPont | 19 | 22 |
| R102 | DuPont | 28 | 36 |
| R104 | DuPont | 13 | 14 |
| R105 | DuPont | 15 | 17 |
| R960 | DuPont | 13 | 12 |
| RCL6 | Millienium | 38 | 44 |
| RCL 188 | Millienium | 86 | 96 |
| Anatase | Millienium | — | 25 |

From this experiment, the alumina surface treatment (DuPont grades) appears to reduce light emission 4-5 times compared to phosphate treatment (RCL 188) and by 2-3 times compared to silica (RCL 6).

The two best grades R104 and R960 and the RCL 188 were compounded into polystyrene to see if the effect was the same in the desired polymer (Experiment 2).

Experiment 2:

The above experiment was repeated for three forms of the $TiO_2$ tested above compounded into polystyrene at ~5 and 15 weight percent using a tungsten light source. Samples were measured in triplicate. The light intensity was read at 15 seconds after insertion into the instrument.

| | Results in polystyrene - 15 seconds after insertion into instrument | | |
|---|---|---|---|
| | Concentration | Background corrected light intensity | |
| Grade | (wt. %) | Mean | Standard Deviation |
| R104 | 16 | 14 | 2 |
| R104 | 5 | 30 | 7 |
| R960 | 19 | 16 | 1 |
| R960 | 6 | 6 | 1 |
| RCL188 | 16 | 84 | 19 |
| RCL188 | 5 | 10 | 1 |
| Polystyrene | 0% $TiO_2$ | 0 | 0 |

Again, the alumina coated $TiO_2$ emitted less light than the silica coated material. For R104, the emitted light decreased with increased $TiO_2$ concentration. The experiments were repeated with the same results. The concentration of $TiO_2$ for the R104 samples was verified by an independent measurement.

7. INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A multi-well plate comprising a plate top having plate top openings and a plate bottom mated to said plate top to define wells of said multi-well plate, said plate bottom comprising a substrate having a top surface with electrodes patterned thereon and a bottom surface with electrical contacts patterned thereon, wherein said electrodes and contacts are patterned to define two or more independently addressable sectors of two or more jointly addressable assay wells, each sector comprising two or more wells with:
   (a) jointly addressable working electrodes on said top surface of said substrate, wherein each of said working electrodes is electrically connected with each other and connected to at least a first of said electrical contacts; and
   (b) jointly addressable counter electrodes on said top surface of said substrate, wherein each of said counter electrodes is electrically connected with each other, but not with said working electrodes, and connected to at least a second of said electrical contacts.

2. The multi-well plate of claim 1, wherein said multi-well plate is a 4 well plate, 6 well plate, 24 well plate, 96 well plate, 384 well plate, 1536 well plate, 6144 well plate or 9600 well plate.

3. The multi-well plate of claim 1, wherein said independently addressable sectors include less than 50% of said wells of said multi-well plate.

4. The multi-well plate of claim 1, wherein said independently addressable sectors include less than 20% of said wells of said multi-well plate.

5. The multi-well plate of claim 1, wherein said independently addressable sectors comprise a 4×4 array of said wells.

6. The multi-well plate of claim 1, wherein said multi-well plate comprises a 2×3 array of independently addressable sectors.

7. The multi-well plate of claim 1, wherein said independently addressable sectors comprise one or more rows or one or more columns of said wells.

8. The multi-well plate of claim 1, wherein said electrodes comprise carbon particles.

9. The multi-well plate of claim 1, wherein said electrodes comprise a printed conductive material.

10. The multi-well plate of claim 1, wherein one or more of said electrodes comprise a plurality of assay domains formed thereon.

11. The multi-well plate of claim 10, wherein said plurality of assay domains comprises at least four assay domains.

12. The multi-well plate of claim 10, wherein said plurality of assay domains comprises at least seven assay domains.

13. The multi-well plate of claim 10, wherein said plurality of assay domains comprises at least ten assay domains.

14. The multi-well plate of claim 1, further comprising a luminescent label in one or more of said wells.

15. The multi-well plate of claim 1, wherein said multi-well plate further includes one or more wells useful in the conduct of a chemiluminescence and/or fluorescence assay.

16. The multi-well plate of claim 1, wherein the inner surface of said wells is substantially free of silicon and silicone.

17. A method of making the multi-well plate of claim 1, comprising:
   (a) forming said patterned electrodes on said top surface and said electrical contacts patterned on said bottom surface, thereby forming said patterned electrodes and contacts to define said independently addressable sectors of jointly addressable working electrodes and said jointly addressable counter electrodes; and
   (b) attaching said plate top having a plurality of openings onto said plate bottom;
   wherein said plurality of openings forms a plurality of wells, each having at least one of said working electrodes.

18. The method of claim 17 wherein said forming step (a) further comprises
   (i) introducing a plurality of through-holes in said substrate; and
   (ii) screen-printing said patterned electrodes and/or said electrical contacts and thereby filling said through-holes with a conducting material to provide an electrical connection between said working electrodes and said electrical contacts.

19. The method of claim 18 wherein said introducing step (i) comprises a method selected from the group consisting of punching, drilling, burning, laser-drilling, machining, etching and a combination thereof.

20. The method of claim 18 wherein said conductive material is a conductive ink.

21. The multi-well plate of claim 1, wherein said electrodes comprise metal-coated pressure sensitive adhesive.

22. The multi-well plate of claim 1, wherein at least one well comprises a surface of said working electrodes and said surface is bounded by a dielectric surface.

23. The multi-well plate of claim 1, wherein at least one of said working electrodes in at least one of said wells of said multi-well plate has one or more assay domains comprising immobilized reagents, said assay domains being defined by openings in one or more dielectric layers supported on said at least one working electrode.

24. The multi-plate of claim 1, wherein said plate top comprises a plurality of rows of openings and said plate bottom comprises said working electrodes and said counter electrodes patterned as strips on said plate bottom, wherein said plate top is affixed to said plate bottom thereby forming a plurality of rows of wells defined by said openings, wherein the bottom of each well comprises an exposed portion of at least one working electrode strip and two exposed edge portions of at least one of said counter electrodes strips.

25. The multi-well plate of claim 1, wherein said plate bottom comprises an insulating substrate and a conductive substrate, wherein said conductive substrate is folded around said insulating substrate forming said electrodes on a first side of said insulating substrate and said electrical contacts on a second side of said insulating substrate.

26. The multi-well plate of claim 1, wherein at least one of said wells comprises a surface of one of said working electrodes, said surface having a plurality of assay domains formed thereon.

27. The multi-well plate of claim 26, wherein said assay domains are independently addressable.

28. The multi-well plate of claim 1, wherein two or more of said wells of said multi-well plate each comprise a working electrode surface formed by applying one or more layers of carbon onto a conductive layer comprising silver.

29. A multi-well plate according to claim 1 wherein said electrodes patterned on said top surface are electrically connected to said electrical contacts patterned on said bottom surface, wherein said substrate further comprises one or more conductive through-holes electrically that provide said electrical connections between said electrodes patterned on said top surface and said electrical contacts patterned on said bottom surface.

* * * * *